US011623911B2

(12) United States Patent
Petrie et al.

(10) Patent No.: US 11,623,911 B2
(45) **Date of Patent: *Apr. 11, 2023**

(54) LIPID COMPRISING DOCOSAPENTAENOIC ACID

(71) Applicants: Commonwealth Scientific and Industrial Research Organisation, Acton (AU); Grains Research and Development Corporation, Barton (AU); Nuseed Nutritional Australia Pty Ltd, Laverton North (AU)

(72) Inventors: James Robertson Petrie, Goulburn (AU); Surinder Pal Singh, Downer (AU); Pushkar Shrestha, Lawson (AU); Jason Timothy McAllister, Portarlington (AU); Robert Charles de Feyter, Monash (AU); Malcolm David Devine, Vernon (CA)

(73) Assignees: COMMONWEALTH SCIENTIFIC AND INDUSTRIAL RESEARCH ORGANISATION, Acton (AU); GRAINS RESEARCH AND DEVELOPMENT CORPORATION, Barton (AU); NUSEED NUTRITIONAL AUSTRALIA PTY LTD., Laverton North (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/146,469

(22) Filed: Sep. 28, 2018

(65) Prior Publication Data

US 2019/0194572 A1 Jun. 27, 2019

Related U.S. Application Data

(63) Continuation of application No. 15/617,642, filed on Jun. 8, 2017, now Pat. No. 10,125,084, which is a (Continued)

(30) Foreign Application Priority Data

Jun. 27, 2014 (AU) ................................ 2014902471
Dec. 18, 2014 (AR) .............................. 20140104761

(51) Int. Cl.
*C07C 69/587* (2006.01)
*C12N 15/82* (2006.01)
(Continued)

(52) U.S. Cl.
CPC .............. *C07C 69/587* (2013.01); *A23D 9/00* (2013.01); *A61K 31/20* (2013.01); *A61K 31/201* (2013.01);
(Continued)

(58) Field of Classification Search
CPC .... C07C 69/587; C12N 15/8247; A23D 9/00; C11B 1/10; A61K 31/20; A61K 31/202; A61K 36/31
See application file for complete search history.

(56) References Cited

U.S. PATENT DOCUMENTS 4,399,216 A 8/1983 Axel
5,004,863 A 4/1991 Umbeck
(Continued)

FOREIGN PATENT DOCUMENTS

AU 667939 1/1994
AU 200059710 B2 12/2000
(Continued)

OTHER PUBLICATIONS

Complaint for Declaratory Judgment, filed by BASF Plant Science, LP, on Sep. 19, 2017, in the United States District Court for the Eastern District of Virginia Alexandria Division, in connection with "*BASF Plant Science, LP* v. *Commonwealth Scientific and Industrial Research Organisation, Grains Research and Development Corporation, and Nuseed Pty, Ltd*", Case No. 2:17-cv-00503.
(Continued)

*Primary Examiner* — Yate' K Cutliff
(74) *Attorney, Agent, or Firm* — Gary J. Gershik

(57) ABSTRACT

The present invention relates to extracted plant lipid or microbial lipid comprising docosapentaenoic acid, and processes for producing the extracted lipid.

38 Claims, 4 Drawing Sheets

Figure 1:
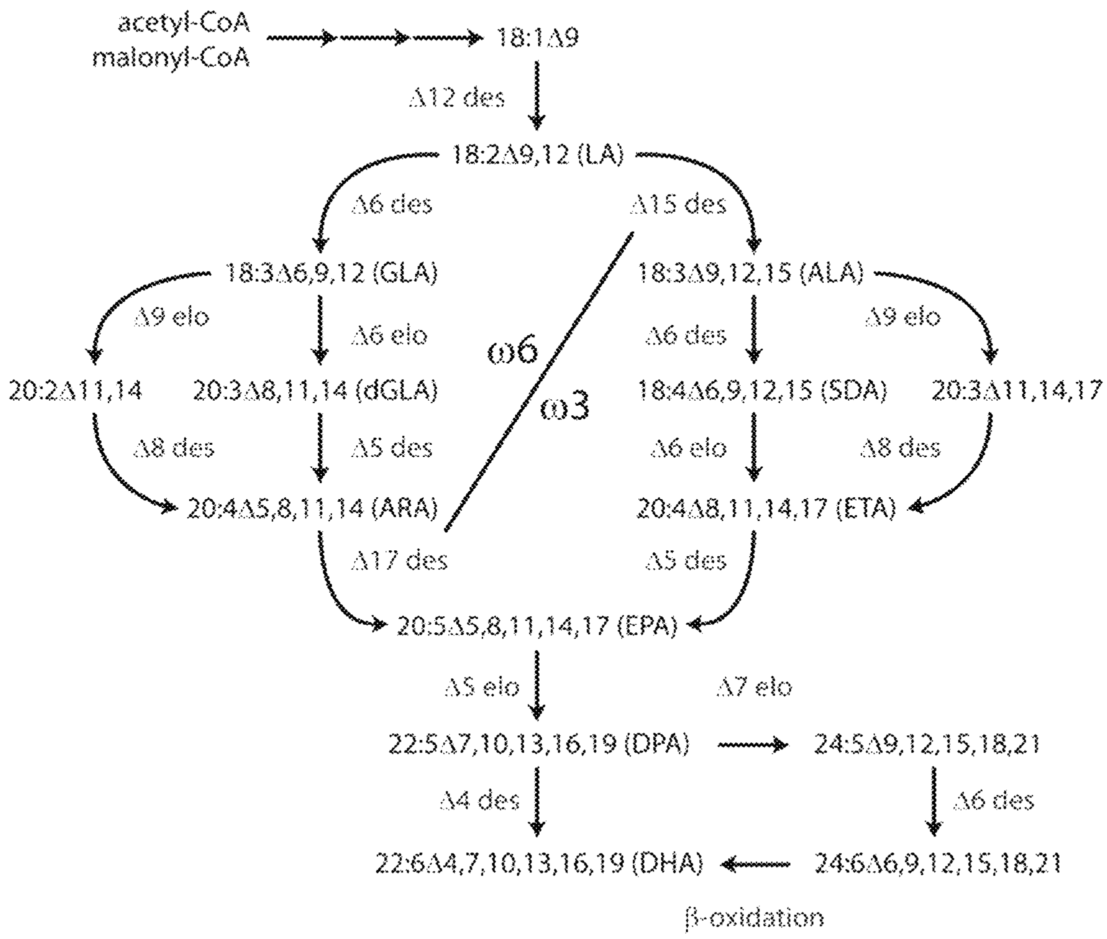

Specification includes a Sequence Listing.

Related U.S. Application Data continuation of application No. 14/743,531, filed on Jun. 18, 2015, now Pat. No. 9,718,759, which is a continuation-in-part of application No. PCT/AU2014/050433, filed on Dec. 18, 2014, and a continuation-in-part of application No. 14/575,756, filed on Dec. 18, 2014, now Pat. No. 9,725,399.

(51) Int. Cl.

| | |
|---|---|
| ***A61K 36/31*** | (2006.01) |
| ***A23D 9/00*** | (2006.01) |
| ***A61K 31/20*** | (2006.01) |
| ***A61K 31/201*** | (2006.01) |
| ***A61K 31/202*** | (2006.01) |
| ***C11B 1/10*** | (2006.01) |

(52) U.S. Cl.

CPC ............ *A61K 31/202* (2013.01); *A61K 36/31* (2013.01); *C11B 1/10* (2013.01); *C12N 15/8247* (2013.01); *A61K 2236/00* (2013.01); *A61K 2236/333* (2013.01)

(56) References Cited

U.S. PATENT DOCUMENTS

| | | | | |
|---|---|---|---|---|
| 5,104,310 | A | 4/1992 | Saltin | |
| 5,159,135 | A | 10/1992 | Umbeck | |
| 5,177,010 | A | 1/1993 | Goldman | |
| 5,362,865 | A | 11/1994 | Austin | |
| 5,416,011 | A | 5/1995 | Hinchee | |
| 5,451,513 | A | 9/1995 | Maliga | |
| 5,463,174 | A | 10/1995 | Moloney | |
| 5,504,200 | A | 4/1996 | Hall | |
| 5,518,908 | A | 5/1996 | Corbin | |
| 5,545,818 | A | 8/1996 | McBride | |
| 5,552,306 | A | 9/1996 | Thomas | |
| 5,569,834 | A | 10/1996 | Hinchee | |
| 5,589,617 | A | 12/1996 | Nehra | |
| 5,608,152 | A | 3/1997 | Kridl | |
| 5,614,393 | A | 3/1997 | Thomas | |
| 5,663,068 | A | 9/1997 | Thomas | |
| 5,668,299 | A | 9/1997 | Debonte | |
| 5,683,898 | A | 11/1997 | Yazawa | |
| 5,689,050 | A | 11/1997 | Thomas | |
| 5,789,220 | A | 8/1998 | Thomas | |
| 5,798,259 | A | 8/1998 | Yazawa | |
| 5,850,026 | A | 12/1998 | DeBonte | |
| 5,859,347 | A | 1/1999 | Brown | |
| 5,869,617 | A | 2/1999 | Fischer | |
| 5,877,402 | A | 3/1999 | Maliga | |
| 5,932,479 | A | 8/1999 | Daniell | |
| 5,952,544 | A | 9/1999 | Browse | |
| 5,968,809 | A | 10/1999 | Knutzon | |
| 5,972,664 | A | 10/1999 | Knutzon | |
| 6,051,754 | A | 4/2000 | Knutzon | |
| 6,075,183 | A | 6/2000 | Knutzon | |
| 6,100,447 | A | 8/2000 | Wu | |
| 6,136,574 | A | 10/2000 | Knutzon | |
| 6,140,486 | A | 10/2000 | Facciotti | |
| 6,194,167 | B1 | 2/2001 | Browse | |
| 6,329,518 | B1 | 12/2001 | Green | |
| 6,342,658 | B1 | 1/2002 | DeBonte | |
| 6,355,861 | B1 | 3/2002 | Thomas | |
| 6,372,965 | B1 | 4/2002 | Lightner | |
| 6,403,349 | B1 | 6/2002 | Mukerji | |
| 6,410,288 | B1 | 6/2002 | Knutzon | |
| 6,428,990 | B1 | 8/2002 | Mukerji | |
| 6,432,684 | B1 | 8/2002 | Mukerji | |
| 6,459,018 | B1 | 10/2002 | Knutzon | |
| 6,492,108 | B1 | 12/2002 | Hillman | |
| 6,541,257 | B2 | 4/2003 | Lemaux | |
| 6,566,583 | B1 | 5/2003 | Facciotti | |
| 6,589,767 | B1 | 7/2003 | Knutzon | |
| 6,620,986 | B1 | 9/2003 | McKeon | |
| 6,635,951 | B1 | 10/2003 | Mukerji | |
| 6,677,145 | B2 | 1/2004 | Mukerji | |
| 6,683,232 | B1 | 1/2004 | Thomas | |
| 6,686,185 | B1 | 2/2004 | Logan | |
| 6,825,017 | B1 | 11/2004 | Browse | |
| 6,825,335 | B1 | 11/2004 | Marin | |
| 6,838,594 | B1 | 1/2005 | Kinney | |
| 6,858,416 | B2 | 2/2005 | Mukerji | |
| 6,864,077 | B1 | 3/2005 | Cahoon | |
| 6,875,595 | B2 | 4/2005 | Kloek | |
| 6,884,921 | B2 | 4/2005 | Browse | |
| 6,897,050 | B1 | 5/2005 | Napier | |
| 6,913,916 | B1 | 7/2005 | Mukerji | |
| 6,936,728 | B2 | 8/2005 | Somerville | |
| 6,958,229 | B2 | 10/2005 | Suzuki | |
| 6,967,243 | B2 | 11/2005 | Debonte | |
| 7,001,772 | B2 | 2/2006 | Roessler | |
| 7,045,683 | B2 | 5/2006 | Mukerji | |
| 7,067,285 | B2 | 6/2006 | Mukerji | |
| 7,067,722 | B2 | 6/2006 | Fillatti | |
| 7,070,970 | B2 | 7/2006 | Mukerji | |
| 7,081,356 | B2 | 7/2006 | Putten | |
| 7,087,432 | B2 | 8/2006 | Qiu | |
| 7,091,005 | B2 | 8/2006 | Petrukhin | |
| 7,109,392 | B1 | 9/2006 | Broglie | |
| 7,135,614 | B1 | 11/2006 | DeBonte | |
| 7,135,623 | B1 | 11/2006 | Rusing | |
| 7,148,336 | B2 | 12/2006 | Fillatti | |
| 7,179,620 | B2 | 2/2007 | Lerchl | |
| 7,179,647 | B2 | 2/2007 | Lerchl | |
| 7,189,559 | B2 | 3/2007 | Damude | |
| 7,192,762 | B2 | 3/2007 | Macool | |
| 7,198,937 | B2 | 4/2007 | Xue | |
| 7,208,297 | B2 | 4/2007 | Mukerji | |
| 7,211,418 | B2 | 5/2007 | Metz | |
| 7,211,656 | B2 | 5/2007 | Mukerji | |
| 7,214,853 | B2 | 5/2007 | Facciotti | |
| 7,217,856 | B2 | 5/2007 | Weaver | |
| 7,220,897 | B2 | 5/2007 | Mukerji | |
| 7,241,619 | B2 | 7/2007 | Mukerji | |
| 7,244,563 | B2 | 7/2007 | Cahoon | |
| 7,247,461 | B2 | 7/2007 | Metz | |
| 7,256,033 | B2 | 8/2007 | Damude | |
| 7,262,343 | B1 | 8/2007 | DeBonte | |
| 7,271,315 | B2 | 9/2007 | Metz | |
| 7,273,746 | B2 | 9/2007 | Yadav | |
| 7,402,735 | B2 | 7/2008 | Browse | |
| 7,411,054 | B2 | 8/2008 | Meyers | |
| 7,504,259 | B2 | 3/2009 | Yadav | |
| 7,537,920 | B2 | 5/2009 | Renz | |
| 7,550,286 | B2 | 6/2009 | Damude | |
| 7,550,651 | B2 | 6/2009 | Damude | |
| 7,589,253 | B2 | 9/2009 | Green | |
| 7,615,679 | B2 | 11/2009 | Lerchl | |
| 7,619,105 | B2 | 11/2009 | Green | |
| 7,659,120 | B2 | 2/2010 | Yadav | |
| 7,659,247 | B2 | 2/2010 | Kretschmar | |
| 7,709,239 | B2 | 5/2010 | Damude | |
| 7,714,185 | B2 | 5/2010 | Napier | |
| 7,736,884 | B2 | 6/2010 | Gunnarsson | |
| 7,777,098 | B2 | 8/2010 | Cirpus | |
| 7,807,849 | B2 | 10/2010 | Singh | |
| 7,834,248 | B2 | 11/2010 | Green | |
| 7,834,250 | B2 * | 11/2010 | Singh | C12Y 114/1900 800/306 |
| 7,838,651 | B2 | 11/2010 | Picataggio | |
| 7,842,852 | B2 | 11/2010 | Cirpus | |
| 7,855,321 | B2 | 12/2010 | Benz | |
| 7,871,804 | B2 | 1/2011 | Cirpus | |
| 7,879,591 | B2 | 2/2011 | Damude | |
| 7,901,928 | B2 | 3/2011 | Yadav | |
| 7,932,438 | B2 | 4/2011 | Singh | |
| 8,013,216 | B2 | 9/2011 | Napier | |
| 8,071,341 | B2 | 12/2011 | Singh | |
| 8,084,074 | B2 | 12/2011 | Kinney | |
| 8,106,226 | B2 | 1/2012 | Singh | |
| 8,119,861 | B2 | 2/2012 | Napier | |
| 8,134,046 | B2 | 3/2012 | Cirpus | |
| 8,158,392 | B1 | 4/2012 | Singh | |

(56) References Cited

U.S. PATENT DOCUMENTS

| | | | |
|---|---|---|---|
| 8,192,964 | B2 | 6/2012 | Knauf |
| 8,288,572 | B2 | 10/2012 | Singh |
| 8,318,914 | B2 | 11/2012 | Bauer |
| 8,455,035 | B2 | 6/2013 | Rein |
| 8,535,917 | B2 | 9/2013 | Singh |
| 8,575,377 | B2 | 11/2013 | Singh |
| 8,716,555 | B2 | 5/2014 | Liu |
| 8,778,644 | B2 | 7/2014 | Singh |
| 8,785,163 | B2 | 7/2014 | Senger |
| 8,785,727 | B2 | 7/2014 | Bauer |
| 8,809,559 | B2 | 8/2014 | Petrie |
| 8,816,106 | B2 | 8/2014 | Damcevski |
| 8,816,111 | B2 | 8/2014 | Petrie |
| 8,822,662 | B2 | 9/2014 | Senger |
| 8,853,383 | B2 | 10/2014 | Bauer |
| 8,853,432 | B2 | 10/2014 | Singh |
| 8,901,374 | B2 | 12/2014 | Bauer |
| 8,921,652 | B2 | 12/2014 | Liu |
| 8,946,460 | B2 | 2/2015 | Petrie |
| 9,090,902 | B2 | 7/2015 | Bauer |
| 9,212,371 | B2 | 12/2015 | Senger |
| 9,347,049 | B2 | 5/2016 | Bauer |
| 9,388,436 | B2 | 7/2016 | Bauer |
| 9,428,757 | B2 | 8/2016 | Senger |
| 9,453,183 | B2 | 9/2016 | Singh |
| 9,458,410 | B2 | 10/2016 | Singh |
| 9,458,477 | B2 | 10/2016 | Senger |
| 9,493,520 | B2 | 11/2016 | Bauer |
| 9,550,718 | B2 | 1/2017 | Petrie |
| 9,556,102 | B2 | 1/2017 | Petrie |
| 9,718,759 | B2 | 8/2017 | Singh |
| 9,725,399 | B2 | 8/2017 | Petrie |
| 2001/0023259 | A1 | 9/2001 | Slabas |
| 2002/0009779 | A1 | 1/2002 | Meyers |
| 2002/0042933 | A1 | 4/2002 | Browse |
| 2002/0065406 | A1 | 5/2002 | Meyers |
| 2002/0076786 | A1 | 6/2002 | Curtis |
| 2002/0107373 | A1 | 8/2002 | Curtis |
| 2002/0108147 | A1 | 8/2002 | Thomas |
| 2002/0111307 | A1 | 8/2002 | Glucksmann |
| 2002/0115178 | A1 | 8/2002 | Meyers |
| 2002/0138874 | A1 | 9/2002 | Mukerji |
| 2002/0146784 | A1 | 10/2002 | Suzuki |
| 2002/0156254 | A1 | 10/2002 | Qiu |
| 2002/0170090 | A1 | 11/2002 | Browse |
| 2002/0194641 | A1 | 12/2002 | Metz |
| 2003/0033622 | A1 | 2/2003 | Lightner |
| 2003/0033633 | A1 | 2/2003 | Lightner |
| 2003/0077747 | A1 | 4/2003 | Hillman |
| 2003/0079250 | A1 | 4/2003 | Fillatti |
| 2003/0082754 | A1 | 5/2003 | Mukerji |
| 2003/0084480 | A1 | 5/2003 | Fillatti |
| 2003/0101486 | A1 | 5/2003 | Facciotti |
| 2003/0104596 | A1 | 6/2003 | Mukerji |
| 2003/0115632 | A1 | 6/2003 | Lardizabal |
| 2003/0131379 | A1 | 7/2003 | Debonte |
| 2003/0134400 | A1 | 7/2003 | Mukerji |
| 2003/0152983 | A1 | 8/2003 | Napier |
| 2003/0157144 | A1 | 8/2003 | Mukerji |
| 2003/0159164 | A1 | 8/2003 | Kopchick |
| 2003/0159173 | A1 | 8/2003 | Wolter |
| 2003/0163844 | A1 | 8/2003 | Lightner |
| 2003/0163845 | A1 | 8/2003 | Mukerji |
| 2003/0166207 | A1 | 9/2003 | Roessler |
| 2003/0167525 | A1 | 9/2003 | Mukerji |
| 2003/0172398 | A1 | 9/2003 | Browse |
| 2003/0172399 | A1 | 9/2003 | Fillatti |
| 2003/0177508 | A1 | 9/2003 | Mukerji |
| 2003/0190733 | A1 | 10/2003 | Mukerji |
| 2003/0196217 | A1 | 10/2003 | Mukerji |
| 2004/0009501 | A1 | 1/2004 | Curtis |
| 2004/0049805 | A1 | 3/2004 | Lerchl |
| 2004/0053234 | A1 | 3/2004 | Winther |
| 2004/0053379 | A1 | 3/2004 | Lerchl |
| 2004/0067226 | A1 | 4/2004 | Petrukhin |
| 2004/0078845 | A1 | 4/2004 | Thomas |
| 2004/0086899 | A1 | 5/2004 | Winther |
| 2004/0098762 | A1 | 5/2004 | Fillatti |
| 2004/0111763 | A1 | 6/2004 | Heinz |
| 2004/0132654 | A1 | 7/2004 | Kumpe |
| 2004/0157221 | A9 | 8/2004 | Curtis |
| 2004/0172682 | A1 | 9/2004 | Kinney |
| 2004/0180414 | A1 | 9/2004 | Putten |
| 2004/0195512 | A1 | 10/2004 | Crosetto |
| 2004/0221335 | A1 | 11/2004 | Shewmaker |
| 2004/0224413 | A1 | 11/2004 | Cahoon |
| 2004/0235127 | A1 | 11/2004 | Metz |
| 2005/0003442 | A1 | 1/2005 | Mukerji |
| 2005/0005328 | A1 | 1/2005 | Mukerji |
| 2005/0005329 | A1 | 1/2005 | Mukerji |
| 2005/0009140 | A1 | 1/2005 | Mukerji |
| 2005/0089865 | A1 | 4/2005 | Napier |
| 2005/0089879 | A1 | 4/2005 | Feussner |
| 2005/0089981 | A1 | 4/2005 | Napier |
| 2005/0100995 | A1 | 5/2005 | Weaver |
| 2005/0112719 | A1 | 5/2005 | Roessler |
| 2005/0164192 | A1 | 7/2005 | Graham |
| 2005/0166271 | A1 | 7/2005 | Feubner |
| 2005/0214761 | A1 | 9/2005 | Lerchl |
| 2005/0239171 | A1 | 10/2005 | Mitterer |
| 2005/0262588 | A1 | 11/2005 | Dehesh |
| 2005/0262589 | A1 | 11/2005 | Fillatti |
| 2005/0262591 | A1 | 11/2005 | Debonte |
| 2013/0309772 | A1 | 11/2005 | Sakagushi |
| 2005/0266440 | A1 | 12/2005 | Metz et al. |
| 2005/0273883 | A1 | 12/2005 | Metz |
| 2005/0273884 | A1 | 12/2005 | Metz |
| 2005/0273885 | A1 | 12/2005 | Singh |
| 2006/0014268 | A1 | 1/2006 | Suzuki |
| 2006/0078973 | A1 | 4/2006 | Renz |
| 2006/0094088 | A1 | 5/2006 | Picataggio |
| 2006/0094092 | A1 | 5/2006 | Damude |
| 2006/0094102 | A1 | 5/2006 | Xue |
| 2006/0110806 | A1 | 5/2006 | Damude |
| 2006/0115881 | A1 | 6/2006 | Damude |
| 2006/0117414 | A1 | 6/2006 | Qiu |
| 2006/0156435 | A1 | 7/2006 | Ursin |
| 2006/0168687 | A1 | 7/2006 | Renz |
| 2006/0174376 | A1 | 8/2006 | Renz |
| 2006/0191042 | A1 | 8/2006 | Fillatti |
| 2006/0195939 | A1 | 8/2006 | Damude |
| 2006/0205047 | A1 | 9/2006 | Putten |
| 2006/0206961 | A1 | 9/2006 | Cirpus |
| 2006/0206963 | A1 | 9/2006 | Voelker |
| 2006/0218668 | A1 | 9/2006 | Cirpus |
| 2006/0246556 | A1 | 11/2006 | Napier |
| 2007/0028326 | A1 | 2/2007 | Cirpus |
| 2007/0059730 | A1 | 3/2007 | Curtis |
| 2007/0061921 | A1 | 3/2007 | Graham |
| 2007/0118929 | A1 | 5/2007 | Damude |
| 2007/0163002 | A1 | 7/2007 | DeBonte |
| 2007/0192902 | A1 | 8/2007 | Qiu |
| 2007/0220634 | A1 | 9/2007 | Metz |
| 2007/0224661 | A1 | 9/2007 | Cirpus |
| 2007/0238648 | A1 | 10/2007 | Brownlie |
| 2007/0244192 | A1 | 10/2007 | Metz |
| 2007/0245431 | A1 | 10/2007 | Metz |
| 2007/0259355 | A1 | 11/2007 | Luy |
| 2007/0261138 | A1 | 11/2007 | Graham |
| 2007/0270494 | A1 | 11/2007 | Metz |
| 2007/0294790 | A1 | 12/2007 | Graham |
| 2008/0005811 | A1 | 1/2008 | Metz |
| 2008/0022422 | A1 | 1/2008 | Weaver |
| 2008/0057495 | A1 | 3/2008 | Ohyama |
| 2008/0063691 | A1 | 3/2008 | Ursin |
| 2008/0076164 | A1 | 3/2008 | Cirpus |
| 2008/0076166 | A1 | 3/2008 | Cirpus |
| 2008/0155705 | A1 | 6/2008 | Zank |
| 2008/0160054 | A1 | 7/2008 | Heinz |
| 2008/0214667 | A1 | 9/2008 | Das |
| 2008/0220143 | A1 | 9/2008 | Kinney |
| 2008/0220500 | A1 | 9/2008 | Winther |
| 2008/0241133 | A1 | 10/2008 | Curtis |
| 2008/0254191 | A1 | 10/2008 | Damude |

(56) References Cited

U.S. PATENT DOCUMENTS

2008/0254195 A1 10/2008 Damude
2008/0260929 A1 10/2008 Ursin
2008/0268539 A1 10/2008 Singh
2009/0093033 A1 4/2009 Luy
2009/0158462 A1 6/2009 Cirpus
2009/0222951 A1 9/2009 Cirpus
2009/0253188 A1 10/2009 Zhu
2009/0320161 A1 12/2009 McGonigle
2010/0088776 A1 4/2010 Bauer
2010/0092640 A1 4/2010 Ursin
2010/0189868 A1 7/2010 Damude
2010/0227924 A1 9/2010 Cirpus et al.
2011/0015415 A1 1/2011 Singh
2011/0016585 A1 1/2011 Periera
2011/0039010 A1 2/2011 Rein
2011/0054198 A1 3/2011 Singh
2011/0059204 A1 3/2011 Jackson
2011/0059496 A1 3/2011 Zhu
2011/0190521 A1 8/2011 Damcevski
2011/0201065 A1 8/2011 Singh
2011/0218348 A1 9/2011 Zhou
2011/0269983 A1 11/2011 Kinney
2011/0314725 A1 12/2011 Petrie
2012/0016144 A1 1/2012 Petrie
2012/0041218 A1 2/2012 Singh et al.
2012/0083615 A1 4/2012 Singh
2012/0215018 A1 8/2012 Singh
2013/0060053 A1 3/2013 Singh
2013/0338387 A1 12/2013 Petrie
2013/0338388 A1 12/2013 Petrie
2014/0011247 A1 1/2014 Singh
2014/0314727 A1 10/2014 Singh
2015/0018571 A1 1/2015 Petrie
2015/0031096 A1 1/2015 Damude et al.
2015/0045567 A1 2/2015 Damcevski
2015/0045569 A1 2/2015 Petrie
2015/0087849 A1 3/2015 Singh
2015/0166928 A1 6/2015 Petrie et al.
2015/0203788 A1 7/2015 Petrie
2015/0203826 A1 7/2015 Marty
2015/0216828 A1 8/2015 Napier
2015/0275243 A1 10/2015 Napier
2015/0353863 A1 12/2015 Petrie
2016/0177220 A1 6/2016 Petrie et al.
2017/0058304 A1 3/2017 Singh
2017/0073712 A1 3/2017 Singh
2017/0211013 A1 7/2017 Petrie
2017/0305834 A1 10/2017 Petrie
2017/0320806 A1 11/2017 Petrie
2017/0321234 A1 11/2017 Singh
2017/0327767 A1 11/2017 Petrie
2017/0327852 A1 11/2017 Singh
2017/0334826 A1 11/2017 Petrie
2017/0349526 A1 12/2017 Petrie
2017/0349527 A1 12/2017 Petrie
2017/0349528 A1 12/2017 Petrie
2017/0349921 A1 12/2017 Singh
2018/0002633 A1 1/2018 Petrie
2018/0008568 A1 1/2018 Petrie
2018/0010141 A1 1/2018 Petrie

FOREIGN PATENT DOCUMENTS

AU 200065607 B2 1/2001
AU 776417 9/2004
AU 776447 9/2004
AU 2005901673 4/2005
AU 2007276257 1/2008
CA 2092588 9/1994
EP 275957 7/1988
EP 256223 2/1998
GB 1206483.8 4/2012
GB 1222184.2 12/2012
JP 2000217582 8/2000
JP 2001095588 4/2001
JP 2001145490 5/2001
JP 2001169780 6/2001
JP 2003116566 4/2003
JP 2004-285182 10/2004
JP 2004-285182 A 10/2004
JP 2011-516067 5/2011
WO WO 1984/02913 8/1984
WO WO 1987/005327 9/1987
WO WO 1989/05852 6/1989
WO WO 1991/002071 2/1991
WO WO 1991/013980 9/1991
WO WO 1993/06712 4/1993
WO WO 1993/23545 A1 11/1993
WO WO 1995/015389 6/1995
WO WO 1995/023230 8/1995
WO WO 1996/10074 4/1996
WO WO 1996/21022 A2 7/1996
WO WO 1997/006269 2/1997
WO WO 1997/21340 6/1997
WO WO 1997/37033 10/1997
WO WO 1997/48814 12/1997
WO WO 1998/01565 A1 1/1998
WO WO 1998/18952 A1 5/1998
WO WO 1998/39468 A1 9/1998
WO WO 1998/46765 A1 9/1998
WO WO 1998/045461 10/1998
WO WO 1998/46763 A1 10/1998
WO WO 1998/46764 10/1998
WO WO 1998/046764 10/1998
WO WO 1998/55625 A1 12/1998
WO WO 1998/56239 A1 12/1998
WO WO 1999/005265 2/1999
WO WO 1999/14314 3/1999
WO WO 1999/016890 4/1999
WO WO 1999/33958 A2 7/1999
WO WO 1999/49050 A2 9/1999
WO WO 1999/61602 A1 12/1999
WO WO 1999/64614 A2 12/1999
WO WO 1999/64616 A2 12/1999
WO WO 2000/12720 A3 3/2000
WO WO 2000/20602 A2 4/2000
WO WO 2000/20603 A1 4/2000
WO WO 2000/21557 A1 4/2000
WO WO 2000/40705 A2 7/2000
WO WO 2000/42195 A2 7/2000
WO WO 00/052183 9/2000
WO WO 2000/053770 9/2000
WO WO 2000/55330 A1 9/2000
WO WO 2000/75341 A1 12/2000
WO WO 2001/02591 A1 1/2001
WO WO 2001/04636 A1 1/2001
WO WO 2002/008401 1/2001
WO WO 2001/014538 3/2001
WO WO 2001/14538 A2 3/2001
WO WO 2001/020001 3/2001
WO WO 01/038512 A2 5/2001
WO WO 2001/38484 5/2001
WO WO 2001/038512 5/2001
WO WO 2001/44485 A1 6/2001
WO WO 2001/059128 8/2001
WO WO 2001/66758 A2 9/2001
WO WO 2001/70777 9/2001
WO WO 2001/75069 A1 10/2001
WO WO 2001/92489 A2 12/2001
WO WO 2001/96363 12/2001
WO WO 2002/08401 A2 1/2002
WO WO 2002/26946 A2 4/2002
WO WO 2002/081668 10/2002
WO WO 2002/81668 A3 10/2002
WO WO 2002/81702 A1 10/2002
WO WO 2002/83869 A3 10/2002
WO WO 2002/83870 A2 10/2002
WO WO 02/092540 A1 11/2002
WO WO 2002/90493 11/2002
WO WO 2002/90493 A2 11/2002
WO WO 2002/092540 A1 11/2002
WO WO 2003/64596 A2 8/2003
WO WO 2003/093482 11/2003
WO WO 2003/93482 A2 11/2003

(56) References Cited

FOREIGN PATENT DOCUMENTS

| | | |
|---|---|---|
| WO | WO 2003/099216 | 12/2003 |
| WO | WO 2003/102138 A2 | 12/2003 |
| WO | WO 2004/005442 | 1/2004 |
| WO | WO 2010/023202 | 3/2004 |
| WO | WO 2004/057001 | 7/2004 |
| WO | WO 2004/71467 A2 | 8/2004 |
| WO | WO 2004/87180 A1 | 10/2004 |
| WO | WO 2004/101757 | 11/2004 |
| WO | WO 2005/07845 A2 | 1/2005 |
| WO | WO 05/012316 A2 | 2/2005 |
| WO | WO 2005/12316 A2 | 2/2005 |
| WO | WO 2005/83053 A2 | 9/2005 |
| WO | WO 2005/83093 A2 | 9/2005 |
| WO | WO 2005/97982 A2 | 10/2005 |
| WO | WO 2005/98033 A1 | 10/2005 |
| WO | WO 2005/103253 | 11/2005 |
| WO | WO 2005/103253 A1 | 11/2005 |
| WO | WO 2005/118814 | 12/2005 |
| WO | WO 2006/008099 | 1/2006 |
| WO | WO 2006/019192 | 2/2006 |
| WO | WO 2006/052871 | 5/2006 |
| WO | WO 2006/064317 A1 | 6/2006 |
| WO | WO 2006/069936 | 7/2006 |
| WO | WO 2005/80578 A2 | 9/2006 |
| WO | WO 2006/127655 | 11/2006 |
| WO | WO 2006/127789 | 11/2006 |
| WO | WO 07/005882 A2 | 1/2007 |
| WO | WO 2007/005727 A1 | 1/2007 |
| WO | WO 2007/042510 | 4/2007 |
| WO | WO 07/092460 A2 | 8/2007 |
| WO | WO 2007/096387 | 8/2007 |
| WO | WO 2007/127381 | 11/2007 |
| WO | WO 2007/133425 | 11/2007 |
| WO | WO 2007/137788 | 12/2007 |
| WO | WO 08/009600 A1 | 1/2008 |
| WO | WO 2008/022963 | 2/2008 |
| WO | WO 2008/040787 A2 | 4/2008 |
| WO | WO 2008/025068 | 6/2008 |
| WO | WO 2008/104559 A1 | 9/2008 |
| WO | WO 2008/124048 A2 | 10/2008 |
| WO | WO 2008/128241 | 10/2008 |
| WO | WO 2008/150892 A2 | 12/2008 |
| WO | WO 2009/016202 | 2/2009 |
| WO | WO 2009/017821 | 2/2009 |
| WO | WO 2003/078639 | 9/2009 |
| WO | WO 2009/124101 A1 | 10/2009 |
| WO | WO 2009/129582 | 10/2009 |
| WO | WO 2010/009500 | 1/2010 |
| WO | WO 2010/057246 | 5/2010 |
| WO | WO 2010/057246 A1 | 5/2010 |
| WO | WO 2010/147900 | 12/2010 |
| WO | WO 2010/147900 A1 | 12/2010 |
| WO | WO 2011/146524 | 11/2011 |
| WO | WO 2013/016546 | 1/2013 |
| WO | WO 2013/016546 A1 | 1/2013 |
| WO | WO 2013/153404 | 10/2013 |
| WO | WO 2013/153404 A1 | 10/2013 |
| WO | WO 2013/185184 | 12/2013 |
| WO | WO 2013/185184 A1 | 12/2013 |
| WO | WO 2013/185184 A2 * | 12/2013 ............... A01H 5/00 |
| WO | WO 2015/089587 | 6/2015 |
| WO | WO 2015/196250 A1 | 12/2015 |

OTHER PUBLICATIONS

Apr. 20, 2018 Amended Complaint for Declaratory Judgment filed by BASF Plant Science, LP in connection with U.S. Pat. No. 7,807,849, issued Oct. 5, 2010 (Singh et al.); U.S. Pat. No. 8,106,226, issued Jan. 31, 2012 (Singh et al.); U.S. Pat. No. 8,288,572, issued Oct. 16, 2012 (Singh et al.); U.S. Pat. No. 8,575,377, issued Nov. 5, 2013 (Singh et al.); U.S. Pat. No. 8,853,432, issued Oct. 7, 2014 (Singh et al.); and U.S. Pat. No. 9,458,410, issued Oct. 4, 2016 (Singh et al.), in the United States District Court for the Eastern District of Virginia Norfolk Division, Civil Action No. 2:17-cv-00503-HCM-LRL.

Jan. 3, 2019 First Amended Counterclaims filed by Commonwealth Scientific and Industrial Research Corporation, Grains Research and Development Corporation, and Nuseed Pty. Ltd. in the United States District Court for the Eastern District of Virginia Norfolk Division, Civil Action No. 2:17-cv-00503-HCM-LRL.

Jan. 11, 2019 BASF Plant Science, LP's Answer and Amended Affirmative Defenses to Counterclaimants' Amended Counterclaims and BASF Plant Science, LP and BASF Plant Science GMBH's Amended Counterclaims Against Counterclaimants (Public Redacted Version), in the United States District Court for the Eastern District of Virginia Norfolk Division, Civil Action No. 2:17-cv-00503-HCM-LRL.

Feb. 27, 2019 Opening Claim Construction Brief of Cargill, Incorporated, in the United States District Court for the Eastern District of Virginia Norfolk Division, Civil Action No. 2:17-cv-00503-HCM-LRL.

Feb. 27, 2019 BASF Plant Science, LP's and BASF Plant Science GMBH's Opening Claim Construction Brief, in the United States District Court for the Eastern District of Virginia Norfolk Division, Civil Action No. 2:17-cv-00503-HCM-LRL.

Feb. 27, 2019 Counterclaimants Commonwealth Scientific and Industrial Research Organisation, Grains Research and Development Corp., and Nuseed Pty Ltd.'s Initial Markman Brief, in the United States District Court for the Eastern District of Virginia Norfolk Division, Civil Action No. 2:17-cv-00503-HCM-LRL.

Mar. 13, 2019 Responsive Claim Construction Brief of Cargill, Incorporated, in the United States District Court for the Eastern District of Virginia Norfolk Division, Civil Action No. 2:17-cv-00503-HCM-LRL.

Mar. 13, 2019 BASF Plant Science, LP's and BASF Plant Science GMBH's Responsive Claim Construction Brief, in the United States District Court for the Eastern District of Virginia Norfolk Division, Civil Action No. 2:17-cv-00503-HCM-LRL.

Mar. 13, 2019 Counterclaimants Commonwealth Scientific and Industrial Research Organisation, Grains Research and Development Corp., and Nuseed Pty Ltd.'s Rebuttal Markman Brief, in the United States District Court for the Eastern District of Virginia Norfolk Division, Civil Action No. 2:17-cv-00503-HCM-LRL.

Apr. 17, 2019 Counterclaimants Commonwealth Scientific and Industrial Research Organisation, Grains Research and Development Corp., and Nuseed Pty Ltd.'s Supplemental Brief on Term 9, in the United States District Court for the Eastern District of Virginia Norfolk Division, Civil Action No. 2:17-cv-00503-HCM-LRL.

Apr. 17, 2019 Cargill, Incorporated's Supplemental Claim Construction Brief Regarding the "Acyl-Coa Substrate" Claim Term, in the United States District Court for the Eastern District of Virginia Norfolk Division, Civil Action No. 2:17-cv-00503-HCM-LRL.

Apr. 30, 2019 Claim Construction Order and Opinion, in the United States District Court for the Eastern District of Virginia Norfolk Division, Civil Action No. 2:17-cv-00503-HCM-LRL.

May 15, 2019 Supplemental Claim Construction Opinion and Order, in the United States District Court for the Eastern District of Virginia Norfolk Division, Civil Action No. 2:17-cv-00503-HCM-LRL.

Oct. 4, 2018 Plaintiff BASF Plant Science, LP's Objections and Responses to Commonwealth Scientific and Industrial Research Organisation's First Set of Interrogatories (Excerpted for Interrogatory Nos. 5 and 7), in the United States District Court for the Eastern District of Virginia Norfolk Division, Civil Action No. 2:17-cv-00503-HCM-LRL.

Oct. 31, 2018 Cargill Incorporated's Responses to Counterclaimant Commonwealth Scientific and Industrial Research Organisation's First Set of Interrogatories (Excerpted for Interrogatory Nos. 5 and 7), in the United States District Court for the Eastern District of Virginia Norfolk Division, Civil Action No. 2:17-cv-00503-HCM-LRL.

Jan. 18, 2019 Plaintiff BASF Plant Science, LP's Supplemental Responses to Commonwealth Scientific and Industrial Research Organisation's Interrogatory Nos. 5 and 7, in the United States

(56) References Cited

OTHER PUBLICATIONS

District Court for the Eastern District of Virginia Norfolk Division, Civil Action No. 2:17-cv-00503-HCM-LRL.
Feb. 25, 2019 Cargill Incorporated's Supplemental Responses to Counterclaimant Commonwealth Scientific and Industrial Research Organisation's First Set of Interrogatories (Excerpted for Interrogatory Nos. 5 and 7), in the United States District Court for the Eastern District of Virginia Norfolk Division, Civil Action No. 2:17-cv-00503-HCM-LRL.
May 13, 2019 BASF Plant Science, LP's Second Supplemental Response to Commonwealth Scientific and Industrial Research Organisation's Interrogatory Nos. 5 and 7, in the United States District Court for the Eastern District of Virginia Norfolk Division, Civil Action No. 2:17-cv-00503-HCM-LRL.
May 13, 2019 Cargill Incorporated's Second Supplemental Responses to Counterclaimant Commonwealth Scientific and Industrial Research Organisation's First Set of Interrogatories, in the United States District Court for the Eastern District of Virginia Norfolk Division, Civil Action No. 2:17-cv-00503-HCM-LRL.
May 13, 2019 BASF Plant Science, LP's and BASF Plant Science Gmbh's Objections and Responses to Commonwealth Scientific and Industrial Organisation's Second Set of Interrogatories (Request Nos. 14-25) (Excerpted), in the United States District Court for the Eastern District of Virginia Norfolk Division, Civil Action No. 2:17-cv-00503-HCM-LRL.
May 29, 2019 Expert Report of Denis J. Murphy, Ph.D. (redacted version), in the United States District Court for the Eastern District of Virginia Norfolk Division, Civil Action No. 2:17-cv-00503-HCM-LRL.
Jul. 1, 2019 Rebuttal Validity Expert Report of Ljerka Kunst, Ph.D., in the United States District Court for the Eastern District of Virginia Norfolk Division, Civil Action No. 2:17-cv-00503-HCM-LRL.
International Search Report, dated Jan. 14, 2015 in connection with PCT International Application No. PCT/AU2014/050340, filed Jun. 18, 2015.
Written Opinion of the International Searching Authority, dated Jan. 14, 2015 in connection with PCT International Application No. PCT/AU2014/050340, filed Jun. 18, 2015.
Demand for International Preliminary Examination filed on May 14, 2015 in connection with PCT International Application No. PCT/AU2014/050340, filed Jun. 18, 2015.
Letter to the International Preliminary Examination Authority filed on Apr. 27, 2016 in connection with PCT International Application No. PCT/AU2014/050340, filed Jun. 18, 2015.
Amended Claims filed on Apr. 27, 2016 in connection with PCT International Application No. PCT/AU2014/050340, filed Jun. 18, 2015.
Second Written Opinion of the International Preliminary Examining Authority, dated May 5, 2016 in connection with PCT International Application No. PCT/AU2014/050340, filed Jun. 18, 2015.
International Search Report, dated Mar. 20, 2015 in connection with PCT International Application No. PCT/AU2014/050433, filed Dec. 18, 2014.
Written Opinion of the International Searching Authority, dated Mar. 20, 2015 in connection with PCT International Application No. PCT/AU2014/050433, filed Dec. 18, 2014.
Green, D. et al., "Measurement of hemostatic factors in EDTA plasma" Am. J. Clin. Pathol., 2008, 130(5): 811-815.
Petrie, J.R. et al., "Metabolic engineering *Camelina sativa* with fish oil-like levels of DHA", PLoS One, Jan. 2014, vol. 9, p. e85061.
Petrie, J.R. et al., "Metabolic engineering plant seed with fish oil-like levels of DHA", PLoS One, 2012. vol. 7, e49165, published online Nov. 7, 2012.
Ruiz-Lopez, N. et al., "Metabolic engineering of the omega-3 long chain polyunsaturated fatty acid biosynthetic pathway into transgenic plants" Journal of Experimental botany, 2012, vol. 63, pp. 2397-2410.
Office Action, dated Dec. 15, 2015 in connection with U.S. Appl. No. 14/575,756.
Response to Office Action, filed Feb. 12, 2016 in connection with U.S. Appl. No. 14/575,756.
Office Action, dated Apr. 15, 2016 in connection with U.S. Appl. No. 14/575,756.
Response to Office Action, filed Aug. 15, 2016 in connection with U.S. Appl. No. 14/575,756.
Notice of Allowance, dated Oct. 12, 2016 in connection with U.S. Appl. No. 14/575,756.
Supplemental Notice of Allowability, dated Nov. 30, 2016 'In connection with U.S. Appl. No. 14/575,756.
Office Action, dated Aug. 8, 2016 in connection with U.S. Appl. No. 14/975,333.
Response to Office Action, filed Nov. 8, 2016 in connection with U.S. Appl. No. 14/975,333.
Demand for International Preliminary Examination filed on Oct. 19, 2015 in connection with PCT International Application No. PCT/AU2014/050433, filed Dec. 18, 2014.
Oct. 10, 2016 International Preliminary Report on Patentability for International Patent Application PCT/AU2015/050340.
Letter to the International Preliminary Examination Authority filed on Apr. 27, 2016 in connection with PCT International Application No. PCT/AU2015/050340.
Amended Claims filed on Apr. 27, 2016 in connection with PCT International Application No. PCT/AU2015/050340.
Second Written Opinion of the International Searchig Authority, dated May 5, 2016 in connection with PCT International Application No. PCT/AU2015/050340.
File History of U.S. Pat. No. 7,807,849, Singh et al., issued Oct. 5, 2010 (U.S. Appl. No. 11/112,882, filed Apr. 22, 2005).
File History of U.S. Patent Application Publication No. 2011/0015415, Singh, et al., published Jan. 20, 2011 (U.S. Appl. No. 12/661,978, filed Mar. 26, 2010.
File History of U.S. Patent Application Publication No. 2012-0041218, Singh et al., published Feb. 16, 2012, (U.S. Appl. No. 13/243,747, filed Sep. 23, 2011.
File History of U.S. Pat. No. 7,834,250, Singh et al., issued Nov. 16, 2010 (U.S. Appl. No. 11/587,092, filed Oct. 20, 2006.
File History of U.S. Pat. No. 7,932,438, Singh et al., issued (U.S. Appl. No. 12/945,708, filed Nov. 12, 2010.
File History of U.S. Patent Application Publication No. 2011/0201065, Singh et al., published Aug. 18, 2011 (U.S. Appl. No. 13/093,252, filed Apr. 25, 2011.
File History of U.S. Pat. No. 8,158,392, Singh et al., issued Apr. 17, 2012 (U.S. Appl. No. 13/311,240, filed Sep. 23, 2011.
File History of U.S. Patent Application Publication No. 2011/0190521, Damcevski et al., published Aug. 4, 2011 (U.S. Appl. No. 12/310,645, filed Feb. 16, 2011.
File History of U.S. Appl. No. 12/989,405, Zhou et al., filed May 16, 2011.
File History of U.S. Pat. No. 7,589,253, Green et al., issued Sep. 15, 2009 (U.S. Appl. No. 09/981,124, filed Oct. 17, 2011.
File History of U.S. Pat. No. 7,834,248, Green et al., issued Nov. 16, 2010 (U.S. Appl. No. 11/699,817, filed Jan. 30, 2007.
File History of U.S. Patent Application No. 2012-0016144, Singh et al., Jan. 19, 2012 (U.S. Appl. No. 13/129,940, filed Sep. 30, 2011.
File History of U.S. Patent Application No. 2014-0314727, Singh et al., Oct. 23, 2014 (U.S. Appl. No. 14/323,512, filed Jul. 3, 2014.
File History of U.S. Patent Application No. 2015-0087849, Singh et al., Mar. 26, 2015 (U.S. Appl. No. 14/503,002, filed Sep. 30, 2014.
File History of U.S. Patent Application No. 2015-0203788, Petrie et al., Jul. 23, 2015 (U.S. Appl. No. 14/600,653, filed Jan. 20, 2015.
File History of U.S. Patent Application No. 2015-0045569, Petrie et al., Feb. 12, 2015 (U.S. Appl. No. 14/464,510, filed Aug. 20, 2014.
Complete File History of U.S. Pat. No. 8,809,559, Petrie et al., issued Aug. 19, 2014.
Complete File History of U.S. Pat. No. 8,816,106, issued Aug. 26, 2014 (Damcevski et al.).
U.S. Appl. No. 11/587,092, filed Oct. 20, 2006, Singh.
U.S. Appl. No. 13/448,107, filed Apr. 16, 2012, Singh.
U.S. Appl. No. 12/661,978, filed Mar. 6, 2010, Singh.
U.S. Appl. No. 13/093,252, filed Apr. 25, 2011, Singh.
U.S. Appl. No. 13/011,779, filed Jan. 21, 2011, Liu.
U.S. Appl. No. 12/989,405, filed May 16, 2011, Zhou.

(56) References Cited

OTHER PUBLICATIONS

U.S. Appl. No. 12/310,645, filed Feb. 16, 2011, Damcevski.
U.S. Appl. No. 13/129,940, filed May 18, 2011, Petrie.
U.S. Appl. No. 13/011,773, filed Jan. 21, 2011, Liu.
U.S. Appl. No. 13/243,747, filed Sep. 23, 2011, Singh.
U.S. Appl. No. 13/171,032, filed Jun. 28, 2011, Petrie.
U.S. Appl. No. 13/311,240, filed Dec. 5, 2011, Singh.
U.S. Appl. No. 13/651,275, filed Oct. 12, 2012, Singh.
International Preliminary Report on Patentability, dated May 24, 2011 in connection with PCT International Application Publication No. PCT/AU2009/001488.
Written Opinion of the International Search Authority, dated Apr. 1, 2010 in connection with PCT International Application Publication No. PCT/AU2009/001488.
International Search Report, dated Apr. 1, 2010 in connection with PCT International Application Publication No. PCT/AU2009/001488.
International Search Report dated Jul. 27, 2009 in connection with PCT International Application No. PCT/AU2009/000517.
Report on Patentability dated Oct. 26, 2010 in connection with PCT International Application No. PCT/AU2009/000517.
Dec. 6, 2013 International Search Report, dated in connection with PCT International Patent Application No. PCT/AU2013/000639.
Dec. 6, 2013 Written Opinion of the International Searching Authority, issued in connection with PCT International Patent Application No. PCT/AU2013/000639.
May 13, 2014 International Preliminary Report on Patentability, issued in connection with PCT International Patent Application No. PCT/AU2013/000639.
Apr. 15, 2014 Demand for International Preliminary Examination, including substitute claim pp. 164-186, filed in connection with PCT International Patent Application No. PCT/AU2013/000639.
PCT International Preliminary Report on Patentability dated Oct. 25, 2006 for PCT International Application Publication No. WO 2005/103253.
PCT International Search Report dated Apr. 1, 2010 for PCT International Application Publication No. WO 2010/057246.
Notification of European publication number dated Jan. 31, 2007 in connection with European Patent Application No. 05733657.0.
Supplementary European Search Report dated Apr. 1, 2008 in connection with European Patent Application No. 05733657.0.
Commincation Pursuant to Article 94(3) EPC issued Feb. 12, 2009 in connection with European Patent Application No. 05733657.0.
Response to Communication from the Examining Division, filed Oct. 22, 2009 in connection with European Application No. EP 05733657.0.
Communication from the Examining Division issued by the European Patent Office dated Aug. 18, 2010 in connection with European Application No. EP 05733657.0.
Response to Communication from the Examining Division, filed Feb. 3, 2011 in connection with European Application No. EP 05733657.0.
Communication from the Examining Division issued by the European Patent Office dated Apr. 6, 2011 in connection with European Application No. EP 05733657.0.
Examination Report dated Mar. 14, 2012 in connection with corresponding European Patent Application No. 05733657.0.
Oct. 17, 2011 Response dated Apr. 6, 2011 Communication from the Examining Division, filed in connection with European Application No. EP05733657.0.
Sep. 24, 2012 Response dated Mar. 14, 2012 Communication from the Examining Division, filed in connection with European Application No. EP05733657.0.
Communication from the Examining Division issued by the European Patent Office dated Nov. 9, 2012 in connection with European Patent Application No. 05733657.0.
Jan. 3, 2013 Response, filed in connection with European Patent Application No. 05733657.0.
May 16, 2013 Response filed in connection with European Patent Application No. 05733657.0.
Aug. 20, 2015 Communication of a Notice of Opposition; issued in connection with European Patent Application No. 05733657.0, including a list of documents cited by the Opponent.
Apr. 5, 2013 Response filed in connection with European Patent Application No. 10184533.7.
European Search Report, issued by the European Patent Office dated Jul. 15, 2011 in connection with European Patent Application No. 11155282.4.
Extended European Search Report, issued by the European Patent Office dated Oct. 25, 2011 in connection with European Patent Application No. 11155282.4.
Sep. 7, 2012 Amendment after receipt of European Search Report, filed in connection with European Patent Application No. 11155282.4.
Mar. 11, 2013 Office Action, issued in connection with European Patent Application No. 11155282.4.
Dec. 27, 2013 Response, filed in connection with European Patent Application No. 11155282.4.
Aug. 21, 2014 Examination Report, issued in connection with European Patent Application No. 11155282.4.
Jun. 26, 2015 Response to Examination Report filed in connection with European patent application 11155282.4.
European Search Report, issued by the European Patent Office dated Jul. 15, 2011 in connection with European Patent Application No. 11155364.0.
Extended European Search Report, issued by the European Patent Office dated Oct. 25, 2011 in connection with European Patent Application No. 11155364.0.
Sep. 10, 2012 Amendment after receipt of European Search Report, filed in connection with European Patent Application No. 11155364.0.
Feb. 13, 2013 OfficeAction issued in connection with European Patent Application No. 11155364.0.
Dec. 4, 2013 Response, filed in connection with European Patent Application No. 11155364.0.
Aug. 13, 2014 Examination Report, issued in connection with European Patent Application No. 11155364.0.
European Search Report, issued by the European Patent Office dated Oct. 25, 2011 in connection with European Patent Application No. 11155266.7.
Extended European Search Report and Opinion dated Feb. 10, 2012 in connection with corresponding European Divisional Patent Application No. 11155266.7.
Rule 69 EPC Communication dated Mar. 19, 2012 in connection with European Divisional Patent Application No. 11155266.7.
Jan. 3, 2013 Response filed in connection with European Patent Application No. 11155266.7.
Examination Report, issued by the Australian Patent Office dated Sep. 6, 2012 in connection with Australian Patent Application No. 2011232757.
Sep. 6, 2013 Response to Australian Examination report, filed in connection with Australian Patent Application No. 2011232757.
Jan. 9, 2014 Office Action, issued in connection with Australian Patent Application No. 2013204296.
Jul. 1, 2015 Response to second Office Action, filed in connection with Australian Patent Application No. 2013204296.
May 8, 2015 Response to Office Action, filed in connection with Vietnamese Patent Application No. 1-2015-00134.
Aug. 13, 2013 Response to Chinese Office Action, filed in connection with Chinese Patent Application No. 2012100061398.
Australian Examination Report dated Nov. 16, 2009 in connection with Australian Patent Application No. 2005235627.
Australian Examination Report dated Mar. 14, 2011 in connection with Australian Patent Application No. 2005235627.
Response to Australian Examination Report filed Feb. 25, 2011 in connection with Australian Patent Application No. 2005235627.
Response to Australian Examination Report filed Apr. 19, 2011 in connection with Australian Patent Application No. 2005235627.
Australian Examination Report dated May 16, 2011 in connection with Australian Patent Application No. 2005235627.
Response to Australian Examination Report filed Jun. 14, 2011 in connection with Australian Patent Application No. 2005235627.

(56) References Cited

OTHER PUBLICATIONS

Chinese Examination Report dated Apr. 10, 2009 in connection with Chinese Patent Application No. 200580020696.3.
Response to Chinese Examination Report filed Jul. 21, 2009 in connection with Chinese Patent Application No. 200580020696.3.
Chinese Examination Report dated Apr. 30, 2010 in connection with Chinese Patent Application No. 200580020696.3.
Response to Chinese Examination Report filed Sep. 15, 2010 in connection with Chinese Patent Application No. 200580020696.3.
Nov. 30, 2011 Request for Re-Examination filed in connection with Chinese Patent Application No. 200580020696.3, including English language translation of submitted claims.
Aug. 18, 2011 Decision of Rejection issued by the Chinese Patent Office in connection with Chinese Patent Application No. 200580020696.3.
Response to Notification of Re-Examination filed on Oct. 18, 2012 in connection with Chinese Patent Application No. 200580020696.3, including English.
Oct. 18, 2012 Request for Reexamination filed in connection with Chinese Patent Application No. 200580020696.3.
Jan. 29, 2013 Office Action issued in connection with Chinese Patent Application No. 201210006139.8.
Nov. 21, 2013 Office Action, issued in connection with Chinese Patent Application No. 201210006139.8.
Jun. 25, 2014 Third Office Action, issued in connection with Chinese Patent Application No. 201210006139.8, including English language translation.
Jan. 20, 2015 Response to Office Action, filed in connection with Chinese patent application 201210006139.8.
Aug. 10, 2015 Fifth Office Action issued in connection with Chinese Patent Application No. 201210006139.8, including English language translation.
Aug. 6, 2014 First Office Action, issued in connection with Chinese Patent Application No. 201310392524.5.
Dec. 22, 2014 Response, filed in connection with Chinese Patent Application No. 201310392524.5.
Mar. 30, 2015 Second Office Action, issued in connection with Chinese Patent Application No. 201310392524.5, including English language translation.
May 22, 2015 Response to Second Office Action, issued in connection with Chinese Patent Application No. 201310392524.5.
Sep. 7, 2015 Decision of Reject, issued in connection with Chinese Patent Application No. 201310392524.5, including English language translation.
Brazilian Technical Opinion dated Mar. 1, 2012 in connection with corresponding Brazilian Patent Application No. PI 0510132-8.
Response filed to Brazilian Technical Opinion filed Mar. 29, 2012 in connection with corresponding Brazilian Patent Application No. PI 0510132-8.
Nov. 21, 2011 Examination report issued in connection with Canadian Patent Application No. 2,563,875.
May 22, 2012 Response to Examination Report, filed in connection with Canadian Patent Application No. 2,563,875.
Nov. 23, 2012 Office Action issued in connection with Canadian Patent Application No. 2,563,875.
Nov. 1, 2013 Office Action, issued in connection with Canadian Patent Application No. 2,563,875.
May 1, 2014 Response to Examination Report, filed in connection with Canadian Patent Application No. 2,563,875.
Mar. 29, 2012 Extended European Search Report and Search Opinion issued in connection with European Patent Application No. 09827035.8.
Oct. 29, 2012 Response to European Search Opinion filed in connection with European Patent Application No. 09827035.8.
Apr. 11, 2014 Response to Examination Report, filed in connection with European Patent Application No. 09827035.8.
Jul. 10, 2014 Third Party Observations, filed in connection with European Patent Application No. 09827035.8.
Apr. 7, 2015 Response to the Oct. 13, 2014 Office Action filed in connection with European patent application 09827035.8.
Aug. 13, 2015 Third Examination Report European Patent Application No. 09827035.8.
Jan. 21, 2016 Response, filed in connection with European Patent Application No. EP09827035.8.
Jun. 16, 2016 Summons to Oral Proceedings, issued in connection with European Patent Application No. 09827035.8.
Jun. 8, 2012 Australian Examination Report issued in connection with Australian Patent Application No. 2009317860.
Dec. 9, 2013 Response filed in connection with Australian Patent Application No. 2009317860.
Jan. 15, 2014 Office Action issued in connection with Australian Patent Application No. 2009317860.
Feb. 7, 2014 Response filed in connection with Australian Patent Application No. 2009317860.
Jan. 22, 2014 Office Action, issued in connection with Australian Patent Application No. 2013204254.
Jan. 22, 2014 Office Action, issued in connection with Australian Patent Application No. 2013204270.
Mar. 19, 2015 Response to First Examination Report filed in connection with Australian Patent Application No. 2013204270.
Sep. 10, 2013 Office Action issued in connection with Chilean Patent Application No. 1162-2011.
Dec. 19, 2013 Response filed in connection with Chilean Patent Application No. 1162-2011, including English Language Claims.
Jul. 22, 2014 Office Action, issued in connection with Chilean Patent Application No. 1162-2011, including English language translation.
Jan. 14, 2013 Chinese First Office Action issued in connection with Chinese Patent Application No. 200980154876.9.
Sep. 16, 2013 Office Action issued in connection with Chinese Patent Application No. 200980154876.9.
May 21, 2014 Chinese Third Office Action, issued in connection with Chinese Patent Application No. 200980154876.9.
Mar. 9, 2015 Response to Office Action filed in connection with Chinese Patent Application 200980154876.9, including Engligh language translation.
Jul. 6, 2015 Chinese Fifth Office Action issued in connection with Chinese Patent Application No. 200980154876.9, including English language translation.
Jan. 27, 2016 Decision of Rejection, issued in connection with Chinese Patent Application No. 200980154876.9, including English Language Translation.
Jun. 22, 2011 New Zealand Examination Report issued in connection with New Zealand Patent Application No. 593097.
Dec. 11, 2012 Response to New Zealand Examination Report filed in connection with New Zealand Patent Application No. 593097.
Jan. 3, 2013 New Zealand Examination Report issued in connection with New Zealand Patent Application No. 593097.
Jan. 8, 2013 Response to New Zealand Examination Report filed in connection with New Zealand Patent Application No. 593097.
May 13, 2014 First Japanese Office Action, issued in connection with Japanese Patent Application No. 2011-535839.
Aug. 13, 2014 Response to First Japanese Office Action, filed in connection with Japanese Patent Application No. 2011-535839.
Mar. 3, 2015 Office Action, issued in connection with Japanese application 2011-535839, including English language translation.
Nov. 2, 2015 Pretrial reexamination report, issued in connection with Japanese Patent Application No. 2011- 535839, including English language translation.
Supplemental European Search Report and Search Opinion dated Jun. 24, 2010 in connection with European Patent Application No. 07784864.6.
Response filed to European Search Opinion dated Jan. 19, 2011 in connection with European Patent Application No. 07784864.6.
European Examination Report dated Jul. 18, 2011 in connection with European Patent Application No. 07784864.6.
Response filed to European Examination Report dated May 15, 2012 in connection with European Patent Application No. 07784864.6.
Written submissions, Amended description pages, Main and AR1 claims filed Sep. 4, 2014 in relation to corresponding European Patent Application No. 07784864.6.

(56) References Cited

OTHER PUBLICATIONS

Result of Consultation from EPO dated Sep. 15, 2014 in relation to corresponding European Patent Application No. 07784864.6.
Revised written submissions filed Sep. 16, 2014 in relation to corresponding European Patent Application No. 07784864.6.
Amended claims filed Sep. 16, 2014 in relation to corresponding European Patent Application No. 07784864.6.
Apr. 1, 2015 Summons to Oral Proceedings, issued in connection with European Patent Application No. 07784864.6.
Australian Examination Report dated Jul. 25, 2012 in connection with Australian Patent Application No. 2007291937.
Aug. 1, 2014 Response to First Canadian Office Action, filed in connection with Canadian Patent Application No. 2,661,697.
Feb. 4, 2014 Office Action, issued in connection with Canadian Patent Application No. 2,661,697.
Aug. 22, 2014 Office Action, issued in connection with Canadian Patent Application No. 2,661,697.
New Zealand Examination Report dated Jul. 29, 2010 in connection with New Zealand Patent Application No. 575809.
Response filed to New Zealand Examination Report filed Dec. 23, 2011 in connection with New Zealand Patent Application No. 575809.
New Zealand Examination Report dated Jan. 24, 2012 in connection with New Zealand Patent Application No. 575809.
Chinese Office Action dated May 17, 2011 in connection with Chinese Patent Application No. 200780040245.5, including English Language translation.
Response filed to Chinese Office Action dated Nov. 30, 2011 in connection with Chinese Patent Application No. 200780040245.5, including English Language translation of claims.
Second Chinese Office Action dated Jun. 6, 2012 in connection with Chinese Patent Application No. 200780040245.5, including English Language translation.
Response filed to Second Chinese Office Action dated Oct. 22, 2012 in connection with Chinese Patent Application No. 200780040245.5.
Third Chinese Office Action dated Feb. 17, 2013 in connection with Chinese Patent Application No. 200780040245.5, including English Language translation.
Response filed to Chinese Office Action dated Jul. 4, 2013 in connection with Chinese Patent Application No. 200780040245.5.
Feb. 23, 2015 First Examiner's Report, issued in connection with Canadian Patent Application No. 2,884,237.
Nov. 25, 2015 Office Action, issued in connection with Canadian Patent Application 2,743,880.
May 25, 2016 Response to Examiner's Report, filed in connection with Canadian Patent Application 2,743,880.
Mar. 7, 2012 presentation at the CSIRO Marine and Atmospheric Research. Science Forum, Hobart (poster presentation) at Hobart, Australia, entitled "New Land Plants Containing Long-chain, Omega-3 Oils" presented by Peter Nichols, first author, Peter Nichols.
Jun. 8, 2012 presentation at the GOED Exchange at Boston, MA, entitled "An Update from Australia: A Global Leader in Long-Chain Omega-3" presented by Peter Nichols, first author, Peter Nichols, 34 slides.
Jul. 2, 2012 presentation at the Australian Marine Scientists Association, Annual Meeting, 2012 at Hobart, Australia, entitled "New Land Plants With Long-Chain Omega-3 Oils: A journey from marine gene discovery to sustainable sources of health-benefitting oils" presented by Peter Nichols, first author, Peter Nichols, 21 slides.
Jul. 13, 2012 presentation at the 20th International conference on plant lipids at Seville, Spain, entitled "Metabolic egineering plant seeds with fish oil-like levels of DHA" presented by James Petrie, first author, James Petrie, 41 slides.
Jul. 16, 2012 presentation at the Australian Institute of Food Science and Technology, Annual Meeting, 2012 at Adelaide, Australia, entitled "New sustainable land plant sources of long-chain omega-3 oils" presented by Peter Nichols, first author, Peter Nichols, 26 slides.
Aug. 2, 2012 presentation at the UniGateway, Business breakfast series at Melbourne, Australia, entitled "Trends and sustainability of LC omega-3 oils from wild and farmed fish, and Progress with new land plant sources" presented by Peter Nichols, first author, Peter Nichols, 10 slides.
Sep. 26, 2012 presentation at the ComBio—Plants and Human Nutrition Symposium, 2012 at Adelaide, Australia, entitled, "Creating Land Plant-Based Sustainable Sources of Essential Long Chain Omega-3 Fatty Acids" presented by Peter Nichols, first author, James Petrie, 24 slides.
Oct. 9, 2012 presentation at the Invited seminar, Department of Plant Science, University of Tasmania at Hobart, Australia, entitled "The Omega-3 Oils story—Sources of Long-chain Omega-3: A Sustainable Future" presented by Peter Nichols, first author, Peter Nichols, 39 slides.
Nov. 14, 2012 presentation at the Novel sources of omega-3, Copenhagen 2012 at Copenhagen, Denmark, entitled "Metabolic engineering plant seeds with fish oil-like levels of DHA" presented by James Petrie, first author, James Petrie, 35 slides.
Mar. 13, 2013 presentation at the Invited seminar, the Biological Club, Hobart at Hobart, Australia, entitled "The Omega-3 Oils story—Sources of Long-chain Omega-3: A Sustainable Future" presented by Peter Nichols, first author, Peter Nichols, 39 slides.
International Search Report dated Jun. 23, 2005 in connection with PCT International Application No. PCT/AU05/000571, filed Apr. 22, 2005.
Written Opinion dated Jun. 23, 2005 in connection with PCT International Application No. PCT/AU2005/000571, filed Apr. 22, 2005.
International Search Report dated Nov. 21, 2007 in connection with International Application No. PCT/AU2007001242, filed Aug. 29, 2007 (CSIRO).
Written Opinion of the International Searching Authority dated Nov. 21, 2007 in connection with International Application No. PCT/AU2007001242, filed Aug. 29, 2007 (CSIRO).
Supplementary European Search Report, dated Feb. 5, 2016 in connection with European Patent Application No. 13803782.5.
Feb. 23, 2016 Communication, issued in connection with European Patent Application No. 13803782.5.
May 12, 2016 Response dated Feb. 23, 2016 Rule 70(2) and 70a(2) Communication, filed in connection with European Patent Application No. 13803782.5.
Jun. 1, 2016 Communication Pursuant to Article 94(3) EPC, issued in connection with European Patent Application No. 13803782.5.
Abbadi, A., et al., (2001) "Transgenic Oilseeds As Sustainable Source of Nutritionally Relevant C20 and C22 Polyunsaturated Fatty Acids?" European Journal of Lipid Science and Technology, 103(2): 106-113.
Abbadi, A., et al., (2004) "Biosynthesis of Very-Long-Chain Polyunsaturated Fatty Acids in Transgenic Oilseeds: Constraints on Their Accumulation," The Plant Cell, 16(10): 2734-3748.
Abdullah, R., Cocking, E. C., & Thompson, J. A. (Dec. 1986) . Efficient plant regeneration from rice protoplasts through somatic embryogenesis. *Biotechnology*, 4, 1087-1090.
The C. Elegans Sequencing Consortium, (1998) "Genome Sequence of the Nematode *C. elegans*: A Platform for Investigating Biology," Science, 282 (5396) : 2012-2018.
Agaba, M., et al., (2004) "Zebrafish cDNA Encoding Multifunctional Fatty Acid Elongase Involved in Production of Eicosapentaenoic (20:5n-3) and Docosahexaenoic (22:6n-3) Acids," Marine Biotechnology, 6(3) : 251-261.
Akiyama, H., et al., (1998) "A Novel Plasmid Recombination Mechanism of the Marine Cyanobacterium *Synechococcus* sp. PCC7002," DNA Research, 5 (6) : 327-334.
Akiyama, H . , et al., (1998) "Nucleotide Sequence of Plasmid pAQ1 of Marine Cyanobacterium *Synechococcus* sp. PCC7002," DNA Research, 5 (2) : 127-129.
Al-Mariri et al. (2002) "Yersinia enterocolitica as a Vehicle for a Naked DNA Vaccine Encoding Brucella abortus Bacterioferritin or P39 Antigen" Infect. Immun. 70:1915-1923.
Altschul, S. F., Madden, T. L., Schäffer, A. A., Zhang, J., Zhang, Z . , Miller, W., & Lipman, D. J. (1997) . Gapped BLAST

(56) References Cited

OTHER PUBLICATIONS and PIS-BLAST: a new generation of protein database search programs. *Nucleic Acids Research*, 25(17), 3389-3402.
Alvarez et al. (2000) "Silencing of HMW glutenins in transgenic wheat expressing extra HMW subunits" Theor Appl Genet 100:319-327.
Armbrust et al. (2004) The genome of the diatom *Thalassiosira pseudonana* : ecology, evolution, and metabolism, Science 306:79-86.
Badami, R. C., & Patil, K. B. (1980) . Structure and occurrence of unusual fatty acids in minor seed oils. *Prog. Lipid Res.*, 19, 119-153.
Bafor et al., Biosynthesis of vernoleate (cis-12- eposyoctadeca-cis-9-enoate) in microsomal preparations from developing endosperm of euphorbia lagascae. Archives of Biochemistry and Biophysics. 1993, 303 (1) :145-151.
Banas et al. In: Williams, J. P. , Molbasher, K.U., Lem, n. W. , (Eds . ) Physiology, biochemistry and molecular biology of plant lipids. Kluwer Academic Publisher, Dordrecht. In Press. "Biosynthesis of an Acetylenic Fatty Acid in Microsomal Preparations from Developing Seeds of Crepis Alpina", 1997, pp. 57-59.
Bates et al. (2007) "Incorporation of Newly Synthesized Fatty Acids into Cytosolic Glycerolipids in Pea Leaves Occurs via Acyl Editing" J. Biol. Chem. 282:31206-31216.
Baumberger et al. (2007) "The Polerovirus Silencing Suppressor P0 Targets ARGONAUTE Proteins for Degradation" Curr. Biol. 17:1609-1614.
Bäumlein, H., et al., (1992) "Cis-Analysis of a Seed Protein Gene Promoter: The Conservative RY Repeat CATGCATC Within the Legumin Box is Essential for Tissue-Specific Expression of a Legumin Gene," The Plant Journal, 2 (2) : 233-239.
Bäumlein, H., et al., (1991) "A Novel Seed Protein Gene From Vicia faba is Developmentally Regulated in Transgenic Tobacco and *Arabidopsis* Plants," Molecular and General Genetics, 225 (3) : 459-467.
Beaudoin, et al., "Production of C20 polyunsaturated fatty acids (PUFAs) by pathway engineering: identification of a PUFA elongase component from Caenorhabditis elegans", Biochemical Society Transactions, vol. 28, Part 6, p. 661-663.
Beaudoin, F., et al., (2000) "Heterologous Reconstitution in Yeast of the Polyunsaturated Fatty Acid Biosynthetic Pathway," Proceedings of the National Academy of Sciences of The United States of America, 97 (12) : 6421-6426.
Beclin et al. (2002) "A Branched Pathway for Transgene-Induced RNA Silencing in Plants" Curr. Biol. 12:684-688.
Berberich, T., et al., (1998) "Two Maize Genes Encoding Omega-3 Fatty Acid Desaturase and Their Differential Expression to Temperature," Plant Molecular Biology, 36(2): 297-306.
Blee et al., Regio- and stereoselectivity of cytochrome P-450 and peroxygenase-dependent formation of CIS-12,13-epoxy-9(Z)-octadecenoic acid (vernolic acid) in euphorbia lagascae. Biochemical and Biophysical Research Communications, 1993, 197(2):778-784.
Blee et al., Mechanism of reaction of fatty acid hydroperoxides with soybean peroxygenase. The Journal of Biological Chemistry. 1993, 268(3):1708-1715.
Blee and Schuber, Efficient epoxidation of unsaturated fatty acids by a hydroperoxide-dependent oxygenase. The Journal of Biological Chemistry. 1990, 265(22):12887-12894.
Bligh and Dyer, Orange-red Flesh in Cod and Haddock. J. Fish. Res. Bd. Canada, 1959, 16(4):449-452.
Bolch, C.J.S., et al., (1999) "Genetic, Morphological, and Toxicological Variation Among Globally Distributed Strains of Nodularia (Cyanobacteria)," Journal of Phycology, 35(2): 339-355.
Bolch, C.J.S., et al., (1999) "Genetic Variation Among Strains of the Toxic Dinoflagellate Gymnodinium Catenatum (Dinophyceae)," Journal of Phycology, 35: 356-367.
Bortolamiol et al. (2007) "The Polerovirus F Box Protein P() Targets ARGONAUTE1 to Suppress RNA Silencing" Euro. J. Biochm. 267:85.
Bouvier (2000) "Identification of neoxanthin synthase as a carotenoid" Eur J. Biochem. 267:6346-6352.
Bozak et al., Sequence analysis of ripening-related cytochrome P-450 cDNAs from avocado fruit. PNAS, 1990, 87:3904-3908.
Brodersen et al. (2008) "Widespread Translational Inhibition by Plant miRNAs and siRNAs" Science 320:1185-1190.
Brosnan et al. (2007) "Nuclear gene silencing directs reception of long-distance mRNA silencing in *Arabidopsis*" Proc. Natl. Acad. Sci U.S.A. 104:14741-14746.
Broun, P., et al., (1998) "A Bifunctional oleate 12- Hydroxylase: Desaturase From *Lesquerella fendleri*," The Plant Journal, 13(2): 201-210.
Brown, M.R., et al., (1997) "Nutritional Properties of Microalgae for Mariculture," Aquaculture, 151(1): 315-331.
Brown et al. (2002) Limnanthes douglasii lysophosphatidic acid acyltransferases: immunological quantification, acyl selectivity and functional replacement of the *Escherichia coli* plsC gene, Biochem J. 364:795-805.
Browse, J.A. and Slack, C.R., (1981) "Catalase Stimulates Linoleate Desaturase Activity in Microsomes From Developing Linseed Cotyledons," Federation of European Biochemical Societies Letters, 131(1): 111-114.
Burgal et al., Metabolic engineering of hydroxy fatty acid production in plants: RcDGAT2 drives dramatic increases in ricinoleate levels in seed oil. Plant Biotechnology Journal, 2008, 6:819-831.
Cahoon, E. B., Ripp, K. G., Hall, S. E., & Kinney, A. J. (2001). Formation of conjugated $\Delta^8$,Δ10-double bonds by $\Delta^{12}$-oleic-acid desaturase-related enzymes. *The Journal of Biological Chemistry*, 276(4), 2637-2643.
Cahoon, E. B., Marillia, E., Stecca, K. L., Hall, S. E., Taylor, D. C., & Kinney, A. J. (2000). Production of factty acid components of meadowfoam oil in somatic soybean embryos. *Plant Physiology*, 124, 243-251.
Cahoon, E. B., Shanklin, J., & Ohlrogge, J. B. (1992). Expression of a coriander desaturase results in petroselinic acid production in transgenic tobacco. *Proc: Natl. Acad. Sci. USA*, 89, 11184-11188.
Cahoon et al., Conjugated fatty acids accumulate to high levels in phospholipids of metabolically engineered soybean and *Arabidopsis* seeds. Phytochemistry, 2006, 67(12) :1166-1176.
Capdevila et al., Cytochrome P-450 anachidonate oxygenase. Methods in Enzymology, 1990, 187:385-394.
Capecchi (1980) "High Efficiency Transformation by Direct Microinjection of DNA into Cultured Mammalian Cells" Cell 22:479-488.
Chapman et al: (2001) "Transgenic Cotton Plants with Increased Seed Oleic Acid Content" Journal of American Chemists' Chemistry; vol. 78 No. 9, 941-947.
Chapman et al. (2004) Transgenic Cotton Plants with Increased Seed Oleic Acid Content. Gen: Dev. 18:1179-1186.
Chen et al. (2004) "Introgression of Salt-Tolerance From Somatic Hybrids Between common Wheat and Thinopyrum Ponticum" Plant Science 167:773-779.
Chen et al. (2010) "MISSA is a Highly Efficient in Vivo DNA Assembly Method for Plant Multiple-Gene Transformation" Plant Physiology, vol. 153, pp. 41-51.
Cheng, M., Jarret, R. L., Li, Z., Xing, A., & Demski, J. W. (1996) . Production of fertile transgenic peanut (*Arachis hypogaea* L.) plants using *Agrobacterium tumefaciens. Plant Cell Reports*, 15, 653-657.
Cheng et al. (2010) Towards the production of high levels of eicosapentaenoic acid in transgenic plants: the effects of different host species, genes and promoters, Transgenic Res 19: 221-229.
Certik M. and Shimizu S., Biosynthesis and regulation of microbial polyunsaturated fatty acid production. J. Biosci Bioeng, 1999; 87 (1) :1-14.
Chica et al. (2005) Semi-rational approaches to engineering enzyme activity: combining the benefits of directed evolution and rational design. Current Opinion in Biothechnology, 16:378-384.
Chikwamba et al. (2003) "Localization of a bacterial protein in starch granules of transgenic maize kernels" Proc. Natl. Acad. Sci. U.S.A. 100:11127-11132.
Chinain, M., et al., "Intraspecific Variation in the Dinoflagellate Gambierdiscus Toxicus (Dinophyceae) . I. Isozyme Analysis," Journal of Phycology, 33: 36-43.

(56) References Cited

OTHER PUBLICATIONS

Christian and Yu, Cytochrome P-450-dependent monooxygenase activity in the velvetbean caterpillar, *Anticarsia gemmatalis hubner*. Comparative Biochemistry and Physiology, 1986, 83C(1):23-27.
Cho, H.P., et al., (1999) "Cloning, Expression, and Nutritional Regulation of the Mammalian Δ-6 Desaturase," The Journal of Biological Chemistry, 274(1): 471-477.
Cho, H.P., et al., (1999) "Cloning, Expression, and Fatty Acid Regulation of the Human Δ-5 Desaturase," The Journal of Biological Chemistry, 274(52): 37335-37339.
Chung et al. (2006) "Effect of 5'UTR introns on gene expression in *Arabidopsis thaliana*" BMC Genomics 7:120.
Clapp et al., The 16-Kilodalton N-Terminal Fragment of Human Prolactin is a Potent Inhibitor of Angiogenesis. Endocrinology, 1993, 133(3):1292-1299.
Clough, S.J. and Bent, A.F., (1998) "Floral Dip: A Simplified Method for Agrobacterium-Mediated Transformation of *Arabidopsis thaliana*," 16(6); 735-743.
Coleman, A.W., (1977) "Sexual and Genetic Isolation in the Cosmopolitan Algal Species *Pandorina Morum*," American Journal of Botany, 64(3): 361-368.
Coutu et al. (2007) "pORE: a modular binary vector series suited for both monocot and dicot plant transformation" Transgenic Res. 16: 771-781.
Cripps, C., Borgeson, C., Blomquist, G. J., & de Renobales, M. (1990). The $\Delta^{12}$-desaturase from the house cricket, *Acheta domesticus* (orthoptera: gryllidae): characterization ad form of the substrate. *Archives of Biochemistry and Biophysics*, 278(1), 46-51.
Crombie, L., & Holloway, S. J. (1984). Origins of conjugated triene fatty acids. The biosynthesis of calendic acid by *Calendula officinalis. J. Chem. Soc., Chem. Commun.*, 15, 953-955.
Crombie, L., & Holloway, S. J. (1985). the biosynthesis of calendic acid, octadeca-(8E,10E,12Z)-trienoic acid, by developing marigold seeds: origins of (E,E,Z) and (Z,E,Z) conjugated triene acids in higher plants. *J. Chem. Soc. Perkin Trans.* 1, 2425-2434.
Cuperus, F. P., & Derksen, J. T. P. (1996). High value-added applications from vernolic acid. In J. Janick (Ed.), *Progress in new crops* (pp. 354-356). Alexandria, VA: ASHS Press.
Curiel et al. (1992) "High-Efficiency Gene Transfer Mediated by Adenovirus Coupled to DNA-Polylysine Complexes" Hum. Gen. Ther. 3:147-154.
Dafny-Yelin et al., Delivery of Multiple Transgenes to Plant Cells, Plant Physiology, Dec. 2007, vol. 145, pp. 1118-11128.
Damude et al., (2007) "Engineering Oilseed Plants for a Sustainable, Land-Based Source of Long Chain Polyunsaturated Fatty Acids", Lipids, 42:179-185.
Damude et al. (2006). Identification of bifunctional delta12/omega3 fatty acid desaturases for improving the ratio of omega3 to omega6 fatty acids in microbes and plants, Proc Natl Acad Sci USA 103: 9446-9451.
Darji et al. (1997) "Oral Somatic Transgene Vaccination Using Attenuated S. typhimurium" Cell 91:765-775.
Denic and Weissman (2007) A molecular caliper mechanism for determining very long-chain fatty acid length, Cell 130:663-677.
De Renobales, M., Cripps, C., Stanley-Samuelson, D. W., Jurenka, R. A., & Blomquist, G. J. (1987). Biosynthesis of linoleic acid in insects. *Trends in Biochemical Sciences*, 12, 364-366.
Ding and Voinett (2007) "Antiviral Immunity Directed by Small RNAs" Cell 130:413-426.
Dobson, G., & Christie, W. W. (2002). Mass spectrometry of fatty acid derivatives. *Eur. J. Lipid Sci. Technol.*, 104, 36-43.
Dolferus et al., Differential Interactions of promoter elements in stress responses of the *Arabidopsis* adh gene. Plant Physiol, 1994, 105:1075-1087.
Domergue, F., et al., (2002) "Cloning and Functional Characterization of Phaeodactylum Tricornutum Front-End Desaturases Involved in Eicosapentaenoic Acid Biosynthesis," European Journal of Biochemistry, 269(16):4105-4113.
Domergue et al., In vivo characterization of the first acyl-CoA $\Delta^6$-desaturase from a member of the plant kingdom, the microalga *Ostreococcus tauri*, Biochem J. 2005, 389, 483-490.
Domergue, F., et al., (2003) "New Insight Into Phaeodactylum tricornutum Fatty Acid Metabolism. Cloning and Functional Characterization of Plastidial and Microsomal Δ12-Fatty Acid Desaturases," Plant Physiology, 131(4): 1648-1660.
Domergue et al., (2003), Acyl Carriers Used as Substrates by the Desaturases and Elongases Involved in Very Long-chian Polyunsaturated Fatty Acids Biosynthesis Reconstituted in Yeast, J. Biol. Chem. 278; 35115-35126.
Drexler, H., et al., (2003) "Metabolic Engineering of Fatty Acids for Breeding of New Oilseed Crops: Strategies, Problems and First Results," Journal of Plant Physiology, 160(7): 779-802.
Dunoyer et al. (2004) "Probing the MicroRNA and Small Interfering RNA Pathways with Virus-Encoded Suppressors of RNA Silencing" The Plant Cell 16:1235-1250.
Dunstan, G.A., et al., (1994) "Essential Polyunsaturated Fatty Acids From 14 Species of *Diatom* (Bacillariophyceae)," Phytochemistry, 35(1): 155-161.
Dyer et al., Engineering plant oils as high-value industrial feedstocks for biorefining: the need for underpinning cell biology research. Physiol Plant, 2008,.
Eglitis et al. (1988) "Retroviral Vectors for Introduction of Genes into Mammalian Cells" Biotechniques 6:608-614.
Engeseth and Stymne, Desaturation of oxygenated fatty acids in lesquerella and other oil seeds. Planta, 1996, 198: 238-245.
Eigenheer et al (2002) "Isolation and molecular characterization of Musca domestica delta-9 desaturase sequences" Insect Molecular Biology 11(6):533-542.
Fay, L., & Richli, U. (1991). Location of double bonds in polyunsaturated fatty acids by gas chromatography-mass spectrometry after 4,4-dimethyloxazoline derivatization. *Journal of Chromatography*, 541, 89-98.
Fennelly et al. (1999) "Mucosal DNA Vaccine Immunization Against Measles with a Highly Attenuated Shigella flexneri Vector" J. Immunol. 162:1603-1610.
Fraser et al. (2004) "Expression of the Isochrysis C18-Δ9 Polyunsaturated Fatty Acid Specific Elongase Component Alters *Arabidopsis* Glycerolipid Profiles" Plant Physiol. 135:859-866.
Fritsche, K., Hornung, E., Peitzsch, N., Renz, A., & Feussner, I. (1999). Isolation and characterization of a calendic acid producing (8,11)-linoleoyl desaturase. *FEBS Letters*, 462, 249-253.
Fuji et al. (2007) "*Arabidopsis* Vacuolar Sorting Mutants (green fluorescent seed) Can Be Identified Efficiently by Secretion of Vacuole-Targeted Green Fluorescent Protein in Their Seeds" Plant Cell 19:597-609.
Fujimura et al. (1985) "Regeneration of Rice Plants from Protoplasts" Plant Tissue Culture Lett. 2:74.
Gallagher,. J.C., (1980) "Population Genetics of Skeletonema Costatum (Bacillariophyceae) in Narragansett Bay," Journal of Phycology, (16)3: 464-474.
Garcia-Maroto, F., et al., (2002) "Cloning and Molecular Characterization of the Δ6-Desaturase From Two Echium Plant Species: Production of GLA by Heterologous Expression in Yeast and Tobacco," Lipids, 37(4): 417-426.
Girke, T., et al., (1998) "Identification of a Novel Δ6- Acyl-Group Desaturase by Targeted Gene Disruption in Physcomitrella patens," The Plant Journal, 15(1): 39-48.
Gleave (1992) "A versatile binary vector system with a T-DNA organisational structure conducive to efficient integration of cloned DNA into the plant genome" Plant Mol. Biol. 20:1203-1207.
Glevin et al (2003) "Agrobacterium-Mediated Plant Transformation: the Biology behind the 'Gene-Jockeying' Tool" Microbiol. Mol. Biol. Rev. 67:16-37.
Glick et al. (2008) "Interaction with host SGS3 is required for suppression of RNA silencing by tomato yellow leaf curl virus V2 protein" Proc. Natl. Acad. Sci U.S.A. 105:157-161.
Graham et al. (1973) "Transformation of Rat Cells by DNA of Human Adenovirus 5" Virology 54:536-539.
Grant, J. E., Cooper, P. A., McAra, A. E., & Frew, T. J. (1995). Transformation of peas (*Pisum sativum* L.) using immature cotyledons. *Plant Cell Reports*, 15, 254-258.

(56) References Cited

OTHER PUBLICATIONS

Grillot-Codrvalin (1999) "Bacteria as gene delivery vectors for mammalian cells" Curr. Opin. Biotech. 10:477-481.
Gul et al. (2006) Sterols and the phytosterol content of oil seed rape (*Brassica napus* L.). Journal of Cell and Molecular Biology, vol. 5, pp. 71-79.
Guil-Guerrero, J.L., et al., (2000) "Occurrence and Characterization of Oils Rich in γ-Linolenic Acid Part I: Echium Seeds From Macaronesia," Phytochemistry, 53(4): 451-456.
Halpin, Gene stacking in transgenic plants-the challenge for 21st century plant biotechnology, Plant Biotechnology Journal (2005, 3, pp. 141-155).
Hamberg and Fahlstadius, On the Specificity of Fatty Acid Epoxygenase in Broad Bean (*Vicia faba* L.). Plant Physiol, 1992, 99:987-998.
Hamilton and Baulcombe (1999) "A Species of Small Antisense RNA in Posttranscriptional Gene Silencing in Plants" Science 286:950-952.
Haseloff, J. and Gerlach, W.L., (1988) "Simple RNA Enzymes With New and Highly Specific Endoribonuclease Activities," Nature, 334: 585-591.
Hastings, N., et al., (2001) "A Vertebrate Fatty Acid Desaturase With Δ5 and Δ6 Activities," Proceedings of The National Academy of Sciences of the United States of America, 98(25): 14304-14309.
Hao, G., Liu, W., O'Conner, M., & Roelofs, W. L. (2002). Acyl-CoA Z9- and Z10-desaturase genes from a New Zealand leafroller moth species, *Planotortrix octo. Insect Biochemistry and Molecular Biology*, 32, 961-966.
Harayama, S. (1998). Artificial evolution by DNA shuffling. *Trends in Biotechnology*, 16(2), 76-82.
Hense et al. (2001) "Eukaryotic expression plasmid transfer from the intracellular bacterium Listeria monocytogenes to host cells" Cell Microbiol. 3:599-609.
Heppard et al., Developmental and Growth Temperature Regulation of Two Different Microsomal ω-6 Desaturase Genes in Soybeans. Plant Physiol, 1996, 110:311-319.
Hoffman et al (2007) "A Small Membrane-peripheral Region Close to the Active Center Determines Regioselectivity of Membrane-bound Fatty Acid Desaturases from Aspergillus nidulans" J. Biol. Chem. 282:26666-26674.
Hoffman et al., (2008) "Metabolic Engineering of ω3-Very Long Chain Polyunsaturated Fatty Acid Production by an Exclusively Acyl-CoA-dependent Pathway", The Journal of Biological Chemistry, 283:22352-22362.
Hong, H., et al., (2002) "Isolation and Characterization of a Δ5 FA Desaturase From Pythium irregulare by Heterologous Expression in *Saccaromyces cerevisiae* and Oilseed Crops," Lipids, 37(9): 863-868.
Horiguchi, G., et al., (1998) "Developmental Regulation of Genes for Microsome and Plastid Omega-3 Fatty Acid Desaturases in Wheat (*Triticum aestivum* L.)," Plant and Cell Physiology, 39(5): 540-544.
Horvath et al. (2000) "The production of recombinant proteins in transgenic barley grains" Proc. Natl. Acad. Sci. U.S.A. 97:1914-1919.
Huang, Y., et al . , (1999) "Cloning of Δ12-and Δ6-Desaturases From Mortierella alpina and Recombinant Production of γ-Linolenic Acid in *Saccharomyces cerevisiae*, " Lipids, 34 (7) : 649-659.
Huang et al. (2004) "How Insulin Binds: the B-Chain a-Helix Contacts the L1 b-Helix of the Insulin Receptor" J. Mol. Biol. 341:529-550.
Hu et al. (2008) "Microalgal triacylglycerols as feedstocks for biofuel production: perspectives and advances" The Plant Journal, 54, 621-639.
Ikeda, K., et al . , (2002) "Transformation of the Fresh Water Cyanobacterium Synechococcus PCC7942 With the Shuttle-Vector pAQ-EX1 Developed for the Marine Cyanobacterium Synechococcus PCC7002," World Journal of Microbiology & Biotechnology, 18 (1) : 55-56.
Inagaki, K., et al., (2002) "Identification and Expression of a Rat Fatty Acid Elongase Involved in the Biosynthesis of C18 Fatty Acids," Bioscience, Biotechnology, and Biochemistry, 66 (3) : 613-621.
Jiang et al. (2014) Isolation and Characterization of the Diatom Phaeodactylum Δ5-Elongase Gene for Transgenic LC-PUFA Production in Pichia pastoris. Mar. Drugs, 12, 1317-1334.
Johansen and Carrington (2001) "Silencing on the Spot. Induction and Suppression of RNA Silencing in the Agrobacterium-Mediated Transient Expression System" Plant Physiol . 126-930-938.
Jones, A.V.M. and Harwood, J.L. , (1980) "Desaturation of Linoleic Acid From Exogenous Lipids by Isolated Chloroplasts," The Biochemical Journal, 190 (3) : 851-854.
Jøstensen et al. (2002) Molecular-phylogenetic, structural and biochemical features of a cold-adapted marine ichtyosporean near the animal-fungal divergence, described from in vitro cultures. Europ. J. Protistol. , 38, 93-104.
Kajikawa, M., et al., (2004) "Isolation and Characterization of Δ6-Desaturase, An ELO-Like Enzyme and Δ5-Desaturase From the Liverwort Marchantia polymorpha and Production of Arachidonic and Eicosapentaenoic Acids in the Methylotrophic Yeast Pichia pastoris," Plant Molecular Biology, 54: 335-352.
Kajikawa et al. (2006) Isolation and functional characterization of fatty acid delta5-elongase gene from the liverwort *Marchantia polymorpha* L, FEBS Lett 580:149-154.
Kang et al. (2008) "Coexpression of Elo-like Enzyme and A4-Desaturases Derived from Thraustochytrium aureum ATCC 34304 and the Production of DHA and DPA in Pichia pastoris" 13:483-490.
Kasschau et al. (2003) "P1/HC-Pro, a Viral Suppressor of RNA Silencing, Interferes with *Arabidopsis* Development and miRNA Function" Devel. Cell 4:205-217.
Khozin et al. (1997) "Elucidation of the Biosynthesis of Eicosapentaenoic Acid in the Microalga Porphyridium cruentum" Plant Physiol. 114:223-230.
Kleiman, R., & Spencer, G. F. (Jan. 1982). Search for new industrial oils: XVI. umbelliflorae-seed oils rich in petroselinic acid. *Journal of the American Oil Chemists' Society*, 59(1), 29-38.
Knipple, D. C., Rosenfield, C., Nielsen, R., You, K. M., & Jeong, S. E. (2002). Evolution of the integral membrane desaturase gene family in moths and flies. *Genetics*, 162, 1737-1752.
Knutzon, D.S., et al., (1998) "Identification of Δ5-Desaturase From Mortierella alpina by Heterologous Expression in Bakers' Yeast and Canola," The Journal of Biological Chemistry, 273(45): 29360-29366.
Koziel et al. (1996) "Optimizing expression of transgenes with an emphasis on post-transcriptional events" Plant Mol. Biol. 32:393-405.
Kroon et al., Identification and functional expression of a type 2 acyl-CoA:diacylglycerol acyltransferase (DGAT2) in developing castor bean seeds which has high homology to the major triglyceride biosynthetic enxyme of fungi and animals. Phytochemistry, 2006, 67:2541-2549.
Kunik et al. (2001) "Genetic transformation of HeLa cells by Agrobacterium" Proc. Natl. Acad. Sci. U.S.A. 98:1871-1876.
Lacroix et al. (2008) "Association of the Agrobacterium T-DNA-protein complex with plant nucleosomes" Proc. Natl. Acad. Sci. U.S.A. 105: 15429-15434.
Laethem et al., Epoxidation of C18 unsaturated fatty acids by cytochromes P4502C2 and P4502CAA. Drug Metabolism and Disposition, 1996, 24(6):664-668.
Lassner (1995) Lysophosphatidic acid acyltransferase from meadowfoam mediates insertion of erucic acid at the sn-2 position of triacylglycerol in transgenic rapeseed oil, Plant Physiol. 109:1389-94.
Lechtenberg et al. (2003) "Neither inverted repeat T-DNA configurations nor arrangements of tandemly repeated transgenes are sufficient to trigger transgene silencing" Plant J. 507-517.
Lee, M., et al., (1998) "Identification of Non-Heme Diiron Proteins That Catalyze Triple Bond and Epoxy Group Formation," Science, 280(5365): 915-918.

(56) References Cited

OTHER PUBLICATIONS

Lenihan-Geels et al. (2013) "Alternative Sources of Omega-3 Fats: Can We Find a Sustainable Substitute for Fish?" Nutrients, 5, 1301-1315.
Leonard, A.E., et al., (2000) "cDNA Cloning and Characterization of Human Δ5-Desaturase Involved in the Biosynthesis of Arachidonic Acid," The Biochemical Journal, 347(Pt 3): 719-724.
Leonard, A.E., et al., (2000) "Cloning of a Human cDNA Encoding a Novel Enzyme Involved in the Elongation of Long-Chain Polyunsaturated Fatty Acids," The Biochemical Journal, 350(Pt 3): 765-770.
Leonard, A.E., et al., (2002) "Identification and Expression of Mammalian Long-Chain Pufa Elongation Enzymes," Lipids, 37(8): 733-740.
Lewis, T., Nichols, P. D., & McMeekin, T. A. (2000). Evaluation of extraction methods for recovery of fatty acids from lipid-producing microheterotrophs. Journal of Microbiological Methods, 43, 107-116.
Lewsey et al. (2007) "Selective targeting of miRNA- regulated plant development by a viral counter-silencing protein" Plant J. 50:240-252.
Lin et al. (2003) "Efficient linking and transfer of multiple genes by a multigene assembly and transformation vector system" Pnas, 100(10): 5962-5967.
Lindbo et. al. (1993) "Induction of a Highly Specific Antiviral State in Transgenic Plants: Implications for Regulation of Gene Expression and Virus Resistance" Plant Cell 5:1749-1759.
Lo, J. et al., (2003) "15,000 Unique Zebrafish EST Clusters and Their Future Use in Microarray for Profiling Gene Expression Patterns During Embryogenesis," Genome Research Letter, 13(3): 455-466.
Lu et al., an analysis of expressed sequence tags of developing castor endosperm using a full-length cDNA library. BMC Plant Biol, 2007, 7(42):1-9.
Lu et al. (1993) "High Efficiency Retroviral Mediated Gene Transduction into Single Isolated Immature and Replatable CD343+ Hematopoietic Stem/Progenitor Cells from Human Umbilical Cord Blood" J. Exp. Med. 178:2089-2096.
Mallory et al (2002) "The amplicon-plus system for high- level expression of transgenes in plants" Nat. Biotech. 20:622-625.
Mansour, M.P., et al., (1999) "The Fatty Acid and Sterol Composition of Five Marine Dinoflagellates," Journal of Phycology, 35(4): 710-720.
Marangoni and Rousseau (1995) "Engineering triacylglycerols: The role of interesterification" Trends in Food Science & Technology 6, 329-335.
Marquardt et al., (2000) "cDNA cloning, genomic structure, and chromosomal localization of three members of the human fatty acid desaturase family." Genomics, 66 (2) :175-183.
Marekov et al. (2009) Sterol composite of rapeseed varieties introduced in Bulgaria. Bulgarian Journal of Agricultural Science, 15(2): 119-122.
Matzke et al. (2001) "RNA: Guiding Gene Silencing" Science 293:1080-1083.
Medlin, L.K. , et al., (1996) "Genetic Characterization of Emiliania huxleyi (Haptophyta) , " Journal of Marine Systems, 9: 13-31.
Meesapyodsuk et al. (2007) Primary structure, regioselectivity, and evolution of the membrane-bound fatty acid desaturases of Claviceps purpurea, J Biol Chem 282: 20191-20199.
Meng et al. (2008) "Hibiscus chlorotic ringspot virus coat protein inhibits trans-acting small interfering RNA biogenesis in *Arabidopsis*" J. Gen. Virol. 89:2349-2358.
Metz, J.G., et al., (2001) "Production of Polyunsaturated Fatty Acids by Polyketide Synthases in Both Prokaryotes and Eukaryotes," Science, 293(5528) : 290-293.
Meyer, A., et al., (2003) "Biosynthesis of Docosahexaenoic Acid in Euglena gracilis: Biochemical and Molecular Evidence for the Involvement of a Δ4-Fatty Acyl Group Desaturase," Biochemistry, 42(32): 9779-9788.
Meyer, A., et al., (2004) "Novel Fatty Acid Elongases and Their Use for the Reconstitution of Docosahexaenoic Acid Biosynthesis," Journal of Lipid Research, 45(10): 1899-1909.
Michaelson, L.V., et al., (1998) "Isolation of a Δ5-Fatty Acid Desaturase Gene From Mortirella alpina," the Journal of Biological Chemistry, 273(30): 19055-19059.
Michaelson, L.V., et al., (1998) "Functional Identification of a Fatty Acid As Desaturase Gene From Caenorhabditis elegans," Federation of European Biochemical Societies Letters, 439(3): 215-218.
Mitchell, A.G. and Martin, C., (1995) "A Novel Cytochrome b5-Like Domain is Linked to the Carboxyl Terminus of the *Saccharomyces cerevisiae* Δ-9 Fatty Acid Desaturase," The Journal of Biological Chemistry, 270(50): 29766-29772.
Moreau et al. (1998) "Lipid Trafficking in Plant Cells" Progress Lip. Res. 37:371-391.
Morimoto et al. (2005) Hot Topic:. Endogenous Production of n-3 and n-6 Fatty Acids in Mammalian Cells. J. Dairy Sci., 88:1142-1146.
Morita, N., et al., (2000) "Biosynthesis of Fatty Acids in the Docosahexaenoic Acid-Producing Bacterium Moritella marina Strain MP-1," Biochemical Society Transactions, 28(6): 943-945.
Mortimer, R. K., & Johnston, J. R. (1986). Genealogy of principal strains of the yeast genetic stock center. *Genetics*, 113, 35-43.
Moto, K., Suzuki, M. G., Hull, J. J., Kurata, R., Takahashi, S., Yamamoto, M., . . . Matsumoto, S. (2004). Involvement of a bifunctional fatty-acyl desaturase in the biosynthesis of the silkmoth, *Bombyx mori*, sex pheromone. *PNAS*, 101(23), 8631-8636.
Murata, N., & Wada, H. (1995). Acyl-lipid desaturases and their importance in the tolerance and acclimatization to cold of cyanobacteria. *Biochem. J.*, 308, 1-8.
Napier, J.A., et al., (1998) "Identification of a Caenorhabditis elegans Δ6-Fatty-Acid-Desaturase by Heterologous Expression in *Saccharomyces cerevisiae*," The Biochemical Journal, 330(Pt 2): 611-614.
Napier, J.A., et al., (1999) "A Growing Family of Cytochrome b5-Domain Fusion Proteins," Trends in Plant Science, 4(1): 2-4.
Napier, J.A., et al., (1999) "Plant Desaturases: Harvesting the Fat of the Land," Current Opinion in Plant Biology, 2(2): 123-127.
Napier (2007) "The Production of Unusual Fatty Acids in Transgenic Plants" Ann. Rev. Plant. Biol. 58:295-319.
Needleman, S. B., & Wunsch, C. D. (1970). A general method applicable to the search for similarities in the amino acid sequence of two proteins. *J. Mol. Biol.*, 48, 443-453.
Niedz et al (1995) "Green fluorescent protein: an in vivo reporter of plant gene expression" Plant Cell Reports 14:403-406.
Nishizawa et al. (2003) "A C-terminal sequence of soybean b-conglycinin a' subunit acts as a vacuolar sorting determinant in seed cells" Plant J. 34:647-659.
Okuley et al. *Arabidopsis* FAD2 Gene Encodes the Enzyme that is Essential for Polyunsaturated Lipid Synthesis. Plant Cell, 1994, 6:147-158.
Ohlrogge and Browse (1995) "Lipid Biosynthesis" Plant Cell 7:957-970.
Ohlrogge and Jaworski (1997) Regulation of Fatty Acid Synthesis. Annu Rev Plant Physiol Plant Mol Biol. 48:109-136.
Ow et al. (1986) "Transient and Stable Expression of the Firefly Luciferase Gene in Plant Cells and Transgenic Plants" Science 234:856-859.
Park and Jeong (2005) "Cloning and Functional Expression of cDNA Encoding Pheromone Δ9 Acyl-CoA Desaturase of the Tobacco Cutworm, *Spodoptera litura* (Lepidoptera: Noctuidae)" Entomological Research, 35(4):253-263.
Parker-Barnes, J.M. , et al . , (2000) "Identification and Characterization of an Enzyme Involved in the Elongation of n-6 and n-3 Polyunsaturated Fatty Acids," Proceedings of the National Academy of Sciences of the United States of America, 97(15): 8284-8289.
Pereira, S . L. , et al., (2004) "A Novel omega3-Fatty Acid Desaturase Involved in the Biosynthesis of Eicosapentaenoic Acid," The Biochemical Journal, 378 (Pt 2): 665-671.
Passorn et al (1999) "Heterologous Expression of Mucor rouxii Δ12-Desaturase Gene in *Saccharomyces cerevisiae*" Biochemical and Biophysical Research Communications 263, 47-51.

(56) References Cited

OTHER PUBLICATIONS

Pereira et al. (2004b) Identification of two novel microalgal enzymes involved in the conversion of the omega3-fatty acid, eicosapentaenoic acid, into docosahexaenoic acid, Biochem. J. 384:357-366.

Petrie et al. (2010a) Metabolic engineering of omega-3 long-chain polyunsaturated fatty acids in plants using an acyl-CoA Delta6-desaturase with omega3-preference from the marine microalga *Micromonas pusilla*, Metab. Eng. 12:233-240.

Petrie et al. (2012) Transgenic production of arachidonic acid in oilseeds, Transgenic Res. 21:139-147.

Petrie et al. (2011) "Expanding the docosahexaenoic acid food web for sustainable production: engineering lower plant pathways into higher plants" AoB Plants Article plr011 (doi:10.1093/aobpla/plr011.

Petrie et al. (2012) "Metabolic Engineering Plant Seeds with Fish Oil-Like Levels of DHA" PLoS ONE, vol. 7, No. 10, e49165.

Petrie et al. (2010) "Rapid expression of transgenes driven by seed-specific constructs in leaf tissue: DHA production" Plant Methods 6:8 (pp. 1-6).

Petrie et al. (2010) "Isolation and Characterisation of a High-Efficiency Desaturase and Elongases from Microalgae for Transgenic LC-PUFA Production" Mar Biotechnol 12:430-438.

Petrie et al. (2013) "Engineered oilseed crops with fish oil DHA levels" Inform, 24(10):648-652.

Pereira et al. (2004) "Identification of two novel microalgal enzymes involved in the conversion of the ω3-fatty acid, eicosapentaenoic acid, into docosahexaenoic acid" Biochem. J. 384:357-366.

Perriman, R., et al., (1992) "Extended Target-Site Specificity for a Hammerhead Ribozyme," Gene, 113(2):157-163.

Peyou-Ndi et al. (2000) Identification and Characterization of an Animal Δ12 Fatty Acid Desaturase Gene by Heterologous Expression in *Saccharomyces cerevisiae*. Archives of Biochemistry and Biophysics, vol. 376, No. 2, pp. 399-408.

Potenza et al. (2004) "Targeting Transgene Expression in Research, Agricultural, and Environmental Applications: Promoters Used in Plant Transformation" In Vitro Cell Dev Biol—Plant 40:1-22.

Qu, B., et al., (2002) "Identification of a cDNA Encoding a Novel C18-Δ9 Polyunsaturated Fatty Acid-Specific Elongating Activity From the Docosahexaenoic Acid(DHA)—Producing Microalga, *Isochrysis galbana*," Federation of European Biochemical Societies Letters, 510(3): 159-165.

Qi, et al., (2004) "Production of Very Long Chain Polyunsaturated Omega-3 and Omega-6 Fatty Acids in Plants", Nature Biotechnology 22:739-745 (published online May 16, 2004).

Qiu, X., Reed, D. W., Hong, H., MacKenzie, S. L., & Covello, P. S. (2001). Identification and analysis of a gene from *Calendula officinalis* encoding a fatty acid conjugase. *Plant Physiology*, 125 847-855.

Qiu, X., et al., (2001) "Identification of a Δ4 Fatty Acid Desaturase From *Thraustochytrium* sp. Involved in the Biosynthesis of Docosahexanoic Acid by Heterologous Expression in *Saccharomyces cerveisiae* and *Brassica juncea*," The Journal of Biological Chemistry, 276(34): 31561-31566.

Reddy, A.S., et al., (1993) "Isolation of a Δ6—Desaturase Gene From the Cyanobacterium *Synechocystis* sp. Strain PCC6803 by Gain-Of-Function Expression in *Anabaena* sp. Strain PCC7120," Plant Molecular Biology, 27: 293-300.

Riddervold et al (2002) "Biochemical and molecular characterizaton of house cricket (*Acheta domesticus*, Orthoptera: Gryllidae) Δ9 desaturase" Insect Biochemistry and Molecular Biology 32, 1731-1740.

Robert et al., Metabolic engineering of *Arabidopsis*to produce nutritionally important DHA in seed oil, Functional Plant Biology, 2005, vol. 32, p. 473-479 (Abstract Only).

Robert et al. (2009) Isolation and characterisation of a delta5-fatty acid elongase from the marine microalga *Pavlova salina*, Marine Biotech 11:410-418.

Rodríguez, S., Hao, G., Liu, W., Piña, B., Rooney, A. P., Camps, F., . . . Fabriàs, G. (2004). Expression and evolution of $\Delta^9$ and $\Delta^{11}$ Expression and *Spodoptera littoralis. Insect Biochemistry and Molecular Biology*, 34, 1315-1328.

Romero et al., An epoxygenase metabolite of arachidonic acid 5,6 epoxy-eicosatrienoic acid mediates angiotensin-induced natriuresis in proximal tubular epithelium. Advances in Prostaglandin, Thromboxane and Leukotriene Research, 1991, 21:205-208.

Rose et al. (1998) "Consensus-degenerate hybrid oligonucleotide primers for amplification of distantly related sequences" Nucleic Acids Res. 26:1628-1635.

Ruiz-Lopez et al. (2012) "Enhancing the accumulation of omega-3 long chain polyunsaturated fatty acids in transgenic *Arabidopsis thaliana* via iterative metabolic engineering and genetic crossing" Transgenic Res, 21:1233-1243.

Ruiz-López et al., (2012) Metabolic engineering of the omega-3 long chain polyunsaturated fatty acid biosynthetic pathway into transgenic plants. Journal of Experimental Botany, 63(7):2397-2410.

Ryckebosch et al. (2012) "Microalgae as an alternative source of omega-3 long chain polyunsaturated fatty acids" Lipid Technology, 24(6): 128-130.

Saito, T., et al., (2000) "A Second Functional Δ5 Fatty Acid Desaturase in the Cellular Slime Mould *Dictyostelium discoideum*," European Journal of Biochemistry, 267(6): 1813-1818.

Sato et al. (2004) Production of gamma-Linolenic Acid Stearidonic Acid in Seeds of Marker-Free Transgenic Soybean, Crop Sci. 44: 646-652.

Saha et al. (2006) "Cytosolic Triacylglycerol Biosynthetic Pathway in Oilseeds. Molecular Cloning and Expression of Peanut Cytosolic Diacylglycerol Acyltransferase" Plant Physiol. 141:1533-1543.

Sakuradani, E., et al., (1999) "Δ6-Fatty Acid Desaturase From an Arachidonic Acid-Producing Mortierella Fungus. Gene Cloning and Its Heterologous Expression in a Fungus, *Aspergillus*," Gene, 238(2): 445-453.

Sakuradani et al (2005) "A novel fungal ω3-desaturase with wide substrate specificity from arachidonic acid-producing Mortierella alpina 1S-4" Appl Microbiol Biotechnol 66: 648-654.

Sayanova, O.V., et al., (1997) "Expression of a Borage Desaturase cDNA Containing an N-Terminal Cytochrome b5 Domain Results in the Accumulation of High Levels of Δ6-Desaturated Fatty Acids in Transgenic Tobacco," Proceedings of the National Academy of Sciences of The United States of America, 94(8): 4211-4216.

Sayanova, O.V., et al., (1999) "Histidine-41 of the Cytochrome b5 Domain of the Borage Δ6 Fatty Acid Desaturase is Essential for Enzyme Activity," Plant Physiology, 121(2): 641-646.

Sayanova, O.V., et al., (2003) "Identification of Primula Fatty Acid Δ6-Desaturases with n-3 Substrate Preferences," Federation of European Biochemical Societies, 542: 100-10.

Sayanova, O.V. and Napier, J.A., (2004) "Eicosapentaenoic Acid: Biosynthetic Routes and the Potential for Synthesis in Transgenic Plants," Phytochemistry, 65(2): 147-158.

Sayanova et al. (2006) A bifunctional Deltal2,Delta15-desaturase from Acanthamoeba castellanii directs the synthesis of highly unusual n-1 series unsaturated fatty acids, J Biol Chem 281: 36533-36541.

Sayanova et al. (2006) Identification of Primula "front-end" desaturases with distinct n-6 or n-3 substrate preferences, Planta 224:1269-1277.

Sayanova, O., Haslam, R., Caleron, M. V., & Napier, J. A. (May 2007). Cloning and characterization of unusual fatty caid desaturases from *Anemone leveillei*: identification of an acyl-coenzyme A $C_{20}$ $\Delta^5$-desaturase responsible for the synthesis of sciadonic acid. *Plant Physiology*, 144, 455-467.

Sayanova et al., The role of delta (6)-desaturase acyl-carrier specificity in the efficient synthesis of long-chain polyunsaturated fatty acids in transgenic plants. Plant Biotechnology Journal, (2012) 10:195-206.

Schubert et al. (2004) "Silencing in Arabidopsis T-DNA Transformants: The Predominant Role of a Gene-Specific RNA Sensing Mechanism versus Position Effects" Plant Cell 16:2561-2572.

Sen et al., (2007) Developments in Directed Evolution for Improving Enzyme Functions. Appl Biochem Biotechnol, 143:212-223.

Serra, M., Gauthier, L. T., Fabrias, G., & Buist, P. H. (2006). $\Delta^{11}$ desaturases of *Trichoplusia ni* and *Spodoptera littoralis* exhibit dual catalytic behaviour. *Insect Biochemistry and Molecular Biology*, 36, 822-825.

(56) References Cited

OTHER PUBLICATIONS

Shanklin, J., & Cahoon, E. B. (1998). Desaturation and related modifications of fatty acids. *Annu. Rev. Plant Physiol. Plant Mol. Biol.*, 49, 611-641.

Shanklin et al., Eight histidine residues are catalytically essential in a membrane-associated iron enzyme, stearoyl-coa desaturase, and are conserved in alkane hydroxylase and xylene monooxygenase. Biochemistry, 1994, 33:12787-12794.

Shippy, R., et al., (1999) "The Hairpin Ribozyme—Discovery, Mechanism, and Development for Gene Therapy," Molecular Biotechnology, 12(1): 117-129.

Shocket et al., Tung tree DGAT1 and DGAT2 have nonredundant functions in triacylglycerol biosynthesis and are localized to different subdomains of the endoplasmic reticulum. Plant Cell, 2006, 18:2294-2313.

Simopoulos, A.P. , (2000) "Symposium: Role of Poultry Products in Enriching the Human Diet With N-3 PUFA," Poultry Science, 79: 961-970.

Simopoulus, A. P. (2000) . Human requirement for N-3 polyunsaturated fatty acids. *Poultry Science*, 79(7), 961-970.

Singh, S., et al., (2001) "Transgenic Expression of a Δ12-Epoxygenase Gene in *Arabidopsis* Seeds Inhibits Accumulation of Linoleic Acid," Planta, 212: 872-879.

Singh et al. (2005) Metabolic engineering of new fatty acids in plants, Curr. Opin. in Plant Biol. 8:197-203.

Slater et al., Metabolic engineering of *Arabidopsis* and *Brassica* for poly (3-hydroxybutyrate-co-3-hydroxyvalerate) copolymer production, Nature Biotechnology, Oct. 1999, vol. 12, 1011-1016.

Smith, N.A. , et al., (2000) "Total Silencing by Intron-Spliced Hairpin RNAs," Nature, 407 (6802) : 319-320.

Smith, C. R., Jr. (1971) . Occurrence of unusual fatty acids in plants. *Progress in the Chemistry of Fats and Other Lipids*, 11, 137, 139-177.

Smith, M. A., Moon, H., Chowrira, G., & Kunst, L. (2003) . Heterologous expression of a fatty acid hydroxylase gene in developing seeds of *Arabidopsis thaliana. Planta*, 217, 507-516.

Speranza and Macedo (2012) "Lipase-mediated production of specific lipids with improved biological and physicochemical properties" Process Biochemistry 47, 1699-1706.

Sperling, P., et al., (2000) "A Bifunctional Δ6-Fatty Acyl Acetylenase/Desaturase From the Moss Ceratodon purpureus," European Journal of Biochemistry, 267(12) : 3801-3811.

Sperling, P. and Heinz, E., (2001) "Desaturases Fused to Their Electron Donor," European Journal of Lipid Science and Technology, 103(3): 158-180.

Sperling et al. (2001) Functional identification of a delta8-sphingolipid desaturase from Borago officinalis, Arch. Biochm. Biophys. 388:293-8.

Sprecher, H., et al., (1995) "Reevaluation of the Pathways for the Biosynthesis of Polyunsaturated Fatty Acids," Journal of Lipid Research, 36(12): 2471-2477.

Spychalla, J.P., et al., (1997) "Identification of an animal omega-3 Fatty Acid Desaturase by Heterologous Expression in Arabidopsis," Proceedings of the National Academy of Sciences of the United States of America, 94(4): 1142-1147.

Stålberg, K., et al., (1993) "Deletion Analysis of a 2S Seed Storage Protein Promoter of *Brassica napus* in Transgenic Tobacco," Plant Molecular Biology, 23(4): 671-683.

Stalker et al (1988) "Purification and Properties of a Nitrilase Specific for the Herbicide Bromoxynil and Corresponding Nucleotide Sequence Analysis of the bxn Gene" J. Biol. Chem. 263:6310-6314.

Stanley-Samuelson et al (1998) "Fatty Acids in Insects: Composition, Metabolism, and Biological Significance" Archives of Insect Biochemistry and Physiology 9:1-33.

Stukey, J. E., McDonough, V. M., & Martin, C. E. (1990). The OLE1 gene of *Saccharomyces cerevisiae* encodes the Δ9 fatty acid desaturase and can be functionally replaced by the rat stearoyl-CoA desaturase gene. *The Journal of Biological Chemistry*, 265(33), 20144-20149.

Sujatha and Sailaja, Stable genetic transformation of castor (*Ricinus communis* L.) via *Agrobacterium tumefaciens*-mediated gene transfer using embryo axes from mature seeds. Plant Cell Rep, 2005, 23:803-810.

Stymne, S., & Appelqvist, L. (1978). The biosynthesis of linoleate from oleoyl-CoA via oleoyl-phosphatidylcholine in microsomes of developing safflower seeds. *Eur. J. Biochem*, 90, 223-229.

Suiyun et al. (2004) "Introgression of salt-tolerance from somatic hybrids between common wheat and Thinopyrum ponticum" Plant Science 773-779.

Takeyama, H., et al., (1997) "Expression of the Eicosapentaenoic Acid Synthesis Gene Cluster From *Shewanella* sp. in a Transgenic Marine Cyanobacterium, *Synechococcus* sp. ," Microbiology, 143 (Pt 8) : 2725-2731.

Thompson, J. D., Gibson, T. J., Plewniak, F., Jeanmougin, F., & Higgins, D. G. (1997) . The CLUSTAL_ X windows interface: flexible strategies for multiple sequence alignment aided by quality analysis tools. *Nucleic Acids Research*, 25(24), 4876-4882.

Thillet et al (1988) "Site-directed Mutagenesis of Mouse Dihydrofolate Reductase" J. Biol. Chem 263:12500-12508.

Tanaka, M., et al., (1999) "Isolation of Clustered Genes That are Notably Homologous to the Eicosapentaenoic Acid Biosynthesis Gene Cluster From the Docosaehexaenoic Acid-Producing Bacterium Vibrio marinus Strain MP-1," Biotechnology Letters, 21(11): 939-945.

Tonon, T., et al., (2003) "Identification of a Very Long Chain Polyunsaturated Fatty Acid Δ4-Desaturase From the Microalga Pavlova lutheri," Federation of European biochemical Societies, 553(3): 440-444.

Toriyama et al., Haploid and diploid plant regeneration from protoplasts of anther callus in rice. Theor Appl Genet, 1986, 73:16-19.

Trautwein, E.A. , (2001) "n-3 Fatty Acids—Physiological and Technical Aspects for Their Use in Food," European Journal of Lipid Science and Technology, 103(1): 45-55.

Truksa et al., (2006) "Metabolic Engineering of Plants to Produce Very Long-Chain Polyunsaturated Fatty Acids", Transgenic Research, 15:131-137.

Tsevegsuren et al., (2003) "Isomers of hexadecenoic and hexadecadienoic acids in Androspace septentrionalis (Primulaceae) seed oil" Lipids 38(11):1173-1178.

Tvrdik, P., et al., (2000) "Role of a New Mammalian Gene Family in the Biosynthesis of Very Long Chain Fatty Acids and Sphingolipids," The Journal of Cell Biology, 149(3): 707-717.

Tzfira & Citovsky (2006) "Agrobacterium-mediated genetic transformation of plants: biology and biotechnology" Curr. Opin. Biotech. 17:147-154.

Untergasser et al. (2012) "One-Step Agrobacterium Mediated Transformation of Eight Genes Essential for Rhizobium Symbiotic Signaling Using the Novel Binary Vector System pHUGE" PLoS ONE, vol. 7, No. 10, e47885.

Valvekens, D., et al., (1988) "Agrobacterium tumefaciens-Mediated Transformation of *Arabidopsis thaliana* Root Explants by Using Kanamycin Selection," Proceedings of the National Academy of Sciences of the United States of America, 85(15) 5536-5540.

Van de Loo, F. J., Broun, P., Turner, S., & Somerville, C. (Jul. 1995). An oleate 12-hydroxylase from *Ricinus communis* L. is a fatty acyl desaturase homolog. *Proc. Natl. Acad. Sci. USA*, 92, 6743-6747.

Venegas-Calerón et al (2010) "An alternative to fish oils: Metabolic engineering of oil-seed crops to produce omega-3 long chain polyunsaturated fatty acids" Progress in Lipid Research 49, 108-119.

Voinnet et al., (2003) "An enhanced transient expression system in plants based on suppression of gene silencing by the p19 protein of tomato bushy stunt virus" Plant J. 33:949-956.

Volkman, J.K., et al., (1989) "Fatty Acid and Lipid Composition of 10 Species of Microalgae Used in Mariculture," Journal of Experimental Marine Biology and Ecology, 128(3): 219-240.

Vrinten et al. (2013) Biosynthesis of Long Chain Polyunsaturated Fatty Acids in the Marine Ichthyosporean Sphaeroforma arctica. Lipids, 48:263-274.

Wada et al (1993) "The desA Gene of the Cyanobacterium *Synechocystis* sp. Strain PCC6803 is the Structural Gene for Δ12 Desaturase" Journal of Bacteriology 175(18):6056-6058.

(56) References Cited

OTHER PUBLICATIONS

Wagner et al. (1992) "Coupling of adenovirus to transferrin-polylysine/DNA complexes greatly enhances receptor-mediated gene delivery and expression of transfected genes" Proc. Natl. Acad. Sci. USA 89:6099-6103.
Wallis, J.G. and Browse, J., (1999) "The Δ8-Desaturase of Euglena gracilis: An Alternate Pathway for Synthesis of 20-Carbon Polyunsaturated Fatty Acids," Archives of Biochemistry and Biophysics, 365(2): 307-316.
Wang, M.B., et al., (1997) "Intron-Mediated Improvement of a Selectable Marker Gene for Plant Transformation Using Agrobacterium Tumefaciens," Journal of Genetics & Breeding, 51: 325-334.
Wang and Hildebrand (1988) "Biosynthesis and Regulation of Linolenic Acid in Higher Plants" Plant Physiol. Biochem. 26(6), 777-792.
Waterbury, J.B. and Willey, J.M., (1988) "Isolation and Growth of Marine Planktonic Cyanobacteria," Methods of Enzymology, 167: 100-105.
Waterhouse, P.M., et al., (1998) "Virus Resistance and Gene Silencing in Plants Can Be Induced by Simultaneous Expression of Sense and Antisense RNA," Proceedings of the National Academy of Sciences of the United States of America, 95(23): 13959-13964.
Watts, J.L. and Browse, J., (1999) "Isolation and Characterization of a Δ5-Fatty Acid Desaturase From Caenorhabditis elegans," Archives of Biochemistry and Biophysics, 362(1): 175-182.
Watts and Browse (1999b) "A Palmitoyl-CoA-Specific Δ9 Fatty Acid Desaturase from Caenorhabditis elegans" Arch. Biochem. Biophys. 362:175-182.
Williams, J.G.K. and Szalay, A.A., (1983) "Stable Integration of Foreign DNA Into the Chromosome of the Cyanobacterium Synechococcus R2," Gene, 24(1): 37-51.
Whitney et al (2003) "Functional characterisation of two cytochrome b5-fusion desaturases from Anemone leveillei : the unexpected identification of a fatty acid Δ6-desaturase" Planta 217: 983-992.
Whittle, E., Cahoon, E. B., Subrahmanyam, S., & Shanklin, J. (2005) . A multifunctional acyl-acyl carrier protein desaturase from *Hedera helix* L. (English ivy) can synthesize 16- and 18-cabon monoene and diene products. *The Journal of Biological Chemistry*, 280(31), 28169-28176.
Wolff, R. L., et al., (1999) "Arachidonic Eicosapentaenoic, and Biosynthetically Related Fatty Acids in the Seed Lipids from a Primitive Gymnosperm, Agathis Robusta" Lipids, 34 (10) :1083-1097.
Wood (2009) A leaf-based assay using interchangeable design principles to rapidly assemble multistep recombinant pathways, Plant Biotechnol J. 7:914-24.
Wu et al. (2005) Stepwise engineering to produce high yields of very long-chain polyunsaturated fatty acids in plants, Nat. Biotech. 23:1013-1017.
Yang et al. (2003) "Expression and localization of human lysozyme in the endosperm of transgenic rice" Planta 216:597-603.
Yazawa, K., (1996) "Production of Eicosapentaenoic Acid From Marine Bacteria," Lipids, 31: S297-300.
Yu, R., et al., (2000) "Production of Eicosapentaenoic Acid by a Recombinant Marine Cyanobacterium, *Synechococcus* sp. , " Lipids, 35(10): 1061-1064.
Zank, T .K . , et al., (2002) "Cloning and Functional Characterization of an Enzyme Involved in the Elongation of Δ6-Polyunsaturated Fatty Acids From the Moss *Physcomitrella patens*," The Plant Journal, 31(3): 255-268.
Zhang et al. (2006) "Cucumber mosaic virus-encoded 2b suppressor inhibits *Arabidopsis* Argonautel cleavage activity to counter plant defense" Gene & Development 20:3255-3268.
Zhang, Q., et al., (2004) "Identification and Characterization of a Novel Δ6-Fatty Acid Desaturase Gene From Rhizopus arrhizus," Federation of European Biochemical Societies Letters, 556(1-3): 81-85.
Zhang et al. (2007a) Identification of a novel bifunctional delta12/delta15 fatty acid desaturase from a basidiomycete, Coprinus cinereus TD#822-2, FEBS Letters 581: 315-319.
Zhang et al. (2008) Identification and characterization of a novel yeast omega3-fatty acid desaturase acting on long-chain n-6 fatty acid substrates from *Pichia pastoris*, Yeast 25: 21-27.
Zhou, X. and Christie, P.J., (1997) "Suppression of Mutant Phenotypes of the Agrobacterium tumefaciens VirB11 ATPase by Overproduction of VirB Proteins," Journal of Bacteriology, 179(18): 5835-5842.
Zhou et al. (2007) "Isolation and characterization of genes from the marine microalga Pavlova salina encoding three front-end desaturases involved in docosahexaenoic acid biosynthesis" Phytochemistry 68, 785-796.
Zhou et al (2008) "Isolation and functional characterization of two independently-evolved fatty acid Δ12-desaturase genes from insects" Insect Molecular Biology 17(6), 667-676.
Zhou, X., Robert, S., Singh, S., & Green, A. (2005). Heterologous production of GLA and SDA by expression of an Echium plantagineum Δ6-desaturase gene. *Plant Science*, 170, 665-673.
Zipfel et al. (2006) "Perception of the Bacterial PAMP EF-Tu by the Receptor EFR Restricts Agrobacterium-Mediated Transformation" Cell 125:749-760.
NCBI Nucleotide Database Accession No. GenBank DQ923084, *Ricinus communis* type 2 acyl-CoA diacylglycerol acyltransferase mRNA, complete cds. Published Sep. 1, 2007.
NCBI Nucleotide Database Accession No. GenBank DQ356682, *Vernicia fordii* type 2 diacylglycerol acyltransferase (DGAT2) mRNA, complete cds. Published Sep. 13, 2006.
Meyer et al. (2003) GenBank Accession No. AY278558, NCBI, pp. 1-2.
Tonon et al. (2003) GenBank Accession No. AY332747, NCBI, pp. 1-2.
Qiu et al. (2001) GenBank Accession No. AF489589, NCBI, pp. 1-2.
Thurmond et al. (2001) GenBank Accession No. AF391543, NCBI, pp. 1-2.
Cho et al. (1999) GenBank Accession No. AF199596, NCBI, pp. 1-2.
Sanger Institute. (2003) GenBank Accession No. NM_069350, NCBI, pp. 1-4.
Knutzon et al. (1998) GenBank Accession No. AF067654, NCBI, pp. 1-2.
Hong et al. (2001) GenBank Accession No. AF419297, NCBI, pp. 1-2.
Saito et al. (1999) GenBank Accession No. AB022097, NCBI, pp. 1-2.
Domergue et al. (2002) GenBank Accession No. AY082392, NCBI, pp. 1-2.
Qiu et al. (2003) GenBank Accession No. AF489588, NCBI, pp. 1-2.
Kajikawa et al. (2004) GenBank Accession No. AY583465, NCBI, pp. 1-2.
Stohr et al. (1998) GenBank Accession No. NM_013402, NCBI, pp. 1-6.
Cho et al., (1999) GenBank Accession No. NM_ 019699, NCBI, pp. 1-3.
Swinburne et al. (1998) GenBank Accession No. 270271, NCBI, pp. 1-11.
Sayanova et al. (1996) GenBank Accession No. U79010, NCBI, pp. 1-2.
Maroto et al. (2001) GenBank Accession No. AY055117, NCBI, pp. 1-2.
Maroto et al. (2001) GenBank Accession No. AY055118, NCBI, pp. 1-2.
Sayanova et al. (2003) GenBank Accession No. AY234127, NCBI, pp. 1-2.
Sayanova et al. (2003) GenBank Accession No. AF536525, NCBI, pp. 1-2.
Sperling et al. (1999) GenBank Accession No. AJ250735, NCBI, pp. 1-2.
Kajikawa et al. (2004) GenBank Accession No. AY583463, NCBI, pp. 1-2.
Knutzon et al. (1998) GenBank Accession No. AF110510, NCBI, pp. 1-2.

(56) References Cited

OTHER PUBLICATIONS

Kobayashi et al. (1998) GenBank Accession No. AB020032, NCBI, pp. 1-2.
Qui et al. (2001) GenBank Accession No. AF419296, NCBI, pp. 1-2.
Aki et al. (2000) GenBank Accession No. AB052086, NCBI, pp. 1-2.
Zhang et al. (2003) GenBank Accession No. AY320288, NCBI, pp. 1-2.
Domergue et al. (2002) GenBank Accession No. AY082393, NCBI, pp. 1-2.
Reddy et al. (1993) GenBank Accession No. L11421, NCBI, pp. 1-2.
HastingS et al. (2000) GenBank Accession No. AF309556, NCBI, pp. 1-2.
Wallis et al. (1991) GenBank Accession No. AF139720, NCBI, pp. 1-2.
Libisch et al. (1999) GenBank Accession No. AF133728, NCBI, pp. 1-2.
Nematode Sequencing project and Gernome Sequencing Center, (2003) GenBank Accession No. NM 069288, NCBI, pp. 1-3.
Zank et al. (2002) GenBank Accession No. AF428243, NCBI, pp. 1-2.
Kajikawa et al. (2004) GenBank Accession No. AY583464, pp. 1-2.
Chaung et al. (1999) GenBank Accession No. AF206662, NCBI, pp. 1-2.
Cirpus et al. (2003) GenBank Accession No. AX951565, NCBI, pp. 1.
Heinz et al. (2001) GenBank Accession No. AX214454, NCBI, pp. 1.
Leonard et al. (2000) GenBank Accession No. AF231981, NCBI, pp. 1-2.
Aki et al. (2001) GenBank Accession No. AB071985, NCBI, pp. 1-2.
Aki et al. (2001) GenBank Accession No. AB071986, NCBI, pp. 1-2.
Tvrdik et al. (1999) GenBank Accession No. AF170907, NCBI, pp. 1-2.
Tvrdik et al. (1999) GenBank Accession No. AF170908, NCBI, pp. 1-2.
Agaba et al. (2004) GenBank Accession No. AF532782, NCBI, pp. 1-2.
Lo et al. (2003) GenBank Accession No. NM_199532, NCBI, pp. 1-2.
Wilkinson et al. (1996) GenBank Accession No. Z68749, NCBI, pp. 1-8.
Mukerji et al. (2002) GenBank Accession No. AX464802, NCBI, pp. 1.
Qi et al. (2001) GenBank Accession No. AF390174, NCBI, pp. 1-2.
Genbank accession AAF19262, Benveniste (1998).
Genbank accession AAL37626, Qi et al. (2001).
GenBank accession AAM09687, Qiu et al. (2001).
GenBank accession AAR20444, Periera et al. (2003).
GenBank accession AAT85661, Kajikawa et al. (2004).
GenBank accession AAV67797, Meyer et al. (2004).
GenBank accession AAV67799, Meyer et al. (2004).
GenBank accession AAV67800, Meyer et al. (2004).
GenBank accession AAW70157, Domergue and Heinz (2004).
GenBank accession AAW70159, Domergue and Heinz (2004).
GenBank accession AAX14505, Tonon et al. (2004).
GenBank accession AAY15135, Zhou et al. (2005).
GenBank accession AAY15136, Zhou et al. (2005).
GenBank accession ABC18313, Huang and Jiang (2005).
GenBank accession ABC18314, Huang and Jiang (2005).
GenBank accession ABL63813, Zhang et al. (2006).
Genbank accession ABL96296, Zhou et al. (2006).
GenBank accession AB094747, Grigoriev et al. (2007).
GenBank accession ABP49078, Li et al. (2007).
GenBank accession ABR67690, Niu et al. (2007).
GenBank accession AY746357, Domergue and Heinz (2004).
GenBank accession BAD11952, Oura and Kajiwara (2003).
Genbank accession BAD91495, Sakuradani et al. (2004).
GenBank accession CAD58540, Napier et al. (2002).
GenBank accession CAI58897, Zank et al. (2005).
GenBank accession CAJ30869, Cirpus et al. (2005).
GenBank accession CAL23339, Cirpus et al. (2006).
GenBank accession CAL55414, (2012).
GenBank accession CAM55882, Cirpus (2006).
GenBank accession EDQ92231, Kuo et al. (2007).
GenBank accession XP_001416454, Grigoriev et al. (2007).
GenBank accession XP_001421073 Grigoriev et al. (2007).
Apr. 3, 2017 Notification on the result of preliminary examination, issued in connection with Vietnamese Patent Application No. 1-2017-00323, including English language.
Feb. 14, 2017 Response to Rule 161(2) and 162 Communication dated Aug. 4, 2017, filed in connection with European Patent Application No. 14870813.4.
Apr. 13, 2017 Complaint for Declaratory Judgment, filed by BASF in connection with U.S. Pat. No. 7,807,849, issued Oct. 5, 2010 (Singh et al.); U.S. Pat. No. 7,834,250, issued Nov. 16, 2010 (Singh et al.); U.S. Pat. No. 8,106,226, issued Jan. 31, 2012 (Singh et al.); U.S. Pat. No. 8,288,572, issued Oct. 16, 2012 (Singh et al.); U.S. Pat. No. 8,575,377, issued Nov. 5, 2013 (Singh et al.); U.S. Pat. No. 8,809,559, issued Aug. 19, 2014 (Petrie et al.); U.S. Pat. No. 8,853,432, issued Oct. 7, 2014 (Singh et al.); and U.S. Pat. No. 9,458,410, issued Oct. 4, 2016 (Singh et al.).
Opsahl-Ferstad et al. (2003) "Biotechnological approaches to modify rapeseed oil composition for applications in aquaculture" Plant Science 165: 349-357.
Letter to the International Preliminary Examination Authority filed on Oct. 19, 2015 in connection with PCT International Application No. PCT/AU2014/050433, filed Dec. 18, 2014.
Amended Claims filed on Oct. 19, 2015 in connection with PCT International Application No. PCT/AU2014/050433, filed Dec. 18, 2014.
U.S. Appl. No. 15/642,207, filed Jul. 5, 2017, Singh.
U.S. Appl. No. 15/642,223, filed Jul. 5, 2017, Petrie.
Sequence alignment demonstrating that the amino acid sequence of GenBank accession No. AY055117 was found to have the same length as protein SEQ ID No. 64 of WO 2005/103253, filed as "D18" in connection with Opposition to European Patent No. EP1756280 (Application No. EP05733657.0).
U.S. Appl. No. 60/564,627, filed Apr. 22, 2004, Singh.
U.S. Appl. No. 60/613,861, filed Sep. 27, 2004, Singh.
U.S. Appl. No. 60/668,705, filed Aug. 30, 2005, Singh.
Sequence alignment demonstrating that the amino acid sequence of GenBank accession No. AY055118 was found to have the same length as protein SEQ ID No. 64 of WO 2005/103253, filed as "D19" in connection with Opposition to European Patent No. EP1756280 (Application No. EP05733657.0).
Reference formula used for the calculation of the melting temperature as regards sequences hybridizing under high stringency conditions, filed as "D20" in connection with Opposition to European Patent No. EP1756280 (Application No. EP05733657.0).
Mar. 29, 2016 Response to the Notice of Opposition, filed by CSIRO in connection with Opposition to European Patent No. EP1756280 (Application No. EP05733657.0).
Jul. 18, 2016 EPO Communication providing Summons to attend Oral Proceedings and Preliminary Opinion, issued in connection with Opposition to European Patent No. EP1756280 (Application No. EP05733657.0).
Jan. 9, 2017 Written Submissions under Rule 116 EPC filed in response to the Summons to Oral Proceedings, filed by CSIRO in connection with Opposition to European Patent No. EP1756280 (Application No. EP05733657.0).
Auxiliary Request I claims, filed with Jan. 9, 2017 Written Submissions under Rule 116 EPC, in response to the Summons to Oral Proceedings, in connection with Opposition to European Patent No. EP1756280 (Application No. EP05733657.0).
Jan. 9, 2017 Written Submissions under Rule 116 EPC filed in response to the Summons to Oral Proceedings, filed by BASF in connection with European Patent Application No. EP05733657.0.

(56) References Cited

OTHER PUBLICATIONS

Huang Y. S., Pereira S. L., Leonard A. E. (2004) "Enzymes for transgenic biosynthesis of long-chain polyunsaturated fatty acids" Biochimie, vol. 86, No. 11, p. 793-798.
Graham, et al. (2004) "The use of very long chain polyunsaturated fatty acids to ameliorate metabolic syndrome: transgenic plants as an alternative sustainable source to fish oils" Nutrition Bulletin, vol. 29, p. 228-233.
Napier JA, Beaudoin F, Michaelson Lv, Sayanova O. (2004) "The production of long chain polyunsaturated fatty acids in transgenic plants by reverse-engineering." Biochimie. Nov. 2004 86(11):785-92.
Napier JA, Beaudoin F, Sayanova O. (2005) "Reverse engineering of long-chain polyunsaturated fatty acid biosynthesis into transgenic plants" European Journal of Lipid Science and Technology 107(4):249-255.
Kinney AJ, Cahoon BB, Hitz WD. "Manipulating desaturase activities in transgenic crop plants." Biochem Soc Trans. Nov. 30, 2002(Pt 6):1099-103.
Voelker Tl, Kinney AJ. "Variations in the Biosynthesis of Seed-Storage Lipids." Annu Rev Plant Physiol Plant Mol Biol. Jun. 2001 52:335-361.
Surinder Singh (2010) "Engineering Complex Fatty Acid Pathways in Seeds: The EPA/DHA Example", submitted as "D31" subsequently renmmumbered as "D34"in connection with Opposition to European Patent No. EP1756280 (Application No. EP05733657.0).
Materials and methods, results and conclusions for experimental data provided by the Opponent. The Opponent's experiments repeated and expanded on the experiment described in Example 5 of the opposed patent EP 1756280 (Annex A); Data table depicting the fatty acid composition of segreagating T2 or T1 seeds from *Arabidopsis* or *Brassica napus* (canola) (Annex B); Media used in *Brassica napus* transformation (Annex C), filed by BASF in connection with Opposition to European Patent No. EP1756280 (Application No. EP05733657.0).
List of documents cited by CSIRO and BASF as of Jan. 16, 2017, in connection Opposition to European Patent No. EP1756280 (Application No. EP05733657.0).
Feb. 21, 2017 Additional Submissions, including list of all documents cited to date and documents "D36", "D37" and "D38" filed in connection with Opposition to European Patent No. EP1756280 (Application No. EP05733657.0).
Mar. 9, 2017 Information about the result of Oral Proceedings, filed in connection with Opposition to European Patent No. EP1756280 (Application No. EP05733657.0).
Aug. 23, 2017 Appeal Brief, filed by BASF in connection with Opposition to European Patent No. EP1756280.
Aug. 30, 2017 Correction to Aug. 23, 2017 Appeal Brief, filed by BASF in connection with Opposition to European Patent No. EP1756280.
Feature-structured claim 1, submitted as "D39" by BASF with Aug. 23, 2017 Appeal Brief, filed by Basf in connection with Opposition to European Patent No. EP1756280.
Heinz (2002) . "Docosahexaenoic acid (DHA) in transgenic oilseeds: which approach will be successful first?" European Journal of Lipid Science and Technology 2002, 104:1-2.
Das et al. (2000) "Polyunsaturated fatty acid-specific elongation enzymes", Biochemical Society Transactions 28(6):658-660.
Presentation "Engineering of LCPUFA biosynthesis" presented by Prof. Heinz at the 1st European Symposium on Plant Lipids held Sep. 10-13, 2003 in Aachen, submitted as "D44" by Basf with Aug. 23, 2017 Appeal Brief, filed by BASF in connection with Opposition to European Patent No. EP1756280.
Evidence of the publication date of D44, submitted as "D44a" by BASF with Aug. 23, 2017 Appeal Brief, filed by BASF in connection with Opposition to European Patent No. EP1756280.
Expert declaration from Dr. Domergue, submitted as "D47" by BASF with Aug. 23, 2017 Appeal Brief, filed by BASF in connection with Opposition to European Patent No. EP1756280.
Leonard et al. (2004) "Elongation of long-chain fatty acids", Progress in Lipid Research 43:36-54.
Experimental data relating to EPA production in different plants, including experimental details, results, a discussion and conclusion, submitted as "D49" by BASF with Aug. 23, 2017 Appeal Brief, filed by BASF in connection with Opposition to European Patent No. EP1756280 including Attachment 1 of D49 ("D52").
Media used in *Brassica* transformation described in D49, submitted as "D49a" by BASF with Aug. 23, 2017 Appeal Brief, filed by BASF in connection with Opposition to European Patent No. EP1756280.
Experimental data on EPA production of segregating seeds, submitted as "D50" by BASF with Aug. 23, 2017 Appeal Brief, filed by BASF in connection with Opposition to European Patent No. EP1756280.
Experimental data on EPA production of homozygous seeds, submitted as "D51" by BASF with Aug. 23, 2017 Appeal Brief, filed by BASF in connection with Opposition to European Patent No. EP1756280.
Aug. 9, 2017 Partial European Search Report, issued in connection with European Patent Application No. 14870813.4.
English language translation of Aug. 11, 2017 Office Action, issued in connection with Eurasian Patent Application No. 201600471.
Sep. 14, 2017 Office Action, issued in connection with Colombian Patent Application No. 15-001155, including English language translation.
English language translation of the Response to Sep. 14, 2017 Office Action, issued in connection with Colombian Patent Application No. 15-001155, including English language translation of amended claims.
Nov. 14, 2017 Extended European Search Report, issued in connection with European Patent Application No. 14870813.4.
Notification on the result of preliminary examination dated Nov. 3, 2016, issued in connection with Vietnamese Patent Application No. 1-2016-02647.
Jan. 11, 2018 Extended European Search Report issued in connection with European patent application 15811918.0.
Jun. 22, 2018 Office Action issued in connection with Eurasian Patent Application No. 201700030.
Jul. 24, 2018 Office Action which issued in connection with corresponding Colombian patent application 2017/0000543 including English translation thereof.
Jun. 7, 2019 First Examination Report issued in connection with Australian Patent Application No. 2015281791.
May 28, 2019 Office Action, issued in connection with Japanese Patent Application No. 2016-575436, including the English Language Translation.
Apr. 10, 2019 Office Action issued in connection with Chilean Patent Application No. 201603351, including the English Language Translation.
Feb. 19, 2019 Office Action, issued in connection with Eurasian Patent Application No. 201700030.
Feb. 12, 2019 Office Action, issued in connection with Israeli Patent Application No. 249842, including the English Language translation.
Dec. 3, 2018 Request for Further Processing and Response to Communication under Rule 70A(2) EPC issued by the European Patent Office in connection with related European Patent Application No. 15811918.0.
Nov. 7, 2018 Office Action, issued in Connection with Columbian Patent Application No. 2017/0000543, including the English language translation.
Oct. 18, 2018 Response to Office Action filed in connection with Columbian Patent Application No. 2017/0000543, including the English Language translation.
Jan. 14, 2020 Office Action issued in connection with Chilean Patent Application No. 201603351, including English language translation thereof.
Nov. 1, 2019 Jury Verdict Form in United States District Court for the Eastern District of Virginia Norfolk Division, Civil Action No. 2:17-cv-00503-HCM-LRL.

(56) References Cited

OTHER PUBLICATIONS

Dec. 23, 2019 Judgment in a Civil Case issued in United States District Court for the Eastern District of Virginia Norfolk Division, Civil Action No. 2:17-cv-00503-HCM-LRL.
Dec. 23, 2019 Opinion and Order Regarding Remedies issued in United States District Court for the Eastern District of Virginia Norfolk Division, Civil Action No. 2:17-cv-00503-HCM-LRL.
Aug. 23, 2019 Counterclaimants' Answer to BASF Plant Science, LP and BASF Plant Science Gmbh's Amended Counterclaims Against Counterclaimants (Public Redacted Version), filed in the United States District Court for the Eastern District of Virginia Norfolk Division, Civil Action No. 2:17-cv-00503-HCM-LRL.
Sep. 4, 2019 BASF/Cargill's Brief in Support of Their Daubert Motion to Exclude Portions of the Testimony of Dr. Ljerka Kunst and Mr. John C. Jarosz (Public Redacted Version), filed in the United States District Court for the Eastern District of Virginia Norfolk Division, Civil Action No. 2:17-cv-00503-HCM-LRL.
Sep. 4, 2019 Counterclaimants' Memorandum in Support of Motion to Exclude Certain Opinions and Preclude Certain Testimony by Defendants' Experts Brian Napper and Dr. Denis Murphy (Public Redacted Version), filed in the United States District Court for the Eastern District of Virginia Norfolk Division, Civil Action No. 2:17-cv-00503-HCM-LRL.
Sep. 4, 2019 Counterclaimants' Memorandum in Support of Motion for Summary Judgment (Public Redacted Version), filed in the United States District Court for the Eastern District of Virginia Norfolk Division, Civil Action No. 2:17-cv-00503-HCM-LRL.
Sep. 6, 2019 Counterclaimants' Memorandum in Support of Motions in Limine (Nos. 1-13) (Public Redacted Version), filed in the United States District Court for the Eastern District of Virginia Norfolk Division, Civil Action No. 2:17-cv-00503-HCM-LRL.
Sep. 6, 2019 BASF's and Cargill's Motions in Limine (Public Redacted Version), filed in the United States District Court for the Eastern District of Virginia Norfolk Division, Civil Action No. 2:17-cv-00503-HCM-LRL.
Sep. 13, 2019 Counterclaimants' Opposition to BASF and Cargill's Daubert Motion to Exclude Portions of the Testimony of Dr. Ljerka Kunst and Mr. John Jarosz (Public Redacted Version), filed in the United States District Court for the Eastern District of Virginia Norfolk Division, Civil Action No. 2:17-cv-00503-HCM-LRL.
Sep. 14, 2019 BASF/Cargill's Memorandum in Opposition to Counterclaimants' Motion for Summary Judgment (Public Redacted Version), filed in the United States District Court for the Eastern District of Virginia Norfolk Division, Civil Action No. 2:17-cv-00503-HCM-LRL.
Sep. 14, 2019 BASF/Cargill's Memorandum in Opposition to Counterclaimants' Daubert Motion (Public Redacted Version), filed in the United States District Court for the Eastern District of Virginia Norfolk Division, Civil Action No. 2:17-cv-00503-HCM-LRL.
Sep. 19, 2019 Counterclaimants' Opposition to BASF's and Cargill's Motions in Limine (Public Redacted Version), filed in the United States District Court for the Eastern District of Virginia Norfolk Division, Civil Action No. 2:17-cv-00503-HCM-LRL.
Sep. 19, 2019 Counterclaimants' Reply in Support of Motion to Exclude Certain Opinions and Preclude Certain Testimony by Defendants' Experts Brian Napper and Dr. Denis Murphy (Public Redacted Version), filed in the United States District Court for the Eastern District of Virginia Norfolk Division, Civil Action No. 2:17-cv-00503-HCM-LRL.
Sep. 19, 2019 BASF/Cargill's Reply Brief in Support of Their Daubert Motion to Exclude Portions of the Testimony of Dr. Ljerka Kunst and Mr. John C. Jarosz (Public Redacted Version), filed in the United States District Court for the Eastern District of Virginia Norfolk Division, Civil Action No. 2:17-cv-00503-HCM-LRL.
Sep. 19, 2019 Counterclaimants' Reply in Support of Motion for Summary Judgment (Public Redacted Version), filed in the United States District Court for the Eastern District of Virginia Norfolk Division, Civil Action No. 2:17-cv-00503-HCM-LRL.
Sep. 30, 2019 BASF/Cargill's Memorandum in Opposition to Counterclaimants' Motions in Limine (Public Redacted Version), filed in the United States District Court for the Eastern District of Virginia Norfolk Division, Civil Action No. 2:17-cv-00503-HCM-LRL.
Sep. 27, 2019 Transcript of Proceedings (Motions Hearing) in the United States District Court for the Eastern District of Virginia Norfolk Division, Civil Action No. 2:17-cv-00503-HCM-LRL.
Oct. 3, 2019 Proposed Final Pretrial Order in the United States District Court for the Eastern District of Virginia Norfolk Division, Civil Action No. 2:17-cv-00503-HCM-LRL.
Oct. 8, 2019 BASF's Brief Supporting Trial by Jury of BASF's MTEA-Based Claims and Defenses (Public Redacted Version), filed in the United States District Court for the Eastern District of Virginia Norfolk Division, Civil Action No. 2:17-cv-00503-HCM-LRL.
Oct. 8, 2019 CSIRO, Nuseed, and GRDC's Memorandum in Support of Excluding BASF's MTEA Counterclaims and Related Defenses from Trial (Public Redacted Version), filed in the United States District Court for the Eastern District of Virginia Norfolk Division, Civil Action No. 2:17-cv-00503-HCM-LRL.
Oct. 28, 2019 Proponents' Motion Seeking Dismissal of Opponents' Unclean Hands Defense (Public Redacted Version), filed in the United States District Court for the Eastern District of Virginia Norfolk Division, Civil Action No. 2:17-cv-00503-HCM-LRL.
Oct. 28, 2019 BASF/Cargill's Proposed Final Jury Instructions, filed in the United States District Court for the Eastern District of Virginia Norfolk Division, Civil Action No. 2:17-cv-00503-HCM-LRL.
Oct. 28, 2019 Counterclaimants' Final Proposed Jury Instructions—Liability Phase, filed in the United States District Court for the Eastern District of Virginia Norfolk Division, Civil Action No. 2:17-cv-00503-HCM-LRL.
Oct. 29, 2019 Proponents' Trial Brief in Support of Jury Instructions Regarding Continuation Patent Applications, Corroborating Evidence of Conception, and Willful Infringement, filed in the United States District Court for the Eastern District of Virginia Norfolk Division, Civil Action No. 2:17-cv-00503-HCM-LRL.
Oct. 30, 2019 Counterclaimants' Final Proposed Jury Instructions—Liability Phase, filed in the United States District Court for the Eastern District of Virginia Norfolk Division, Civil Action No. 2:17-cv-00503-HCM-LRL.
Oct. 30, 2019 Proponents' Memorandum Regarding a Jury Instruction Concerning Written Description, filed in the United States District Court for the Eastern District of Virginia Norfolk Division, Civil Action No. 2:17-cv-00503-HCM-LRL.
Oct. 30, 2019 Proponents' Brief in Support of Motion Under Fed. R. Civ. P. 50(A), filed in the United States District Court for the Eastern District of Virginia Norfolk Division, Civil Action No. 2:17-cv-00503-HCM-LRL.
Oct. 31, 2019 Opponents' Brief in Support of Motion Under Fed. R. Civ. P. 50(A) Concerning Co-Ownership Under Mtea, Lack of Written Description, and Obviousness, filed in the United States District Court for the Eastern District of Virginia Norfolk Division, Civil Action No. 2:17-cv-00503-HCM-LRL.
Oct. 31, 2019 Proponents' Proposed Jury Instruction on MTEA, filed in the United States District Court for the Eastern District of Virginia Norfolk Division, Civil Action No. 2:17-cv-00503-HCM-LRL.
Oct. 31, 2019 Proponents' Supplemental Memorandum in Support of its Motion for Judgment as a Matter of Law to Address Additional Bases for Relief Under Fed. R. Civ. Proc. 50, filed in the United States District Court for the Eastern District of Virginia Norfolk Division, Civil Action No. 2:17-cv-00503-HCM-LRL.
Dec. 2, 2019 Proponents' Memorandum in Support of Motions for Judgment as a Matter of Law and a New Trial as to Jury Issues Not Decided by Verdict Under Fed. R. Civ. P. 50(B) and 59, filed in the United States District Court for the Eastern District of Virginia Norfolk Division, Civil Action No. 2:17-cv-00503-HCM-LRL.
Dec. 16, 2019 Opponents' Brief in Opposition to Proponents' Motions for Judgment as a Matter of Law and a New Trial as to Jury Issues Not Decided by Verdict Under Fed. R. Civ. P. 50(B) and 59,

(56) References Cited

OTHER PUBLICATIONS filed in the United States District Court for the Eastern District of Virginia Norfolk Division, Civil Action No. 2:17-cv-00503-HCM-LRL.
Dec. 23, 2019 Proponents' Reply Brief in Support of Their Motion for Judgment as a Matter of Law and Motion for a New Trial as to Jury Issues Not Decided by Verdict, filed in the United States District Court for the Eastern District of Virginia Norfolk Division, Civil Action No. 2:17-cv-00503-HCM-LRL.
Aug. 15, 2019 Opinion and Order on Motions to Seal issued in the United States District Court for the Eastern District of Virginia Norfolk Division, Civil Action No. 2:17cv-00503-HCM-LRL.
Jan. 11, 2019 BASF Plant Science, LP's Answer and Amended Affirmative Defenses to Counterclaimants' Amended Counterclaims and BASF Plant Science, LP and BASF Plant Science GMBH's Amended Counterclaims Against Counterclaimants (Public Redacted Version filed Aug. 25, 2019), in the United States District Court for the Eastern District of Virginia Norfolk Division, Civil Action No. 2:17-cv-00503-HCM-LRL.
Nov. 6, 2018 Protective Order Signed by District Judge Henry C. Morgan, Jr in the United States District Court for the Eastern District of Virginia Norfolk Division, Civil Action No. 2:17-cv-00503-HCM-LRL.
Jan. 21, 2020 Opponent's Brief in Support of their Renewed Motion for Judgment as a Matter of Law Under Fed. R. Civ. p. 50(b) or, in the Alternative, for a New Trial Pursuant to Rule 59(a).
Jan. 21, 2020 Proponent's Memorandum in Support of Motions for Judgment as a Matter of Law and a New Trial under Fed. R. Civ. P. 50(b) and 59.
Aug. 20, 2019 Office Action which issued in connection with corresponding Colombian Patent Application No. 2017/0000543, including English translation thereof.
Sep. 6, 2019 Office Action which issued in connection with corresponding Mexican Patent Application No. MX/a/2016/017355 including English translation thereof.
Nov. 22, 2019 Office Action which issued in connection with corresponding Chinese Patent Application No. 201510342019.9 including English translation thereof.
Jan. 13, 2020 Office Action which issued in connection with corresponding Philippine Patent Application No. 1-2016-502586.
Feb. 25, 2020 Examination Report which issued in connection with counterpart Malaysian Patent Application No. PI 2016704757.
Feb. 27, 2020 First Examination Report issued in connection with corresponding European patent application 15811918.0.
Jun. 2, 2020 Response to a Second Examination Report filed in connection with corresponding Australian patent application 2015281791.
May 26, 2020 Response to a First Examination Report issued in connection with corresponding Australian patent application 2015281791.
Mar. 17, 2020 Second Office Action issued in connection with corresponding Japanese patent application 2016-575436, including English language translation.
English translation of Feb. 18, 2020 Office Action issued in connection with corresponding Ukrainian patent application No. a201613628.
Jul. 20, 2020 Office Action issued in connection with Mexican Patent Application No. MX/a/2016/017355 including English language translation thereof.
Jul. 27, 2020 Response to Jan. 13, 2020 Office Action filed in connection with Philippines Patent Application No. 1-2016-502586.
Oct. 27, 2020 Second Office Action issued in connection with Chinese Patent Application No. 201510342019.9, including English translation thereof.
Oct. 27, 2020 Second Examination Report issued in connection with Chinese Patent Application No. 201510342019.9.
Dec. 9, 2020 Resolution issued in connection with Colombian Patent Application No. 2017/0000543, including English translation thereof.
Jan. 4, 2021 Office Action issued in connection with Chilean Patent Application No. 201903571, including English translation thereof.
Jan. 4, 2021 Search Report issued in connection with Chilean Patent Application No. 201903571, including English translation thereof.
Dec. 30, 2020 Office Action issued in connection with Peruvian Patent Application No. 2775-2016, including English translation thereof.
Kaur, G et al. "Docosapentanoic acid (22:5n-3): A review of its biological effects", Progress in Lipid Research, 50: 28-34 (Dec. 31, 2011).
Yazdi, P et al. "A review of the biologic and pharmacological role of docosapentanoic acid", FWOORes, 2: 256 (2013).
Feb. 12, 2021 Examination Report issued in connection with Indian Patent Application No. 201717001088, including English translation thereof.
Feb. 15, 2021 Technical Examination Report issued in connection with Brazilian Patent Application No. BR 11 2016 030705 4, including English translation thereof.
Feb. 26, 2021 Subsequent Substantive Examination Report issued In connection with Philippine Patent Application No. 1-2016-502586.
Mar. 9, 2021 Third Office Action issued in connection with Chinese Patent Application No. 201510342019.9, including English translation thereof.
Mar. 26, 2021 Office Action issued in connection with Colombian Patent Application No. 2017/0000543, including English translation thereof.
Apr. 23, 2021 Second Office Action issued in connection with Chilean Patent Application No. 201903571, including English translation thereof.
Apr. 28, 2021 Office Action issued in connection with Vietnamese Patent Application No. 1-2017-00323, including English translation thereof.
May 7, 2021 Third Office Action issued in connection with Mexican Patent Application No. MX/a/2016/017355, including English translation thereof.
Dec. 4, 2020 Request for Further Processing and Response to Feb. 27, 2020 Official Communication Pursuant to Art. 94(3) EPC filed in connection with European Patent Application No. 15811918.0.
Dec. 29, 2021 Fourth Office Action issued in connection with Chinese Patent Application No. 201510342019.9.
Oct. 21, 2021 Office Action issued in connection with Canadian Patent Application No. 2,953,008.
Feb. 21, 2022 Response to Oct. 21, 2021 filed in connection with Canadian Patent Application No. 2,953,008.
May 11, 2022 Office Action issued in connection with Canadian Patent Application No. 2,953,008.
Apr. 28, 2022 Written Opinion issued in connection with Chilean Patent Application No. 201603351 including English language translation thereof.
Sep. 13, 2021 Written Opinion issued in connection with Chilean Patent Application No. 201903571 including English language translation thereof.
Feb. 9, 2022 Written Opinion issued in connection with Chilean Patent Application No. 202001535 including English language translation thereof.
Aug. 13, 2021 Decision of Rejection issued in connection with Chinese Patent Application No. 201510342019.9 including English language translation thereof.
Jun. 13, 2022 Office Action issued in connection with Chinese Patent Application No. 201510342019.9 including English language translation thereof.
Feb. 18, 2022 Communication pursuant to Article 94(3) EPC issued in connection with European Patent Application No. 15811918.0.
Aug. 10, 2021 Response to Feb. 12, 2021 Office Action filed in connection with Indian Patent Application No. 201717001088.
May 10, 2022 Office Action issued in connection with Japanese Patent Application No. 2021-043379 including English language translation thereof.
May 31, 2022 Notice of Preliminary Rejection issued in connection with Korean Patent Application No. 10-2017-7002195 including English language translation thereof.

(56) References Cited

OTHER PUBLICATIONS

Jul. 30, 2021 Office Action issued in connection with Malaysian Patent Application No. PI 2016704757.
Sep. 28, 2021 Response to Jul. 30, 20210ffice Action filed in connection with Malaysian Patent Application No. PI 2016704757.
Aug. 19, 2021 Second Office Action issued in connection with Peruvian Patent Application No. 2775-2016 including English language translation thereof.
Jul. 9, 2021 Response to Mar. 11, 20210ffice Action filed in connection with Philippine Patent Application No. 1-2016-502586.
Aug. 24, 2021 Office Action issued in connection with Philippine Patent Application No. 1-2016-502586.
Oct. 22, 2021 Response to Aug. 24, 2021 Office Action filed in connection with Philippine Patent Application No. 1-2016-502586.
Dec. 7, 2021 Office Action issued in connection with Philippine Patent Application No. 1-2016-502586.
Jun. 3, 2022 Office Action issued in connection with Philippine Patent Application No. 1-2016-502586.

* cited by examiner

A)

5α-cholestan-3β-ol

B)

campesterol sitosterol brassicasterol stigmasterol avenasterol

LIPID COMPRISING DOCOSAPENTAENOIC ACID

CROSS REFERENCE TO RELATED APPLICATIONS

This application is a continuation of U.S. application Ser. No. 15/617,642 filed Jun. 8, 2017, now U.S. Pat. No. 10,125,084, issued Nov. 13, 2018, which is a continuation of U.S. application Ser. No. 14/743,531, filed Jun. 18, 2015, now U.S. Pat. No. 9,718,759, issued Aug. 1, 2018, which is a continuation-in-part of PCT International Application No. PCT/AU2014/050433, filed Dec. 18, 2014, and of U.S. application Ser. No. 14/575,756, filed Dec. 18, 2014, now U.S. Pat. No. 9,725,399, claiming priority of Argentinian Patent Application No. 20140104761, filed Dec. 18, 2014, and Australian Patent Application No. 2014902471, filed Jun. 27, 2014, the contents of each of which are hereby incorporated by reference in their entirety.

REFERENCE TO A SEQUENCE LISTING

This application incorporates-by-reference nucleotide and/or amino acid sequences which are present in the file named "190311_87180-BAA_Substitute_Sequence-_Listing_DH.txt", which is 173 kilobytes in size, and which was created Mar. 8, 2019 in the IBM-PC machine format, having an operating system compatibility with MS-Windows, which is contained in the text file filed Mar. 11, 2019 as part of this application.

FIELD OF THE INVENTION

The present invention relates to lipid comprising docosapentaenoic acid, obtained from plant cells or microbial cells, and processes for producing and using the lipid.

BACKGROUND OF THE INVENTION

Omega-3 long-chain polyunsaturated fatty acids (LC-PUFA) are now widely recognized as important compounds for human and animal health. These fatty acids may be obtained from dietary sources or by conversion of linoleic (LA, 18:2ω6) or α-linolenic (ALA, 18:30ω3) fatty acids, both of which are regarded as essential fatty acids in the human diet. While humans and many other vertebrate animals are able to convert LA or ALA, obtained from plant sources to C22 they carry out this conversion at a very low rate. Moreover, most modern societies have imbalanced diets in which at least 90% of polyunsaturated fatty acids (PUFA) are of the ω6 fatty acids, instead of the 4:1 ratio or less for ω6:ω3 fatty acids that is regarded as ideal (Trautwein, 2001). The immediate dietary source of LC-PUFAs such as eicosapentaenoic acid (EPA, 20:5ω3), docosapentaenoic acid (DPA) and docosahexaenoic acid (DHA, 22:6ω3) for humans is mostly from fish or fish oil. Health professionals have therefore recommended the regular inclusion of fish containing significant levels of LC-PUFA into the human diet. Increasingly, fish-derived LC-PUFA oils are being incorporated into food products and in infant formula, for example. However, due to a decline in global and national fisheries, alternative sources of these beneficial health-enhancing oils are needed.

Flowering plants, in contrast to animals, lack the capacity to synthesise polyunsaturated fatty acids with chain lengths longer than 18 carbons. In particular, crop and horticultural plants along with other angiosperms do not have the enzymes needed to synthesize the longer chain ω3 fatty acids such as EPA, docosapentaenoic acid (DPA, 22:5ω3) and DHA that are derived from ALA. An important goal in plant biotechnology is therefore the engineering of crop plants which produce substantial quantities of LC-PUFA, thus providing an alternative source of these compounds.

LC-PUFA Biosynthesis Pathways

Biosynthesis of LC-PUFAs in organisms such as microalgae, mosses and fungi usually occurs as a series of oxygen-dependent desaturation and elongation reactions (FIG. 1). The most common pathway that produces EPA in these organisms includes a Δ6-desaturation, Δ6-elongation and Δ5-desaturation (termed the Δ6-desaturation pathway) whilst a less common pathway uses a Δ9-elongation, Δ8-desaturation and Δ5-desaturation (termed the Δ9-desaturation pathway). These consecutive desaturation and elongation reactions can begin with either the ω6 fatty acid substrate LA, shown schematically as the upper left part of FIG. 1 (ω6) or the ω3 substrate ALA through to EPA, shown as the lower right part of FIG. 1 (ω3). If the initial Δ6-desaturation is performed on the ω6 substrate LA, the LC-PUFA product of the series of three enzymes will be the ω6 fatty acid ARA. LC-PUFA synthesising organisms may convert ω6 fatty acids to ω3 fatty acids using an ω3-desaturase, shown as the Δ17-desaturase step in FIG. 1 for conversion of arachidonic acid (ARA, 20:4ω6) to EPA. Some members of the ω3-desaturase family can act on a variety of substrates ranging from LA to ARA. Plant ω3-desaturases often specifically catalyse the Δ15-desaturation of LA to ALA, while fungal and yeast ω3-desaturases may be specific for the Δ17-desaturation of ARA to EPA (Pereira et al., 2004a; Zank et al., 2005). Some reports suggest that non-specific ω3-desaturases may exist which can convert a wide variety of ω6 substrates to their corresponding ω3 products (Zhang et al., 2008).

The conversion of EPA to DHA in these organisms occurs by a Δ5-elongation of EPA to produce DPA, followed by a Δ4-desaturation to produce DHA (FIG. 1). In contrast, mammals use the so-called "Sprecher" pathway which converts DPA to DHA by three separate reactions that are independent of a Δ4-desaturase (Sprecher et al., 1995).

The front-end desaturases generally found in plants, mosses, microalgae, and lower animals such as *Caenorhabditis elegans* predominantly accept fatty acid substrates esterified to the sn-2 position of a phosphatidylcholine (PC) substrate. These desaturases are therefore known as acyl-PC, lipid-linked, front-end desaturases (Domergue et al., 2003). In contrast, higher animal front-end desaturases generally accept acyl-CoA substrates where the fatty acid substrate is linked to CoA rather than PC (Domergue et al., 2005). Some microalgal desaturases and one plant desaturase are known to use fatty acid substrates esterified to CoA (Table 2).

Each PUFA elongation reaction consists of four steps catalysed by a multi-component protein complex: first, a condensation reaction results in the addition of a 2C unit from malonyl-CoA to the fatty acid, resulting in the formation of a β-ketoacyl intermediate. This is then reduced by NADPH, followed by a dehydration to yield an enoyl intermediate. This intermediate is finally reduced a second time to produce the elongated fatty acid. It is generally thought that the condensation step of these four reactions is substrate specific whilst the other steps are not. In practice, this means that native plant elongation machinery is capable of elongating PUFA providing that the condensation enzyme (typically called an 'elongase') specific to the PUFA is introduced, although the efficiency of the native plant elongation machinery in elongating the non-native PUFA substrates may be low. In 2007 the identification and characterisation of the yeast elongation cycle dehydratase was published (Denic and Weissman, 2007).

PUFA desaturation in plants, mosses and microalgae naturally occurs to fatty acid substrates predominantly in the acyl-PC pool whilst elongation occurs to substrates in the acyl-CoA pool. Transfer of fatty acids from acyl-PC molecules to a CoA carrier is performed by phospholipases (PLAs) whilst the transfer of acyl-CoA fatty acids to a PC carrier is performed by lysophosphatidyl-choline acyltransferases (LPCATs) (Singh et al., 2005).

Engineered Production of LC-PUFA

Most LC-PUFA metabolic engineering has been performed using the aerobic Δ6-desaturation/elongation pathway. The biosynthesis of γ-linolenic acid (GLA, 18:30ω6) in tobacco was first reported in 1996 using a Δ6-desaturase from the cyanobacterium *Synechocystis* (Reddy and Thomas, 1996). More recently, GLA has been produced in crop plants such as safflower (73% GLA in seedoil, WO 2006/127789) and soybean (28% GLA; Sato et al., 2004). The production of LC-PUFA such as EPA and DHA involves more complicated engineering due to the increased number of desaturation and elongation steps involved. EPA production in a land plant was first reported by Qi et al. (2004) who introduced genes encoding a Δ9-elongase from *Isochrysis galbana*, a Δ8-desaturase from *Euglena gracilis* and a Δ5-desaturase from *Mortierella alpina* into *Arabidopsis* yielding up to 3% EPA. This work was followed by Abbadi et al. (2004) who reported the production of up to 0.8% EPA in flax seed using genes encoding a Δ6-desaturase and Δ6-elongase from *Physcomitrella patens* and a Δ5-desaturase from *Phaeodactylum tricornutun*.

The first report of DHA production was in WO 04/017467 where the production of 3% DHA in soybean embryos is described, but not seed, by introducing genes encoding the *Saprolegnia diclina* Δ6-desaturase, *Mortierella alpina* Δ6-desaturase, *Mortierella alpina* Δ5-desaturase, *Saprolegnia diclina* Δ4-desaturase, *Saprolegnia diclina* Δ17-desaturase, *Mortierella alpina* Δ6-elongase and *Pavlova lutheri* Δ5-elongase. The maximal EPA level in embryos also producing DHA was 19.6%, indicating that the efficiency of conversion of EPA to DHA was poor (WO 2004/071467). This finding was similar to that published by Robert et al. (2005), where the flux from EPA to DHA was low, with the production of 3% EPA and 0.5% DHA in *Arabidopsis* using the *Danio rerio* Δ5/6-desaturase, the *Caenorhabditis elegans* Δ6-elongase, and the *Pavlova salina* Δ5-elongase and Δ4-desaturase. Also in 2005, Wu et al. published the production of 25% ARA, 15% EPA, and 1.5% DHA in *Brassica juncea* using the *Pythium irregulare* Δ6-desaturase, a *Thraustochytrid* Δ5-desaturase, the *Physcomitrella patens* Δ6-elongase, the *Calendula officianalis* Δ12-desaturase, a *Thraustochytrid* Δ5-elongase, the *Phytophthora infestans* Δ17-desaturase, the *Oncorhyncus mykiss* LC-PUFA elongase, a *Thraustochytrid* Δ4-desaturase and a *Thraustochytrid* LPCAT (Wu et al., 2005). Summaries of efforts to produce oil-seed crops which synthesize ω3 LC-PUFAs is provided in Venegas-Caleron et al. (2010) and Ruiz-Lopez et al. (2012). As indicated by Ruiz-Lopez et al. (2012), results obtained to date for the production of DHA in transgenic plants has been no where near the levels seen in fish oils. More recently, Petrie et al (2012) reported the production of about 15% DHA in *Arabidopsis thaliana* seeds, and WO2013/185184 reported the production of certain seedoils having between 7% and 20% DHA. However, there are no reports of production of plant oils having more than 20% DHA.

There are no reports of the production of DPA in recombinant cells to significant levels without concomitant production of DHA. Indeed, the present inventors are unaware of any published suggestion or motivation to produce DPA in recombinant cells without production of DHA.

There therefore remains a need for more efficient production of LC-PUFA in recombinant cells, in particular of DPA in seeds of oilseed plants.

SUMMARY OF THE INVENTION

Few organisms produce oil with DPA greater than 1-2%, and hence there are limited, if any, options for producing DPA on a large scale from natural sourses. The present inventors have identified methods and plants for producing lipid with much higher levels of DPA than natural sources.

In a first aspect, the invention provides extracted lipid, preferably extracted plant lipid or extracted microbial lipid, comprising fatty acids in an esterified form, the fatty acids comprising oleic acid, palmitic acid, ω6 fatty acids which comprise linoleic acid (LA), ω3 fatty acids which comprise α-linolenic acid (ALA) and docosapentaenoic acid (DPA), and optionally one or more of stearidonic acid (SDA), eicosapentaenoic acid (EPA), and eicosatetraenoic acid (ETA), wherein the level of DPA in the total fatty acid content of the extracted lipid is between about 7% and 35%. In embodiments of this aspect, the level of DPA in the total fatty acid content of the extracted lipid is about 7%, about 8%, about 9%, about 10%, about 12%, about 15%, about 18%, about 20%, about 22%, about 24%, about 26%, about 28%, about 30%, between about 7% and about 28%, between about 7% and about 25%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%.

In an embodiment of the above aspect, DHA is present at a level of less than 2% or less than 0.5% of the total fatty acid content of the extracted lipid and more preferably is absent from the total fatty acid content of the lipid.

In another aspect, the invention provides extracted lipid, preferably extracted plant lipid or extracted microbial lipid, comprising fatty acids in an esterified form, the fatty acids comprising docosapentaenoic acid (DPA), wherein at least 35% of the DPA esterified in the form of triacylglycerol (TAG) is esterified at the sn-2 position of the TAG. In an embodiment, the extracted lipid is further characterised by one or more or all of (i) it comprises fatty acids comprising oleic acid, palmitic acid, ω6 fatty acids which comprise linoleic acid (LA), ω3 fatty acids which comprise α-linolenic acid (ALA) and optionally one or more of stearidonic acid (SDA), eicosapentaenoic acid (EPA), and eicosatetraenoic acid (ETA), (ii) at least about 40%, at least about 45%, at least about 48%, between 35% and about 60%, or between 35% and about 50%, of the DPA esterified in the form of triacylglycerol (TAG) is esterified at the sn-2 position of the TAG, and (iii) the level of DPA in the total fatty acid content of the extracted lipid is between about 1% and 35%, or between about 7% and 35% or between about 20.1% and 35%. In embodiments of this aspect, the level of DPA in the total fatty acid content of the extracted lipid is about 7%, about 8%, about 9%, about 10%, about 12%, about 15%, about 18%, about 20%, about 22%, about 24%, about 26%, about 28%, about 30%, between about 7% and about 28%, between about 7% and about 25%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%. In preferred embodiments, the extracted lipid is characterised by (i) and (ii), (i) and (iii) or (ii) and (iii), more preferably all of (i), (ii) and (iii). Preferably, the extracted lipid is further characterised by a level of palmitic acid in the total fatty acid content of the extracted lipid which is between about 2% and 16%, and a level of myristic acid (C14:0) in the total fatty acid content of the extracted lipid, if present, is less than 1%.

Embodiments of each of the above aspects are described in further detail below. As the skilled person would understand, any features of an embodiment described which are broader than the corresponding feature in an above aspect do not apply to that aspect.

In an embodiment, the extracted lipid has one or more of the following features i) the level of palmitic acid in the total fatty acid content of the extracted lipid is between about 2% and 18%, between about 2% and 16%, between about 2% and 15%, or between about 3% and about 10%, ii) the level of myristic acid (C14:0) in the total fatty acid content of the extracted lipid is less than 6%, less than 3%, less than 2%, less than 1%, or about 0.1%, iii) the level of oleic acid in the total fatty acid content of the extracted lipid is between about 1% and about 30%, between about 3% and about 30%, between about 6% and about 30%, between 1% and about 20%, between about 30% and about 60%, about 45% to about 60%, about 30%, or between about 15% and about 30%, iv) the level of linoleic acid (LA) in the total fatty acid content of the extracted lipid is between about 4% and about 35%, between about 4% and about 20%, between about 4% and about 17%, or between about 5% and about 10%, v) the level of α-linolenic acid (ALA) in the total fatty acid content of the extracted lipid is between about 4% and about 40%, between about 7% and about 40%, between about 10% and about 35%, between about 20% and about 35%, between about 4% and 16%, or between about 2% and 16%, vi) the level of γ-linolenic acid (GLA) in the total fatty acid content of the extracted lipid is less than 4%, less than about 3%, less than about 2%, less than about 1%, less than about 0.5%, between 0.05% and about 7%, between 0.05% and about 4%, between 0.05% and about 3%, or between 0.05% and about 2%, vii) the level of stearidonic acid (SDA) in the total fatty acid content of the extracted lipid is less than about 10%, less than about 8%, less than about 7%, less than about 6%, less than about 4%, less than about 3%, between about 0.05% and about 7%, between about 0.05% and about 6%, between about 0.05% and about 4%, between about 0.05% and about 3%, between about 0.05% and about 10%, or between 0.05% and about 2%, viii) the level of eicosatetraenoic acid (ETA) in the total fatty acid content of the extracted lipid is less than about 6%, less than about 5%, less than about 4%, less than about 1%, less than about 0.5%, between 0.05% and about 6%, between 0.05% and about 5%, between 0.05% and about 4%, between 0.05% and about 3%, or between 0.05% and about 2%, ix) the level of eicosatrienoic acid (ETrA) in the total fatty acid content of the extracted lipid is less than 4%, less than about 2%, less than about 1%, between 0.05% and 4%, between 0.05% and 3%, or between 0.05% and about 2%, or between 0.05% and about 1%, x) the level of eicosapentaenoic acid (EPA) in the total fatty acid content of the extracted lipid is between 4% and 15%, less than 4%, less than about 3%, less than about 2%, between 0.05% and 10%, between 0.05% and 5%, between 0.05% and about 3%, or between 0.05% and about 2%, xi) the lipid comprises ω6-docosapentaenoic acid ($22:5^{\Delta 4,7,10,13,16}$) in its fatty acid content, xii) the lipid comprises less than 0.1% of ω6-docosapentaenoic acid ($22:5^{\Delta 4,7,10,13,16}$) in its fatty acid content, xiii) the lipid comprises less than 0.1% of one or more or all of SDA, EPA and ETA in its fatty acid content, xiv) the level of total saturated fatty acids in the total fatty acid content of the extracted lipid is between about 4% and about 25%, between about 4% and about 20%, between about 6% and about 20%, or between about 6% and about 12%, xv) the level of total monounsaturated fatty acids in the total fatty acid content of the extracted lipid is between about 4% and about 40%, between about 4% and about 35%, between about 8% and about 25%, between 8% and about 22%, between about 15% and about 40% or between about 15% and about 35%, xvi) the level of total polyunsaturated fatty acids in the total fatty acid content of the extracted lipid is between about 20% and about 75%, between 30% and 75%, between about 50% and about 75%, about 60%, about 65%, about 70%, about 75%, or between about 60% and about 75%, xvii) the level of total ω6 fatty acids in the total fatty acid content of the extracted lipid is between about 35% and about 50%, between about 20% and about 35%, between about 6% and 20%, less than 20%, less than about 16%, less than about 10%, between about 1% and about 16%, between about 2% and about 10%, or between about 4% and about 10%, xviii) the level of new ω6 fatty acids in the total fatty acid content of the extracted lipid is less than about 10%, less than about 8%, less than about 6%, less than 4%, between about 1% and about 20%, between about 1% and about 10%, between 0.5% and about 8%, or between 0.5% and 4%, xix) the level of total ω3 fatty acids in the total fatty acid content of the extracted lipid is between 36% and about 65%, between 36% and about 70%, between 40% and about 60%, between about 30% and about 60%, between about 35% and about 60%, between 40% and about 65%, between about 30% and about 65%, between about 35% and about 65%, about 35%, about 40%, about 45%, about 50%, about 55%, about 60%, about 65% or about 70%, xx) the level of new ω3 fatty acids in the total fatty acid content of the extracted lipid is between 21% and about 45%, between 21% and about 35%, between about 23% and about 35%, between about 25% and about 35%, between about 27% and about 35%, about 23%, about 25%, about 27%, about 30%, about 35%, about 40% or about 45%, xxi) the ratio of total ω6 fatty acids: total ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 1.0, about 0.1, about 0.10 to about 0.4, or about 0.2, xxii) the ratio of new ω6 fatty acids: new ω3 fatty acids in the fatty acid content of the extracted lipid is between about 1.0 and about 3.0, between about 0.02 and about 0.1, between about 0.1 and about 1, between about 0.1 and about 0.5, less than about 0.50, less than about 0.40, less than about 0.30, less than about 0.20, less than about 0.15, about 0.02, about 0.05, about 0.1, about 0.2 or about 1.0, xxiii) the fatty acid composition of the lipid is based on an efficiency of conversion of oleic acid to LA by Δ12-desaturase of at least about 60%, at least about 70%, at least about 80%, between about 60% and about 98%, between about 70% and about 95%, or between about 75% and about 90%, xxiv) the fatty acid composition of the lipid is based on an efficiency of conversion of ALA to SDA by Δ6-desaturase of at least about 30%, at least about 40%, at least about 50%, at least about 60%, at least about 70%, between about 30% and about 70%, between about 35% and about 60%, or between about 50% and about 70%, xxv) the fatty acid composition of the lipid is based on an efficiency of conversion of SDA to ETA acid by Δ6-elongase of at least about 60%, at least about 70%, at least about 75%, between about 60% and about 95%, between about 70% and about 88%, or between about 75% and about 85%, xxvi) the fatty acid composition of the lipid is based on an efficiency of conversion of ETA to EPA by Δ5-desaturase of at least about 60%, at least about 70%, at least about 75%, between about 60% and about 99%, between about 70% and about 99%, or between about 75% and about 98%, xxvii) the fatty acid composition of the lipid is based on an efficiency of conversion of EPA to DPA by Δ5-elongase of at least about 80%, at least about 85%, at least about 90%, between about 50% and about 99%, between about 85% and about 99%, between about 50% and about 95%, or between about 85% and about 95%, xxviii) the fatty acid composition of the lipid is based on an efficiency of conversion of oleic acid to DPA of at least about 10%, at least about 15%, at least about 20%, at least about 25%, about 20%, about 25%, about 30%, between about 10% and about 50%, between about 10% and about 30%, between about 10% and about 25% or between about 20% and about 30%, xxix) the fatty acid composition of the lipid is based on an efficiency of conversion of LA to DPA of at least about 15%, at least about 20%, at least about 22%, at least about 25%, at least about 30%, at least about 40%, about 25%, about 30%, about 35%, about 40%, about 45%, about 50%, between about 15% and about 50%, between about 20% and about 40%, or between about 20% and about 30%, xxx) the fatty acid composition of the lipid is based on an efficiency of conversion of ALA toDPA of at least about 17%, at least about 22%, at least about 24%, at least about 30%, about 30%, about 35%, about 40%, about 45%, about 50%, about 55%, about 60%, between about 22% and about 70%, between about 17% and about 55%, between about 22% and about 40%, or between about 24% and about 40%, xxxi) the total fatty acid in the extracted lipid has less than 1.5% C20:1, less than 1% C20:1 or about 1% C20:1, xxxii) the triacylglycerol (TAG) content of the lipid is at least about 70%, at least about 80%, at least about 90%, at least 95%, between about 70% and about 99%, or between about 90% and about 99%, xxxiii) the lipid comprises diacylglycerol (DAG), which DAG preferably comprises DPA, xxxiv) the lipid comprises less than about 10%, less than about 5%, less than about 1%, or between about 0.001% and about 5%, free (non-esterified) fatty acids and/or phospholipid, or is essentially free thereof, xxxv) at least 70%, at least 72% or at least 80%, of the DPA esterified in the form of TAG is in the sn-1 or sn-3 position of the TAG, xxxvi) the most abundant DPA-containing TAG species in the lipid is DPA/18:3/18:3 (TAG 58:12), the lipid comprises tri-DPA TAG (TAG 66:18), and xxxvii) the level of DPA in the total fatty acid content of the extracted lipid is about 7%, about 8%, about 9%, about 10%, about 12%, about 15%, about 18%, about 20%, about 22%, about 24%, about 26%, about 28%, about 31%, between about 7% and about 31%, between about 7% and about 28%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%, optionally wherein the level of DHA is less than 0.5% of the total fatty acid content of the extracted lipid.

In another embodiment, the extracted lipid has one or more of the following features i) the level of palmitic acid in the total fatty acid content of the extracted plant lipid is between 2% and 15%, ii) the level of myristic acid (C14:0) in the total fatty acid content of the extracted plant lipid is about 0.1%, iii) the level of oleic acid in the total fatty acid content of the extracted plant lipid is between 1% and 30%, iv) the level of linoleic acid (LA) in the total fatty acid content of the extracted plant lipid is between 4% and 20%, v) the level of α-linolenic acid (ALA) in the total fatty acid content of the extracted plant lipid is between 4% and 40%, vi) the level of γ-linolenic acid (GLA) in the total fatty acid content of the extracted plant lipid is between 0.05% and 7%, vii) the level of stearidonic acid (SDA) in the total fatty acid content of the extracted plant lipid is between 0.05% and 10%, viii) the level of eicosatetraenoic acid (ETA) in the total fatty acid content of the extracted plant lipid is less than 6%, ix) the level of eicosatrienoic acid (ETrA) in the total fatty acid content of the extracted plant lipid is less than 4%, x) the extracted plant lipid comprises less than 0.1% of ω6-docosapentaenoic acid ($22:5^{\Delta4,7,10,13,16}$) in its fatty acid content, xi) the level of new ω6 fatty acids in the total fatty acid content of the extracted plant lipid is less than 10%, xii) the ratio of total ω6 fatty acids: total ω3 fatty acids in the fatty acid content of the extracted plant lipid is between 1.0 and 3.0, or between 0.1 and 1, xiii) the ratio of new ω6 fatty acids: new ω3 fatty acids in the fatty acid content of the extracted plant lipid is between 1.0 and 3.0, between 0.02 and 0.1, or between 0.1 and 1, xiv) the fatty acid composition of the extracted plant lipid is based on an efficiency of conversion of oleic acid to DPA of at least 10%, xv) the fatty acid composition of the extracted plant lipid is based on an efficiency of conversion of LA to DPA of at least 15%, xvi) the fatty acid composition of the extracted plant lipid is based on an efficiency of conversion of ALA to DPA of at least 17%, xvii) the total fatty acid in the extracted plant lipid has less than 1.5% C20:1, and xviii) the triacylglycerol (TAG) content of the extracted plant lipid is at least 70%, and may be characterised by one or more of the following features xix) the extracted plant lipid comprises diacylglycerol (DAG) which comprises DPA, xx) the extracted plant lipid comprises less than 10% free (non-esterified) fatty acids and/or phospholipid, or is essentially free thereof, xxi) at least 70% of the DPA esterified in the form of TAG is in the sn-1 or sn-3 position of the TAG, xxii) the most abundant DPA-containing TAG species in the extracted plant lipid is DPA/18:3/18:3 (TAG 58:12), and xxiii) the extracted plant lipid comprises tri-DPA TAG (TAG 66:18).

In an embodiment, the level of eicosapentaenoic acid (EPA) in the total fatty acid content of the extracted plant lipid is between 0.05% and 10%.

In a further embodiment, the level of DHA in the total fatty acid content of the extracted plant lipid is less than 2%, preferably less than 1%, or between 0.1% and 2%, more preferably is not detected. Preferably, the plant, or part thereof such as seed, or microbial cell has no polynucleotide encoding a Δ4-desaturase, or has no Δ4-desaturase polypeptide. In another embodiment, the extracted lipid is in the form of an oil, wherein at least about 90%, least about 95%, at least about 98%, or between about 95% and about 98%, by weight of the oil is the lipid.

Preferably, the extracted lipid is *Brassica* sp. seedoil lipid or *Camelina sativa* seedoil lipid.

In a preferred embodiment of the first aspect above, the lipid or oil, preferably a seedoil, more preferably a *Brassica* sp. seedoil or *Camelina sativa* seedoil, has the following features: in the total fatty acid content of the lipid or oil, the level of DPA is between about 7% and 30% or between about 7% and 35%, the level of palmitic acid is between about 2% and about 16%, the level of myristic acid is less than 1%, the level of oleic acid is between about 1% and about 30%, the level of LA is between about 4% and about 35%, ALA is present, the level of total saturated fatty acids in the total fatty acid content of the extracted lipid is between about 4% and about 25%, the ratio of total ω6 fatty acids: total ω3 fatty acids in the fatty acid content of the extracted lipid is between 0.05 and about 3.0, and the triacylglycerol (TAG) content of the lipid is at least about 70%, and optionally the lipid is essentially free of cholesterol and/or the lipid comprises tri-DPA TAG (TAG 66:15). More preferably, the lipid or oil, preferably a seedoil, additionally has one or more or all of the following features: at least 70% of the DPA is esterified at the sn-1 or sn-3 position of triacylglycerol (TAG), ALA is present at a level of between 4% and 40% of the total fatty acid content, GLA is present and/or the level of GLA is less than 4% of the total fatty acid content, the level of SDA is between 0.05% and about 10%, the level of ETA is less than about 4%, the level of EPA is between 0.05% and about 10%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the ratio of new ω6 fatty acids: new ω3 fatty acids in the fatty acid content of the extracted lipid is between about 0.03 and about 3.0, preferably less than about 0.50, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of EPA to DPA by Δ5-elongase of between about 50% and about 95%, an efficiency of conversion of oleic acid to DPA of at least about 10%. Most preferably, at least 81% of the DPA is esterified at the sn-1 or sn-3 position of triacylglycerol (TAG).

In another preferred embodiment of the second aspect above, the lipid or oil, preferably a seedoil, more preferably a *Brassica* sp. seedoil or *Camelina sativa* seedoil, comprising DPA has the following features: in the total fatty acid content of the lipid or oil, the level of palmitic acid is between about 2% and about 16%, the level of myristic acid is less than 1%, the level of oleic acid is between about 1% and about 30%, the level of LA is between about 4% and about 35%, ALA is present, the level of total saturated fatty acids in the total fatty acid content of the extracted lipid is between about 4% and about 25%, the ratio of total ω6 fatty acids: total ω3 fatty acids in the fatty acid content of the extracted lipid is between 0.05 and about 3.0, the triacylglycerol (TAG) content of the lipid is at least about 70%, and optionally the lipid comprises tri-DPA TAG (TAG 66:15), wherein at least 35% of the DPA esterified in the form of triacylglycerol (TAG) is esterified at the sn-2 position of the TAG. More preferably, the lipid or oil, preferably a seedoil, additionally has one or more or all of the following features: ALA is present at a level of between 4% and 40% of the total fatty acid content, GLA is present and/or the level of GLA is less than 4% of the total fatty acid content, the level of SDA is between 0.05% and about 10%, the level of ETA is less than about 4%, the level of EPA is between 0.05% and about 10%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the ratio of new ω6 fatty acids: new ω3 fatty acids in the fatty acid content of the extracted lipid is between about 0.03 and about 3.0, preferably less than about 0.50, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of EPA to DPA by Δ5-elongase of between about 50% and about 95%, an efficiency of conversion of oleic acid to DPA of at least about 10%.

In the context of the extracted lipid or oil of the invention, in an embodiment the level of DPA in the extracted lipid or oil has not been increased, or is substantially the same as, the level of DPA in the lipid or oil of the plant part or microbe prior to extraction. In other words, no procedure has been performed to increase the level of DPA in the lipid or oil relative to other fatty acids post-extraction. As would be apparent, the lipid or oil may subsequently be treated by fractionation or other procedures to alter the fatty acid composition.

In another preferred embodiment, the lipid or oil, preferably a seedoil and more preferably a *Brassica* seedoil such as mustard oil or canola oil or *C. sativa* seedoil, has the following features: in the total fatty acid content of the lipid or oil, the level of DPA is between about 7% and 35%, the level of palmitic acid is between about 2% and about 16%, the level of myristic acid is less than about 6% and preferably less than 1%, the level of oleic acid is between about 1% and about 30%, the level of LA is between about 4% and about 35%, ALA is present, the level of SDA is between about 0.05% and about 10%, the level of ETA is less than about 6%, the level of EPA is between about 0.05% and about 10%. DHA is, or preferably is not, detectable in the lipid or oil. Preferably, DHA, if present, is present at a level of not more than 2% or not more than 0.5% of the total fatty acid content of the lipid or oil and more preferably is absent from the total fatty acid content of the lipid or oil. Optionally, the lipid is essentially free of cholesterol and/or the lipid comprises tri-DPA TAG (TAG 66:15). More preferably, the lipid or oil, preferably a seedoil, additionally has one or more or all of the following features: at least 70% of the DPA is esterified at the sn-1 or sn-3 position of triacylglycerol (TAG), ALA is present at a level of between 4% and 40% of the total fatty acid content, GLA is present and/or the level of GLA is less than 4% of the total fatty acid content, the level of SDA is between 0.05% and about 10%, the level of ETA is less than about 4%, the level of EPA is between 0.05% and about 10%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the ratio of new ω6 fatty acids: new ω3 fatty acids in the fatty acid content of the extracted lipid is between about 0.03 and about 3.0, preferably less than about 0.50, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of EPA to DPA by Δ5-elongase of between about 50% and about 95%, an efficiency of conversion of oleic acid to DPA of at least about 10%. In an embodiment, at least 81% of the DPA is esterified at the sn-1 or sn-3 position of triacylglycerol (TAG). Alternatively, at least 35% of the DPA esterified in the form of TAG is esterified at the sn-2 position of TAG.

In a further embodiment, the extracted lipid of the invention further comprises one or more sterols, preferably plant sterols.

In another embodiment, the extracted lipid is in the form of an oil, and comprises less than about 10 mg of sterols/g of oil, less than about 7 mg of sterols/g of oil, between about 1.5 mg and about 10 mg of sterols/g of oil, or between about 1.5 mg and about 7 mg of sterols/g of oil.

Examples of sterols which can be in the extracted lipid include, but are not necessarily limited to, one or more or all of campesterol/24-methylcholesterol, Δ5-stigmasterol, eburicol, β-sitosterol/24-ethylcholesterol, Δ5-avenasterol/isofucosterol, Δ7-stigmasterol/stigmast-7-en-3β-ol, and Δ7-avenasterol.

In an embodiment, the plant species is one listed in Table 11, such as canola, and the level of sterols are about the same as that listed in Table 11 for that particular plant species. The plant species may be *B. napus*, mustard (*B. juncea*) or *C. sativa* and comprise a level of sterols about that found in wild-type mustard *B. napus*, mustard or *C. sativa* extracted oil, respectively.

In an embodiment, the extracted plant lipid comprises one or more or all of campesterol/24-methylcholesterol, Δ5-stigmasterol, eburicol, β-sitosterol/24-ethylcholesterol, Δ5-avenasterol/isofucosterol, Δ7-stigmasterol/stigmast-7-en-3β-ol, and Δ7-avenasterol, or which has a sterol content essentially the same as wild-type canola oil.

In an embodiment, the extracted lipid has a sterol content essentially the same as wild-type canola oil, mustard oil or *C. sativa* oil.

In an embodiment, the extracted lipid comprises less than about 0.5 mg of cholesteroUg of oil, less than about 0.25 mg of cholesterol/g of oil, between about 0 mg and about 0.5 mg of cholesterol/g of oil, or between about 0 mg and about 0.25 mg of cholesterol/g of oil, or which is essentially free of cholesterol.

In a further embodiment, the lipid is an oil, preferably oil from an oilseed. Examples of such oils include, but are not limited to, *Brassica* sp. oil such as for example canola oil or mustard oil, *Gossypium hirsutum* oil, *Linum usitatissimum* oil, *Helianthus* sp. oil, *Carthamus tinctorius* oil, *Glycine max* oil, *Zea mays* oil, *Arabidopsis thaliana* oil, *Sorghum bicolor* oil, *Sorghum vulgare* oil, *Avena sativa* oil, *Trifolium* sp. oil, *Elaesis guineenis* oil, *Nicotiana benthamiana* oil, *Hordeum vulgare* oil, *Lupinus angustifolius* oil, *Oryza sativa* oil, *Oryza glaberrima* oil, *Camelina sativa* oil, *Crambe abyssinica* oil, *Miscanthus*x*giganteus* oil, or *Miscanthus sinensis* oil. More preferably, the oil is a *Brassica* sp. oil, a *Camelina sativa* oil or a *Glycine max* (soybean) oil. In an embodiment the lipid comprises or is *Brassica* sp. oil such as *Brassica napus* oil or *Brassica juncea* oil, *Gossypium hirsutum* oil, *Linum usitatissimum* oil, *Helianthus* sp. oil, *Carthamus tinctorius* oil, *Glycine max* oil, *Zea mays* oil, *Elaesis guineenis* oil, *Nicotiana benthamiana* oil, *Lupinus angustifolius* oil, *Camelina sativa* oil, *Crambe abyssinica* oil, *Miscanthus*×*giganteus* oil, or *Miscanthus sinensis* oil. In a further embodiment, the oil is canola oil, mustard (*B. juncea*) oil, soybean (*Glycine max*) oil, *Camelina sativa* oil or *Arabidopsis thaliana* oil. In an alternative embodiment, the oil is a plant oil other than *A. thaliana* oil and/or other than *C. sativa* oil. In an embodiment, the plant oil is an oil other than *G. max* (soybean) oil. In an embodiment, the oil was obtained from a plant grown under standard conditions, for Example as described in Example 1, or from a plant grown in the field or in a glasshouse under standard conditions.

In a further aspect, the invention provides a process for producing extracted plant lipid or microbial lipid, comprising the steps of i) obtaining a plant part, preferably *Brassica* seed or *Camelina sativa* seed, or microbial cells comprising lipid, the lipid comprising fatty acids in an esterified form, the fatty acids comprising oleic acid, palmitic acid, ω6 fatty acids which comprise linoleic acid (LA), ω3 fatty acids which comprise α-linolenic acid (ALA) and docosapentaenoic acid (DPA), and optionally one or more of stearidonic acid (SDA), eicosapentaenoic acid (EPA), and eicosatetraenoic acid (ETA), wherein the level of DPA in the total fatty acid content of the lipid of the plant part or microbial cells between about 7% and 35%, and ii) extracting lipid from the plant part or microbial cells, wherein the level of DPA in the total fatty acid content of the extracted lipid is between about 7% and 35%. In an embodiment, the level of DPA in the total fatty acid content of the extracted lipid is between about 7% and 20%, or between 20.1% and 35%. In an embodiment, the level of DPA is between 7% and 20% or between 20.1% and 30%, preferably between 20.1% and 35%, more preferably between 30% and 35%. In an embodiment, the level of DPA in the total fatty acid content of the extracted lipid is between 8% and 20% or between 10% and 20%, preferably between 11% and 20% or between 12% and 20%.

In an embodiment of the above aspect, the invention provides a process for producing extracted plant lipid or microbial lipid, comprising the steps of i) obtaining a plant part, preferably *Brassica* seed or *C. sativa* seed, or microbial cells comprising lipid, the lipid comprising fatty acids in an esterified form, wherein the lipid has a fatty acid composition comprising oleic acid, palmitic acid, ω6 fatty acids which comprise linoleic acid (LA), ω3 fatty acids which comprise α-linolenic acid (ALA) and docosapentaenoic acid (DPA), and one or more of stearidonic acid (SDA), eicosapentaenoic acid (EPA), and eicosatetraenoic acid (ETA), wherein (i) the level of DPA in the total fatty acid content of the extracted lipid is between 7% and 30% or between 7% and 35%, preferably between 30% and 35%, (ii) the level of palmitic acid in the total fatty acid content of the extracted lipid is between 2% and 16%, (iii) the level of myristic acid (C14:0) in the total fatty acid content of the extracted lipid is less than 6%, preferably less than 1%, (iv) the level of oleic acid in the total fatty acid content of the extracted lipid is between 1% and 30%, (v) the level of linoleic acid (LA) in the total fatty acid content of the extracted lipid is between 4% and 35%, (vi) the level of α-linolenic acid (ALA) in the total fatty acid content of the extracted lipid is between 4% and 40%, (vii) the level of eicosatrienoic acid (ETrA) in the total fatty acid content of the extracted lipid is less than 4%, (viii) the level of total saturated fatty acids in the total fatty acid content of the extracted lipid is between 4% and 25%, (ix) the ratio of total ω6 fatty acids: total ω3 fatty acids in the fatty acid content of the extracted lipid is between 0.05 and 1, (x) the triacylglycerol (TAG) content of the lipid is at least 70%, and (xi) at least 70% of the DPA esterified in the form of TAG is in the sn-1 or sn-3 position of the TAG and ii) extracting lipid from the plant part, wherein the level of DPA in the total fatty acid content of the extracted lipid is between about 7% and 30% or between 7% and 35%, preferably between 30% and 35%. Preferably, at least 81% or at least 90% of the DPA esterified in the form of TAG is in the sn-1 or sn-3 position of the TAG.

In another aspect, the present invention provides a process for producing extracted lipid, comprising the steps of i) obtaining cells, preferably a plant part comprising the cells or microbial cells, more preferably *Brassica* seed or *C. sativa* seed, comprising lipid, the lipid comprising fatty acids in an esterified form, the fatty acids comprising docosapentaenoic acid (DPA), wherein at least 35% of the DPA esterified in the form of triacylglycerol (TAG) is esterified at the sn-2 position of the TAG, and ii) extracting lipid from the cells, wherein at least 35% of the DPA esterified in the form of triacylglycerol (TAG) in the total fatty acid content of the extracted lipid is esterified at the sn-2 position of the TAG. In an embodiment, the extracted lipid produced by the process is further characterised by one or more or all of (i) it comprises fatty acids comprising oleic acid, palmitic acid, ω6 fatty acids which comprise linoleic acid (LA), ω3 fatty acids which comprise α-linolenic acid (ALA) and optionally one or more of stearidonic acid (SDA), eicosapentaenoic acid (EPA), and eicosatetraenoic acid (ETA), (ii) at least about 40%, at least about 45%, at least about 48%, between 35% and about 60%, or between 35% and about 50%, of the DPA esterified in the form of triacylglycerol (TAG) is esterified at the sn-2 position of the TAG, and (iii) the level of DPA in the total fatty acid content of the extracted lipid is between about 1% and 35%, or between about 7% and 35% or between about 20.1% and 35%. In embodiments of this aspect, the level of DPA in the total fatty acid content of the extracted lipid is about 7%, about 8%, about 9%, about 10%, about 12%, about 15%, about 18%, about 20%, about 22%, about 24%, about 26%, about 28%, about 30%, between about 7% and about 28%, between about 7% and about 25%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%. In preferred embodiments, the extracted lipid is characterised by (i) and (ii), (i) and (iii) or (ii) and (iii), more preferably all of (i), (ii) and (iii). Preferably, the extracted lipid is further characterised by a level of palmitic acid in the total fatty acid content of the extracted lipid which is between about 2% and 16%, and a level of myristic acid (C14:0) in the total fatty acid content of the extracted lipid, if present, is less than 1%.

In an embodiment of the above aspect, the invention provides a process for producing extracted lipid, comprising the steps of i) obtaining cells, preferably a plant part comprising the cells or microbial cells, more preferably *Brassica* seed or *C. sativa* seed, comprising lipid, the lipid comprising fatty acids in an esterified form, the fatty acids comprising docosapentaenoic acid (DPA), and further comprising oleic acid, palmitic acid, cob fatty acids which comprise linoleic acid (LA), ω3 fatty acids which comprise α-linolenic acid (ALA), and one or more of stearidonic acid (SDA), eicosapentaenoic acid (EPA), and eicosatetraenoic acid (ETA), wherein (i) the level of palmitic acid in the total fatty acid content of the extracted lipid is between 2% and 16%, (ii) the level of myristic acid (C14:0) in the total fatty acid content of the extracted lipid is less than 1%, (iii) the level of oleic acid in the total fatty acid content of the extracted lipid is between 1% and 30%, (iv) the level of linoleic acid (LA) in the total fatty acid content of the extracted lipid is between 4% and 35%, (v) the level of α-linolenic acid (ALA) in the total fatty acid content of the extracted lipid is between 4% and 40%, (vi) the level of eicosatrienoic acid (ETrA) in the total fatty acid content of the extracted lipid is less than 4%, (vii) the level of total saturated fatty acids in the total fatty acid content of the extracted lipid is between 4% and 25%, (viii) the ratio of total ω6 fatty acids: total ω3 fatty acids in the fatty acid content of the extracted lipid is between 0.05 and 1, (ix) the triacylglycerol (TAG) content of the lipid is at least 70%, and (x) at least 35% of the DPA esterified in the form of triacylglycerol (TAG) is esterified at the sn-2 position of the TAG, and ii) extracting lipid from the plant part, wherein at least 35% of the DPA esterified in the form of triacylglycerol (TAG) in the total fatty acid content of the extracted lipid is esterified at the sn-2 position of the TAG.

The step of obtaining the plant part or microbial cells may comprise harvesting plant parts, preferably seed, from plants that produce the plant parts, recovery of the microbial cells from cultures of such cells, or obtaining the plant parts or microbial cells by purchase from a producer or supplier, or by importation. The process may comprise a step of determining the fatty acid composition of the lipid in a sample of the plant parts or microbial cells, or of the extracted lipid.

In a preferred embodiment, the extracted lipid obtained by a process of the invention has, where relevant, one or more of the features defined herein, for example as defined above in relation to the first two aspects.

Embodiments of above aspects of the invention are described in further detail below. As the skilled person would understand, any features described of embodiments which are broader than the corresponding feature in an above aspect do not apply to that aspect.

In an embodiment, the plant part is a seed, preferably an oilseed. Examples of such seeds include, but are not limited to, *Brassica* sp., *Gossypium hirsutum, Linum usitatissimum, Helianthus* sp., *Carthamus tinctorius, Glycine max, Zea mays, Arabidopsis thaliana, Sorghum bicolor, Sorghum vulgare, Avena sativa, Trifolium* sp., *Elaesis guineenis, Nicotiana benthamiana, Hordeum vulgare, Lupinus angustifolius, Oryza sativa, Oryza glaberrima, Camelina sativa,* or *Crambe abyssinica*, preferably a *Brassica* sp. seed, a *C. sativa* seed or a *G. max* (soybean) seed, more preferably a *Brassica napus, B. juncea* or *C. sativa* seed. In an embodiment, the plant part is a seed, preferably an oilseed such as *Brassica* sp. such as *Brassica napus* or *Brassica juncea, Gossypium hirsutum, Linum usitatissimwn, Helianthus* sp., *Carthamus tinctorius, Glycine max, Zea mays, Elaesis guineenis, Nicotiana benthamiana, Lupinus angustifolius, Camelina sativa,* or *Crambe abyssinica*, preferably a *Brassica napus, B juncea* or *C. sativa* seed. In an embodiment, the seed is canola seed, mustard seed, soybean seed, *Camelina sativa* seed or *Arabidopsis thaliana* seed. In an alternate embodiment, the seed is a seed other than *A. thaliana* seed and/or other than *C. sativa* seed. In an embodiment, the seed is a seed other than soybean seed. In an embodiment, the plant part is *Brassica* sp. seed. The plant part is preferably *Brassica* sp. seed or *Camelina sativa* seed. In an embodiment, the seed was obtained from a plant grown under standard conditions, for Example as described in Example 1, or from a plant grown in the field or in a glasshouse under standard conditions.

In another embodiment, the seed comprises at least about 18 mg, at least about 22 mg, at least about 26 mg, between about 18 mg and about 100 mg, between about 22 mg and about 70 mg, about 80 mg, between about 30 mg and about 80 mg, or between about 24 mg and about 50 mg, of DPA per gram of seed.

In a further embodiment, the plant part such as a seed comprises exogenous polynucleotides encoding one of the following sets of enzymes;

i) an ω3-desaturase, a Δ6-desaturase, a Δ5-desaturase, a Δ6-elongase and a Δ5-elongase, ii) a Δ15-desaturase, a Δ6-desaturase, a Δ5-desaturase, a Δ6-elongase and a Δ5-elongase, iii) a Δ12-desaturase, a Δ6-desaturase, a Δ5-desaturase, a Δ6-elongase and an Δ5-elongase, iv) a Δ12-desaturase, a ω3-desaturase and/or a Δ5-desaturase, a Δ6-desaturase, a Δ5-desaturase, a Δ6-elongase and an Δ5-elongase, v) an ω3-desaturase, a Δ8-desaturase, a Δ5-desaturase, a Δ9-elongase and an Δ5-elongase, vi) a Δ15-desaturase, a Δ8-desaturase, a Δ5-desaturase, a Δ9-elongase and a Δ5-elongase, vii) a Δ12-desaturase, a Δ8-desaturase, a Δ5-desaturase, a Δ9-elongase and an Δ5-elongase, viii) a Δ12-desaturase, a ω3-desaturase and/or a Δ15-desaturase, a Δ8-desaturase, a Δ5-desaturase, a Δ9-elongase and an Δ5-elongase, and wherein each polynucleotide is operably linked to one or more promoters that are capable of directing expression of said polynucleotides in a cell of the plant part.

In a further embodiment, the plant part such as a seed or recombinant cells such as microbial cells comprise exogenous polynucleotides encoding one of the following sets of enzymes;

i) an ω3-desaturase and/or a Δ15-desaturase, a Δ6-desaturase, a Δ5-desaturase, a Δ6-elongase and a Δ5-elongase, ii) a Δ12-desaturase, a Δ6-desaturase, a Δ5-desaturase, a Δ6-elongase and an Δ5-elongase, iii) a Δ12-desaturase, a ω3-desaturase and/or a Δ15-desaturase, a Δ6-desaturase, a Δ5-desaturase, a Δ6-elongase and an Δ5-elongase, iv) an ω3-desaturase and/or a Δ15-desaturase, a Δ8-desaturase, a Δ5-desaturase, a Δ9-elongase and a Δ5-elongase, v) a Δ12-desaturase, a Δ8-desaturase, a Δ5-desaturase, a Δ9-elongase and an Δ5-elongase, vi) a Δ12-desaturase, a ω3-desaturase and/or a Δ15-desaturase, a Δ8-desaturase, a Δ5-desaturase, a Δ9-elongase and an Δ5-elongase, and wherein each polynucleotide is operably linked to one or more promoters that are capable of directing expression of said polynucleotides in a cell of the plant part or the cells.

In an embodiment, if the plant part or cell comprises lipid comprising fatty acids in an esterified form, the fatty acids comprising docosapentaenoic acid (DPA), wherein at least 35% of the DPA and/or DHA (if present) esterified in the form of triacylglycerol (TAG) is esterified at the sn-2 position of the TAG, the plant part such as a seed or recombinant cells such as microbial cells comprise an exogenous polynucleotide encoding an 1-acyl-glycerol-3-phosphate acyltransferase (LPAAT), wherein the polynucleotide is operably linked to one or more promoters that are capable of directing expression of the polynucleotide in a cell of the plant part or the cells. In a further embodiment, the cell comprises exogenous polynucleotides encoding one of the following sets of enzymes;

i) an 1-acyl-glycerol-3-phosphate acyltransferase (LPAAT), an ω3-desaturase, a Δ6-desaturase, a Δ5-desaturase, a Δ6-elongase and a Δ5-elongase, ii) an 1-acyl-glycerol-3-phosphate acyltransferase (LPAAT), a Δ15-desaturase, a Δ6-desaturase, a Δ5-desaturase, a Δ6-elongase, and a Δ5-elongase, iii) an 1-acyl-glycerol-3-phosphate acyltransferase (LPAAT), a Δ12-desaturase, a Δ6-desaturase, a Δ5-desaturase, a Δ6-elongase and a Δ5-elongase, iv) an 1-acyl-glycerol-3-phosphate acyltransferase (LPAAT), a Δ12-desaturase, a ω3-desaturase and/or a Δ15-desaturase, a Δ6-desaturase, a Δ5-desaturase, a Δ6-elongase and an Δ5-elongase, v) an 1-acyl-glycerol-3-phosphate acyltransferase (LPAAT), an ω3-desaturase, a Δ8-desaturase, a Δ5-desaturase, a Δ9-elongase and a Δ5-elongase, vi) an 1-acyl-glycerol-3-phosphate acyltransferase (LPAAT), a Δ15-desaturase, a Δ8-desaturase, a Δ5-desaturase, a Δ9-elongase, and a Δ5-elongase, vii) an 1-acyl-glycerol-3-phosphate acyltransferase (LPAAT), a Δ12-desaturase, a Δ8-desaturase, a Δ5-desaturase, a Δ9-elongase and a Δ5-elongase, viii) an 1-acyl-glycerol-3-phosphate acyltransferase (LPAAT), a Δ12-desaturase, a ω3-desaturase and/or a Δ15-desaturase, a Δ8-desaturase, a Δ5-desaturase, a Δ9-elongase, and a Δ5-elongase, wherein each polynucleotide is operably linked to one or more promoters that are capable of directing expression of said polynucleotides in the cell. Preferably, the LPAAT can use a C22 polyunsaturated fatty acyl-CoA substrate such as DPA-CoA.

Preferably, the plant, or part thereof such as seed, or microbial cell has no polynucleotide encoding a Δ4-desaturase, or has no Δ4-desaturase polypeptide.

In an embodiment, the Δ12-desaturase also has ω3-desaturase and/or Δ15-desaturase activity, i.e. the activities are conferred by a single polypeptide. Alternatively, the Δ12-desaturase does not have ω3-desaturase activity and does not have Δ15-desaturase activity i.e. the Δ12-desaturase is a separate polypeptide to the polypeptide having ω3-desaturase activity and/or Δ15-desaturase.

In yet a further embodiment, the plant part such as a seed or recombinant cells such as microbial cells have one or more or all of the following features:

i) the Δ12-desaturase converts oleic acid to linoleic acid in one or more cells of the plant part or in the recombinant cells with an efficiency of at least about 60%, at least about 70%, at least about 80%, between about 60% and about 95%, between about 70% and about 90%, or between about 75% and about 85%, ii) the ω3-desaturase converts ω6 fatty acids to ω3 fatty acids in one or more cells of the plant part or in the recombinant cells with an efficiency of at least about 65%, at least about 75%, at least about 85%, between about 65% and about 95%, between about 75% and about 91%, or between about 80% and about 91%, iii) the Δ6-desaturase converts ALA to SDA in one or more cells of the plant part or in the recombinant cells with an efficiency of at least about 20%, at least about 30%, at least about 40%, at least about 50%, at least about 60%, at least about 70%, between about 30% and about 70%, between about 35% and about 60%, or between about 50% and about 70%, iv) the Δ6-desaturase converts linoleic acid to γ-linolenic acid in one or more cells of the plant part or in the recombinant cells with an efficiency of less than about 5%, less than about 2.5%, less than about 1%, between about 0.1% and about 5%, between about 0.5% and about 2.5%, or between about 0.5% and about 1%, v) the Δ6-elongase converts SDA to ETA in one or more cells of the plant part or in the recombinant cells with an efficiency of at least about 60%, at least about 70%, at least about 75%, between about 60% and about 95%, between about 70% and about 80%, or between about 75% and about 80%, vi) the Δ5-desaturase converts ETA to EPA in one or more cells of the plant part or in the recombinant cells with an efficiency of at least about 60%, at least about 70%, at least about 75%, at least about 80%, at least about 90%, between about 60% and about 95%, between about 70% and about 95%, or between about 75% and about 95%, vii) the Δ5-elongase converts EPA to DPA in one or more cells of the plant part or in the recombinant cells with an efficiency of at least about 80%, at least about 85%, at least about 90%, between about 50% and about 90%, or between about 85% and about 95%, ix) the efficiency of conversion of oleic acid to DPA in one or more cells of the plant part or in the recombinant cells is at least about 10%, at least about 15%, at least about 20%, at least about 25%, about 20%, about 25%, about 30%, between about 10% and about 50%, between about 10% and about 30%, between about 10% and about 25%, or between about 20% and about 30%, x) the efficiency of conversion of LA to DPA in one or more cells of the plant part or in the recombinant cells is at least about 15%, at least about 20%, at least about 22%, at least about 25%, at least about 30%, about 25%, about 30%, about 35%, between about 15% and about 50%, between about 20% and about 40%, or between about 20% and about 30%, xi) the efficiency of conversion of ALA to DPA in one or more cells of the plant part or in the recombinant cells is at least about 17%, at least about 22%, at least about 24%, at least about 30%, about 30%, about 35%, about 40%, between about 17% and about 55%, between about 22% and about 35%, or between about 24% and about 35%, xi) one or more cells of the plant part or the recombinant cells comprise at least about 25%, at least about 30%, between about 25% and about 40%, or between about 27.5% and about 37.5%, more ω3 fatty acids than corresponding cells lacking the exogenous polynucleotides, xii) the Δ6-desaturase preferentially desaturates α-linolenic acid (ALA) relative to linoleic acid (LA), xiii) the Δ6-elongase also has Δ9-elongase activity, xiv) the Δ12-desaturase also has Δ15-desaturase activity, xv) the Δ6-desaturase also has Δ8-desaturase activity, xvi) the Δ8-desaturase also has Δ6-desaturase activity or does not have Δ6-desaturase activity, xvii) the Δ15-desaturase also has ω3-desaturase activity on GLA, xviii) the ω3-desaturase also has Δ15-desaturase activity on LA, xix) the ω3-desaturase desaturates both LA and/or GLA, xx) the ω3-desaturase preferentially desaturates GLA relative to LA, xxi) one or more or all of the desaturases, preferably the Δ6-desaturase and/or the Δ5-desaturase, have greater activity on an acyl-CoA substrate than a corresponding acyl-PC substrate, xxii) the Δ6-desaturase has greater Δ6-desaturase activity on ALA than LA as fatty acid substrate, xxiii) the Δ6-desaturase has greater Δ6-desaturase activity on ALA-CoA as fatty acid substrate than on ALA joined to the sn-2 position of PC as fatty acid substrate, xxiv) the Δ6-desaturase has at least about a 2-fold greater Δ6-desaturase activity, at least 3-fold greater activity, at least 4-fold greater activity, or at least 5-fold greater activity, on ALA as a substrate compared to LA, xxv) the Δ6-desaturase has greater activity on ALA-CoA as fatty acid substrate than on ALA joined to the sn-2 position of PC as fatty acid substrate, xxvi) the Δ6-desaturase has at least about a 5-fold greater Δ6-desaturase activity or at least 10-fold greater activity, on ALA-CoA as fatty acid substrate than on ALA joined to the sn-2 position of PC as fatty acid substrate, xxvii) the desaturase is a front-end desaturase, and xxviii) the Δ6-desaturase has no detectable Δ5-desaturase activity on ETA.

In yet a further embodiment, the plant part such as a seed, preferably a *Brassica* seed or a *C. sativa* seed, or the recombinant cell such as microbial cells has one or more or all of the following features i) the Δ12-desaturase comprises amino acids having a sequence as provided in SEQ ID NO:4, a biologically active fragment thereof, or an amino acid sequence which is at least 50% identical to SEQ ID NO:4, ii) the ω3-desaturase comprises amino acids having a sequence as provided in SEQ ID NO:6, a biologically active fragment thereof, or an amino acid sequence which is at least 50% identical to SEQ ID NO:6, iii) the Δ6-desaturase comprises amino acids having a sequence as provided in SEQ ID NO:9, a biologically active fragment thereof, or an amino acid sequence which is at least 50% identical to SEQ ID NO:9, iv) the Δ6-elongase comprises amino acids having a sequence as provided in SEQ ID NO:16, a biologically active fragment thereof such as SEQ ID NO:17, or an amino acid sequence which is at least 50% identical to SEQ ID NO:16 and/or SEQ ID NO:17, v) the Δ5-desaturase comprises amino acids having a sequence as provided in SEQ ID NO:20, a biologically active fragment thereof, or an amino acid sequence which is at least 50% identical to SEQ ID NO:20, and vi) the Δ5-elongase comprises amino acids having a sequence as provided in SEQ ID NO:25, a biologically active fragment thereof, or an amino acid sequence which is at least 50% identical to SEQ ID NO:25.

In an embodiment, the plant part such as a seed or the recombinant cells such as microbial cells further comprise(s) an exogenous polynucleotide encoding a diacylglycerol acyltransferase (DGAT), monoacylglycerol acyltransferase (MGAT), glycerol-3-phosphate acyltransferase (GPAT), 1-acyl-glycerol-3-phosphate acyltransferase (LPAAT) preferably an LPAAT which can use a C22 polyunsaturated fatty acyl-CoA substrate such as DPA-CoA, acyl-CoA:lysophosphatidylcholine acyltransferase (LPCAT), phospholipase $A_2$ ($PLA_2$), phospholipase C (PLC), phospholipase D (PLD), CDP-choline diacylglycerol choline phosphotransferase (CPT), phoshatidylcholine diacylglycerol acyltransferase (PDAT), phosphatidylcholine:diacylglycerol choline phosphotransferase (PDCT), acyl-CoA synthase (ACS), or a combination of two or more thereof.

In another embodiment, the plant part such as a seed or the recombinant cells such as microbial cells further comprise(s) an introduced mutation or an exogenous polynucleotide which down regulates the production and/or activity of an endogenous enzyme in a cell of the plant part selected from FAE1, DGAT, MGAT, GPAT, LPAAT, LPCAT, $PLA_2$, PLC, PLD, CPT, PDAT, a thioesterase such as FATB, or a Δ12-desaturase, or a combination of two or more thereof.

In a further embodiment, at least one, or preferably all, of the promoters are seed specific promoters. In an embodiment, at least one, or all, of the promoters have been obtained from an oil biosynthesis or accumulation gene such as a gene encoding oleosin, or from a seed storage protein genes such as a gene encoding conlinin.

In another embodiment, the promoter(s) directing expression of the exogenous polynucleotides encoding the Δ5-elongase initiate expression of the polynucleotides in developing seed of the plant or the recombinant cells such as the microbial cells before, or reach peak expression before, the promoter(s) directing expression of the exogenous polynucleotides encoding the Δ12-desaturase and the ω3-desaturase.

In a further embodiment, the exogenous polynucleotides are covalently linked in a DNA molecule, preferably a T-DNA molecule, integrated into the genome of cells of the plant part or the recombinant cells such as the microbial cells and preferably where the number of such DNA molecules integrated into the genome of the cells of the plant part or the recombinant cells is not more than one, two or three, or is two or three.

In yet another embodiment, the plant part comprises at least two different, exogenous polynucleotides each encoding a Δ6-desaturase which have the same or different amino acid sequences.

In a further embodiment, the total oil content of the plant part comprising the exogenous polynucleotides is at least about 40%, at least about 50%, at least about 60%, at least about 70%, between about 50% and about 80%, or between about 80% and about 100% of the total oil content of a corresponding plant part lacking the exogenous polynucleotides. In a further embodiment, the seed comprising the exogenous polynucleotides has a seed weight at least about 40%, at least about 50%, at least about 60%, at least about 70%, between about 50% and about 80%, or between about 80% and about 100% of the weight of a corresponding seed lacking the exogenous polynucleotides.

In another embodiment, the lipid is in the form of an oil, preferably a seedoil from an oilseed, and wherein at least about 90%, or about least 95%, at least about 98%, or between about 95% and about 98%, by weight of the lipid is triacylglycerols.

In a further embodiment, the process further comprises treating the lipid to increase the level of DPA as a percentage of the total fatty acid content. For example, the treatment comprises hydrolysis of the esterified fatty acids to produce free fatty acids, or transesterification. For example, the lipid such as canola oil may be treated to convert the fatty acids in the oil to alkyl esters such as methyl or ethyl esters, which may then be fractionated to enrich the lipid or oil for the DPA. In embodiments, the fatty acid composition of the lipid after such treatment comprises at least 40%, at least 50%, at least 60%, at least 70%, at least 80% or at least 90% DPA. In an embodiment, the level of DHA in the total fatty acid content of the lipid after treatment is less than 2.0% or less than 0.5%, preferably is not detect in the lipid.

Also provided is lipid, or oil comprising the lipid, such as free fatty acids or alkyl esters, produced using a process of the invention.

In another aspect, the present invention provides a process for producing methyl or ethyl esters of polyunsaturated fatty acids, the process comprising reacting triacylglycerols in extracted plant lipid, or during the process of extraction, with methanol or ethanol, respectively, wherein the extracted plant lipid comprises fatty acids esterified in the form of TAG, the fatty acids comprising oleic acid, palmitic acid, ω6 fatty acids which comprise linoleic acid (LA), ω3 fatty acids which comprise α-linolenic acid (ALA), and docosapentaenoic acid (DPA), and optionally one or more of stearidonic acid (SDA), eicosapentaenoic acid (EPA), and eicosatetraenoic acid (ETA), wherein the level of DPA in the total fatty acid content of the extracted lipid is between about 7% and 35%, preferably between 20.1% and 30% or between 20.1% and 35%, thereby producing the methyl or ethyl esters of polyunsaturated fatty acids.

In another aspect, the present invention provides a process for producing methyl or ethyl esters of docosapentaenoic acid (DPA), the process comprising reacting triacylglycerols (TAG) in extracted plant lipid, or during the process of extraction, with methanol or ethanol, respectively, wherein the extracted plant lipid comprises fatty acids in an esterified form, the fatty acids comprising docosapentaenoic acid (DPA), wherein at least 35% of the DPA esterified in the form of TAG is esterified at the sn-2 position of the TAG, thereby producing the methyl or ethyl esters of polyunsaturated fatty acids.

In a preferred embodiment, the lipid which is used in the process of the above two aspects has one or more of the features defined herein in the context of the extracted lipid or oil of the invention.

In another aspect, the present invention provides an oilseed plant or part thereof such as a seed, preferably a *Brassica* plant or a *C. sativa* plant, comprising lipid in its seed, or a microbial cell, comprising a) lipid comprising fatty acids in an esterified form, and b) exogenous polynucleotides encoding one of the following sets of enzymes;

i) a Δ12-desaturase, a ω3-desaturase and/or Δ15-desaturase, a Δ6-desaturase, a Δ5-desaturase, a Δ6-elongase and an Δ5-elongase, ii) a Δ12-desaturase, a ω3-desaturase and/or Δ15-desaturase, a Δ8-desaturase, a Δ5-desaturase, a Δ9-elongase and an Δ5-elongase, iii) a ω3-desaturase and/or Δ15-desaturase, a Δ6-desaturase, a Δ5-desaturase, a Δ6-elongase and an Δ5-elongase, or iv) a ω3-desaturase and/or Δ15-desaturase, a Δ8-desaturase, a Δ5-desaturase, a Δ9-elongase and an Δ5-elongase, wherein each polynucleotide is operably linked to one or more seed-specific promoters that are capable of directing expression of said polynucleotides in developing seed of the plant, or one or more promoters that are capable of directing expression of said polynucleotides in the microbial cell, wherein the fatty acids comprise oleic acid, palmitic acid, ω6 fatty acids which comprise linoleic acid (LA) and optionally γ-linolenic acid (GLA), ω3 fatty acids which comprise α-linolenic acid (ALA), stearidonic acid (SDA), and docosapentaenoic acid (DPA), and optionallyeicosapentaenoic acid (EPA) and/or eicosatetraenoic acid (ETA), and wherein the level of DPA in the total fatty acid content of the lipid of the seed or microbial cell is between 7% and 35%. In a preferred embodiment of this aspect, DHA is present at a level of less than 2% or less than 0.5% of the total fatty acid content of the lipid of the seed and of the extracted lipid and more preferably is not detected in the total fatty acid content of the lipids.

In another aspect, the present invention provides a cell, preferably a cell in or from a plant such as an oilseed plant or part thereof such as a seed, or an oilseed plant or part thereof, preferably a *Brassica* plant or a *C. sativa* plant, or a microbial cell, comprising a) fatty acids in an esterified form, the fatty acids comprising docosapentaenoic acid (DPA), wherein at least 35% of the DPA esterified in the form of triacylglycerol (TAG) is esterified at the sn-2 position of the TAG, and b) exogenous polynucleotides encoding one of the following sets of enzymes;

i) an 1-acyl-glycerol-3-phosphate acyltransferase (LPAAT), an ω3-desaturase, a Δ6-desaturase, a Δ5-desaturase, a Δ6-elongase and a Δ5-elongase, ii) an 1-acyl-glycerol-3-phosphate acyltransferase (LPAAT), a Δ15-desaturase, a Δ6-desaturase, a Δ5-desaturase, a Δ6-elongase and a Δ5-elongase, iii) an 1-acyl-glycerol-3-phosphate acyltransferase (LPAAT), a Δ12-desaturase, a Δ6-desaturase, a Δ5-desaturase, a Δ6-elongase and a Δ5-elongase, iv) an 1-acyl-glycerol-3-phosphate acyltransferase (LPAAT), a Δ12-desaturase, a ω3-desaturase and/or a Δ15-desaturase, a Δ6-desaturase, a Δ5-desaturase, a Δ6-elongase and an Δ5-elongase, v) an 1-acyl-glycerol-3-phosphate acyltransferase (LPAAT), an ω3-desaturase, a Δ8-desaturase, a Δ5-desaturase, a Δ9-elongase, and a Δ5-elongase, vi) an 1-acyl-glycerol-3-phosphate acyltransferase (LPAAT), a Δ15-desaturase, a Δ8-desaturase, a Δ5-desaturase, a Δ9-elongase and a Δ5-elongase, vii) an 1-acyl-glycerol-3-phosphate acyltransferase (LPAAT), a Δ12-desaturase, a Δ8-desaturase, a Δ5-desaturase, a Δ9-elongase and a Δ5-elongase, viii) an 1-acyl-glycerol-3-phosphate acyltransferase (LPAAT), a Δ12-desaturase, a ω3-desaturase and/or a Δ15-desaturase, a Δ8-desaturase, a Δ5-desaturase, a Δ9-elongase and a Δ5-elongase, wherein each polynucleotide is operably linked to one or more promoters that are capable of directing expression of said polynucleotides in the cell. Preferably, the LPAAT can use a C22 polyunsaturated fatty acyl-CoA substrate such as DPA-CoA and the level of DPA in the total fatty acid content of the extracted lipid is between about 1% and 35%, or between about 7% and 35% or between about 20.1% and 35%. In embodiments, at least about 40%, at least about 45%, at least about 48%, between 35% and about 60%, or between 35% and about 50%, of the DPA esterified in the form of triacylglycerol (TAG) is esterified at the sn-2 position of the TAG.

In preferred embodiments of each of the above two aspects, the Δ15-desaturase is a fungal Δ15-desaturase and the ω3-desaturase is a fungal ω3-desaturase.

In a preferred embodiment, the oilseed plant, microbial cell or cell of the invention has, where relevant, one or more of the features defined herein, for example as defined above in relation to extracted plant lipid, extracted microbial lipid or a process for the production thereof.

Examples of oilseed plants include, but are not limited to, *Brassica* sp., *Gossypium hirsutum, Linum usitatissimum, Helianthus* sp., *Carthamus tinctorius, Glycine max, Zea mays, Arabidopsis thaliana, Sorghum bicolor, Sorghum vulgare, Avena sativa, Trifolium* sp., *Elaesis guineenis, Nicotiana benthamiana, Hordeum vulgare, Lupinus angustifolius, Oryza sativa, Oryza glaberrima, Camelina sativa*, or *Crambe abyssinica*. In an embodiment, the plant is a *Brassica* sp. plant, a *C. sativa* plant or a *G. max* (soybean) plant. In an embodiment, the oilseed plant is a canola, *B. juncea, Glycine max, Camelina sativa* or *Arabidopsis thaliana* plant. In an alternate embodiment, the oilseed plant is other than *A. thaliana* and/or other than *C. sativa*. In an embodiment, the oilseed plant is a plant other than *G. max* (soybean). The plant is preferably *Brassica* sp. or *Camelina sativa*. In an embodiment, the oilseed plant is in the field, or was grown in the field, or was grown in a glasshouse under standard conditions, for example as described in Example 1.

In an embodiment, one or more of the desaturases used in a process of the invention or present in a cell, or plant or part thereof of the invention, is capable of using an acyl-CoA substrate. In a preferred embodiment, one or more of the Δ6-desaturase, Δ5-desaturase and Δ8-desaturase, if present, is capable of using an acyl-CoA substrate, preferably each of the i) Δ6-desaturase and Δ5-desaturase or ii) Δ5-desaturase and Δ8-desaturase is capable of using an acyl-CoA substrate. In an embodiment, a Δ12-desaturase and/or an ω3-desaturase is capable of using an acyl-CoA substrate. The acyl-CoA substrate is preferably an ALA-CoA for Δ6-desaturase, ETA-CoA for Δ5-desaturase, and ETrA-CoA for Δ8-desaturase, oleoyl-CoA for the Δ12-desaturase, or one or more of LA-CoA, GLA-CoA, and ARA-CoA for ω3-desaturase.

In an embodiment, mature, harvested seed of the plant has a DPA content of at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed, about 80 mg per gram seed, or between about 30 mg and about 80 mg per gram seed.

In a further aspect, the present invention provides a *Brassica napus, B. juncea* or *Camelina sativa* plant which is capable of producing seed comprising DPA, wherein mature, harvested seed of the plant has a DPA content of at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed, about 80 mg per gram seed, or between about 30 mg and about 80 mg per gram seed.

In another aspect, the present invention provides a plant cell of a plant of the invention comprising the exogenous polynucleotides defined herein.

Also provided is a plant part, preferably a seed, or recombinant cells such as microbial cells which has one or more of the following features i) is from a plant of the invention, ii) comprises lipid as defined herein, or iii) can be used in a process of the invention.

In yet another aspect, the present invention provides mature, harvested *Brassica napus, B. juncea* or *Camelina sativa* seed comprising DPA and a moisture content of between about 4% and about 15% by weight, preferably between about 6% and about 8% by weight or between about 4% and about 8% by weight, more preferably between about 4% and about 6% by weight, wherein the DPA content of the seed is at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed, about 80 mg per gram seed, or between about 30 mg and about 80 mg per gram seed.

In an embodiment, the cell of the invention, the oilseed plant of the invention, the *Brassica napus, B. juncea* or *Camelina sativa* plant of the invention, the plant part of the invention, or the seed of the invention, can be used to produce extracted lipid comprising one or more or all of the features defined herein.

In yet a further aspect, the present invention provides a method of producing a plant or cell which can be used to produce extracted lipid of the invention, the method comprising a) assaying the level of DPA in lipid produced by one or more plant parts such as seeds or recombinant cells such as microbial cells from a plurality of plants or recombinant cells such as microbial cells, each plant or recombinant cell such as a microbial cell comprising one or more exogenous polynucleotides encoding one of the following sets of enzymes;

i) an ω3-desaturase, a Δ6-desaturase, a Δ5-desaturase, a Δ6-elongase and a Δ5-elongase, ii) a Δ15-desaturase, a Δ6-desaturase, a Δ5-desaturase, a Δ6-elongase and a Δ5-elongase, iii) a Δ12-desaturase, a Δ6-desaturase, a Δ5-desaturase, a Δ6-elongase and an Δ5-elongase, iv) a Δ12-desaturase, a ω3-desaturase or a Δ15-desaturase, a Δ6-desaturase, a Δ5-desaturase, a Δ6-elongase and an Δ5-elongase, v) an ω3-desaturase, a Δ8-desaturase, a Δ5-desaturase, a Δ9-elongase and an Δ5-elongase, vi) a Δ15-desaturase, a Δ8-desaturase, a Δ5-desaturase, a Δ9-elongase and a Δ5-elongase, vii) a Δ12-desaturase, a Δ8-desaturase, a Δ5-desaturase, a Δ9-elongase and an Δ5-elongase, viii) a Δ12-desaturase, a ω3-desaturase or a Δ15-desaturase, a Δ8-desaturase, a Δ5-desaturase, a Δ9-elongase and an Δ5-elongase, ix) an ω3-desaturase, a Δ6-desaturase, a Δ5-desaturase, a Δ6-elongase and a Δ5-elongase, x) a Δ15-desaturase, a Δ6-desaturase, a Δ5-desaturase, a Δ6-elongase and a Δ5-elongase, or xi) a Δ12-desaturase, a Δ6-desaturase, a Δ5-desaturase, a Δ6-elongase and an Δ5-elongase, wherein each polynucleotide is operably linked to one or more promoters that are capable of directing expression of said polynucleotides in a cell of a plant part or recombinant cell, and b) identifying a plant or recombinant cell, from the plurality of plants or recombinant cells, which can be used to produce extracted plant lipid or cell lipid of the invention in one or more of its parts, and c) optionally, producing progeny plants or recombinant cells from the identified plant or recombinant cell, or seed therefrom.

In an embodiment, the plant or recombinant cell further comprises an exogenous polynucleotide encoding an LPAAT as defined herein.

Preferably, the progeny plant is at least a second or third generation removed from the identified plant, and is preferably homozygous for the one or more polynucleotides. More preferably, the one or more polynucleotides are present in the progeny plant at only a single insertion locus. That is, the invention provides such a method which can be used as a screening method to identify a plant or seed therefrom from a plurality of transformed candidate plants or seeds, wherein the identified plant or its progeny plant produces lipid of the invention, preferably in its seed. Such a plant or progeny plant or its seed is selected if it produces lipid of the invention, in particular having the specified DPA level, or is not selected if it does not produce lipid of the invention.

In an embodiment, the exogenous polynucleotide(s) present in a cell such as a microbial cell, or plant or part thereof as defined herein, become stably integrated into the genome of the cell, plant or the plant part such as seed. Preferably, the exogenous polynucleotide(s) become stably integrated into the genome of the cell, plant or plant part such as seed at a single locus in the genome, and is preferably homozygous for the insertion. More preferably, the plant, plant part or seed is further characterised in that it is lacking exogenous polynucleotides other than one or more T-DNA molecules. That is, no exogenous vector sequences are integrated into the genome other than the T-DNA sequences.

In an embodiment, before step a) the method includes introducing the one or more exogenous polynucleotides into one or more cells of the plant.

Also provided is a plant produced using a method of the invention, and seeds of such plants.

In an embodiment, the plant of the invention is both male and female fertile, preferably has levels of both male and female fertility that are at least 70% relative to, or preferably are about the same as, a corresponding wild-type plant. In an embodiment, the pollen produced by the plant of the invention or the plant produced from the seed of the invention is 90-100% viable as determined by staining with a viability stain. For example, the pollen viability may be assessed as described in Example 1.

In another aspect, the present invention provides a method of producing seed, the method comprising, a) growing a plant of the invention, or a plant which produces a part of the invention, preferably in a field as part of a population of at least 1000 or 2000 or 3000 such plants or in an area of at least 1 hectare or 2 hectares or 3 hectares planted at a standard planting density, alternatively in a glasshouse under standard conditions, b) harvesting seed from the plant or plants, and c) optionally, extracting lipid from the seed, preferably to produce oil with a total DPA yield of at least 60 kg or 70 kg or 80 kg DPA/hectare.

In an embodiment, the plant, plant cell, plant part or seed, or recombinant cell, of the invention has one or more of the following features i) its oil is as defined herein, or ii) the plant part or seed or recombinant cell is capable of being used in a process of the invention.

For example, the seed can be used to produce a plant of the invention. The plant may be grown in the field or in a glasshouse under standard conditions, for example as described in Example 1.

In a further aspect, the present invention provides lipid, or oil, produced by, or obtained from, using the process of the invention, the cell of the invention, the oilseed plant of the invention, the *Brassica* sp., *Brassica napus, B. juncea, G. max* or *Camelina sativa* plant of the invention, the plant part of the invention, the seed of the invention, or the plant, plant cell, plant part or seed of the invention. Preferably, the lipid or oil is purified to remove contaminants such as nucleic acid (DNA and/or RNA), protein and/or carbohydrate, or pigments such as chlorophyll. The lipid or oil may also be purified to enrich the proportion of TAG, for example by removal of free fatty acids (FFA) or phospholipid.

In an embodiment, the lipid or oil is obtained by extraction of oil from an oilseed. Examples of oil from oilseeds include, but are not limited to, canola oil (*Brassica napus, Brassica rapa* ssp.), mustard oil (*Brassica juncea*), other *Brassica* oil, sunflower oil (*Helianthus annus*), linseed oil (*Linum usitatissimum*), soybean oil (*Glycine max*), safflower oil (*Carthamus tinctorius*), corn oil (*Zea mays*), tobacco oil (*Nicotiana tabacum*), peanut oil (*Arachis hypogaea*), palm oil, cottonseed oil (*Gossypium hirsutum*), coconut oil (*Cocos nucifera*), avocado oil (*Persea americana*), olive oil (*Olen europaea*), cashew oil (*Anacardium occidentale*), *Macadamia* oil (*Macadamia intergrifolia*), almond oil (*Prunus amygdalus*) or *Arabidopsis* seed oil (*Arabidopsis thaliana*).

In an embodiment, a cell (recombinant cell) of, or used in, the invention is a microbial cell such as a cell suitable for fermentation, preferably an oleaginous microbial cell which is capable of accumulating triacylglycerols to a level of at least 25% on a weight basis. Preferred fermentation processes are anaerobic fermentation processes, as are well known in the art. Suitable fermenting cells, typically microorganisms are able to ferment, i.e., convert, sugars, such as glucose or maltose, directly or indirectly into the desired fatty a cids. Examples of fermenting microorganisms include fungal organisms, such as yeast. As used herein, "yeast" includes *Saccharomyces* spp., *Saccharomyces cerevisiae, Saccharomyces carlbergensis, Candida* spp., *Kluveromyces* spp., *Pichia* spp., *Hansenula* spp., *Trichoderma* spp., *Lipomyces starkey*, and preferably *Yarrowia lipolytica.*

In a further aspect, the present invention provides fatty acid produced by, or obtained from, using the process of the invention, the cell of the invention, the oilseed plant of the invention, the *Brassica* sp., *Brassica napus, B. juncea, G. max* or *Camelina sativa* plant of the invention, the plant part of the invention, the seed of the invention, or the plant, plant cell, plant part or seed of the invention. Preferably the fatty acid is DPA. The fatty acid may be in a mixture of fatty acids having a fatty acid composition as described herein, or may be enriched so that the fatty acid, preferably DPA, comprises at least 40% or at least 90% of the fatty acid content of the mixture. In an embodiment, the fatty acid is non-esterified. Alternatively, the fatty acid is esterified such as, for example, to a methyl, ethyl, propyl or butyl group.

Also provided is seedmeal obtained from seed of the invention or obtained from a plant of the invention. Preferred seedmeal includes, but not necessarily limited to, *Brassica* sp., *Brassica napus, B. juncea, Camelina sativa* or *Glycine max* seedmeal. In an embodiment, the seedmeal comprises an exogenous polynucleotide(s) and/or genentic constructs as defined herein. In a preferred embodiment, the seedmeal retains some of the lipid or oil produced in the seed from which the seedmeal is obtained, but at a low level (for example, less than 2% by weight) after extraction of most of the lipid or oil. The seedmeal may be used as an animal feed or as an ingredient in food production.

In another aspect, the present invention provides a composition comprising one or more of the lipid or oil of the invention, the fatty acid of the invention, the cell according of the invention, the oilseed plant of the invention, the *Brassica* sp., *Brassica napus, B. juncea, Glycine max* or *Camelina sativa* plant of the invention, the plant part of the invention, the seed of the invention, or the seedmeal of the invention. In embodiments, the composition comprises a carrier suitable for pharmaceutical, food or agricultural use, a seed treatment compound, a fertiliser, another food or feed ingredient, or added protein or vitamins.

Also provided is feedstuffs, cosmetics or chemicals comprising one or more of the lipid or oil of the invention, the fatty acid of the invention, the cell according of the invention, the oilseed plant of the invention, the *Brassica* sp., *Brassica napus, B. juncea, Glycine max* or *Camelina sativa* plant of the invention, the plant part of the invention, the seed of the invention, the seedmeal of the invention, or the composition of the invention. A preferred feedstuff is infant formula comprising the lipid or oil of the invention.

In another aspect, the present invention provides a method of producing a feedstuff, preferably infant formula, the method comprising mixing one or more of the lipid or oil of the invention, the fatty acid of the invention, the cell according of the invention, the oilseed plant of the invention, the *Brassica* sp., *Brassica napus, B. juncea, Glycine max* or *Camelina saliva* plant of the invention, the plant part of the invention, the seed of the invention, the seedmeal of the invention, or the composition of the invention, with at least one other food ingredient. The method may comprise steps of blending, cooking, baking, extruding, emulsifying or otherwise formulating the feedstuff, or packaging the feedstuff, or of analysing the amount of lipid or oil in the feedstuff.

In another aspect, the present invention provides a method of treating or preventing a condition which would benefit from a PUFA, preferably DPA, the method comprising administering to a subject one or more of the lipid or oil of the invention, the fatty acid of the invention, the cell according of the invention, the oilseed plant of the invention, the *Brassica* sp., *Brassica napus, B. juncea, Glycine max* or *Camelina sativa* plant of the invention, the plant part of the invention, the seed of the invention, the seedmeal of the invention, the composition of the invention, or the feedstuff of the invention. In a preferred embodiment, the PUFA is administered in the form of a pharmaceutical composition comprising an ethyl ester of the PUFA. The subject may be a human or an animal other than a human.

Examples of conditions which would benefit from a PUFA include, but are not limited to, elevated serum triglyceride levels, elevated serum cholesterol levels such as elevated LDL cholesterol levels, cardiac arrhythmia's, angioplasty, inflammation, asthma, psoriasis, osteoporosis, kidney stones, AIDS, multiple sclerosis, rheumatoid arthritis, Crohn's disease, schizophrenia, cancer, foetal alcohol syndrome, attention deficient hyperactivity disorder, cystic fibrosis, phenylketonuria, unipolar depression, aggressive hostility, adrenoleukodystophy, coronary heart disease, hypertension, diabetes, obesity, Alzheimer's disease, chronic obstructive pulmonary disease, ulcerative colitis, restenosis after angioplasty, eczema, high blood pressure, platelet aggregation, gastrointestinal bleeding, endometriosis, premenstrual syndrome, myalgic encephalomyelitis, chronic fatigue after viral infections or an ocular disease.

Also provided is the use of one or more of the lipid or oil of the invention, the fatty acid of the invention, the cell according of the invention, the oilseed plant of the invention, the *Brassica* sp., *Brassica napus, B. juncea, Glycine max* or *Camelina sativa* plant of the invention, the plant part of the invention, the seed of the invention, the seedmeal of the invention, the composition of the invention, or the feedstuff of the invention for the manufacture of a medicament for treating or preventing a condition which would benefit from a PUFA preferably DPA.

The production of the medicament may comprise mixing the oil of the invention with a pharmaceutically acceptable carrier, for treatment of a condition as described herein. The method may comprise firstly purifying the oil and/or transesterification, and/or fractionation of the oil to increase the level of DPA. In a particular embodiment, the method comprises treating the lipid or oil such as canola oil to convert the fatty acids in the oil to alkyl esters such as methyl or ethyl esters. Further treatment such as fractionation or distillation may be applied to enrich the lipid or oil for the DPA. In a preferred embodiment, the medicament comprises ethyl esters of DPA. In an even more preferred embodiment, the level of ethyl esters of DPA in the medicament is between 30% and 50%, or at least 80% or at least about 85% or at least 90% or at least about 95%. The medicament may further comprise ethyl esters of EPA, such as between 30% and 50%, or at least 90%, of the total fatty acid content in the medicament. Such medicaments are suitable for administration to human or animal subjects for treatment of medical conditions as described herein.

In another aspect, the present invention provides a method of trading seed, comprising obtaining seed of the invention, and trading the obtained seed for pecuniary gain.

In an embodiment, obtaining the seed comprises cultivating plants of the invention and/or harvesting the seed from the plants.

In another embodiment, obtaining the seed further comprises placing the seed in a container and/or storing the seed.

In a further embodiment, obtaining the seed further comprises transporting the seed to a different location.

In yet another embodiment, the method further comprises transporting the seed to a different location after the seed is traded.

In a further embodiment, the trading is conducted using electronic means such as a computer.

In yet a further aspect, the present invention provides a process of producing bins of seed comprising:

a) swathing, windrowing and/or reaping above-ground parts of plants comprising seed of the invention, b) threshing and/or winnowing the parts of the plants to separate the seed from the remainder of the plant parts, and c) sifting and/or sorting the seed separated in step b), and loading the sifted and/or sorted seed into bins, thereby producing bins of seed.

In an embodiment, where relevant, the lipid or oil, preferably seedoil, of, or useful for, the invention has fatty levels about those provided in a Table in the Examples section.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Aerobic DPA biosynthesis pathways.

Figure 2:
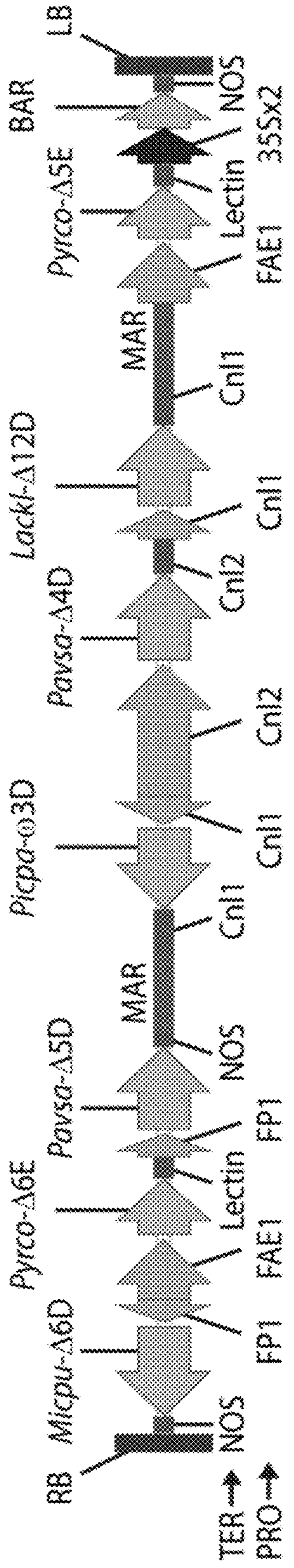

FIG. 2. Map of the T-DNA insertion region between the left and right borders of pJP3416-GA7. RB denotes right border; LB, left border; TER, transcription terminator/polyadenylation region; PRO, promoter; Coding regions are indicated above the arrows, promoters and terminators below the arrows. Micpu-Δ6D, *Micromonas pusilla* Δ6-desaturase; Pyrco-Δ6E, *Pyramimonas cordata* Δ6-elongase; Pavsa-Δ5D, *Pavlova salina* Δ5-desaturase; Picpa-ω3D, *Pichia pastoris* ω3-desaturase; Pavsa-Δ4D, *P. sauna* Δ4-desaturase; Lackl-Δ12D, *Lachancea kluyveri* Δ12-desaturase; Pyrco-Δ5E, *Pyramimonas cordata* Δ5-elongase. NOS denotes the *Agrobacterium tumefaciens* nopaline synthase transcription terminator/polyadenylation region; FP1, *Brassica napus* truncated napin promoter; FAE1, *Arabidopsis thaliana* FAE1 promoter; Lectin, *Glycine max* lectin transcription terminator/polyadenylation region; Cn11 and Cn12 denotes the *Linum usitatissimum* conlinin1 or conlinin2 promoter or terminator. MAR denotes the Rb7 matrix attachment region from *Nicotiana tabacum.*

Figure 3:
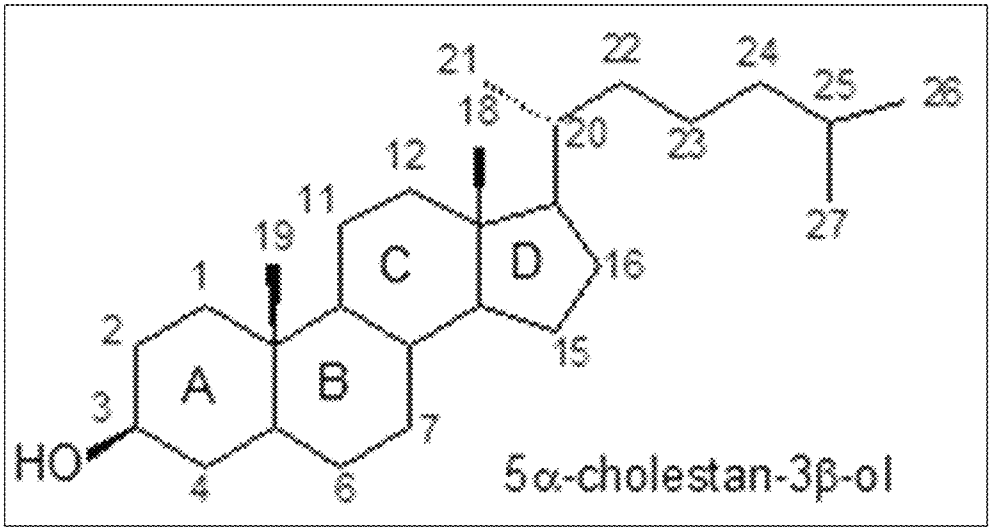
Figure 3:
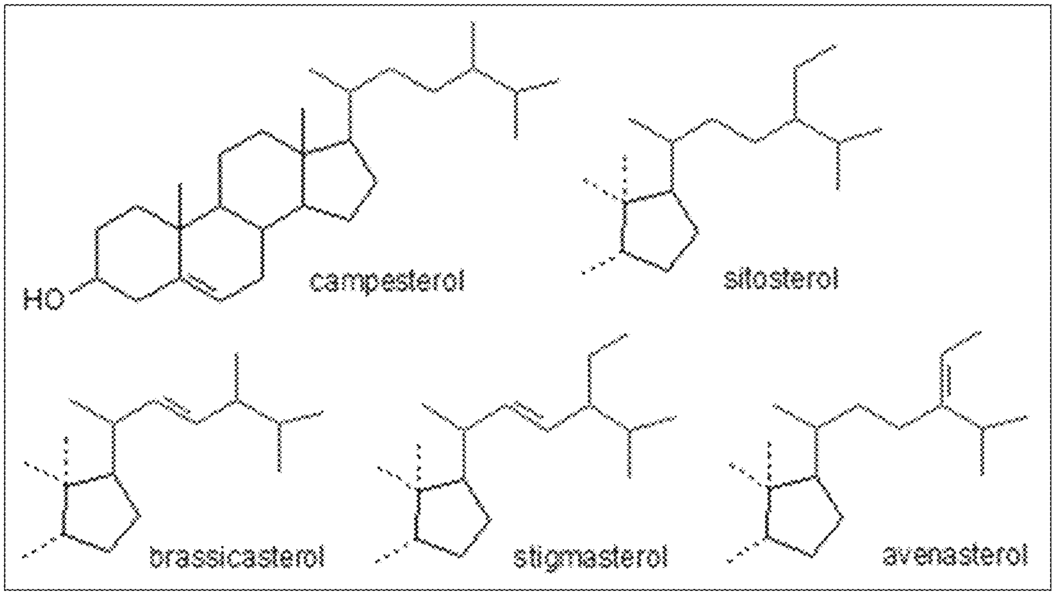

FIG. 3. (A) Basic phytosterol structure with ring and side chain numbering. (B) Chemical structures of some of the phytosterols.

Figure 4:
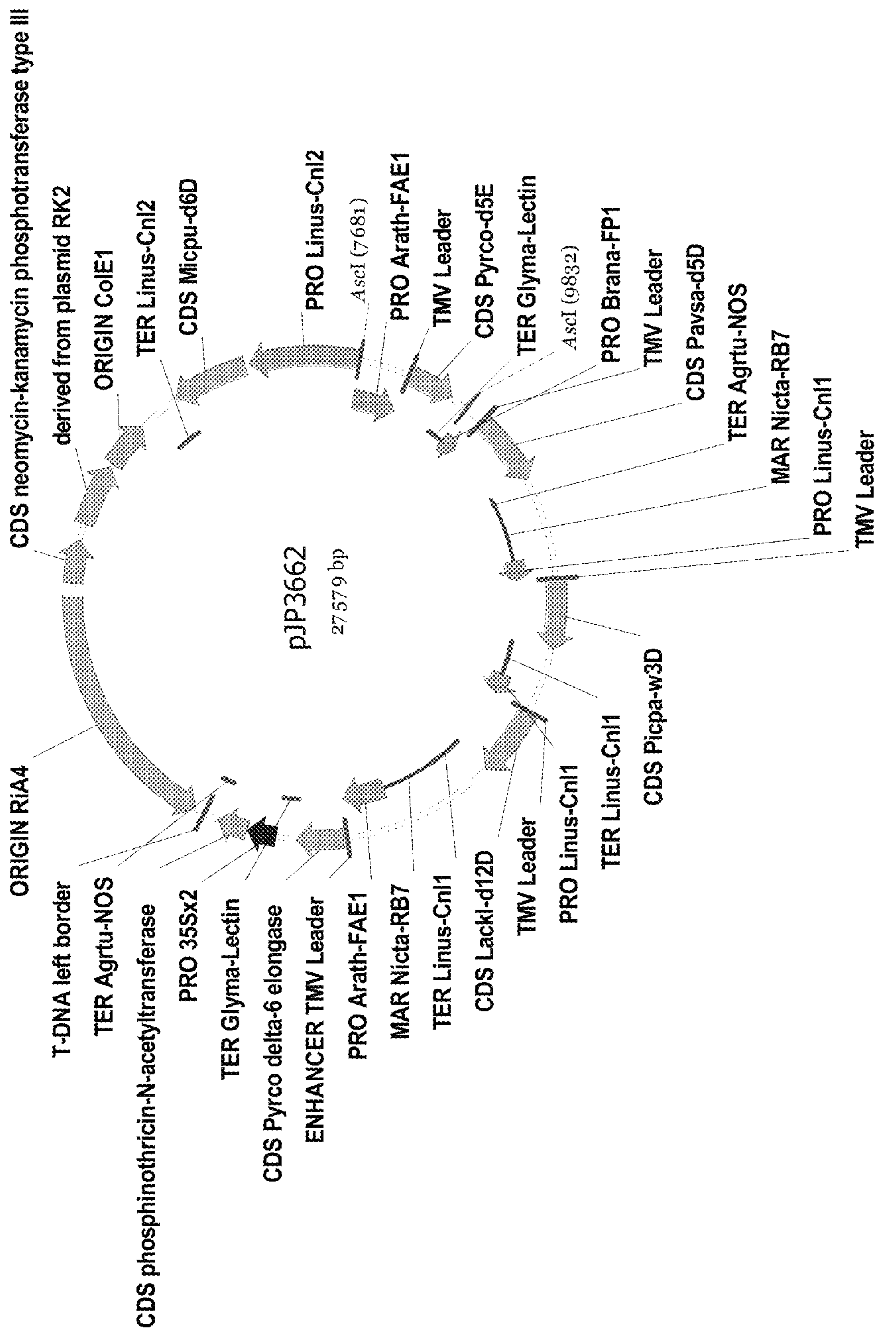

FIG. 4. Map of the T-DNA insertion region between the left and right borders of pJP3662. RB denotes right border; LB, left border; TER, transcription terminator/polyadenylation region; PRO, promoter; Coding regions are indicated above the arrows, promoters and terminators below the arrows. Micpu-Δ6D, *Micromonas pusilla* Δ6-desaturase; Pyrco-Δ6E, *Pyramimonas cordata* Δ6-elongase; Pavsa-Δ5D, *Pavlova salina* Δ5-desaturase; Picpa-ω3D, *Pichia pastoris* ω3-desaturase; Lackl-Δ12D, *Lachancea kluyveri* Δ12-desaturase; Pyrco-Δ5E, *Pyramimonas cordata* Δ5-elongase. NOS denotes the *Agrobacterium tumefaciens* nopaline synthase transcription terminator/polyadenylation region; FP1, *Brassica napus* truncated napin promoter; FAE1, *Arabidopsis thaliana* FAE1 promoter; Lectin, *Glycine max* lectin transcription terminator/polyadenylation region; Cn11 denotes the *Linum usitatissimum* conlinin1 promoter or terminator. MAR denotes the Rb7 matrix attachment region from *Nicotiana tabacum.*

KEY TO THE SEQUENCE LISTING

SEQ ID NO:1—pJP3416-GA7 nucleotide sequence.

SEQ ID NO:2—pGA7-mod_B nucleotide sequence.

SEQ ID NO:3—Codon-optimized open reading frame for expression of *Lachancea kluyveri* Δ12 desaturase in plants.

SEQ ID NO:4—*Lachancea kluyveri* Δ12-desaturase.

SEQ ID NO:5—Codon-optimized open reading frame for expression of *Pichia pastoris* ω3 desaturase in plants.

SEQ ID NO:6—*Pichia pastoris* ω3 desaturase.

SEQ ID NO:7—Open reading frame encoding *Micromonas pusilla* Δ6-desaturase.

SEQ ID NO:8—Codon-optimized open reading frame for expression of *Micromonas pusilla* Δ6-desaturase in plants.

SEQ ID NO:9—*Micromonas pusilla* Δ6-desaturase.

SEQ ID NO:10—Open reading frame encoding *Ostreococcus lucimarinus* Δ6-desaturase.

SEQ ID NO:11—Codon-optimized open reading frame for expression of *Ostreococcus lucimarinus* Δ6-desaturase in plants.

SEQ ID NO:12—*Ostreococcus lucimarinus* Δ6-desaturase.

SEQ ID NO:13—*Ostreococcus tauri* Δ6-desaturase.

SEQ ID NO:14—Open reading frame encoding *Pyramimonas cordata* Δ6-elongase.

SEQ ID NO:15—Codon-optimized open reading frame for expression of *Pyramimonas cordata* Δ6-elongase in plants (truncated at 3' end and encoding functional elongase).

SEQ ID NO:16—*Pyramimonas cordata* Δ6-elongase.

SEQ ID NO:17—Truncated *Pyramimonas cordata* Δ6-elongase.

SEQ ID NO:18—Open reading frame encoding *Pavlova salina* Δ5-desaturase.

SEQ ID NO:19—Codon-optimized open reading frame for expression of *Pavlova salina* Δ5-desaturase in plants.

SEQ ID NO:20—*Pavlova salina* Δ5-desaturase.

SEQ ID NO:21—Open reading frame encoding *Pyramimonas cordata* Δ5-desaturase.

SEQ ID NO:22—*Pyramimonas cordata* Δ5-desaturase.

SEQ ID NO:23—Open reading frame encoding *Pyramimonas cordata* Δ5-elongase.

SEQ ID NO:24—Codon-optimized open reading frame for expression of *Pyramimonas cordata* Δ5-elongase in plants.

SEQ ID NO:25—*Pyramimonas cordata* Δ5-elongase.

SEQ ID NO:26—Open reading frame encoding *Pavlova salina* Δ4-desaturase.

SEQ ID NO:27—Codon-optimized open reading frame for expression of *Pavlova salina* Δ4-desaturase in plants.

SEQ ID NO:28—*Pavlova salina* Δ4-desaturase.

SEQ ID NO:29—*Isochrysis galbana* Δ9-elongase.

SEQ ID NO:30—Codon-optimized open reading frame for expression of *Emiliania huxleyi* Δ9-elongase in plants.

SEQ ID NO:31—*Emiliania huxleyi* CCMP1516 Δ9-elongase.

SEQ ID NO:32—Open reading frame encoding *Pavlova pinguis* Δ9-elongase.

SEQ ID NO:33—*Pavlova pinguis* Δ9-elongase.

SEQ ID NO:34—Open reading frame encoding *Pavlova salina* Δ9-elongase.

SEQ ID NO:35—*Pavlova salina* Δ9-elongase.

SEQ ID NO:36—Open reading frame encoding *Pavlova salina* Δ8-desaturase.

SEQ ID NO:37—*Pavlova salina* Δ8-desaturase.

SEQ ID NO:38—V2 viral suppressor.

SEQ ID NO:39—Open reading frame encoding V2 viral suppressor.

SEQ ID NO: 40—*Arabidopsis thaliana* LPAAT2.

SEQ ID NO: 41—*Limnanthes alba* LPAAT.

SEQ ID NO: 42—*Saccharomyces cerevisiae* LPAAT.

SEQ ID NO: 43—*Micromonas pusilla* LPAAT.

SEQ ID NO: 44—*Mortierella alpina* LPAAT.

SEQ ID NO: 45—*Braccisa napus* LPAAT.

SEQ ID NO: 46—*Brassica napus* LPAAT.

SEQ ID NO: 47—*Phytophthora infestans* ω3 desaturase.

SEQ ID NO: 48—*Thalassiosira pseudonana* ω3 desaturase.

SEQ ID NO: 49—*Pythium irregulare* ω3 desaturase.

SEQ ID NO's: 50 to 58—Oligonucleotide primers/probes.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, fatty acid synthesis, transgenic plants, recombinant cells, protein chemistry, and biochemistry).

Unless otherwise indicated, the protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al. (editors), Current Protocols in Molecular Biology, Greene Pub. Associates and Wiley-Interscience (1988, including all updates until present), Ed Harlow and David Lane (editors), Antibodies: A Laboratory Manual, Cold Spring Harbour Laboratory, (1988), and J. E. Coligan et al. (editors), Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about" unless stated to the contrary, refers to +/−10%, more preferably +/−5%, more preferably +/−1% of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

As used herein, the terms "extracted plant lipid" and "isolated plant lipid" refer to a lipid composition which has been extracted from, for example by crushing, a plant or part thereof such as seed. The extracted lipid can be a relatively crude composition obtained by, for example, crushing a plant seed, or a more purified composition where most, if not all, of one or more or each of the water, nucleic acids, proteins and carbohydrates derived from the plant material have been removed. Examples of purification methods are described below. In an embodiment, the extracted or isolated plant lipid comprises at least about 60%, at least about 70%, at least about 80%, at least about 90%, or at least about 95% (w/w) lipid by weight of the composition. The lipid may be solid or liquid at room temperature, when liquid it is considered to be an oil. In an embodiment, extracted lipid of the invention has not been blended with another lipid such as DPA produced by another source (for example, DPA from fish oil). In an embodiment, following extraction the ratio of one or more or all of, oleic acid to DPA, palmitic acid to DPA, linoleic acid to DPA, and total ω6 fatty acids: total ω3 fatty acids, has not been significantly altered (for example, no greater than a 10% or 5% alteration) when compared to the ratio in the intact seed or cell. In an another embodiment, the extracted plant lipid has not been exposed to a procedure, such as hydrogenation or fractionation, which may alter the ratio of one or more or all of, oleic acid to DPA, palmitic acid to DPA, linoleic acid to DPA, and total ω6 fatty acids: total ω3 fatty acids, when compared to the ratio in the intact seed or cell. When the extracted plant lipid of the invention is comprised in an oil, the oil may further comprise non-fatty acid molecules such as sterols.

As used herein, the terms "extracted plant oil" and "isolated plant oil" refer to a substance or composition comprising extracted plant lipid or isolated plant lipid and which is a liquid at room temperature. The oil is obtained from a plant or part thereof such as seed. The extracted or isolated oil can be a relatively crude composition obtained by, for example, crushing a plant seed, or a more purified composition where most, if not all, of one or more or each of the water, nucleic acids, proteins and carbohydrates derived from the plant material have been removed. The composition may comprise other components which may be lipid or non-lipid. In an embodiment, the oil composition comprises at least about 60%, at least about 70%, at least about 80%, at least about 90%, or at least about 95% (w/w) extracted plant lipid. In an embodiment, extracted oil of the invention has not been blended with another oil such as DPA produced by another source (for example, DPA from fish oil). In an embodiment, following extraction, the ratio of one or more or all of, oleic acid to DPA, palmitic acid to DPA, linoleic acid to DPA, and total ω6 fatty acids: total ω3 fatty acids, has not been significantly altered (for example, no greater than a 10% or 5% alteration) when compared to the ratio in the intact seed or cell. In an another embodiment, the extracted plant oil has not been exposed to a procedure, such as hydrogenation or fractionation, which may alter the ratio of one or more or all of, oleic acid to DPA, palmitic acid to DPA, linoleic acid to DPA, and total ω6 fatty acids: total ω3 fatty acids, when compared to the ratio in the intact seed or cell. Extracted plant oil of the invention may comprise non-fatty acid molecules such as sterols.

As used herein, terms such as "extracted microbial lipid" or "extracted microbial oil" have analogous meanings as the corresponding terms "extracted plant lipid" and "extracted plant oil" respectively, with the main difference being the source of the lipid or oil.

As used herein, an "oil" is a composition comprising predominantly lipid and which is a liquid at room temperature. For instance, oil of the invention preferably comprises at least 75%, at least 80%, at least 85% or at least 90% lipid by weight. Typically, a purified oil comprises at least 90% triacylglycerols (TAG) by weight of the lipid in the oil. Minor components of an oil such as diacylglycerols (DAG), free fatty acids (FFA), phospholipid and sterols may be present as described herein.

As used herein, the term "fatty acid" refers to a carboxylic acid (or organic acid), often with a long aliphatic tail, either saturated or unsaturated. Typically fatty acids have a carbon-carbon bonded chain of at least 8 carbon atoms in length, more preferably at least 12 carbons in length. Preferred fatty acids of the invention have carbon chains of 18-22 carbon atoms (C18, C20, C22 fatty acids), more preferably 20-22 carbon atoms (C20, C22) and most preferably 22 carbon atoms (C22). Most naturally occurring fatty acids have an even number of carbon atoms because their biosynthesis involves acetate which has two carbon atoms. The fatty acids may be in a free state (non-esterified) or in an esterified form such as part of a triglyceride, diacylglyceride, monoacylglyceride, acyl-CoA (thio-ester) bound or other bound form. The fatty acid may be esterified as a phospholipid such as a phosphatidylcholine, phosphatidylethanolamine, phosphatidylserine, phosphatidylglycerol, phosphatidy-linositol or diphosphatidylglycerol forms. In an embodiment, the fatty acid is esterified to a methyl or ethyl group, such as, for example, a methyl or ethyl ester of a C20 or C22 PUFA. Preferred fatty acids are the methyl or ethyl esters of EPA or DPA, or EPA, DPA and DHA, or EPA and DPA.

"Saturated fatty acids" do not contain any double bonds or other functional groups along the chain. The term "saturated" refers to hydrogen, in that all carbons (apart from the carboxylic acid [—COOH] group) contain as many hydrogens as possible. In other words, the omega (ω) end contains 3 hydrogens (—CH3—) and each carbon within the chain contains 2 hydrogens (—CH2—).

"Unsaturated fatty acids" are of similar form to saturated fatty acids, except that one or more alkene functional groups exist along the chain, with each alkene substituting a singly-bonded "—CH2—CH2—" part of the chain with a doubly-bonded "—CH═CH—" portion (that is, a carbon double bonded to another carbon). The two next carbon atoms in the chain that are bound to either side of the double bond can occur in a cis or trans configuration, preferably in the cis configuration. In an embodiment, the lipid or oil or the invention has a fatty acid composition which comprises less than 1% fatty acids having a carbon-carbon double bond in the trans configuration (trans fatty acids).

As used herein, the term "monounsaturated fatty acid" refers to a fatty acid which comprises at least 12 carbon atoms in its carbon chain and only one alkene group (carbon-carbon double bond) in the chain. As used herein, the terms "polyunsaturated fatty acid" or "PUFA" refer to a fatty acid which comprises at least 12 carbon atoms in its carbon chain and at least two alkene groups (carbon-carbon double bonds).

As used herein, the terms "long-chain polyunsaturated fatty acid" and "LC-PUFA" refer to a fatty acid which comprises at least 20 carbon atoms in its carbon chain and at least two carbon-carbon double bonds, and hence include VLC-PUFAs. As used herein, the terms "very long-chain polyunsaturated fatty acid" and "VLC-PUFA" refer to a fatty acid which comprises at least 22 carbon atoms in its carbon chain and at least three carbon-carbon double bonds. Ordinarily, the number of carbon atoms in the carbon chain of the fatty acids refers to an unbranched carbon chain. If the carbon chain is branched, the number of carbon atoms excludes those in sidegroups. In one embodiment, the long-chain polyunsaturated fatty acid is an ω3 fatty acid, that is, having a desaturation (carbon-carbon double bond) in the third carbon-carbon bond from the methyl end of the fatty acid. In another embodiment, the long-chain polyunsaturated fatty acid is an ω6 fatty acid, that is, having a desaturation (carbon-carbon double bond) in the sixth carbon-carbon bond from the methyl end of the fatty acid. In a further embodiment, the long-chain polyunsaturated fatty acid is selected from the group consisting of; arachidonic acid (ARA, 20:4Δ5,8,11,14; ω6), eicosatetraenoic acid (ETA, 20:4Δ8,11,14,17, ω3), eicosapentaenoic acid (EPA, 20:5Δ5,8,11,14,17; ω3), docosapentaenoic acid (DPA, 22:5Δ7,10,13,16,19, ω3), or docosahexaenoic acid (DHA, 22:6Δ4,7,10,13,16,19, ω3). The LC-PUFA may also be dihomo-γ-linoleic acid (DGLA) or eicosatrienoic acid (ETrA, 20:3Δ11,14,17, ω3). It would readily be apparent that the LC-PUFA that is produced according to the invention may be a mixture of any or all of the above and may include other LC-PUFA or derivatives of any of these LC-PUFA. In a preferred embodiment, the ω3 fatty acids are at least DPA, or DPA and DHA, or EPA, DPA and DHA, or EPA and DPA. In an embodiment, DPA is present at a level of between about 7% and 30% or 35% and DHA is either absent or, if present, is present at a level of less than 2.0%, preferably less than 1.0%, more preferably less than 0.5% of the total fatty acid composition and most preferably absent or undetectable. This may be accomplished by the absence of a Δ4-desaturase activity in the cell. In an embodiment, the level of DPA is greater than the level of EPA, more preferably greater than the level of each of EPA and DHA, most preferably greater than the combined level of EPA and DHA. In this embodiment, DHA may be absent or, if present, is present at a level of less than 0.5% of the total fatty acid composition.

Furthermore, as used herein the terms "long-chain polyunsaturated fatty acid" (LC-PUFA) and "very long-chain polyunsaturated fatty acid" (VLC-PUFA) refer to the fatty acid being in a free state (non-esterified) or in an esterified form such as part of a triglyceride (triacylglycerol), diacylglyceride, monoacylglyceride, acyl-CoA bound or other bound form. In the triglyceride, the LC-PUFA or VLC-PUFA such as DPA may be esterified at the sn-1/3 or sn-2 positions, or the triglyceride may comprise two or three acyl groups selected from LC-PUFA and VLC-PUFA acyl groups. For example, the triglyceride may comprise DPA at both of the sn-1 and sn-3 positions. The fatty acid may be esterified as a phospholipid such as a phosphatidylcholine (PC), phosphatidylethanolamine, phosphatidylserine, phosphatidylglycerol, phosphatidyl-inositol or diphosphatidylglycerol forms. Thus, the LC-PUFA may be present as a mixture of forms in the lipid of a cell or a purified oil or lipid extracted from cells, tissues or organisms. In preferred embodiments, the invention provides oil comprising at least 75% or at least 85% triacylglycerols, with the remainder present as other forms of lipid such as those mentioned, with at least said triacylglycerols comprising the LC-PUFA. The oil may subsequently be further purified or treated, for example by hydrolysis with a strong base to release the free fatty acids, or by transesterification, distillation or the like.

As used herein, "total ω6 fatty acids" or "total ω6 fatty acid content" or the like refers to the sum of all the ω6 fatty acids, esterified and non-esterified, in the extracted lipid, oil, recombinant cell, plant part or seed, as the context determines, expressed as a percentage of the total fatty acid content. These ω6 fatty acids include (if present) LA, GLA, DGLA, ARA, EDA and ω6-DPA, and exclude any ω3 fatty acids and monounsaturated fatty acids. The ω6 fatty acids present in the plants, seeds, lipid or oils of the invention are all included in the class of polyunsaturated fatty acids (PUFA).

As used herein, "new ω6 fatty acids" or "new ω6 fatty acid content" or the like refers to the sum of all the ω6 fatty acids excluding LA, esterified and non-esterified, in the extracted lipid, oil, recombinant cell, plant part or seed, as the context determines, expressed as a percentage of the total fatty acid content. These new ω6 fatty acids are the fatty acids that are produced in the cells, plants, plant parts and seeds of the invention by the expression of the genetic constructs (exogenous polynucleotides) introduced into the cells, and include (if present) GLA, DGLA, ARA, EDA and ω6-DPA, but exclude LA and any ω3 fatty acids and monounsaturated fatty acids. Exemplary total ω6 fatty acid contents and new ω6 fatty acid contents are determined by conversion of fatty acids in a sample to FAME and analysis by GC, as described in Example 1.

As used herein, "total ω3 fatty acids" or "total ω3 fatty acid content" or the like refers to the sum of all the ω3 fatty acids, esterified and non-esterified, in the extracted lipid, oil, recombinant cell, plant part or seed, as the context determines, expressed as a percentage of the total fatty acid content. These ω3 fatty acids include (if present) ALA, SDA, ETrA, ETA, EPA, DPA and DHA, and exclude any ω6 fatty acids and monounsaturated fatty acids. The ω3 fatty acids present in the plants, seeds, lipid or oils of the invention are all included in the class of polyunsaturated fatty acids (PUFA).

As used herein, "new ω3 fatty acids" or "new ω3 fatty acid content" or the like refers to the sum of all the ω3 fatty acids excluding ALA, esterified and non-esterified, in the extracted lipid, oil, recombinant cell, plant part or seed, as the context determines, expressed as a percentage of the total fatty acid content. These new ω3 fatty acids are the ω3 fatty acids that are produced in the cells, plants, plant parts and seeds of the invention by the expression of the genetic constructs (exogenous polynucleotides) introduced into the cells, and include (if present) SDA, ETrA, ETA, EPA, DPA and DHA, but exclude ALA and any ω6 fatty acids and monounsaturated fatty acids. Exemplary total ω3 fatty acid contents and new ω3 fatty acid contents are determined by conversion of fatty acids in a sample to FAME and analysis by GC, as described in Example 1.

As the skilled person would appreciate, the term "obtaining a plant part" as a step in the process of the invention can include obtaining one or more plant parts for use in the process. Obtaining the plant part includes harvesting the plant part from a plant such as with a mechanical harvester, or purchasing the plant part, or receiving the plant part from a supplier. In another example, obtaining a plant part may be acquiring the plant from someone else who has harvested the plant part.

The desaturase, elongase and acyl transferase proteins and genes encoding them that may be used in the invention are any of those known in the art or homologues or derivatives thereof. Examples of such genes and encoded protein sizes are listed in Table 1. The desaturase enzymes that have been shown to participate in LC-PUFA biosynthesis all belong to the group of so-called "front-end" desaturases. Preferred proteins, or combinations of proteins, are those encoded by the genetic constructs provided herein as SEQ ID NOs: 1 and 2.

As used herein, the term "front-end desaturase" refers to a member of a class of enzymes that introduce a double bond between the carboxyl group and a pre-existing unsaturated part of the acyl chain of lipids, which are characterized structurally by the presence of an N-terminal cytochrome b5 domain, along with a typical fatty acid desaturase domain that includes three highly conserved histidine boxes (Napier et al., 1997).

Activity of any of the elongases or desaturases for use in the invention may be tested by expressing a gene encoding the enzyme in a cell such as, for example, a plant cell or preferably in somatic embryos or transgenic plants, and determining whether the cell, embryo or plant has an increased capacity to produce LC-PUFA compared to a comparable cell, embryo or plant in which the enzyme is not expressed.

In one embodiment one or more of the desaturases and/or elongases for use in the invention can purified from a microalga, i.e. is identical in amino acid sequence to a polypeptide which can be purified from a microalga.

Whilst certain enzymes are specifically described herein as "bifunctional", the absence of such a term does not necessarily imply that a particular enzyme does not possess an activity other than that specifically defined.

TABLE 1

Cloned genes involved in LC-PUFA biosynthesis

| Enzyme | Type of organism | Species | Accession Nos. | Protein size (aa's) | References |
|---|---|---|---|---|---|
| Δ4-desaturase | Protist | *Euglena gracilis* | AY278558 | 541 | Meyer et al., 2003 |
| | Algae | *Pavlova lutherii* | AY332747 | 445 | Tonon et al., 2003 |
| | | *Isochrysis galbana* | AAV33631 | 433 | Pereira et al., 2004b |
| | | *Pavlova salina* | AAY15136 | 447 | Zhou et al., 2007 |
| | Thraustochytrid | *Thraustochytrium aureum* | AAN75707<br>AAN75708<br>AAN75709<br>AAN75710 | 515 | N/A |
| | | *Thraustochytrium* sp. ATCC21685 | AAM09688 | 519 | Qiu et al. 2001 |
| Δ5-desaturase | Mammals | *Homo sapiens* | AF199596 | 444 | Cho et al., 1999b<br>Leonard et al., 2000b |
| | Nematode | *Caenorhabditis elegans* | AF11440, NM_069350 | 447 | Michaelson et al., 1998b; Watts and Browse, 1999b |
| | Fungi | *Mortierella alpina* | AF067654 | 446 | Michaelson et al., 1998a; Knutzon et al., 1998 |
| | | *Pythium irregulare* | AF419297 | 456 | Hong et al., 2002a |
| | | *Dictyostelium discoideum* | AB022097 | 467 | Saito et al., 2000 |
| | | *Saprolegnia diclina* | | 470 | WO02081668 |
| | Diatom | *Phaeodactylum tricornutum* | AY082392 | 469 | Domergue et al., 2002 |
| | Algae | *Thraustochytrium* sp | AF489588 | 439 | Qiu et al., 2001 |
| | | *Thraustochytrium aureum* | | 439 | WO02081668 |
| | | *Isochrysis galbana* | | 442 | WO02081668 |
| | Moss | *Marchantia polymorpha* | AY583465 | 484 | Kajikawa et al., 2004 |
| Δ6-desaturase | Mammals | *Homo sapiens* | NM_013402 | 444 | Cho et al., 1999a; Leonard et al., 2000 |
| | | *Mus musculus* | NM_019699 | 444 | Cho et al., 1999a |
| | Nematode | *Caenorhabditis elegans* | Z70271 | 443 | Napier et al., 1998 |
| | Plants | *Borago officinales* | U79010 | 448 | Sayanova et al., 1997 |
| | | *Echium* | AY055117<br>AY055118 | | Garcia-Maroto et al., 2002 |
| | | *Primula vialii* | AY234127 | 453 | Sayanova et al., 2003 |
| | | *Anemone leveillei* | AF536525 | 446 | Whitney et al., 2003 |
| | Mosses | *Ceratodon purpureus* | AJ250735 | 520 | Sperling et al., 2000 |
| | | *Marchantia polymorpha* | AY583463 | 481 | Kajikawa et al., 2004 |
| | | *Physcomitrella patens* | CAA11033 | 525 | Girke et al., 1998 |
| | Fungi | *Mortierella alpina* | AF110510<br>AB020032 | 457 | Huang et al., 1999; Sakuradani et al., 1999 |
| | | *Pythium irregulare* | AF419296 | 459 | Hong et al., 2002a |
| | | *Mucor circinelloides* | AB052086 | 467 | NCBI* |
| | | *Rhizopus* sp. | AY320288 | 458 | Zhang et al., 2004 |
| | | *Saprolegnia diclina* | | 453 | WO02081668 |
| | Diatom | *Phaeodactylum tricornutum* | AY082393 | 477 | Domergue et al., 2002 |
| | Bacteria | *Synechocystis* | L11421 | 359 | Reddy et al., 1993 |
| | Algae | *Thraustochytrium aureum* | | 456 | WO02081668 |
| Bifunctional Δ5/Δ6-desaturase | Fish | *Danio rerio* | AF309556 | 444 | Hastings et al., 2001 |
| C20 Δ8-desaturase | Algae | *Euglena gracilis* | AF139720 | 419 | Wallis and Browse, 1999 |
| | Plants | *Borago officinales* | AAG43277 | 446 | Sperling et al., 2001 |
| Δ6-elongase | Nematode | *Caenorhabditis elegans* | NM_069288 | 288 | Beaudoin et al., 2000 |
| | Mosses | *Physcomitrella patens* | AF428243 | 290 | Zank et al., 2002 |
| | | *Marchantia polymorpha* | AY583464 | 290 | Kajikawa et al., 2004 |
| | Fungi | *Mortierella alpina* | AF206662 | 318 | Parker-Barnes et al., 2000 |
| | Algae | *Pavlova lutheri*** | | 501 | WO 03078639 |
| | | *Thraustochytrium* | AX951565 | 271 | WO 03093482 |
| | | *Thraustochytrium* sp** | AX214454 | 271 | WO 0159128 |
| PUFA-elongase | Mammals | *Homo sapiens* | AF231981 | 299 | Leonard et al., 2000b; Leonard et al., 2002 |
| | | *Rattus norvegicus* | AB071985 | 299 | Inagaki et al., 2002 |
| | | *Rattus norvegicus*** | AB071986 | 267 | Inagaki et al., 2002 |
| | | *Mus musculus* | AF170907 | 279 | Tvrdik et al., 2000 |
| | | *Mus musculus* | AF170908 | 292 | Tvrdik et al., 2000 |
| | Fish | *Danio rerio* | AF532782 | 291 (282) | Agaba et al., 2004 |
| | | *Danio rerio*** | NM_199532 | 266 | Lo et al., 2003 |
| | Worm | *Caenorhabditis elegans* | Z68749 | 309 | Abbott et al., 1998<br>Beaudoin et al., 2000 |

TABLE 1-continued

Cloned genes involved in LC-PUFA biosynthesis

| Enzyme | Type of organism | Species | Accession Nos. | Protein size (aa's) | References |
|---|---|---|---|---|---|
| | Algae | *Thraustochytrium aureum*** | AX464802 | 272 | WO 0208401-A2 |
| | | *Pavlova lutheri*** | | 320 | WO 03078639 |
| Δ9-elongase | Algae | *Isochrysis galbana* | AF390174 | 263 | Qi et al., 2002 |
| | | *Euglena gracilis* | | 258 | WO 08/128241 |
| Δ5-elongase | Algae | *Ostreococcus tauri* | AAV67798 | 300 | Meyer et al., 2004 |
| | | *Pyramimonas cordata* | | 268 | WO 2010/057246 |
| | | *Pavlova* sp. CCMP459 | AAV33630 | 277 | Pereira et al., 2004b |
| | | *Pavlova salina* | AAY15135 | 302 | Robert et al., 2009 |
| | Diatom | *Thalassiosira pseudonana* | AAV67800 | 358 | Meyer et al., 2004 |
| | Fish | *Oncorhynchus mykiss* | CAM55862 | 295 | WO 06/008099 |
| | Moss | *Marchantia polymorpha* | BAE71129 | 348 | Kajikawa et al., 2006 |

*http://www.ncbi.nlm.nih.gov/

**Function not proven/not demonstrated

Desaturases

As used herein, the term "desaturase" refers to an enzyme which is capable of introducing a carbon-carbon double bond into the acyl group of a fatty acid substrate which is typically in an esterified form such as, for example, acyl-CoA esters. The acyl group may be esterified to a phospholipid such as phosphatidylcholine (PC), or to acyl carrier protein (ACP), or in a preferred embodiment to CoA. Desaturases generally may be categorized into three groups accordingly. In one embodiment, the desaturase is a front-end desaturase.

As used herein, a "Δ4-desaturase" refers to a protein which performs a desaturase reaction that introduces a carbon-carbon double bond at the $4^{th}$ carbon-carbon bond from the carboxyl end of a fatty acid substrate. The "Δ4-desaturase" is at least capable of converting DPA to DHA. Preferably, the "Δ4-desaturase" is capable of converting DPA-CoA to DHA-CoA, i.e. it is an acyl-CoA desaturase. In an embodiment, the "Δ4-desaturase" is capable of converting DPA esterified at the sn-2 position of PC to DHA-PC. Preferably the Δ4-desaturase has greater activity on DPA-CoA than on DPA-PC. The desaturation step to produce DHA from DPA is catalysed by a Δ4-desaturase in organisms other than mammals, and a gene encoding this enzyme has been isolated from the freshwater protist species *Euglena gracilis* and the marine species *Thraustochytrium* sp. (Qiu et al., 2001; Meyer et al., 2003). In one embodiment, the Δ4-desaturase comprises amino acids having a sequence as provided in SEQ ID NO:28, or a *Thraustochytrium* sp. Δ4-desaturase, a biologically active fragment thereof, or an amino acid sequence which is at least 80% identical to SEQ ID NO:28. In an embodiment, a plant, plant part (such as seed) or cell of, or used in, the invention which produces high levels of DPA, such as 5% to 35% of the total extractable fatty acid content is DPA, does not comprise a gene encoding a functional Δ4-desaturase.

As used herein, a "Δ5-desaturase" refers to a protein which performs a desaturase reaction that introduces a carbon-carbon double bond at the $5^{th}$ carbon-carbon bond from the carboxyl end of a fatty acid substrate. In an embodiment, the fatty acid substrate is ETA and the enzyme produces EPA. Preferably, the "Δ5-desaturase" is capable of converting ETA-CoA to EPA-CoA, i.e. it is an acyl-CoA desaturase. In an embodiment, the "Δ5-desaturase" is capable of converting ETA esterified at the sn-2 position of PC. Preferably the Δ5-desaturase has greater activity on ETA-CoA than on ETA-PC. Examples of Δ5-desaturases are listed in Ruiz-Lopez et al. (2012) and Petrie et al. (2010a) and in Table 1 herein. In one embodiment, the Δ5-desaturase comprises amino acids having a sequence as provided in SEQ ID NO:20, a biologically active fragment thereof, or an amino acid sequence which is at least 80% identical to SEQ ID NO:20. In another embodiment, the Δ5-desaturase comprises amino acids having a sequence as provided in SEQ ID NO:22, a biologically active fragment thereof, or an amino acid sequence which is at least 53% identical to SEQ ID NO:22. In another embodiment, the Δ5-desaturase is from *Thraustochytrium* sp or *Emiliania huxleyi*.

As used herein, a "Δ6-desaturase" refers to a protein which performs a desaturase reaction that introduces a carbon-carbon double bond at the $6^{th}$ carbon-carbon bond from the carboxyl end of a fatty acid substrate. In an embodiment, the fatty acid substrate is ALA and the enzyme produces SDA. Preferably, the "Δ6-desaturase" is capable of converting ALA-CoA to SDA-CoA, i.e. it is an acyl-CoA desaturase. In an embodiment, the "Δ6-desaturase" is capable of converting ALA esterified at the sn-2 position of PC. Preferably the Δ6-desaturase has greater activity on ALA-CoA than on ALA-PC. The Δ6-desaturase may also have activity as a Δ5-desaturase, being termed a Δ5/Δ6 bifunctional desaturase, so long as it has greater Δ6-desaturase activity on ALA than Δ5-desaturase activity on ETA. Examples of Δ6-desaturases are listed in Ruiz-Lopez et al. (2012) and Petrie et al. (2010a) and in Table 1 herein. Preferred Δ6-desaturases are from *Micromonas pusilla, Pythium irregulare* or *Ostreococcus taurii*.

In an embodiment, the Δ6-desaturase is further characterised by having at least two, preferably all three and preferably in a plant cell, of the following: i) greater Δ6-desaturase activity on α-linolenic acid (ALA, 18:3Δ9, 12,15, ω3) than linoleic acid (LA, 18:2Δ9,12, ω6) as fatty acid substrate; ii) greater Δ6-desaturase activity on ALA-CoA as fatty acid substrate than on ALA joined to the sn-2 position of PC as fatty acid substrate; and iii) Δ8-desaturase activity on ETrA. Examples of such Δ6-desaturases are provided in Table 2.

In an embodiment the Δ6-desaturase has greater activity on an ω3 substrate than the corresponding ω6 substrate and has activity on ALA to produce octadecatetraenoic acid (stearidonic acid, SDA, 18:4Δ6,9,12, 15, ω3) with an efficiency of at least 30%, more preferably at least 40%, or most preferably at least 50% when expressed from an exogenous polynucleotide in a recombinant cell such as a plant cell, or at least 35% when expressed in a yeast cell. In one embodiment, the Δ6-desaturase has greater activity, for example, at least about a 2-fold greater Δ6-desaturase activity, on ALA than LA as fatty acid substrate. In another embodiment, the Δ6-desaturase has greater activity, for example, at least about 5 fold greater Δ6-desaturase activity or at least 10-fold greater activity, on ALA-CoA as fatty acid substrate than on ALA joined to the sn-2 position of PC as fatty acid substrate. In a further embodiment, the Δ6-desaturase has activity on both fatty acid substrates ALA-CoA and on ALA joined to the sn-2 position of PC.

TABLE 2

Desaturases demonstrated to have activity on an acyl-CoA substrate

| Enzyme | Type of organism | Species | Accession Nos. | Protein size (aa's) | References |
|---|---|---|---|---|---|
| Δ6-desaturase | Algae | *Mantoniella squamata* | CAQ30479 | 449 | Hoffmann et al., 2008 |
| | | *Ostreococcus tauri* | AAW70159 | 456 | Domergue et al., 2005 |
| | | *Micromonas pusilla* | EEH58637 | | Petrie et al., 2010a (SEQ ID NO: 7) |
| Δ5-desaturase | Algae | *Mantoniella squamata* | CAQ30478 | 482 | Hoffmann et al., 2008 |
| | Plant | *Anemone leveillei* | N/A | | Sayanova et al., 2007 |
| ω3-desaturase | Fungi | *Pythium aphanidermatum* | FW362186.1 | 359 | Xue et al., 2012; WO2008/054565 |
| | Fungi (oomycete) | *Phytophthora sojae* | FW362214.1 | 363 | Xue et al., 2012; WO2008/054565 |
| | Fungi (oomycete) | *Phytophthora ramorum* | FW362213.1 | 361 | Xue et al., 2012; WO2008/054565 |

In one embodiment, the Δ6-desaturase has no detectable Δ5-desaturase activity on ETA. In another embodiment, the Δ6-desaturase comprises amino acids having a sequence as provided in SEQ ID NO:9, SEQ ID NO:12 or SEQ ID NO:13, a biologically active fragment thereof, or an amino acid sequence which is at least 77% identical to SEQ ID NO:9, SEQ ID NO:12 or SEQ ID NO:13. In another embodiment, the Δ6-desaturase comprises amino acids having a sequence as provided in SEQ ID NO:12 or SEQ ED NO:13, a biologically active fragment thereof, or an amino acid sequence which is at least 67% identical to one or both of SEQ ID NO:12 or SEQ ID NO:13. The Δ6-desaturase may also have Δ8-desaturase activity.

As used herein, a "Δ8-desaturase" refers to a protein which performs a desaturase reaction that introduces a carbon-carbon double bond at the $8^{th}$ carbon-carbon bond from the carboxyl end of a fatty acid substrate. The Δ8-desaturase is at least capable of converting ETrA to ETA. Preferably, the Δ8-desaturase is capable of converting ETrA-CoA to ETA-CoA, i.e. it is an acyl-CoA desaturase. In an embodiment, the Δ8-desaturase is capable of converting ETrA esterified at the sn-2 position of PC. Preferably the Δ8-desaturase has greater activity on ETrA-CoA than on ETrA-PC. The Δ8-desaturase may also have activity as a Δ6-desaturase, being termed a Δ6/Δ8 bifunctional desaturase, so long as it has greater Δ8-desaturase activity on ETrA than Δ6-desaturase activity on ALA. Examples of Δ8-desaturases are listed in Table 1. In one embodiment, the Δ8-desaturase comprises amino acids having a sequence as provided in SEQ ID NO:37, a biologically active fragment thereof, or an amino acid sequence which is at least 80% identical to SEQ ID NO:37.

As used herein, an "ω3-desaturase" refers to a protein which performs a desaturase reaction that introduces a carbon-carbon double bond at the 3rd carbon-carbon bond from the methyl end of a fatty acid substrate. A ω3-desaturase therefore may convert LA to ALA and GLA to SDA (all C18 fatty acids), or DGLA to ETA and/or ARA to EPA (C20 fatty acids). Some ω3-desaturases (group I) have activity only on C18 substrates, such as plant and cyanobacteria) ω3-desaturases. Such ω3-desaturases are also Δ15-desaturases. Other ω3-desaturases have activity on C20 substrates with no activity (group II) or some activity (group III) on C18 substrates. Such ω3-desaturases are also Δ17-desaturases. Preferred ω3-desaturases are group III type which convert LA to ALA, GLA to SDA, DGLA to ETA and ARA to EPA, such as the *Pichia pastoris* ω3-desaturase (SEQ ID NO: 6). Examples of ω3-desaturases include those described by Pereira et al. (2004a) (*Saprolegnia diclina* ω3-desaturase, group II), Horiguchi et al. (1998), Berberich et al. (1998) and Spychalla et al. (1997) (*C. elegans* ω3-desaturase, group III). In a preferred embodiment, the ω3-desaturase is a fungal ω3-desaturase. As used herein, a "fungal ω3-desaturase" refers to an ω3-desaturase which is from a fungal source, including an oomycete source, or a variant thereof whose amino acid sequence is at least 95% identical thereto. Genes encoding numerous ω3-desaturases have been isolated from fungal sources such as, for example, from *Phytophthora infestans* (Accession No. CAJ30870, WO2005083053; SEQ ID NO: 47), *Saprolegnia diclina* (Accession No. AAR20444, Pereira et al., 2004a & U.S. Pat. No. 7,211,656), *Pythium irregulare* (WO2008022963, Group II; SEQ ID NO: 49), *Mortierella alpina* (Sakuradani et al., 2005; Accession No. BAD91495; WO2006019192), *Thalassiosira pseudonana* (Armbrust et al., 2004; Accession No. XP_002291057; WO2005012316, SEQ ID NO: 48), *Lachancea kluyveri* (also known as *Saccharomyces kluyveri*; Oura et al., 2004; Accession No. AB118663). Xue et al. (2012) describes ω3-desaturases from the oomycetes *Pythium aphanidermatum, Phytophthora sojae*, and *Phytophthora ramorum* which were able to efficiently convert ω6 fatty acid substrates to the corresponding ω3 fatty acids, with a preference for C20 substrates, i.e. they had stronger Δ17-desaturase activity than Δ15-desaturase activity. These enzymes lacked Δ12-desaturase activity, but could use fatty acids in both acyl-CoA and phospholipid fraction as substrates.

In a more preferred embodiment, the fungal ω3-desaturase is the *Pichia pastoris* (also known as *Komagataella pastoris*) ω3-desaturase/Δ15-desaturase (Zhang et al., 2008;

Accession No. EF116884; SEQ ID NO: 6), or a polypeptide which is at least 95% identical thereto.

In an embodiment, the ω3-desaturase is at least capable of converting one of ARA to EPA, DGLA to ETA, GLA to SDA, both ARA to EPA and DGLA to ETA, both ARA to EPA and GLA to SDA, or all three of these.

In one embodiment, the ω3-desaturase has Δ17-desaturase activity on a C20 fatty acid which has at least three carbon-carbon double bonds, preferably ARA. In another embodiment, the ω3-desaturase has Δ15-desaturase activity on a C18 fatty acid which has three carbon-carbon double bonds, preferably GLA. Preferably, both activities are present.

As used herein, a "Δ12-desaturase" refers to a protein which performs a desaturase reaction that introduces a carbon-carbon double bond at the $12^{th}$ carbon-carbon bond from the carboxyl end of a fatty acid substrate. Δ12-desaturases typically convert either oleoyl-phosphatidylcholine or oleoyl-CoA to linoleoyl-phosphatidylcholine (18:1-PC) or linoleoyl-CoA (18:1-CoA), respectively. The subclass using the PC linked substrate are referred to as phospholipid-dependent Δ12-desaturases, the latter sublclass as acyl-CoA dependent Δ12-desaturases. Plant and fungal Δ12-desaturases are generally of the former subclass, whereas animal Δ12-desaturases are of the latter subclass, for example the Δ12-desaturases encoded by genes cloned from insects by Zhou et al. (2008). Many other Δ12-desaturase sequences can be easily identified by searching sequence databases.

As used herein, a "Δ15-desaturase" refers to a protein which performs a desaturase reaction that introduces a carbon-carbon double bond at the 15th carbon-carbon bond from the carboxyl end of a fatty acid substrate. Numerous genes encoding Δ15-desaturases have been cloned from plant and fungal species. For example, U.S. Pat. No. 5,952,544 describes nucleic acids encoding plant Δ15-desaturases (FAD3). These enzymes comprise amino acid motifs that were characteristic of plant Δ15-desaturases. WO200114538 describes a gene encoding soybean FAD3. Many other Δ15-desaturase sequences can be easily identified by searching sequence databases.

As used herein, a "Δ17-desaturase" refers to a protein which performs a desaturase reaction that introduces a carbon-carbon double bond at the $17^{th}$ carbon-carbon bond from the carboxyl end of a fatty acid substrate. A Δ17-desaturase is also regarded as an ω3-desaturase if it acts on a C20 substrate to introduce a desaturation at the ω3 bond.

In a preferred embodiment, the Δ12-desaturase and/or Δ15-desaturase is a fungal Δ12-desaturase or fungal Δ15-desaturase. As used herein, a "fungal Δ12-desaturase" or "a fungal Δ15-desaturase" refers to a Δ12-desaturase or Δ15-desaturase which is from a fungal source, including an oomycete source, or a variant thereof whose amino acid sequence is at least 95% identical thereto. Genes encoding numerous desaturases have been isolated from fungal sources. U.S. Pat. No. 7,211,656 describes a Δ12 desaturase from *Saprolegnia diclina*. WO2009016202 describes fungal desaturases from *Helobdella robusta, Laccaria bicolor, Lottia gigantea, Microcoleus chthonoplastes, Monosiga brevicollis, Mycosphaerella fijiensis, Mycospaerella graminicola, Naegleria gruben, Nectria haematococca, Nematostella vectensis, Phycomyces blakesleeanus, Trichoderma resii, Physcomitrella patens, Postia placenta, Selaginella moellendotffii* and *Microdochium nivale*. WO2005/012316 describes a Δ12-desaturase from *Thalassiosira pseudonana* and other fungi. WO2003/099216 describes genes encoding fungal Δ12-desaturases and Δ15-desaturases isolated from *Neurospora crassa, Aspergillus nidulans, Botrytis cinerea* and *Mortierella alpina*. WO2007133425 describes fungal Δ15 desaturases isolated from: *Saccharomyces kluyveri, Mortierella alpina, Aspergillus nidulans, Neurospora crassa, Fusarium graminearum, Fusarium moniliforme* and *Magnaporthe grisea*. A preferred Δ12 desaturase is from *Phytophthora sojae* (Ruiz-Lopez et al., 2012).

A distinct subclass of fungal Δ12-desaturases, and of fungal Δ15-desaturases, are the bifunctional fungal Δ12/Δ15-desaturases. Genes encoding these have been cloned from *Fusarium monoliforme* (Accession No. DQ272516, Damude et al., 2006), *Acanthamoeba castellanii* (Accession No. EF017656, Sayanova et al., 2006), *Perkinsus marinus* (WO2007042510), *Claviceps purpurea* (Accession No. EF536898, Meesapyodsuk et al., 2007) and *Coprinus cinereus* (Accession No. AF269266, Zhang et al., 2007).

In another embodiment, the ω3-desaturase has at least some activity on, preferably greater activity on, an acyl-CoA substrate than a corresponding acyl-PC substrate. As used herein, a "corresponding acyl-PC substrate" refers to the fatty acid esterified at the sn-2 position of phosphatidylcholine (PC) where the fatty acid is the same fatty acid as in the acyl-CoA substrate. For example, the acyl-CoA substrate may be ARA-CoA and the corresponding acyl-PC substrate is sn-2 ARA-PC. In an embodiment, the activity is at least two-fold greater. Preferably, the ω3-desaturase has at least some activity on both an acyl-CoA substrate and its corresponding acyl-PC substrate and has activity on both C18 and C20 substrates. Examples of such ω3-desaturases are known amongst the cloned fungal desaturases listed above.

In a further embodiment, the ω3-desaturase comprises amino acids having a sequence as provided in SEQ ID NO:6, a biologically active fragment thereof, or an amino acid sequence which is at least 60% identical to SEQ ID NO:6, preferably at least 90% or at least 95% identical to SEQ ID NO:6.

In yet a further embodiment, a desaturase for use in the present invention has greater activity on an acyl-CoA substrate than a corresponding acyl-PC substrate. In another embodiment, a desaturase for use in the present invention has greater activity on an acyl-PC substrate than a corresponding acyl-CoA substrate, but has some activity on both substrates. As outlined above, a "corresponding acyl-PC substrate" refers to the fatty acid esterified at the sn-2 position of phosphatidylcholine (PC) where the fatty acid is the same fatty acid as in the acyl-CoA substrate. In an embodiment, the greater activity is at least two-fold greater. In an embodiment, the desaturase is a Δ5 or Δ6-desaturase, or an ω3-desaturase, examples of which are provided, but not limited to, those listed in Table 2. To test which substrate a desaturase acts on, namely an acyl-CoA or an acyl-PC substrate, assays can be carried out in yeast cells as described in Domergue et al. (2003 and 2005). Acyl-CoA substrate capability for a desaturase can also be inferred when an elongase, when expressed together with the desturase, has an enzymatic conversion efficiency in plant cells of at least about 90% where the elongase catalyses the elongation of the product of the desaturase. On this basis, the Δ5-desaturase and Δ4-desaturases expressed from the GA7 construct (see, Example 2, FIG. 2 and SEQ ID NO:1) and variants thereof (Example 3) are capable of desaturating their respective acyl-CoA substrates, ETA-CoA and DPA-CoA.

Elongases

Biochemical evidence suggests that the fatty acid elongation consists of 4 steps: condensation, reduction, dehydration and a second reduction. In the context of this invention, an "elongase" refers to the polypeptide that catalyses the condensing step in the presence of the other members of the elongation complex, under suitable physiological conditions. It has been shown that heterologous or homologous expression in a cell of only the condensing component ("elongase") of the elongation protein complex is required for the elongation of the respective acyl chain. Thus, the introduced elongase is able to successfully recruit the reduction and dehydration activities from the transgenic host to carry out successful acyl elongations. The specificity of the elongation reaction with respect to chain length and the degree of desaturation of fatty acid substrates is thought to reside in the condensing component. This component is also thought to be rate limiting in the elongation reaction.

As used herein, a "Δ5-elongase" is at least capable of converting EPA to DPA. Examples of Δ5-elongases include those disclosed in WO2005/103253. In one embodiment, the Δ5-elongase has activity on EPA to produce DPA with an efficiency of at least 60%, more preferably at least 65%, more preferably at least 70% or most preferably at least 80% or 90%. In a further embodiment, the Δ5-elongase comprises an amino acid sequence as provided in SEQ ID NO:25, a biologically active fragment thereof, or an amino acid sequence which is at least 47% identical to SEQ ID NO:25. In a further embodiment, the Δ6-elongase is from *Ostreococcus taurii* or *Ostreococcus lucimarinus* (US2010/088776).

As used herein, a "Δ6-elongase" is at least capable of converting SDA to ETA. Examples of Δ6-elongases include those listed in Table 1. In one embodiment, the elongase comprises amino acids having a sequence as provided in SEQ ID NO:16, a biologically active fragment thereof (such as the fragment provided as SEQ ID NO:17), or an amino acid sequence which is at least 55% identical to one or both of SEQ ID NO:16 or SEQ ID NO:17. In an embodiment, the Δ6-elongase is from *Physcomitrella patens* (Zank et al., 2002; Accession No. AF428243) or *Thalassiosira pseudonana* (Ruiz-Lopez et al., 2012).

As used herein, a "Δ9-elongase" is at least capable of converting ALA to ETrA. Examples of Δ9-elongases include those listed in Table 1. In one embodiment, the Δ9-elongase comprises amino acids having a sequence as provided in SEQ ID NO:29, a biologically active fragment thereof, or an amino acid sequence which is at least 80% identical to SEQ ID NO:29. In another embodiment, the Δ9-elongase comprises amino acids having a sequence as provided in SEQ ID NO:31, a biologically active fragment thereof, or an amino acid sequence which is at least 81% identical to SEQ ID NO:31. In another embodiment, the Δ9-elongase comprises amino acids having a sequence as provided in SEQ ID NO:33, a biologically active fragment thereof, or an amino acid sequence which is at least 50% identical to SEQ ID NO:33. In another embodiment, the Δ9-elongase comprises amino acids having a sequence as provided in SEQ ID NO:35, a biologically active fragment thereof, or an amino acid sequence which is at least 50% identical to SEQ ID NO:35. In a further embodiment, the Δ9-elongase has greater activity on an ω6 substrate than the corresponding ω3 substrate, or the converse.

As used herein, the term "has greater activity on an ω6 substrate than the corresponding ω3 substrate" refers to the relative activity of the enzyme on substrates that differ by the action of an ω3 desaturase. Preferably, the ω6 substrate is LA and the ω03 substrate is ALA.

An elongase with Δ6-elongase and Δ9-elongase activity is at least capable of (i) converting SDA to ETA and (ii) converting ALA to ETrA and has greater Δ6-elongase activity than Δ9-elongase activity. In one embodiment, the elongase has an efficiency of conversion on SDA to produce ETA which is at least 50%, more preferably at least 60%, and/or an efficiency of conversion on ALA to produce ETrA which is at least 6% or more preferably at least 9%. In another embodiment, the elongase has at least about 6.5 fold greater Δ6-elongase activity than Δ9-elongase activity. In a further embodiment, the elongase has no detectable Δ5-elongase activity.

Other Enzymes

The transgenes introduced into the recombinant cell such as a microbial cell, or transgenic plant or part thereof may also encode an LPAAT. As used herein, the term "1-acyl-glycerol-3-phosphate acyltransferase" (LPAAT), also termed lysophosphatidic acid-acyltransferase or acylCoA-lysophosphatidate-acyltransferase, refers to a protein which acylates sn-1-acyl-glycerol-3-phosphate (sn-1 G-3-P) at the sn-2 position to form phosphatidic acid (PA). Thus, the term "1-acyl-glycerol-3-phosphate acyltransferase activity" refers to the acylation of sn-1 G-3-P at the sn-2 position to produce PA (EC 2.3.1.51). Preferred LPAATs are those that can use a polyunsaturated C22 acyl-CoA as substrate to transfer the polyunsaturated C22 acyl group to the sn-2 position of LPA, forming PA. In an embodiment, the polyunsaturated C22 acyl-CoA is DPA-CoA. Such LPAATs are exemplified in Example 6 and can be tested as described therein. In an embodiment, an LPAAT useful for the invention comprises amino acids having a sequence as provided in any one of SEQ ID NOs: 40 to 46, a biologically active fragment thereof, or an amino acid sequence which is at least 40% identical to any one or more of SEQ ID NOs: 40 to 46. In another embodiment, the LPAAT does not have amino acids having a sequence as provided in any one of SEQ ID NO: 44. In a preferred embodiment, an LPAAT useful for the invention which can use a C22 polyunsaturated fatty acyl-CoA substrate, preferably DPA-CoA, comprises amino acids having a sequence as provided in any one of SEQ ID NOs: 41, 42 and 44, a biologically active fragment thereof, or an amino acid sequence which is at least 40% identical to any one or more of SEQ ID NOs: 41, 42 and 44. In a preferred embodiment, an LPAAT useful for the invention which can use a C22 polyunsaturated fatty acyl-CoA substrate, preferably DPA-CoA, comprises amino acids having a sequence as provided in any one of SEQ ID NOs: 41 or 42, a biologically active fragment thereof, or an amino acid sequence which is at least 40% identical to any one or both of SEQ ID NOs: 41 and 42. In an embodiment, the LPAAT is preferably the *Mortierella alpina* LPAAT whose amino acid sequence is set forth as SEQ ID NO: 44 or another LPAAT which is capable of using DPA-CoA as a substrate to transfer the DPA to LPA, forming PA having DPA at the sn-2 position.

The transgenes introduced into the recombinant cell, transgenic plant or part thereof may also encode a DGAT. As used herein, the term "diacylglycerol acyltransferase" (EC 2.3.1.20; DGAT) refers to a protein which transfers a fatty acyl group from acyl-CoA to a diacylglycerol substrate to produce a triacylglycerol. Thus, the term "diacylglycerol acyltransferase activity" refers to the transfer of acyl-CoA to diacylglycerol to produce triacylglycerol. There are three known types of DGAT referred to as DGAT1, DGAT2 and DGAT3 respectively. DGAT1 polypeptides typically have 10 transmembrane domains, DGAT2 typically have 2 transmembrane domains, whilst DGAT3 is typically soluble. Examples of DGAT1 polypeptides include polypeptides encoded by DGAT1 genes from *Aspergillus fumigatus* (Accession No. XP_755172), *Arabidopsis thaliana* (CAB44774), *Ricinus communis* (AAR11479), *Vernicia for-*

*dii* (ABC94472), *Vernonia galamensis* (ABV21945, ABV21946), *Euonymus alatus* (AAV31083), *Caenorhabditis elegans* (AAF82410), *Rattus norvegicus* (NP_445889), *Homo sapiens* (NP_036211), as well as variants and/or mutants thereof. Examples of DGAT2 polypeptides include polypeptides encoded by DGAT2 genes from *Arabidopsis thaliana* (Accession No. NP_566952), *Ricinus communis* (AAY16324), *Vernicia fordii* (ABC94474), *Mortierella ramanniana* (AAK84179), *Homo sapiens* (Q96PD7, Q58HT5), *Bos taurus* (Q70VD8), *Mus musculus* (AAK84175), *Micromonas* CCMP1545, as well as variants and/or mutants thereof. Examples of DGAT3 polypeptides include polypeptides encoded by DGAT3 genes from peanut (*Arachis hypogaea*, Saha, et al., 2006), as well as variants and/or mutants thereof.

Polypeptides/Peptides

The terms "polypeptide" and "protein" are generally used interchangeably.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length. The polypeptide or class of polypeptides may have the same enzymatic activity as, or a different activity than, or lack the activity of, the reference polypeptide. Preferably, the polypeptide has an enzymatic activity of at least 10%, at least 50%, at least 75% or at least 90%, of the activity of the reference polypeptide.

As used herein a "biologically active" fragment is a portion of a polypeptide defined herein which maintains a defined activity of a full-length reference polypeptide, for example possessing desaturase and/or elongase activity or other enzyme activity. Biologically active fragments as used herein exclude the full-length polypeptide. Biologically active fragments can be any size portion as long as they maintain the defined activity. Preferably, the biologically active fragment maintains at least 10%, at least 50%, at least 75% or at least 90%, of the activity of the full length protein.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired enzyme activity.

Mutant (altered) peptides can be prepared using any technique known in the art. For example, a polynucleotide defined herein can be subjected to in vitro mutagenesis or DNA shuffling techniques as broadly described by Harayama (1998). Products derived from mutated/altered DNA can readily be screened using techniques described herein to determine if they possess, for example, desaturase or elongase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites which are not conserved amongst naturally occurring desaturases or elongases. These sites are preferably substituted in a relatively conservative manner in order to maintain enzyme activity. Such conservative substitutions are shown in Table 3 under the heading of "exemplary substitutions".

In a preferred embodiment a mutant/variant polypeptide has only, or not more than, one or two or three or four conservative amino acid changes when compared to a naturally occurring polypeptide. Details of conservative amino acid changes are provided in Table 3. As the skilled person would be aware, such minor changes can reasonably be predicted not to alter the activity of the polypeptide when expressed in a recombinant cell.

TABLE 3

Exemplary amino acid substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |

TABLE 3-continued

| Exemplary amino acid substitutions. | |
|---|---|
| Original Residue | Exemplary Substitutions |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Polynucleotides

The invention also provides for the use of polynucleotides which may be, for example, a gene, an isolated polynucleotide, a chimeric genetic construct such as a T-DNA molecule, or a chimeric DNA. It may be DNA or RNA of genomic or synthetic origin, double-stranded or single-stranded, and combined with carbohydrate, lipids, protein or other materials to perform a particular activity defined herein. The term "polynucleotide" is used interchangeably herein with the term "nucleic acid molecule".

In an embodiment, the polynucleotide is non-naturally occurring. Examples of non-naturally occurring polynucleotides include, but are not limited to, those that have been mutated (such as by using methods described herein), and polynucleotides where an open reading frame encoding a protein is operably linked to a promoter to which it is not naturally associated (such as in the constructs described herein).

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals in which case the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA). Introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins described herein and a complementary nucleotide sequence to any one of the above.

As used herein, a "chimeric DNA" or "chimeric genetic construct" or similar refers to any DNA molecule that is not a native DNA molecule in its native location, also referred to herein as a "DNA construct". Typically, a chimeric DNA or chimeric gene comprises regulatory and transcribed or protein coding sequences that are not found operably linked together in nature i.e. that are heterologous with respect to each other. Accordingly, a chimeric DNA or chimeric gene may comprise regulatory sequences and coding sequences that are derived from different sources, or regulatory sequences and coding sequences derived from the same source, but arranged in a manner different than that found in nature.

An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. Foreign or exogenous genes may be genes that are inserted into a non-native organism, native genes introduced into a new location within the native host, or chimeric genes. A "transgene" is a gene that has been introduced into the genome by a transformation procedure. The terms "genetically modified", "transgenic" and variations thereof include introducing genes into cells by transformation or transduction, mutating genes in cells and altering or modulating the regulation of a gene in a cell or organisms to which these acts have been done or their progeny. A "genomic region" as used herein refers to a position within the genome where a transgene, or group of transgenes (also referred to herein as a cluster), have been inserted into a cell, or an ancestor thereof. Such regions only comprise nucleotides that have been incorporated by the intervention of man such as by methods described herein.

The term "exogenous" in the context of a polynucleotide refers to the polynucleotide when present in a cell in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide operably linked to a promoter suitable of driving transcription of the open reading frame in a cell of interest.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polynucleotides may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above). It is thus apparent that polynucleotides can be either from a naturally occurring source or recombinant. Preferred polynucleotides are those which have coding regions that are codon-optimised for translation in plant cells, as is known in the art.

Recombinant Vectors

Recombinant expression can be used to produce recombinant cells, or plants or plant parts of the invention. Recombinant vectors contain heterologous polynucleotide sequences, that is, polynucleotide sequences that are not naturally found adjacent to polynucleotide molecules defined herein that preferably are derived from a species other than the species from which the polynucleotide molecule(s) are derived. The vector can be either RNA or DNA and typically is a plasmid. Plasmid vectors typically include additional nucleic acid sequences that provide for easy selection, amplification, and transformation of the expression cassette in prokaryotic cells, e.g., pUC-derived vectors, pSK-derived vectors, pGEM-derived vectors, pSP-derived vectors, pBS-derived vectors, or preferably binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells. The recombinant vector may comprise more than one polynucleotide defined herein, for example three, four, five or six polynucleotides defined herein in combination, preferably a chimeric genetic construct described herein, each polynucleotide being operably linked to expression control sequences that are operable in the cell of interest. Preferably the expression control sequences include, or are all, heterologous promoters i.e. are heterologous with respect to the coding regions they control. More than one polynucleotide defined herein, for example 3, 4, 5 or 6 polynucleotides, preferably 7 or 8 polynucleotides each encoding a different polypeptide, are preferably covalently joined together in a single recombinant vector, preferably within a single T-DNA molecule, which may then be introduced as a single molecule into a cell to form a recombinant cell according to the invention, and preferably integrated into the genome of the recombinant cell, for example in a transgenic plant. The integration into the genome may be into the nuclear genome or into a plastid genome in the transgenic plant. Thereby, the polynucleotides which are so joined will be inherited together as a single genetic locus in progeny of the recombinant cell or plant. The recombinant vector or plant may comprise two or more such recombinant vectors, each containing multiple polynucleotides, for example wherein each recombinant vector comprises 3, 4, 5 or 6 polynucleotides.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

When there are multiple promoters present, each promoter may independently be the same or different. Preferably, at least 3 and up to a maximum of 6 different promoter sequences are used in the recombinant vector to control expression of the exogenous polynucleotides.

Recombinant molecules such as the chimeric DNAs or genetic constructs may also contain (a) one or more secretory signals which encode signal peptide sequences, to enable an expressed polypeptide defined herein to be secreted from the cell that produces the polypeptide or which provide for localisation of the expressed polypeptide, for example for retention of the polypeptide in the endoplasmic reticulum (ER) in the cell or transfer into a plastid, and/or (b) contain fusion sequences which lead to the expression of nucleic acid molecules as fusion proteins. Examples of suitable signal segments include any signal segment capable of directing the secretion or localisation of a polypeptide defined herein. Recombinant molecules may also include intervening and/or untranslated sequences surrounding and/or within the nucleic acid sequences of nucleic acid molecules defined herein.

To facilitate identification of transformants, the nucleic acid construct desirably comprises a selectable or screenable marker gene as, or in addition to, the foreign or exogenous polynucleotide. By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked. The actual choice of a marker is not crucial as long as it is functional (i.e., selective) in combination with the cells of choice such as a plant cell.

Examples of selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), or preferably a bar gene conferring resistance against bialaphos as, for example, described in WO91/02071.

Preferably, the nucleic acid construct is stably incorporated into the genome of the cell, such as the plant cell. Accordingly, the nucleic acid may comprise appropriate elements which allow the molecule to be incorporated into the genome, preferably the right and left border sequences of a T-DNA molecule, or the construct is placed in an appropriate vector which can be incorporated into a chromosome of the cell.

Expression

As used herein, an expression vector is a DNA vector that is capable of transforming a host cell and of effecting expression of one or more specified polynucleotide molecule(s). Expression vectors of the present invention can direct gene expression in plant cells or in recombinant cells such as microbial cells. Expression vectors useful for the invention contain regulatory sequences such as transcription control sequences, translation control sequences, origins of replication, and other regulatory sequences that are compatible with the recombinant cell and that control the expression of polynucleotide molecules of the present invention. In particular, polynucleotides or vectors useful for the present invention include transcription control sequences. Transcription control sequences are sequences which control the initiation, elongation, and termination of transcription. Particularly important transcription control sequences are those which control transcription initiation, such as promoter and enhancer sequences. Suitable transcription control sequences include any transcription control sequence that can function in at least one of the recombinant cells of the present invention. The choice of the regulatory sequences used depends on the target organism such as a plant and/or target organ or tissue of interest. Such regulatory sequences may be obtained from any eukaryotic organism such as plants or plant viruses, or may be chemically synthesized. A variety of such transcription control sequences are known to those skilled in the art. Particularly preferred transcription control sequences are promoters active in directing transcription in plants, either constitutively or stage and/or tissue specific, depending on the use of the plant or parts thereof.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, and the light-inducible promoter from the small subunit of the ribulose-1,5-bis-phosphate carboxylase.

For the purpose of expression in source tissues of the plant, such as the leaf, seed, root or stem, it is preferred that the promoters utilized in the present invention have relatively high expression in these specific tissues. Many examples are well known in the art. A variety of plant gene promoters that are regulated in response to environmental, hormonal, chemical, and/or developmental signals, also can be used for expression of genes in plant cells, or it may also be advantageous to employ organ-specific promoters.

As used herein, the term "seed specific promoter" or variations thereof refer to a promoter that preferentially, when compared to other plant tissues, directs gene transcription in a developing seed of a plant, preferably a *Brassica* sp., *Camelina sativa* or *G. max* plant. In an embodiment, the seed specific promoter is expressed at least 5-fold more strongly in the developing seed of the plant relative to the leaves and/or stems of the plant, and is preferably expressed more strongly in the embryo of the developing seed compared to other plant tissues. Preferably, the promoter only directs expression of a gene of interest in the developing seed, and/or expression of the gene of interest in other parts of the plant such as leaves is not detectable by Northern blot analysis and/or RT-PCR. Typically, the promoter drives expression of genes during growth and development of the seed, in particular during the phase of synthesis and accumulation of storage compounds in the seed. Such promoters may drive gene expression in the entire plant storage organ or only part thereof such as the seedcoat, or cotyledon(s), preferably in the embryos, in seeds of dicotyledonous plants or the endosperm or aleurone layer of a seeds of monocotyledonous plants.

Preferred promoters for seed-specific expression include i) promoters from genes encoding enzymes involved in fatty acid biosynthesis and accumulation in seeds, such as fatty acid desaturases and elongases, ii) promoters from genes encoding seed storage proteins, and iii) promoters from genes encoding enzymes involved in carbohydrate biosynthesis and accumulation in seeds. Seed specific promoters which are suitable are the oilseed rape napin gene promoter (U.S. Pat. No. 5,608,152), the *Vicia faba* USP promoter (Baumlein et al., 1991), the *Arabidopsis* oleosin promoter (WO98/45461), the *Phaseolus vulgaris* phaseolin promoter (U.S. Pat. No. 5,504,200), the *Brassica* Bce4 promoter (WO91/13980) or the legumin LeB4 promoter from *Vicia faba* (Baumlein et al., 1992), and promoters which lead to the seed-specific expression in monocots such as maize, barley, wheat, rye, rice and the like. Notable promoters which are suitable are the, barley Ipt2 or Ipt1 gene promoter (WO95/15389 and WO95/23230) or the promoters described in WO99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the *Sorghum* kasirin gene, the rye secalin gene). Other promoters include those described by Broun et al. (1998), Potenza et al. (2004), US20070192902 and US20030159173. In an embodiment, the seed specific promoter is preferentially expressed in defined parts of the seed such as the embryo, cotyledon(s) or the endosperm. Examples of such specific promoters include, but are not limited to, the FP1 promoter (Ellerstrom et al., 1996), the pea legumin promoter (Perrin et al., 2000), the bean phytohemagglutnin promoter (Perrin et al., 2000), the conlinin 1 and conlinin 2 promoters for the genes encoding the flax 2S storage proteins (Cheng et al., 2010), the promoter of the FAE1 gene from *Arabidopsis thaliana*, the BnGLP promoter of the globulin-like protein gene of *Brassica napus*, the LPXR promoter of the peroxiredoxin gene from *Linum usitatissimum*.

The 5' non-translated leader sequence can be derived from the promoter selected to express the heterologous gene sequence of the polynucleotide of the present invention, or preferably is heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene or a flax conlinin gene are commonly used in this capacity. The 3' transcribed, non-translated regions containing the polyadenylate signal of *Agrobacterium* tumor-inducing (Ti) plasmid genes are also suitable.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules defined herein include, but are not limited to, integration of the polynucleotide molecule into one or more host cell chromosomes, addition of stability sequences to mRNAs, substitutions or modifications of transcription control signals (e.g., promoters, operators, enhancers), substitutions or modifications of translational control signals (e.g., ribosome binding sites, Shine-Dalgarno sequences), modification of polynucleotide molecules to correspond to the codon usage of the host cell, and the deletion of sequences that destabilize transcripts.

Transgenic Plants

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. The term "plant part" refers to all plant parts that comprise the plant DNA, including vegetative structures such as, for example, leaves or stems, roots, floral organs or structures, pollen, seed, seed parts such as an embryo, endosperm, scutellum or seed coat, plant tissue such as, for example, vascular tissue, cells and progeny of the same, as long as the plant part synthesizes lipid according to the invention.

A "transgenic plant", "genetically modified plant" or variations thereof refers to a plant that contains a gene construct ("transgene") not found in a wild-type plant of the same species, variety or cultivar. Transgenic plants as defined in the context of the present invention include plants and their progeny which have been genetically modified using recombinant techniques to cause production of the lipid or at least one polypeptide defined herein in the desired plant or plant organ. Transgenic plant cells and transgenic plant parts have corresponding meanings. A "transgene" as referred to herein has the normal meaning in the art of biotechnology and includes a genetic sequence which has been produced or altered by recombinant DNA or RNA technology and which has been introduced into a plant cell. The transgene may include genetic sequences derived from a plant cell which may be of the same species, variety or cultivar as the plant cell into which the transgene is introduced or of a different species, variety or cultivar, or from a cell other than a plant cell. Typically, the transgene has been introduced into the cell, such as a plant, by human manipulation such as, for example, by transformation but any method can be used as one of skill in the art recognizes.

The terms "seed" and "grain" are used interchangeably herein. "Grain" refers to mature grain such as harvested grain or grain which is still on a plant but ready for harvesting, but can also refer to grain after imbibition or germination, according to the context. Mature grain or seed commonly has a moisture content of less than about 18-20%, preferably less than 10%. *Brassica* seed such as canola seed typically has a moisture content of about 4-8% or 6-8% when mature, preferably between about 4% to about 6%. "Developing seed" as used herein refers to a seed prior to maturity, typically found in the reproductive structures of the plant after fertilisation or anthesis, but can also refer to such seeds prior to maturity which are isolated from a plant.

As used herein, the term "obtaining a plant part" or "obtaining a seed" refers to any means of obtaining a plant part or seed, respectively, including harvesting of the plant parts or seed from plants in the field or in containment such as a glasshouse or growth chamber, or by purchase or receipt from a supplier of the plant parts or seed. Standard growth conditions in a glasshouse include 22-24° C. daytime temperature and 16-18° C. night-time temperature, with natural sunlight. The seed may be suitable for planting i.e. able to germinate and produce progeny plants, or alternatively has been processed in such a way that it is no longer able to germinate, e.g. cracked, polished or milled seed which is useful for food or feed applications, or for extraction of lipid of the invention.

As used herein, the term "plant storage organ" refers to a part of a plant specialized to storage energy in the form of, for example, proteins, carbohydrates, fatty acids and/or oils. Examples of plant storage organs are seed, fruit, tuberous roots, and tubers. A preferred plant storage organ is seed.

The plants or plant parts of the invention or used in the invention are preferably phenotypically normal. As used herein, the term "phenotypically normal" refers to a genetically modified plant or plant organ, particularly a storage organ such as a seed, tuber or fruit not having a significantly reduced ability to grow and reproduce when compared to an unmodified plant or plant organ. In an embodiment, the genetically modified plant or plant organ which is phenotypically normal has an ability to grow or reproduce which is essentially the same as an isogenic plant or organ not comprising the exogenous polynucleotide(s). Preferably, the biomass, growth rate, germination rate, storage organ size, pollen viability, male and female fertility, seed size and/or the number of viable seeds produced is not less than 90% of that of a plant lacking said exogenous polynucleotide when grown under identical conditions. Preferably the pollen viability of the plant of the invention, or plants produced from seed of the invention, is about 100% relative to the pollen viability of a corresponding wild-type plant. This term does not encompass features of the plant which may be different to the wild-type plant but which do not affect the usefulness of the plant for commercial purposes such as, for example, a ballerina phenotype of seedling leaves.

Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, *sorghum*, millet, cassava, barley, or pea), or other legumes. The plants may be grown for production of edible roots, tubers, leaves, stems, flowers or fruit. The plants may be vegetables or ornamental plants. The plants of, or useful for, the invention may be: corn (*Zea mays*), canola (*Brassica napus, Brassica rapa* ssp.), mustard (*Brassica juncea*), flax (*Linum usitatissimum*), alfalfa (*Medicago sativa*), rice (*Oryza sativa*), rye (*Secale cerale*), *sorghum* (*Sorghum bicolour, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), *Macadamia* (*Macadamia intergrifolia*), almond (*Prunus amygdalus*), sugar beets (*Beta vulgaris*), oats, or barley.

In a preferred embodiment, the plant is an angiosperm.

In an embodiment, the plant is an oilseed plant, preferably an oilseed crop plant. As used herein, an "oilseed plant" is a plant species used for the commercial production of oils from the seeds of the plant. The oilseed plant may be oil-seed rape (such as canola), maize, sunflower, soybean, *sorghum*, flax (linseed) or sugar beet. Furthermore, the oilseed plant may be other *Brassicas*, cotton, peanut, poppy, mustard, castor bean, sesame, sunflower, safflower, *Camelina, Crambe* or nut producing plants. The plant may produce high levels of oil in its fruit, such as olive, oil palm or coconut. Horticultural plants to which the present invention may be applied are lettuce, endive, or vegetable *Brassicas* including cabbage, broccoli, or cauliflower. The present invention may be applied in tobacco, cucurbits, carrot, strawberry, tomato, or pepper.

In a further preferred embodiment, the non-transgenic plant used to produce a transgenic plant of the invention produces oil, especially in the seed, which has i) less than 20%, less than 10% or less than 5% 18:2 fatty acids and/or ii) less than 10% or less than 5% 18:3 fatty acids.

In a preferred embodiment, the transgenic plant or part thereof is homozygous for each and every gene (exogenous polynucleotide) that has been introduced (transgene) so that its progeny do not segregate for the desired phenotype. The transgenic plant may also be heterozygous for the introduced transgene(s), preferably uniformly heterozygous for the transgene, such as for example in F1 progeny which have been grown from hybrid seed. Such plants may provide advantages such as hybrid vigour, well known in the art, or may be used in plant breeding or backcrossing.

Where relevant, the transgenic plant or part thereof may also comprise additional transgenes encoding enzymes involved in the production of LC-PUFAs such as, but not limited to, a Δ6-desaturase, a Δ9-elongase, a Δ8-desaturase, a Δ6-elongase, a Δ5-desaturase, an ω3-desaturase, a Δ5-elongase, diacylglycerol acyltransferase, LPAAT, a Δ17-desaturase, a Δ15-desaturase and/or a Δ12 desaturase. Examples of such enzymes with one of more of these activities are known in the art and include those described herein. In specific examples, the transgenic plant at least comprises a set of exogenous polynucleotides encoding;

a) a Δ5-desaturase, a Δ6-desaturase, a Δ5-elongase and a Δ6-elongase, b) a Δ5-desaturase, a Δ8-desaturase, a Δ5-elongase and a Δ9-elongase, c) a Δ5-desaturase, a Δ6-desaturase, a Δ5-elongase, a Δ6-elongase, and a Δ15-desaturase, d) a Δ5-desaturase, a Δ8-desaturase, a Δ5-elongase, a Δ9-elongase, and a Δ15-desaturase, e) a Δ5-desaturase, a Δ6-desaturase, a Δ5-elongase, a Δ6-elongase, and a Δ17-desaturase, f) a Δ5-desaturase, a Δ8-desaturase, a Δ5-elongase, a Δ9-elongase, and a Δ17-desaturase, g) an ω3-desaturase or a Δ15-desaturase, a Δ6-desaturase, a Δ5-desaturase, a Δ6-elongase and a Δ5-elongase, h) an ω3-desaturase or a Δ15-desaturase, a Δ8-desaturase, a Δ5-desaturase, a Δ9-elongase and a Δ5-elongase, i) a Δ12-desaturase, a ω3-desaturase or a Δ15-desaturase, a Δ6-desaturase, a Δ5-desaturase, a Δ6-elongase and an Δ5-elongase, j) a Δ12-desaturase, a ω3-desaturase or a Δ15-desaturase, a Δ8-desaturase, a Δ5-desaturase, a Δ9-elongase and an Δ5-elongase, k) an 1-acyl-glycerol-3-phosphate acyltransferase (LPAAT), an ω3-desaturase, a Δ6-desaturase, a Δ5-desaturase, a Δ6-elongase and a Δ5-elongase, l) an 1-acyl-glycerol-3-phosphate acyltransferase (LPAAT), a Δ15-desaturase, a Δ6-desaturase, a Δ5-desaturase, a Δ6-elongase and a Δ5-elongase, m) an 1-acyl-glycerol-3-phosphate acyltransferase (LPAAT), a Δ12-desaturase, a Δ6-desaturase, a Δ5-desaturase, a Δ6-elongase and a Δ5-elongase, n) an 1-acyl-glycerol-3-phosphate acyltransferase (LPAAT), a Δ12-desaturase, a ω3-desaturase and/or a Δ15-desaturase, a Δ6-desaturase, a Δ5-desaturase, a Δ6-elongase and an Δ5-elongase, o) an 1-acyl-glycerol-3-phosphate acyltransferase (LPAAT), an ω3-desaturase, a Δ8-desaturase, a Δ5-desaturase, a Δ9-elongase, and a Δ5-elongase, p) an 1-acyl-glycerol-3-phosphate acyltransferase (LPAAT), a Δ15-desaturase, a Δ8-desaturase, a Δ5-desaturase, a Δ9-elongase, and a Δ5-elongase, q) an 1-acyl-glycerol-3-phosphate acyltransferase (LPAAT), a Δ12-desaturase, a Δ8-desaturase, a Δ5-desaturase, a Δ9-elongase, and a Δ5-elongase, or r) an 1-acyl-glycerol-3-phosphate acyltransferase (LPAAT), a Δ12-desaturase, a ω3-desaturase and/or a Δ15-desaturase, a Δ8-desaturase, a Δ5-desaturase, a Δ9-elongase, and an Δ5-elongase.

In an embodiment, the exogenous polynucleotides encode set of polypeptides which are a *Pythium irregulare* Δ6-desaturase, a *Thraustochytrid* Δ5-desaturase or an *Emiliana huxleyi* Δ5-desaturase, a *Physcomitrella patens* Δ6-elongase, a *Thraustochytrid* Δ5-elongase or an *Ostreocccus taurii* Δ5-elongase, and a *Phytophthora infestans* ω3-desaturase or a *Pythium irregulare* ω3-desaturase.

In an embodiment, plants of, or used for, the invention are grown in the field, preferably as a population of at least 1,000, 1,000,000 or 2,000,000 plants that are essentially the same, or in an area of at least 1 hectare or 2 hectares. Planting densities differ according to the plant species, plant variety, climate, soil conditions, fertiliser rates and other factors as known in the art. For example, canola is typically grown at a planting density of 1.2-1.5 million plants per hectare. Plants are harvested as is known in the art, which may comprise swathing, windrowing and/or reaping of plants, followed by threshing and/or winnowing of the plant material to separate the seed from the remainder of the plant parts often in the form of chaff. Alternatively, seed may be harvested from plants in the field in a single process, namely combining.

Transformation of Plants

Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

As used herein, the terms “stably transforming”, “stably transformed” and variations thereof refer to the integration of the exogenous nucleic acid molecules into the genome of the cell such that they are transferred to progeny cells during cell division without the need for positively selecting for their presence. Stable transformants, or progeny thereof, can be selected by any means known in the art such as Southern blots on chromosomal DNA or in situ hybridization of genomic DNA. Preferably, plant transformation is performed as described in the Examples herein.

*Agrobacterium*-mediated transfer is a widely applicable system for introducing genes into plant cells because DNA can be introduced into cells in whole plant tissues or plant organs or explants in tissue culture, for either transient expression or for stable integration of the DNA in the plant cell genome. The use of *Agrobacterium*-mediated plant integrating vectors to introduce DNA into plant cells is well known in the art (see, for example, U.S. Pat. Nos. 5,177,010, 5,104,310, 5,004,863 or 5,159,135) including floral dipping methods using *Agrobacterium* or other bacteria that can transfer DNA into plant cells. The region of DNA to be transferred is defined by the border sequences, and the intervening DNA (T-DNA) is usually inserted into the plant genome. Further, the integration of the T-DNA is a relatively precise process resulting in few rearrangements. In those plant varieties where *Agrobacterium*-mediated transformation is efficient, it is the method of choice because of the facile and defined nature of the gene transfer. Preferred *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required.

In another alternative embodiment, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932479, and WO99/05265).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

A transgenic plant formed using *Agrobacterium* or other transformation methods typically contains a single genetic locus on one chromosome. Such transgenic plants can be referred to as being hemizygous for the added gene(s). More preferred is a transgenic plant that is homozygous for the added gene(s); i.e., a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both exogenous genes or loci. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Enhancing Exogenous RNA Levels and Stabilized Expression

Silencing Suppressors

In an embodiment, a plant cell, plant or plant part comprises an exogenous polynucleotide encoding a silencing suppressor protein.

Post-transcriptional gene silencing (PTGS) is a nucleotide sequence-specific defense mechanism that can target both cellular and viral mRNAs for degradation PTGS occurs in plants or fungi stably or transiently transformed with foreign (heterologous) or endogenous DNA and results in the reduced accumulation of RNA molecules with sequence similarity to the introduced nucleic acid.

It has widely been considered that co-expression of a silencing suppressor with a transgene of interest will increase the levels of RNA present in the cell transcribed from the transgene. Whilst this has proven true for cells in vitro, significant side-effects have been observed in many whole plant co-expression studies. More specifically, as described in Mallory et al. (2002), Chapman et al. (2004), Chen et al. (2004), Dunoyer et al. (2004), Zhang et al. (2006), Lewsey et al. (2007) and Meng et al. (2008) plants expressing silencing suppressors, generally under constitutive promoters, are often phenotypically abnormal to the extent that they are not useful for commercial production.

Recently, it has been found that RNA molecule levels can be increased, and/or RNA molecule levels stabilized over numerous generations, by limiting the expression of the silencing suppressor to a seed of a plant or part thereof (WO2010/057246). As used herein, a "silencing suppressor protein" or SSP is any polypeptide that can be expressed in a plant cell that enhances the level of expression product from a different transgene in the plant cell, particularly over repeated generations from the initially transformed plant. In an embodiment, the SSP is a viral silencing suppressor or mutant thereof. A large number of viral silencing suppressors are known in the art and include, but are not limited to P19, V2, P38, Pe-Po and RPV-P0. In an embodiment, the viral silencing suppressor comprises amino acids having a sequence as provided in SEQ ID NO:38, a biologically active fragment thereof, or an amino acid sequence which is at least 50% identical to SEQ ID NO:38 and which has activity as a silencing suppressor.

As used herein, the terms "stabilising expression", "stably expressed", "stabilised expression" and variations thereof refer to level of the RNA molecule being essentially the same or higher in progeny plants over repeated generations, for example at least three, at least five or at least 10 generations, when compared to isogenic plants lacking the exogenous polynucleotide encoding the silencing suppressor. However, this term(s) does not exclude the possibility that over repeated generations there is some loss of levels of the RNA molecule when compared to a previous generation, for example not less than a 10% loss per generation.

The suppressor can be selected from any source e.g. plant, viral, mammal etc. See WO2010/057246 for a list of viruses from which the suppressor can be obtained and the protein (eg B2, P14 etc) or coding region designation for the suppressor from each particular virus. Multiple copies of a suppressor may be used. Different suppressors may be used together (e.g., in tandem).

RNA Molecules

Essentially any RNA molecule which is desirable to be expressed in a plant seed can be co-expressed with the silencing suppressor. The encoded polypeptides may be involved in metabolism of oil, starch, carbohydrates, nutrients, etc., or may be responsible for the synthesis of proteins, peptides, fatty acids, lipids, waxes, oils, starches, sugars, carbohydrates, flavors, odors, toxins, carotenoids. hormones, polymers, flavonoids, storage proteins, phenolic acids, alkaloids, lignins, tannins, celluloses, glycoproteins, glycolipids, etc, preferably the biosynthesis or assembly of TAG.

In a particular example, the plants produced increased levels of enzymes for oil production in plants such as *Brassicas*, for example canola or sunflower, safflower, flax, cotton, soya bean, *Camelina* or maize.

Levels of LC-PUFA Produced

The levels of the LC-PUFA or combination of LC-PUFAs that are produced in the recombinant cell or plant part such as seed are of importance. The levels may be expressed as a composition (in percent) of the total fatty acid that is a particular LC-PUFA or group of related LC-PUFA, for example the ω3 LC-PUFA or the ω6 LC-PUFA, or the VLC-PUFA, or other which may be determined by methods known in the art. The level may also be expressed as a LC-PUFA content, such as for example the percentage of LC-PUFA in the dry weight of material comprising the recombinant cells, for example the percentage of the weight of seed that is LC-PUFA. It will be appreciated that the LC-PUFA that is produced in an oilseed may be considerably higher in terms of LC-PUFA content than in a vegetable or a grain that is not grown for oil production, yet both may have similar LC-PUFA compositions, and both may be used as sources of LC-PUFA for human or animal consumption.

The levels of LC-PUFA may be determined by any of the methods known in the art. In a preferred method, total lipid is extracted from the cells, tissues or organisms and the fatty acid converted to methyl esters before analysis by gas chromatography (GC). Such techniques are described in Example 1. The peak position in the chromatogram may be used to identify each particular fatty acid, and the area under each peak integrated to determine the amount. As used herein, unless stated to the contrary, the percentage of particular fatty acid in a sample is determined as the area under the peak for that fatty acid as a percentage of the total area for fatty acids in the chromatogram. This corresponds essentially to a weight percentage (w/w). The identity of fatty acids may be confirmed by GC-MS. Total lipid may be separated by techniques known in the art to purify fractions such as the TAG fraction. For example, thin-layer chromatography (TLC) may be performed at an analytical scale to separate TAG from other lipid fractions such as DAG, acyl-CoAs or phospholipid in order to determine the fatty acid composition specifically of TAG.

In one embodiment, the sum total of ARA, EPA, DPA and DHA in the fatty acids in the extracted lipid is between about 21% and about 40% of the total fatty acids in the cell. In a further embodiment, the total fatty acid in the cell has less than 1% C20:1. In preferred embodiments, the extractable TAG in the cell comprises the fatty acids at the levels referred to herein. Each possible combination of the features defining the lipid as described herein is also encompassed.

The level of production of LC-PUFA in the recombinant cell, plant or plant part such as seed may also be expressed as a conversion percentage of a specific substrate fatty acid to one or more product fatty acids, which is also referred to herein as a "conversion efficiency" or "enzymatic efficiency". This parameter is based on the fatty acid composition in the lipid extracted from the cell, plant, plant part or seed, i.e., the amount of the LC-PUFA formed (including other LC-PUFA derived therefrom) as a percentage of one or more substrate fatty acids (including all other fatty acids derived therefrom). The general formula for a conversion percentage is: 100×(the sum of percentages of the product LC-PUFA and all products derived therefrom)/(the sum of the percentages of the substrate fatty acid and all products derived therefrom). With regard to DPA, for example, this may be expressed as the ratio of the level of DPA (as a percentage in the total fatty acid content in the lipid) to the level of a substrate fatty acid (e.g. OA, LA, ALA, SDA, ETA or EPA) and all products including DPA derived from the substrate. The conversion percentage or efficiency of conversion can be expressed for a single enzymatic step in a pathway, or for part or the whole of a pathway.

Specific conversion efficiencies are calculated herein according to the formulae:

1. OA to DPA=100×(% DHA+% DPA)/(sum % for OA, LA, GLA, DGLA, ARA, EDA, ALA, SDA, ETrA, ETA, EPA, DPA and DHA).
2. LA to DPA=100×(% DHA+DPA)/(sum % for LA, GLA, DGLA, ARA, EDA, ALA, SDA, ETrA, ETA, EPA, DPA and DHA).
3. ALA to DPA=100×(% DHA+% DPA)/(sum % for ALA, SDA, ETrA, ETA, EPA, DPA and DHA).
4. EPA to DPA=100×(% DHA+DPA)/(sum % for EPA, DPA and DHA).
5. DPA to DHA (Δ4-desaturase efficiency)=100×(% DHA)/(sum % for DPA and DHA).
6. Δ12-desaturase efficiency=100×(sum % for LA, GLA, DGLA, ARA, EDA, ALA, SDA, ETrA, ETA, EPA, DPA and DHA)/(sum % for OA, LA, GLA, DGLA, ARA, EDA, ALA, SDA, ETrA, ETA, EPA, DPA and DHA).
7. ω3-desaturase efficiency=100×(sum % for ALA, SDA, ETrA, ETA, EPA, DPA and DHA)/(sum % for LA, GLA, DGLA, ARA, EDA, ALA, SDA, ETrA, ETA, EPA, DPA and DHA).
8. OA to ALA=100×(sum % for ALA, SDA, ETrA, ETA, EPA, DPA and DHA)/(sum % for OA, LA, GLA, DGLA, ARA, EDA, ALA, SDA, ETrA, ETA, EPA, DPA and DHA).
9. Δ6-desaturase efficiency (on ω3 substrate ALA)=100× (sum % for SDA, ETA, EPA, DPA and DHA)/(% ALA, SDA, ETrA, ETA, EPA, DPA and DHA).
10. Δ6-elongase efficiency (on ω3 substrate SDA)=100× (sum % for ETA, EPA, DPA and DHA)/(sum % for SDA, ETA, EPA, DPA and DHA).
11. Δ5-desaturase efficiency (on ω3 substrate ETA)=100× (sum % for EPA, DPA and DHA)/(sum % for ETA, EPA, DPA and DHA).
12. Δ5-elongase efficiency (on ω3 substrate EPA)=100× (sum % for DPA and DHA)/(sum % for EPA, DPA and DHA).

The fatty acid composition of the lipid, preferably seedoil, of the invention, is also characterised by the ratio of ω6 fatty acids:ω3 fatty acids in the total fatty acid content, for either total ω6 fatty acids:total ω3 fatty acids or for new ω6 fatty acids:new ω3 fatty acids. The terms total ω6 fatty acids, total ω3 fatty acids, new ω6 fatty acids and new ω3 fatty acids have the meanings as defined herein. The ratios are calculated from the fatty acid composition in the lipid extracted from the cell, plant, plant part or seed, in the manner as exemplified herein. It is desirable to have a greater level of ω3 than ω6 fatty acids in the lipid, and therefore an ω6:ω3 ratio of less than 1.0 is preferred. A ratio of 0.0 indicates a complete absence of the defined ω6 fatty acids; a ratio of 0.03 was achieved. Such low ratios can be achieved through the combined use of a Δ6-desaturase which has an ω3 substrate preference together with an ω3-desaturase, particularly a fungal ω3-desaturase such as the *Pichia pastoris* ω3-desaturase as exemplified herein.

The yield of LC-PUFA per weight of seed may also be calculated based on the total oil content in the seed and the % DPA in the oil. For example, if the oil content of canola seed is about 40% (w/w) and about 12% of the total fatty acid content of the oil is DPA, the DPA content of the seed is about 4.8% or about 48 mg per gram of seed. At a DPA content of about 21%, canola seed or *Camelina sativa* seed has a DPA content of about 84 mg per gram of seed. The present invention therefore provides *Brassica napus, B. juncea* and *Cainelina sativa* plants, and seed obtained therefrom, comprising at least about 80 mg or at least about 84 mg DPA per gram seed. The seed has a moisture content as is standard for harvested mature seed after drying down (4-15% moisture). The invention also provides a process for obtaining oil, comprising obtaining the seed and extracting the oil from the seed, and uses of the oil and methods of obtaining the seed comprising harvesting the seeds from the plants according to the invention.

The amount of DPA produced per hectare can also be calculated if the seed yield per hectare is known or can be estimated. For example, canola in Australia typically yields about 2.5 tonnes seed per hectare, which at 40% oil content yields about 1000 kg of oil. At 20.1% DPA in the total oil, this provides about 200 kg of DPA per hectare. If the oil content is reduced by 50%, this still provides about 100 kg DPA/ha.

Evidence to date suggests that some desaturases expressed heterologously in yeast or plants have relatively low activity in combination with some elongases. This may be alleviated by providing a desaturase with the capacity of to use an acyl-CoA form of the fatty acid as a substrate in LC-PUFA synthesis, and this is thought to be advantageous in recombinant cells particularly in plant cells. A particularly advantageous combination for efficient DPA synthesis is a fungal ω3-desaturase, for example such as the *Pichia pastoris* ω3-desaturase (SEQ ID NO: 6), with a Δ6-desaturase which has a preference for ω3 acyl substrates such as, for example, the *Micromonas pusilla* Δ6-desaturase (SEQ ID NO: 9), or variants thereof which have at least 95% amino acid sequence identity.

As used herein, the term "essentially free" means that the composition (for example lipid or oil) comprises little (for example, less than about 0.5%, less than about 0.25%, less than about 0.1%, or less than about 0.01%) or none of the defined component. In an embodiment, "essentially free" means that the component is undetectable using a routine analytical technique, for example a specific fatty acid (such as ω6-docosapentaenoic acid) cannot be detected using gas chromatography as outlined in Example 1.

In an embodiment, extracted lipid, extracted oil, a plant or part thereof such as a seed (of the invention or used in a process/method of the invention), a feedstuff, or a composition of the invention does not comprise all-cis-6,9,12,15,18-heneicosapentaenoic acid (n-3 HPA).

Production of Oils

Techniques that are routinely practiced in the art can be used to extract, process, and analyze the oils produced by cells, plants, seeds, etc of the instant invention. Typically, plant seeds are cooked, pressed, and extracted to produce crude oil, which is then degummed, refined, bleached, and deodorized. Generally, techniques for crushing seed are known in the art. For example, oilseeds can be tempered by spraying them with water to raise the moisture content to, e.g., 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the oil droplets, and agglomerates protein particles, all of which facilitate the extraction process.

In an embodiment, the majority of the seed oil is released by passage through a screw press. Cakes expelled from the screw press are then solvent extracted, e.g., with hexane, using a heat traced column. Alternatively, crude oil produced by the pressing operation can be passed through a settling tank with a slotted wire drainage top to remove the solids that are expressed with the oil during the pressing operation. The clarified oil can be passed through a plate and frame filter to remove any remaining fine solid particles. If desired, the oil recovered from the extraction process can be combined with the clarified oil to produce a blended crude oil.

Once the solvent is stripped from the crude oil, the pressed and extracted portions are combined and subjected to normal oil processing procedures. As used herein, the term "purified" when used in connection with lipid or oil of the invention typically means that that the extracted lipid or oil has been subjected to one or more processing steps of increase the purity of the lipid/oil component. For example, a purification step may comprise one or more or all of the group consisting of: degumming, deodorising, decolourising, drying and/or fractionating the extracted oil. However, as used herein, the term "purified" does not include a transesterification process or other process which alters the fatty acid composition of the lipid or oil of the invention so as to increase the DPA content as a percentage of the total fatty acid content. Expressed in other words, the fatty acid composition of the purified lipid or oil is essentially the same as that of the unpurified lipid or oil.

Degumming

Degumming is an early step in the refining of oils and its primary purpose is the removal of most of the phospholipids from the oil, which may be present as approximately 1-2% of the total extracted lipid. Addition of ~2% of water, typically containing phosphoric acid, at 70-80° C. to the crude oil results in the separation of most of the phospholipids accompanied by trace metals and pigments. The insoluble material that is removed is mainly a mixture of phospholipids and triacylglycerols and is also known as lecithin. Degumming can be performed by addition of concentrated phosphoric acid to the crude seedoil to convert non-hydratable phosphatides to a hydratable form, and to chelate minor metals that are present. Gum is separated from the seedoil by centrifugation.

Alkali Refining

Alkali refining is one of the refining processes for treating crude oil, sometimes also referred to as neutralization. It usually follows degumming and precedes bleaching. Following degumming, the seedoil can treated by the addition of a sufficient amount of an alkali solution to titrate all of the fatty acids and phosphoric acids, and removing the soaps thus formed. Suitable alkaline materials include sodium hydroxide, potassium hydroxide, sodium carbonate, lithium hydroxide, calcium hydroxide, calcium carbonate and ammonium hydroxide. This process is typically carried out at room temperature and removes the free fatty acid fraction. Soap is removed by centrifugation or by extraction into a solvent for the soap, and the neutralised oil is washed with water. If required, any excess alkali in the oil may be neutralized with a suitable acid such as hydrochloric acid or sulphuric acid.

Bleaching

Bleaching is a refining process in which oils are heated at 90-120° C. for 10-30 minutes in the presence of a bleaching earth (0.2-2.0%) and in the absence of oxygen by operating with nitrogen or steam or in a vacuum. This step in oil processing is designed to remove unwanted pigments (carotenoids, chlorophyll, gossypol etc), and the process also removes oxidation products, trace metals, sulphur compounds and traces of soap.

Deodorization

Deodorization is a treatment of oils and fats at a high temperature (200-260° C.) and low pressure (0.1-1 mm Hg). This is typically achieved by introducing steam into the seedoil at a rate of about 0.1 ml/minute/100 ml of seedoil. After about 30 minutes of sparging, the seedoil is allowed to cool under vacuum. The seedoil is typically transferred to a glass container and flushed with argon before being stored under refrigeration. This treatment improves the colour of the seedoil and removes a majority of the volatile substances or odorous compounds including any remaining free fatty acids, monoacylglycerols and oxidation products.

Winterisation

Winterization is a process sometimes used in commercial production of oils for the separation of oils and fats into solid (stearin) and liquid (olein) fractions by crystallization at sub-ambient temperatures. It was applied originally to cottonseed oil to produce a solid-free product. It is typically used to decrease the saturated fatty acid content of oils.

Transesterification

As used herein, "transesterification" means a process that exchanges the fatty acids within and between TAGs or transfers the fatty acids to another alcohol to form an ester. This may initially involve releasing fatty acids from the TAGs as free fatty acids or it may directly produce fatty acid esters, preferably fatty acid methyl esters or ethyl esters. In a transesterification reaction of the TAG with an alcohol such as methanol or ethanol, the alkyl group of the alcohol forms an ester linkage with the acyl groups (including the DPA) of the TAG. When combined with a fractionation process, transesterification can be used to modify the fatty acid composition of lipids (Marangoni et al., 1995). Transesterification can use either chemical (e.g. strong acid or base catalysed) or enzymatic means, the latter using lipases which may be position-specific (sn-1/3 or sn-2 specific) for the fatty acid on the TAG, or having a preference for some fatty acids over others (Speranza et al, 2012). The fatty acid fractionation to increase the concentration of LC-PUFA in an oil can be achieved by any of the methods known in the art, such as, for example, freezing crystallization, complex formation using urea, molecular distillation, supercritical fluid extraction, counter current chromatography and silver ion complexing. Complex formation with urea is a preferred method for its simplicity and efficiency in reducing the level of saturated and monounsaturated fatty acids in the oil (Gamez et al., 2003). Initially, the TAGs of the oil are split into their constituent fatty acids, often in the form of fatty acid esters, by hydrolysis under either acid or base catalysed reaction conditions, whereby one mol of TAG is reacted with at least 3 mol of alcohol (e.g. ethanol for ethyl esters or methanol for methyl esters) with excess alcohol used to enable separation of the formed alkyl esters and the glycerol that is also formed, or by lipases. These free fatty acids or fatty acid esters, which are usually unaltered in fatty acid composition by the treatment, may then be mixed with an ethanolic solution of urea for complex formation. The saturated and monounsaturated fatty acids easily complex with urea and crystallize out on cooling and may subsequently be removed by filtration. The non-urea complexed fraction is thereby enriched with LC-PUFA.

Feed Stuffs

The present invention includes compositions which can be used as feedstuffs. For purposes of the present invention, "feedstuffs" include any food or preparation for human or animal consumption which when taken into the body (a) serve to nourish or build up tissues or supply energy; and/or (b) maintain, restore or support adequate nutritional status or metabolic function. Feedstuffs of the invention include nutritional compositions for babies and/or young children such as, for example, infant formula, and seedmeal of the invention.

Feedstuffs of the invention comprise, for example, a cell of the invention, a plant of the invention, the plant part of the invention, the seed of the invention, an extract of the invention, the product of the method of the invention, the product of the fermentation process of the invention, or a composition along with a suitable carrier(s). The term "carrier" is used in its broadest sense to encompass any component which may or may not have nutritional value. As the skilled addressee will appreciate, the carrier must be suitable for use (or used in a sufficiently low concentration) in a feedstuff such that it does not have deleterious effect on an organism which consumes the feedstuff.

The feedstuff of the present invention comprises an oil, fatty acid ester, or fatty acid produced directly or indirectly by use of the methods, cells or plants disclosed herein. The composition may either be in a solid or liquid form. Additionally, the composition may include edible macronutrients, protein, carbohydrate, vitamins, and/or minerals in amounts desired for a particular use. The amounts of these ingredients will vary depending on whether the composition is intended for use with normal individuals or for use with individuals having specialized needs, such as individuals suffering from metabolic disorders and the like.

Examples of suitable carriers with nutritional value include, but are not limited to, macronutrients such as edible fats, carbohydrates and proteins. Examples of such edible fats include, but are not limited to, coconut oil, borage oil, fungal oil, black current oil, soy oil, and mono- and diglycerides. Examples of such carbohydrates include (but are not limited to): glucose, edible lactose, and hydrolyzed starch. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the feedstuff compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the feedstuff compositions of the present invention can be of semi-purified or purified origin. By semi-purified or purified is meant a material which has been prepared by purification of a natural material or by de novo synthesis.

A feedstuff composition of the present invention may also be added to food even when supplementation of the diet is not required. For example, the composition may be added to food of any type, including (but not limited to): margarine, modified butter, cheeses, milk, yogurt, chocolate, candy, snacks, salad oils, cooking oils, cooking fats, meats, fish and beverages.

Additionally, fatty acids produced in accordance with the present invention or host cells transformed to contain and express the subject genes may also be used as animal food supplements to alter an animal's tissue, egg or milk fatty acid composition to one more desirable for human or animal consumption. Examples of such animals include sheep, cattle, horses, poultry such as chickens and the like.

Furthermore, feedstuffs of the invention can be used in aquaculture to increase the levels of fatty acids in fish or crustaceans such as, for example, prawns for human or animal consumption. Preferred fish are salmon.

Preferred feedstuffs of the invention are the plants, seed and other plant parts such as leaves and stems which may be used directly as food or feed for humans or other animals. For example, animals may graze directly on such plants grown in the field or be fed more measured amounts in controlled feeding. The invention includes the use of such plants and plant parts as feed for increasing the LC-PUFA levels in humans and other animals.

In an embodiment, a feedstuff is infant formula comprising the lipid or oil of the invention. As used herein, "infant formula" means a non-naturally occurring composition that satisfies at least a portion of the nutrient requirements of an infant. An "infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. As used herein, "non-naturally occurring" means that the product is not found in nature but has been produced by human intervention. As used herein, the infant formula of the invention excludes pure human breast milk (Koletzko et al., 1988) and pure milk produced by non-human animals, although the infant formula of the invention may comprise components derived from milk such as milk proteins or carbohydrates, for example whey proteins or lactose. The infant formula of the invention excludes naturally occurring meats such as beef, seal meat, whale meat or fish, although the infant formula of the invention may comprise components such as proteins from these sources. The infant formula of the invention always comprises lipid comprising the DPA of the invention, preferably at a level of between 0.05% to about 0.5% by weight of the total fatty acid content. The DPA may be present as TAG, as phospholipid or as non-esterified fatty acid, or a mixture thereof.

Lipid or oil of the invention can be incorporated into infant formula using procedures known in the art. For example, the skilled person can readily produce infant formula of the invention generally using the procedures described in WO 2008/027991, US20150157048, US2015094382 and US20150148316, where the DPA is added in addition to, or instead of, one or more of the polyunsaturated fatty acids described therein.

In one example, the infant formula comprises DPA (ie omega-3 DPA as described herein), optionally with prebiotics, especially polydextrose (PDX) and galacto-oligosaccharides (GOS), lactoferrin from a non-human source, and other long-chain polyunsaturated fatty acids (LC-PUFAs). In some embodiments, the nutritional composition further comprises SDA and/or gamma-linolenic acid (GLA). In certain embodiments, the infant formula comprises up to about 7 g/100 kcal of a fat or lipid source, more preferably about 3 g/100 kcal to about 7 g/100 kcal of a fat or lipid source, wherein the fat or lipid source comprises at least about 0.5 g/100 kcal, and more preferably from about 1.5 g/100 kcal to about 7 g/100 kcal; up to about 7 g/100 kcal of a protein or protein equivalent source, more preferably about 1 g/100 kcal to about 7 g/100 kcal of a protein source or protein equivalent source; and at least about 5 g/100 kcal of a carbohydrate, more preferably about 5 g to about 25 g/100 kcal of a carbohydrate. The infant formula may further comprise one or more or all of 1) at least about 10 mg/100 kcal of lactoferrin, more preferably from about 10 mg/100 kcal to about 200 mg/100 kcal of lactoferrin; 2) about 0.1 g/100 kcal to about 1 g/100 kcal of a prebiotic composition comprising PDX and GOS; and 3) at least about 5 mg/100 kcal of an additional LC-PUFA (i.e., an LC-PUFA other than DPA) comprising DHA, more preferably from about 5 mg/100 kcal to about 75 mg/100 kcal of an additional LC-PUFA comprising DHA.

In an embodiment, the ratio of DPA:DHA in the total fatty acid content of the infant formula is between 1:3 and 2:1. EPA may also be present but is preferable absent. If present, the ratio of EPA:DPA In the total fatty acid content is preferably less than 1:2, more preferably less than 1:5. ARA may also be absent but is preferably present, preferably the ratio of ARA:DPA in the total fatty acid content is between 1:3 and 2:1. Most preferably, the levels of each LC-PUFA in the infant formula is about the same as found in any human breast milk, which naturally show variation based on a mother's age, genetic factors, dietary intake and nutritional status. For example, see Koletzko et al. (1988). In a preferred embodiment, the infant formula does not contain detectable levels of heneicosapentaenoic acid (HPA, 21:5ω3)

The infant formula may refer to, for example, liquids, powders, gels, pastes, solids, concentrates, suspensions, or ready-to-use forms of enteral formulas, oral formulas, formulas for infants.

Prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide and gentio-oligosaccharides.

Lactoferrin may also be also included in the nutritional composition of the present disclosure. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively.

The protein or protein equivalent source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

Suitable carbohydrate sources can be any used in the art, e.g., lactose, glucose, fructose, corn syrup solids, maltodextrins, sucrose, starch, rice syrup solids, and the like. The amount of the carbohydrate component in the nutritional composition is at least about 5 g/100 kcal and typically can vary from between about 5 g and about 25 g/100 kcal. In some embodiments, the amount of carbohydrate is between about 6 g and about 22 g/100 kcal. In other embodiments, the amount of carbohydrate is between about 12 g and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes. Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

Preferably, one or more vitamins and/or minerals may also be added to the infant formula in amounts sufficient to supply the daily nutritional requirements of a subject. It is to be understood by one of ordinary skill in the art that vitamin and mineral requirements will vary, for example, based on the age of the child. The nutritional composition may optionally include, but is not limited to, one or more of the following vitamins or derivations thereof: vitamin B1 (thiamin, thiamin pyrophosphate, TPP, thiamin triphosphate, TTP, thiamin hydrochloride, thiamin mononitrate), vitamin B2 (riboflavin, flavin mononucleotide, FMN, flavin adenine dinucleotide, FAD, lactoflavin, ovoflavin), vitamin B3 (niacin, nicotinic acid, nicotinamide, niacinamide, nicotinamide adenine dinucleotide, NAD, nicotinic acid mononucleotide, NicMN, pyridine-3-carboxylic acid), vitamin B3-precursor tryptophan, vitamin B6 (pyridoxine, pyridoxal, pyridoxamine, pyridoxine hydrochloride), pantothenic acid (pantothenate, panthenol), folate (folic acid, folacin, pteroylglutamic acid), vitamin B12 (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin3, 1,25,-dihydroxyvitamin D), vitamin E (α-tocopherol, α-tocopherol acetate, α-tocopherol succinate, α-tocopherol nicotinate, α-tocopherol), vitamin K (vitamin K1, phylloquinone, naphthoquinone, vitamin K2, menaquinone-7, vitamin K3, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof. Further, the nutritional composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound. The minerals can be added to nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the infant formula of, or produced using the invention, does not comprise human or animal breast milk or an extract thereof comprising DPA.

In another embodiment, the level of omega-6 DPA in the total fatty acid content of the infant formula is less than 2%, preferably less than 1%, or between 0.1% and 2%, more preferably is absent.

Compositions

The present invention also encompasses compositions, particularly pharmaceutical compositions, comprising one or more of the fatty acids and/or resulting oils produced using the methods of the invention, preferably in the form of ethyl esters of the fatty acids.

A pharmaceutical composition may comprise one or more of the fatty acids and/or oils, in combination with a standard, well-known, non-toxic pharmaceutically-acceptable carrier, adjuvant or vehicle such as phosphate-buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride, and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as ethoxylated isostearyl alcohols, polyoxyethylene sorbitol and sorbitan esters, microcrystalline cellulose, aluminum metahydroxide, bentonite, agar-agar, and tragacanth or mixtures of these substances.

Solid dosage forms such as tablets and capsules can be prepared using techniques well known in the art. For example, fatty acids produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant fatty acid (s).

For intravenous administration, the fatty acids produced in accordance with the present invention or derivatives thereof may be incorporated into commercial formulations.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of fatty acid, especially LC-PUFA, is desirable. However, it will be appreciated that any amount of fatty acid will be beneficial to the subject.

Possible routes of administration of the pharmaceutical compositions of the present invention include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants to form a spray or inhalant.

The dosage of the composition to be administered to the patient may be determined by one of ordinary skill in the art and depends upon various factors such as weight of the patient, age of the patient, overall health of the patient, past history of the patient, immune status of the patient, etc.

Additionally, the compositions of the present invention may be utilized for cosmetic purposes. It may be added to pre-existing cosmetic compositions such that a mixture is formed or a fatty acid produced according to the subject invention may be used as the sole "active" ingredient in a cosmetic composition.

EXAMPLES

Example 1. Materials and Methods

Expression of Genes in Plant Cells in a Transient Expression System

Exogenous genetic constructs were expressed in plant cells in a transient expression system essentially as described by Voinnet et al. (2003) and Wood et al. (2009).

Gas Chromatography (GC) Analysis of Fatty Acids

FAME were analysed by gas chromatography using an Agilent Technologies 7890A GC (Palo Alto, Calif., USA) equipped with a 30 m SGE-BPX70 column (70% cyanopropyl polysilphenylene-siloxane, 0.25 mm inner diameter, 0.25 mm film thickness), an FID, a split/splitless injector and an Agilent Technologies 7693 Series auto sampler and injector. Helium was used as the carrier gas. Samples were injected in split mode (50:1 ratio) at an oven temperature of 150° C. After injection, the oven temperature was held at 150° C. for 1 min then raised to 210° C. at 3° C. $min^{-1}$, again raised to 240° C. at 50° C. $min^{-1}$ and finally holding for 1.4 min at 240° C. Peaks were quantified with Agilent Technologies ChemStation software (Rev B.04.03 (16), Palo Alto, Calif., USA) based on the response of the known amount of the external standard GLC-411 (Nucheck) and C17:0-ME internal standard.

Liquid Chromatography-Mass Spectrometry (LC-MS) Analysis of Lipids

Total lipids were extracted from freeze-dried developing seeds, twelve days after flowering (daf), and mature seeds after adding a known amount of tri-C17:0-TAG as an internal quantitation standard. The extracted lipids were dissolved into 1 mL of 10 mM butylated hydroxytoluene in butanol:methanol (1:1 v/v) per 5 mg dry material and analysed using an Agilent 1200 series LC and 6410b electrospray ionisation triple quadrupole LC-MS. Lipids were chromatographically separated using an Ascentis Express RP-Amide column (50 mm×2.1 mm, 2.7 μm, Supelco) operating a binary gradient with a flow rate of 0.2 mL/min. The mobile phases were: A. 10 mM ammonium formate in $H_2O$:methanol:tetrahydrofuran (50:20:30 v/v/v); B. 10 mM ammonium formate in $H_2O$:methanol:tetrahydrofuran (5:20:75, v/v/v). Multiple reaction monitoring (MRM) lists were based on the following major fatty acids: 16:0, 18:0, 18:1, 18:2, 18:3, 18:4, 20:1, 20:2, 20:3, 20:4, 20:5, 22:4, 22:5, 22:6 using a collision energy of 30 V and fragmentor of 60 V. Individual MRM TAG was identified based on ammoniated precursor ion and product ion from neutral loss of 22:6. TAG was quantified using a 10 μM tristearin external standard.

Lipid Profiling with LC-MS

The extracted total lipids were analysed using an Agilent 1200 series LC coupled to an Agilent 6410B electrospray ionisation QQQ-MS (Agilent, Palo Alto, Calif., USA). A 5 μL injection of each total lipid extract was chromatographically separated with an Ascentis Express RP-Amide 50 mm×2.1 mm, 2.7 μm HPLC column (Sigma-Aldrich, Castle Hill, Australia) using a binary gradient with a flow rate of 0.2 mL/min. The mobile phases were: A. 10 mM ammonium formate in $H_2O$:methanol:tetrahydrofuran (50:20:30, v/v/v.); B. 10 mM ammonium formate in $H_2O$:methanol:tetrahydrofuran (5:20:75, v/v/v.). Selected neutral lipids (TAG and DAG) and phospholipids (PL, including PC, PE, PI, PS, PA, PG) were analysed by multiple reaction monitoring (MRM) using a collision energy of 30 V and fragmentation energy of 60 V. Neutral lipids were targeted on the following major fatty acids: 16:0 (palmitic acid), 18:0 (stearic acid), 18:10ω9 (oleic acid, OA), 18:20ω6 (linoleic acid, LA), 18:30ω3 (α-linolenic acid, ALA), 18:4ω3 (stearidonic acid, SDA), 20:1, 20:2, 20:3, 20:4ω3, 20:5ω3, 22:4ω3, 22:5ω3, 22:6ω3, while phospholipids were scanned containing $C_{16}$, $C_{18}$, $C_{20}$ and $C_{22}$ species with double bonds of 0-3, 0-4, 0-5, 4-6 respectively.

Individual MRM TAG was identified based on ammoniated precursor ion and product ion from neutral loss of 20:1, SDA, EPA and DHA. TAG and DAG were quantified using the 50 μM tristearin and distearin as external standards. PL were quantified with 10 uM of di-18:0-PC, di-17:0-PA, di-17:0-PE, 17:0-17:1-PG, di-18:1-PI and di-17:0-PS external standards (Avanti Polar Lipids, Alabaster, Ala., USA). Selected TAG, DAG and PL species were further confirmed by Agilent 6520 Q-TOF MS/MS.

Determination of Seed Fatty Acid Profile and Oil Content

Where seed oil content was to be determined, seeds were dried in a desiccator for 24 h and approximately 4 mg of seed was transferred to a 2 ml glass vial containing Teflon-lined screw cap. 0.05 mg triheptadecanoin dissolved in 0.1 ml toluene was added to the vial as internal standard.

Seed FAME were prepared by adding 0.7 ml of 1N methanolic HCl (Supelco) to the vial containing seed material, vortexed briefly and incubated at 80° C. for 2 h. After cooling to room temperature, 0.3 ml of 0.9% NaCl (w/v) and 0.1 ml hexane was added to the vial and mixed well for 10 min in Heidolph Vibramax 110. The FAME was collected into 0.3 ml glass insert and analysed by GC with a flame ionization detector (FID) as mentioned earlier.

The peak area of individual FAME were first corrected on the basis of the peak area responses of known amount of the same FAMEs present in a commercial standard GLC-411 (NU-CHEK PREP, INC., USA). GLC-411 contains equal amounts of 31 fatty acids (% by wt), ranging from C8:0 to C22:6. In case of fatty acids, which were not present in the standard, the inventors took the peak area responses of the most similar FAME. For example, peak area response of FAMEs of 16:1d9 was used for 16:1d7 and FAME response of C22:6 was used for C22:5. The corrected areas were used to calculate the mass of each FAME in the sample by comparison to the internal standard mass. Oil is stored mainly in the form of TAG and its weight was calculated based on FAME weight. Total moles of glycerol was determined by calculating moles of each FAMES and dividing total moles of FAMEs by three. TAG was calculated as the sum of glycerol and fatty acyl moieties using a relation: % oil by weight=100×((41×total mol FAME/3)+(total g FAME−(15×total mol FAME)))/g seed, where 41 and 15 are molecular weights of glycerol moiety and methyl group, respectively.

Analysis of the Sterol Content of Oil Samples

Samples of approximately 10 mg of oil together with an added aliquot of C24:0 monol as an internal standard were saponified using 4 mL 5% KOH in 80% MeOH and heating for 2 h at 80° C. in a Teflon-lined screw-capped glass tube. After the reaction mixture was cooled, 2 mL of Milli-Q water were added and the sterols were extracted into 2 mL of hexane: dichloromethane (4:1 v/v) by shaking and vortexing. The mixture was centrifuged and the sterol extract was removed and washed with 2 mL of Milli-Q water. The sterol extract was then removed after shaking and centrifugation. The extract was evaporated using a stream of nitrogen gas and the sterols silylated using 200 mL of BSTFA and heating for 2 h at 80° C.

For GC/GC-MS analysis of the sterols, sterol-OTMSi derivatives were dried under a stream of nitrogen gas on a heat block at 40° C. and then re-dissolved in chloroform or hexane immediately prior to GC/GC-MS analysis. The sterol-OTMS derivatives were analysed by gas chromatography (GC) using an Agilent Technologies 6890A GC (Palo Alto, Calif., USA) fitted with an Supelco Equity™-1 fused silica capillary column (15 m×0.1 mm i.d., 0.1 μm film thickness), an FID, a split/splitless injector and an Agilent Technologies 7683B Series auto sampler and injector. Helium was the carrier gas. Samples were injected in splitless mode at an oven temperature of 120° C. After injection, the oven temperature was raised to 270° C. at 10° C. $min^{-1}$ and finally to 300° C. at 5° C. $min^{-1}$. Peaks were quantified with Agilent Technologies ChemStation software (Palo Alto, Calif., USA). GC results are subject to an error of ±5% of individual component areas.

GC-mass spectrometric (GC-MS) analyses were performed on a Finnigan Thermoquest GCQ GC-MS and a Finnigan Thermo Electron Corporation GC-MS; both systems were fitted with an on-column injector and Thermoquest Xcalibur software (Austin, Tex., USA). Each GC was fitted with a capillary column of similar polarity to that described above. Individual components were identified using mass spectral data and by comparing retention time data with those obtained for authentic and laboratory standards. A full procedural blank analysis was performed concurrent to the sample batch.

RT-PCR Conditions

Reverse transcription-PCR (RT-PCR) amplification was typically carried out using the Superscript III One-Step RT-PCR system (Invitrogen) in a volume of 25 μL using 10 pmol of the forward primer and 30 pmol of the reverse primer, $MgSO_4$ to a final concentration of 2.5 mM, 400 ng of total RNA with buffer and nucleotide components according to the manufacturer's instructions. Typical temperature regimes were: 1 cycle of 45° C. for 30 minutes for the reverse transcription to occur; then 1 cycle of 94° C. for 2 minutes followed by 40 cycles of 94° C. for 30 seconds, 52° C. for 30 seconds, 70° C. for 1 minute; then 1 cycle of 72° C. for 2 minutes before cooling the reaction mixtures to 5° C.

Determination of Copy-Number of Transgenes by Digital PCR

To determine the copy-number of transgenes in a transgenic plant, a digital PCR method was used as follows. This method could also be used to determine whether a plant was transgenic for the genetic constructs described herein. About a centimetre square of leaf tissue was harvested from each individual plant and placed in a collection microtube (Qiagen). The samples were then freeze dried for 24 to 48 hr. For breaking up the samples for DNA extraction, stainless steel ball bearings were added to each dried sample and the tubes shaken on a Qiagen Tissue lyser. 3754 of extraction buffer (0.1M Tris-HCl pH8, 0.05M EDTA pH8 and L25% SDS) was added to each tube, the mixtures incubated at 65° C. for 1 hr, and then cooled before 187 μL of 6M ammonium acetate (4° C.) was added to each tube with thorough mixing. The samples were then centrifuged for 30 min at 3000 rpm. The supernatant from each tube was removed into new microtubes each containing 220 μL of isopropanol for precipitation of the DNA at room temperature for 5 min. DNA was collected by centrifuging the tubes at 3000 rpm for 30 min, the DNA pellets washed with 320 μL of 70% ethanol and dried before resuspension of the DNA in 225 μL of water. Non-dissolved material was pelleted by centrifugation at 3000 rpm for 20 min, and 150 μL of each supernatant transferred to 96-well plates for long term storage.

For efficient and quantitative digital PCR (ddPCR) the DNA was digested with restriction enzymes prior to amplification reactions, to ensure that multiple copies of the transgenes or multiple insertions were physically separated. Aliquots of the DNA preparations were therefore digested with EcoRI and BamHI, together, in 20 μL volumes using 10× EcoRI buffer, 5 μL of DNA and about 4 units of each enzyme per sample, incubated overnight at 37° C.

The primers used in these PCR reactions were designed using Primer3 software to confirm that primers for the reference and target genes were not predicted to interact, or such interaction would not be a problem under the conditions used. The reference gene used in the assay was the canola Hmg (high mobility group) gene, present at one gene per canola genome (Weng et al., 2004). Since canola is an allotetraploid, it was taken that there were 4 copies of the Hmg gene, i.e. 2 alleles of each of the two genes, in *Brassica napes*. The reference gene reactions used the pair of primers and a dual-labelled probe, as follows: Sense primer, Can11 GCGAAGCACATCGAGTCA (SEQ ID NO:50); Antisense primer, Can12 GGTTGAGGTGGTAGCTGAGG (SEQ ID NO:51); Probe, Hmg-P3 5'-Hex/TCTCTAC/zen/CCGTCTCACATGACGC/3IABkFQ/-3' (SEQ ID NO:52). The amplification product size was 73 bp.

In one target gene amplification reaction which detected a region of the PPT selectable marker gene to screen all of the transgenic plants, the sense primer was Can17, ATACAAGCACGGTGGATGG (SEQ ID NO:53); the antisense primer, Can18 TGGTCTAACAGGTCTAGGAGGA (SEQ ID NO:54); the probe, PPT-P3 5'-/FAM/TGGCAAAGA/zen/GATTTCGAGCTTCCTGC/3IABkFQ/-3' (SEQ ID NO:55). The size of this target gene amplification product was 82 bp. On some occasions, a second target gene assay was performed in parallel to detect partial insertions of the T-DNA. This second assay detected a region of the Δ6-desaturase gene using a sense primer, Can23 CAAGCACCGTAGTAAGAGAGCA (SEQ ID NO:56), the antisense primer, Can24 CAGACAGCCTGAGGTTAGCA (SEQ ID NO:57); the probe, D6des-P3 5'-/FAM/TCCCCACTT/zen/CTTAGCGAAAGGAACGA/3IAB kFQ/-3' (SEQ ID NO:58). The size of this target gene amplification product was 89 bp. Reactions routinely used 2 μL of the digested DNA preparations. Reaction composition per sample: reference sense primer (10 pM), 1 μL; reference antisense primer (10 pM), 1 μL; reference gene probe (10 pM), 0.5 μL; target gene sense primer (10 pM), 1 μL; target gene antisense primer (10 pM), 1 μL; target gene probe (10 pM), 0.5 μL; ddPCR reagent mix, 12.5 μL; water 5.5 μL; in a total volume of 25 μL.

The mixtures were then placed into a QX100 droplet generator, which partitioned each sample into 20000 nanoliter-sized droplets. This was done in 8-well cartridges until all of the samples were processed and transferred to a 96-well PCR plate. This plate was then heat sealed with a pierceable foil using a plate sealer machine. The samples were then treated under the following reaction conditions: 95° C., 10 min, ramping at 2.5° C./s; then 39 cycles of 94° C., 30 s ramping at 2.5° C./s; 61° C., 1 min, ramping at 2.5° C./s; 98° C., 10 min, followed by cooling to 12° C. Following the amplification reactions of the DNA in the droplets, the plate was placed in a QX100 droplet reader which analysed each droplet individually using a two-color detection system (set to detect FAM or Hex). The droplet digital PCR data were viewed as either a 1-D plot with each droplet from a sample plotted on the graph of fluorescence intensity, or a 2-D plot in which fluorescence (FAM) was plotted against fluorescence (Hex) for each droplet. The software measured the number of positive and negatives droplets for each fluorophore (FAM or Hex) in each sample. The software then fitted the fraction of positive droplets to a Poisson algorithm to determine the concentration of the target DNA molecule in units of copies/4 input. The copy number variation was calculated using the formula: CNV=(A/B)*Nb, where A=concentration of target gene, B=concentration of reference gene, and Nb=4, the number of copies of the reference gene in the genome.

Assessment of Pollen Viability

Fluorescein diacetate (FDA) was dissolved in acetone at 2 mg/ml to provide a stock solution. FDA dilutions were prepared just before use by adding drops of the FDA stock solution to 2 ml of a sucrose solution (0.5 M) until saturation was reached as indicated by the appearance of persistent cloudiness.

Propidium iodide (PI) was dissolved in sterile distilled water at 1 mg/ml to provide a stock solution. Just before use, 100 μl of the stock solution was added to 10 ml of sterile distilled water to make a working solution. To check the ratio of viable and non-viable pollen, PI and FDA stock solutions were mixed in 2:3 ratio.

Transgenic and wild-type canola and mustard plants were grown under standard conditions in a glasshouse at 22±2° C.

with a 16 hr photoperiod per day. Mature flower buds which were ready to open in the next day were labelled and collected on the following morning at 9-10 am. Pollen from opened flowers were stained with the FDA/PI mixture and visualized using a Leica MZFLIII fluorescence microscope. GFP-2, a 510 nm long pass emission filter (transmitting red and green light) with a 480/40 nm excitation filter was used to detect viable and non-viable pollen. Non-viable pollen which took up the PI stain appeared red under the fluorescence microscope whereas viable pollen appeared bright green when stained with PI and FDA.

Example 2. Stable Expression of a Transgenic DHA Pathway in *Camelina sativa* Seeds The binary vector pJP3416-GA7 (see FIG. 2 and SEQ ID NO:1) was introduced into *A. tumefaciens* strain AGL1 and cells from a culture of the transformed *Agrobacterium* used to treat *C. sativa* flowering plants using a floral dip method for transformation (Lu and Kang, 2008). After growth and maturation of the plants, the $T_1$ seeds from the treated plants were harvested, sown onto soil and the resultant plants treated by spraying with the herbicide BASTA to select for plants which were transgenic for, and expressing, the bar selectable marker gene present on the T-DNA of pJP3416-GA7. Surviving $T_1$ plants which were tolerant to the herbicide were grown to maturity after allowing them to self-fertilise, and the resultant $T_2$ seed harvested. Five transgenic plants were obtained, only three of which contained the entire T-DNA.

Lipid was extracted from a pool of approximately twenty seeds from each of the three plants that contained the entire T-DNA. Two of the pooled samples contained very low, barely detectable levels of DHA, but the third pool contained about 4.7% DHA. Therefore, lipid was extracted from 10 individual $T_2$ seeds from this plant and the fatty acid composition analysed by GC. The fatty acid composition data of the individual seeds for this transformed line is also shown in Table 4. Compiled data from the total seed lipid profiles (Table 4) are shown in Table 5.

DHA was present in six of the 10 individual seeds. The four other seeds did not have DHA and were presumed to be null segregants which did not have the T-DNA, based on hemizygosity of the T-DNA insertion in the parental plant. Extracted lipid from the single seed with the highest level of DHA had 9.0% DHA while the sum of the percentages for EPA, DPA and DHA was 11.4%.

TABLE 4

Fatty acid composition of total seed lipids from transgenic $T_2$ *Camelina sativa* seeds transformed with the T-DNA from pJP3416-GA7. The fatty acid composition is shown for a pooled seed batch (FD5.46) and for 10 single seeds ranked (left to right) from highest to lowest DHA.

| Fatty acid | FD5.46 pooled | # 2 | # 4 | # 8 | # 7 | # 9 | # 1 | # 3 | # 5 | # 6 | # 10 |
|---|---|---|---|---|---|---|---|---|---|---|---|
| 14:0 | 0 | 0.2 | 0.2 | 0.1 | 0.2 | 0.2 | 0.2 | 0.2 | 0.1 | 0.2 | 0.2 |
| 16:0 | 11.6 | 12.1 | 12.3 | 12.1 | 13.2 | 12.3 | 12.8 | 11.9 | 11.4 | 11.5 | 11.7 |
| 16:1 | 0.9 | 0.0 | 0.1 | 0.1 | 0.0 | 0.2 | 0.0 | 0.2 | 0.2 | 0.2 | 0.2 |
| 16:3 | 0.3 | 0 | 0.0 | 0.0 | 0.0 | 0.0 | 0.0 | 0.0 | 0.0 | 0.0 | 0.0 |
| 18:0 | 3.7 | 3.3 | 3.2 | 3.2 | 3.0 | 3.1 | 3.9 | 3.3 | 3.1 | 3.2 | 3.2 |
| 18:1 | 10.8 | 8.0 | 8.0 | 8.6 | 8.5 | 9.4 | 11.0 | 10.2 | 8.3 | 9.4 | 8.6 |
| 18:1 Δ11 | 1.7 | 1.3 | 1.4 | 1.4 | 1.7 | 1.4 | 1.5 | 1.3 | 1.3 | 1.3 | 1.3 |
| 18:2 | 24.7 | 18.2 | 19.5 | 19.2 | 18.5 | 20.1 | 23.8 | 32.2 | 30.3 | 29.8 | 31.6 |
| 18:3ω3 | 27.4 | 26.7 | 26.6 | 27.3 | 28.9 | 28.2 | 27.4 | 28.3 | 79.7 | 29.5 | 28.2 |
| 18:3ω6 | 0.2 | 1.4 | 0.3 | 0.3 | 0.4 | 0.2 | 0.5 | 0.0 | 0.5 | 0.4 | 0.6 |
| 20:0 | 1.6 | 1.4 | 1.3 | 1.4 | 1.2 | 1.4 | 1.4 | 1.8 | 9.1 | 1.9 | 2.0 |
| 18:4ω3 | 2.2 | 6.8 | 6.4 | 5.7 | 7.2 | 5.7 | 4.1 | 0.0 | 0.0 | 0.0 | 0.0 |
| 20:1 Δ 11 | 5.3 | 4.4 | 4.6 | 4.8 | 3.3 | 4.1 | 3.5 | 4.4 | 6.1 | 5.8 | 5.5 |
| 20:1iso | 0.4 | 0.3 | 0.3 | 0.3 | 0.3 | 0.3 | 0.0 | 0.5 | 0.6 | 0.5 | 0.5 |
| 20:2ω6 | 0.8 | 0.8 | 0.9 | 0.8 | 0.6 | 0.8 | 0.7 | 1.3 | 1.5 | 1.4 | 1.4 |
| 20:3ω3 | 0.6 | 0.8 | 0.8 | 0.8 | 0.7 | 0.8 | 0.7 | 0.6 | 0.7 | 0.7 | 0.6 |
| 22:0 | 0.4 | 0.5 | 0.5 | 0.5 | 0.4 | 0.5 | 0.5 | 0.6 | 0.6 | 0.6 | 0.6 |
| 20:4ω3 | 0.2 | 0.3 | 0.3 | 0.3 | 0.4 | 0.4 | 0.5 | 0.0 | 0.0 | 0.0 | 0.0 |
| 22:1 | 1.1 | 1.1 | 1.2 | 1.1 | 0.5 | 0.9 | 0.8 | 1.6 | 2.2 | 1.9 | 2.0 |
| 20:5ω3 | 0.7 | 1.3 | 1.6 | 1.5 | 1.6 | 1.1 | 1.7 | 0.0 | 0.0 | 0.0 | 0.1 |
| 22:2ω6 | 0.1 | 0.0 | 0.0 | 0.0 | 0.0 | 0.0 | 0.0 | 0.2 | 0.3 | 0.2 | 0.2 |
| 22:4ω6 + 22:3ω3 | 0.3 | 0.9 | 0.3 | 0.3 | 0.0 | 0.3 | 0.0 | 0.4 | 0.6 | 0.5 | 0.5 |
| 24:0 | 0.3 | 0.3 | 0.3 | 0.3 | 0.0 | 0.3 | 0.0 | 0.4 | 0.4 | 0.4 | 0.4 |
| 24:1 | 0.3 | 0.4 | 0.4 | 0.3 | 0.0 | 0.3 | 0.0 | 0.5 | 0.6 | 0.5 | 0.5 |
| 22:5ω3 | 0.3 | 1.1 | 1.2 | 1.1 | 1.1 | 0.9 | 0.8 | 0.0 | 0.0 | 0.0 | 0.0 |
| 22:6ω3 | 4.7 | 9.0 | 8.5 | 8.3 | 8.3 | 7.1 | 4.9 | 0.0 | 0.0 | 0.0 | 0.0 |

TABLE 5

Compiled data from the total seed lipid profiles from transgenic seed as shown in Table 4. Calculations do not include the 'minor fatty acids' in Table 4.

| Parameter | FD5.46 pooled | # 2 | # 4 | # 8 | # 7 | # 9 | # 1 | # 3 | # 5 | # 6 | # 10 |
|---|---|---|---|---|---|---|---|---|---|---|---|
| total ω3 (% of total FA) | 36.1 | 46 | 45.4 | 45 | 48.2 | 44.2 | 40.1 | 28.9 | 29.9 | 30.2 | 28.9 |
| total ω6 (% of total FA) | 25.8 | 20.4 | 20.7 | 20.3 | 19.5 | 21.1 | 25 | 33.7 | 32.6 | 31.8 | 33.8 |
| ω3/ω6 ratio | 1.40 | 2.25 | 2.19 | 2.22 | 2.47 | 2.09 | 1.60 | 0.86 | 0.92 | 0.95 | 0.86 |
| ω6/ω3 ratio | 0.71 | 0.44 | 0.46 | 0.45 | 0.40 | 0.48 | 0.62 | 1.17 | 1.09 | 1.05 | 1.17 |
| total novel ω3 (% of total FA) | 8.1 | 18.5 | 18 | 16.9 | 18.6 | 15.2 | 12 | 0 | 0 | 0 | 0.1 |

TABLE 5-continued

Compiled data from the total seed lipid profiles from transgenic seed as shown in Table 4. Calculations do not include the 'minor fatty acids' in Table 4.

| Parameter | FD5.46 pooled | # 2 | # 4 | # 8 | # 7 | # 9 | # 1 | # 3 | # 5 | # 6 | # 10 |
|---|---|---|---|---|---|---|---|---|---|---|---|
| total novel ω6 (% of total FA) | 1.1 | 2.2 | 1.2 | 1.1 | 1 | 1 | 1.2 | 1.5 | 2.3 | 2 | 2.2 |
| novel ω3/ω6 ratio | 7.36 | 8.41 | 15.00 | 15.36 | 18.60 | 15.20 | 10.00 | | | | 0.05 |
| novel ω6/ω3 ratio | 0.14 | 0.12 | 0.07 | 0.07 | 0.05 | 0.07 | 0.10 | | | | 22.00 |
| OA to EPA efficiency | 8.2% | 15.6% | 15.5% | 15.1% | 15.1% | 12.8% | 10.5% | 0.0% | 0.0% | 0.0% | 0.1% |
| OA to DHA efficiency | 6.7% | 12.3% | 11.6% | 11.5% | 11.4% | 10.0% | 7.0% | 0.0% | 0.0% | 0.0% | 0.0% |
| LA to EPA efficiency | 9.2% | 17.2% | 17.1% | 16.7% | 16.2% | 13.9% | 11.4% | 0.0% | 0.0% | 0.0% | 0.2% |
| LA to DHA efficiency | 7.6% | 13.6% | 12.9% | 12.7% | 12.3% | 10.9% | 7.5% | 0.0% | 0.0% | 0.0% | 0.0% |
| ALA to EPA efficiency | 15.8% | 24.8% | 24.9% | 24.2% | 22.8% | 20.6% | 18.5% | 0.0% | 0.0% | 0.0% | 0.3% |
| ALA to DHA efficiency | 13.0% | 19.6% | 18.7% | 18.4% | 17.2% | 16.1% | 12.2% | 0.0% | 0.0% | 0.0% | 0.0% |
| total saturates | 17.6 | 17.8 | 17.8 | 17.6 | 18 | 17.8 | 18.1 | 18.2 | 17.7 | 17.8 | 18.1 |
| total monounsaturates | 19.8 | 15.5 | 16 | 16.6 | 14.3 | 16.6 | 16.8 | 18.7 | 19.3 | 19.6 | 18.6 |
| total polyunsaturates | 62.5 | 66.6 | 66.4 | 65.6 | 67.7 | 65.6 | 65.1 | 63 | 63.1 | 62.5 | 63.2 |
| total C20 | 9.6 | 9.3 | 9.8 | 9.9 | 8.1 | 8.9 | 8.5 | 8.6 | 11 | 10.3 | 10.1 |
| total C22 | 5.4 | 10.3 | 10 | 9.7 | 9.4 | 8.3 | 5.7 | 0.6 | 0.9 | 0.7 | 0.7 |
| C20/C22 ratio | 1.78 | 0.90 | 0.98 | 1.02 | 0.86 | 1.07 | 1.49 | 14.33 | 12.22 | 14.71 | 14.43 |

Homozygous seed from this line was obtained in the T4 generation. Up to 10.3% DHA was produced in event FD5-46-18-110 with an average of 7.3% DHA observed across the entire T4 generation. A subsequent generation (T5) was established to further test the stability of PUFA production over multiple generations, particularly the DHA. The maximum DHA levels observed was found to be stable in the fifth generation, even though the pooled seed DHA content had not stabilised until the T4 generation due to the presence of multiple transgenic loci. T₅ seed batches were also germinated on MS media in vitro alongside parental *C. sativa* seed with no obvious difference in germination efficiency or speed observed. Further generations of the transgenic line (T6, T7 generations etc) did not show any reduction in the seed DHA level. The transgenic plants were fully male and female fertile, and the pollen showed about 100% viability as for the wild-type plants. Analysis of the oil content of the seeds having different levels of DHA did not identify a correlation between DHA level and oil content, contrary to the correlation seen in *Arabidopsis thaliana*.

In several further transgenic lines, the DHA content of single seeds from independent events exceeded 12%. The transgenic:null ratio of these lines was found to be between approximately 3:1 and 15:1. Analysis of representative fatty acid profiles from the top DHA samples from each construct found only 1.2-1.4% GLA with no other new ω6 PUFA detected. In contrast, new ω3 PUFA (SDA) ω3 LC-PUFA (ETA, EPA, DPA, DHA) were found to accumulate to 18.5% with a DHA level of 9.6% of the total fatty acid content. Δ6-desaturation was 32% and EPA was 0.8% of the total fatty acid content. The Δ5-elongation efficiency was 93% and Δ6-elongation efficiency was 60%. DHA was detected in the polar seed lipid fraction of GA7 lines.

It was noted that the segregation ratios observed (~3:1 to ~15:1) indicated that one or, at most, two transgenic loci were required to produce fish oil-like levels of DHA in *C. sativa*. This had important implications for the ease with which the transgenic trait can be bred as well as for transgene stability.

Homozygous seed was planted out across several glasshouses to generate a total of over 600 individual plants. Oil was extracted from the seed using a variety of methods including soxhlet, acetone and hexane extractions.

$^{13}$C NMR regiospecificity analysis was performed on the transgenic *C. sativa* seed oil to determine the positional distribution of the ω3 LC-PUFA on TAG. An event with approximately equal EPA and DHA was selected to maximise response for these fatty acids and the ratio of sn-1,3 to sn-2 was found to be 0.75:0.25 for EPA and 0.86:0.14 for DHA where an unbiased distribution would be 0.66:0.33. That is, 75% of the EPA and 86% of the DHA were located at the sn-1,3 position of TAG. This indicated that both fatty acids were preferentially located on the sn-1,3 positions in *C. sativa* TAG although the preference for EPA was weaker than for DHA. The finding that DHA was predominantly found on sn-1,3 was similar to results previously reported in *A. thaliana* seed (Petrie et al., 2012).

Since only a small number of independent transgenic lines were obtained in the transformation experiment described above, further *C. sativa* transformations were performed using the GA7-modB construct (Example 3). More transformants were obtained and homozygous lines producing in excess of 20.1% DHA are identified.

Example 3. Modifications to T-DNAs Encoding DHA Pathways in Plant Seeds

In order to improve the DHA production level in *B. napus* beyond the levels described in WO2013/185184, the binary vectors pJP3416-GA7-modA, pJP3416-GA7-modB, pJP3416-GA7-modC, pJP3416-GA7-modD, pJP3416-GA7-modE and pJP3416-GA7-modF were constructed as described in WO2013/185184 and tested in transgenic plants. These binary vectors were variants of the pJP3416-GA7 construct and were designed to further increase the synthesis of DHA in plant seeds, particularly by improving Δ6-desaturase and Δ6-elongase functions. SDA had been observed to accumulate in some seed transformed with the GA7 construct due to a relatively low Δ6 elongation efficiency compared to the Δ5-elongase, so amongst other modifications, the two elongase gene positions were switched in the T-DNA.

The two elongase coding sequences in pJP3416-GA7 were switched in their positions on the T-DNA to yield pJP3416-GA7-modA by first cloning a new *P. cordata* Δ6-elongase cassette between the Sbfl sites of pJP3416-GA7 to replace the *P. cordata* Δ5-elongase cassette. This construct was further modified by exchanging the FP1 promoter driving, the *M. pusilla* Δ6-desaturase with a conlinin Cn12 promoter (pLuCn12) to yield pJP3416-GA7-modB. This modification was made in an attempt to increase the Δ6-desaturase expression and thereby enzyme efficiency.

It was thought that the Cn12 promoter might yield higher expression of the transgene in *B. napus* than the truncated napin promoter.

Eight transgenic pJP3416-GA7-modB *A. thaliana* events and 15 transgenic pJP3416-GA7-modG *A. thaliana* events were generated. Between 3.4% and 7.2% DHA in pooled pJP3416-GA7-modB seed was observed and between 0.6 and 4.1% DHA in pooled T2 pJP3416-GA7-modG seed was observed. Several of the highest pJP3416-GA7-modB events were sown out on selectable media and surviving seedlings taken to the next generation. Seed is being analysed for DHA content. Since the pooled T1 seeds represented populations that were segregating for the transgenes and included any null segregants, it is expected that the homozygous seeds from progeny plants would have increased levels of DHA, up to 30% of the total fatty acid content in the seed oil. The other modified constructs were used to transform *A. thaliana*. Although only a small number of transformed lines were obtained, none yielded higher levels of DHA than the modB construct.

The pJP3416-GA7-modB construct was also used to generate transformed *B. napus* plants of cultivar Oscar and of a series of breeding lines designated NX002, NX003, NX005, NX050, NX052 and NX054. A total of 1558 transformed plants were obtained including 77 independent transformed plants (T0) for the Oscar transformation, and 1480 independent plants for the breeding lines including 189 for NX005 which is a line having a high oleic acid content in its seedoil by virtue of mutations in FAD2 genes. The other breeding lines had higher levels of LA and ALA. Transgenic plants which exhibited more than 4 copies of the T-DNA as determined by a digital PCR method (Example 1) were discarded; about 25% of the T0 plants were discarded by this criterion. About 53% of the T0 transgenic plants had 1 or 2 copies of the T-DNA as determined by the digital PCR method, 12% had about 3 copies and 24% 4 or more copies. Seed (T1 seed) was harvested from about 450 of the transgenic lines after self-fertilisation, achieved by bagging the plants during flowering to avoid out-crossing. T1 seed are harvested from the remainder of the transgenic plants when mature. About 1-2% of the plant lines were either male or female sterile and produced no viable seeds, these T0 plants were discarded.

Pools of seed (20 T1 seeds in each pool) were tested for levels of DHA in the pooled seed oil, and lines which showed the highest levels were selected. In particular, lines having a DHA content of at least 2% of the total fatty content in the pooled T1 seeds were selected. About 15% of the transgenic lines were selected in this way; the other 85% were discarded. Some of these were designated lines CT132-5 (in cultivar Oscar), CT133-15, -24, -63, -77, -103, -129 and -130 (in NX005). Selected lines in NX050 included CT136-4, -8, -12, -17, -19, -25, -27, -49 and -51. Twenty seeds from selected lines including CT132.5 and 11 seeds from CT133.15 were imbibed and, after two days, oil was extracted from a half cotyledon from each of the individual seeds.

The other half cotyledons with embryonic axes were kept and cultured on media to maintain the specific progeny lines. The fatty acid composition in the oil was determined; the data is shown in Table 6 for CT132.5. The DHA level in ten of the 20 seeds analysed was in the range of 7-20% of the total fatty acid content as determined by the GC analysis. Other seeds had less than 7% DHA and may have contained a partial (incomplete) copy of the T-DNA from pJP3416-GA7-modB. The transgenic line appeared to contain multiple transgene insertions that were genetically unlinked. The seeds of transgenic line CT133.15 exhibited DHA levels in the range 0-5%. Seeds with no DHA were likely to be null segregants. These data confirmed that the modB construct performed well for DHA production in canola seed.

Twenty or 40 individual seeds (T2 seeds) obtained from each of multiple T1 plants, after self-fertilisation, from the selected transformed lines were tested individually for fatty acid composition. Seeds comprising DHA at levels greater than 20% were identified (Table 7). Two representative samples, CT136-27-18-2 and CT136-27-18-19 had 21.2% and 22.7% DHA, respectively. The total ω3 fatty acid content in these seeds was about 60% as a percentage of the total fatty acid content, and the ω6 content was less than 10%. Further sets of 20 or 40 T2 seeds from each of the T1 plants were tested for fatty acid composition. Seeds comprising up to 34.3% DHA were identified, for example in seed CT136-27-47-25 (Table 9). The fatty acid composition for seedoil obtained from CT136-27-47-25 is shown in Table 9. The fatty acid composition included 34.3% DHA together with about 1.5% DPA, 0.6% EPA and 0.5% ETA. The SDA level was about 7.5%, ALA about 21.9% and LA about 6.9%. The new ω6 PUFA exhibited 1.1% GLA but no detectable ω6-C20 or -C22 LC-PUFA. Total saturated fatty acids: 9.6%; monounsaturated fatty acids, 12.5%; total PUFA, 75.2%; total ω6-PUFA (including LA), 7.2%; total ω3-PUFA, 66.9%; the ratio of total ω6:ω3 fatty acids, 9.3:1; new ω6:new ω3 fatty acids, 37:1. The efficiencies of each of the enzymatic steps from oleic acid to DHA were as follows: Δ12-desaturase, 90%; Δ15/ω3-desaturase, 89%; Δ6-desaturase, 67%; Δ6-elongase, 83%; Δ5-desaturase, 99%; Δ5-elongase, 98%; Δ4-desaturase, 96%. The overall efficiency of conversion of oleic acid to DHA was about 50%. It was therefore clear that seeds producing DHA in the range of 20.1-35% of the total fatty acid content of the seedoil could be identified and selected, including seeds having between 20.1% and 30% DHA or between 30% and 35% DHA in the total fatty acid content.

The oil content in some seeds was decreased from about 44% in wild-type seeds to about 31-39% in some of the DHA producing seeds, but was was similar to wild-type levels in other DHA producing seeds.

Various transformed plant lines which were producing DHA at levels of at least 10% in T2 seed are crossed and the F1 progeny selfed in order to produce F2 progeny which are homozygous for multiple T-DNA insertions. Seedoil from homozygous seed is analysed and up to 30% or 35% of the total fatty acid content in the seed oil is DHA.

The TAG in the oil obtained from CT136-27-18-2 and CT136-27-18-19 was analysed by $^{13}C$ NMR regiospecificity assay for positional distribution of the DHA on the glycerol backbone of the TAG molecules. The DHA was preferentially linked at the sn-1,3 position. More than 70%, indeed more than 90% of the DHA was in the sn-1,3 position.

In several further transgenic lines, the DHA content of single seeds from independent events exceeded 12%. The transgenic:null ratio of these lines was found to be approximately 3:1, corresponding to a single transgenic locus, or 15:1, corresponding to two transgenic loci. Analysis of representative fatty acid profiles from the samples from each construct with the highest levels of DHA found only 1.2-1.4% GLA with no other new ω6 PUFA detected. In contrast, new ω3 PUFA (SDA) and ω3 LC-PUFA (ETA, EPA, DPA, DHA) accumulated to a sum of 25.8% for the modF construct and 21.9% for the modG construct compared to 18.5% for the GA7-transformed seed. The DHA levels in the oil from these seeds were 9.6%, 12.4% and 11.5%, respectively. Δ6-desaturation was found to be lower in the GA7- transformed seeds than the modF- and modG-transformed seeds (32% vs 47% and 43%) and this resulted in a reduction of ALA in the modF and modG seeds relative to GA7. Another noteworthy difference was the accumulation of EPA in the modF seed (3.3% vs 0.8% in the other two transgenic seeds) and this was reflected in the reduced Δ5-elongation observed in modF (80%) seed relative to GA7 and modG seeds (93% and 94%). There was a slight increase in Δ6-elongation in these seeds (66% vs 60% and 61%) although the amount of SDA actually increased due to the slightly more active Δ6-desaturation. DHA was detected in the polar seed lipid fraction of GA7 lines.

The fatty acid composition was analysed of the lipid in the T1 seed of 70 independent transgenic plants of the *B. napus* breeding line NX54 transformed with the T-DNA of the modB construct. It was observed that one of these transgenic plants produced seed having DPA but no DHA in the seedoil. The T1 seed of this line (CT-137-2) produced about 4% DPA without any detectable DHA in the T1 pooled seed. The inventors tested whether this was caused by inactivation of the Δ4-desaturase gene in that particular inserted T-DNA, through a spontaneous mutation. PCR analysis and DNA sequencing showed the presence of a deletion, which was defined as having deleted nucleotides 12988-15317 of the T-DNA of GA7-modB (SEQ ID NO: 2). The deleted nucleotides correspond to a portion of the Linus Cn12 promoter driving expression of the Δ4-desaturase coding region as well as the Δ4-desaturase coding region itself, explaining why the seeds transformed with the T-DNA comprising the deletion did not produce DHA.

Around 50 T1 seeds from this transgenic line were germinated and one emerged cotyledon from each analysed for fatty acid composition in the remaining oil. Selected seedlings exhibiting more than 5% DPA were then grown to maturity and T2 seed harvested. Pooled seed fatty acid compositions are shown in Table 8; more than 7% DPA was observed in these lines. T4 seed was produced from the *B. napus* DPA line CT-137-2 and analysed for fatty acid profile. Up to 13% DPA was observed in pooled mature seed samples.

Oil from seeds having about 10% DPA was treated with mild alkali to hydrolyse the fatty acids.

Another transgenic line designated B0003-514 exhibited about 10-16% DPA in T2 seed. Seed containing 15.8% DPA, 0.2-0.9% DHA and 0.1-2.5% EPA was selected. The T2 seed population showed a 1:2:1 segregation ration for high:medium:no DPA, indicating the presence of a single genetic locus for DPA production in that transgenic line.

Oil was extracted by a screw press from seed samples producing LC-PUFA, thereby producing seedmeal.

Construct Design

Whilst the focus of this experiment was the demonstration of DHA and DPA production in an oilseed crop species, the results noted above were also interesting from a construct design perspective. First, switching the Δ6- and Δ5-elongase coding region locations in the modF construct resulted in the intended profile change with more EPA accumulated due to lower Δ5-elongation. A concomitant increase in Δ6-elongation was observed but this did not result in lower SDA levels. This was due to an increase in M-desaturation in the modF transformed seed, caused by adding an extra *M. pusilla* Δ6-desaturase expression cassette as well as by replacing the truncated napin promoter (FP1) with a more highly active flax conlinin2 promoter. The somewhat lower increase in Δ6-desaturation observed with the modG construct was caused by capitalising on the highly expressed Δ5-elongase cassette in GA7. Switching the positions of the Δ6-desaturase and Δ5-elongase coding regions resulted in greater Δ6-desaturation. Δ5-elongase activity was not reduced in this instance due to the replacement of the FP1 promoter with the Cn12 promoter.

These data confirmed that the modB, modF and modG constructs performed well for DHA production in *Camelina* seed, as for *Arabidopsis* and canola.

The inventors considered that, in general, the efficiency of rate-limiting enzyme activities in the DHA pathway can be greater in multicopy T-DNA transformants compared to single-copy T-DNA transformants, or can be increased by inserting into the T-DNA multiple genes encoding the enzyme which might be limiting in the pathway. Evidence for the possible importance of multi-copy transformants was seen in the *Arabidopsis* seeds transformed with the GA7 construct, where the highest yielding DHA event had three T-DNAs inserted into the host genome. The multiple genes can be identical, or preferably are different variants that encode the same polypeptide, or are under the control of different promoters which have overlapping expression patterns. For example, increased expression could be achieved by expression of multiple Δ6-desaturase coding regions, even where the same protein is produced. In pJP3416-GA7-modF and pJP3416-GA7-modC, for instance, two versions of the *M. pusilla* Δ6-desaturase were present and expressed by different promoters. The coding sequences had different codon usage and therefore different nucleotide sequences, to reduce potential silencing or co-suppression effects but resulting in the production of the same protein.

TABLE 6

Fatty acid composition of lipid in germinating T1 transgenic *B. napus* seeds containing the T-DNA from the GA7-modB construct. The lipids also contained 0.1-0.3% of each of C16:1, C16:3, C24:0 and C24:1, and no C20:1Δ11.

| Seed | C14:0 | C16:0 | C18:0 | C18:1 | C18:1Δ11 | C18:2 | C18:3ω6 | C18:3ω3 | C20:0 | C18:4ω3 |
|---|---|---|---|---|---|---|---|---|---|---|
| 1 | 0.1 | 4.2 | 1.8 | 29.9 | 2.5 | 9.9 | 0.1 | 38.4 | 0.5 | 0.8 |
| 2 | 0.1 | 4.7 | 4.0 | 23.0 | 2.3 | 7.4 | 0.3 | 29.3 | 1.0 | 4.3 |
| 3 | 0.1 | 3.7 | 1.8 | 55.1 | 1.9 | 4.7 | 0.2 | 15.2 | 0.8 | 1.8 |
| 4 | 0.1 | 4.6 | 2.9 | 22.1 | 1.8 | 6.6 | 0.4 | 26.5 | 1.0 | 7.2 |
| 5 | 0.1 | 4.0 | 1.7 | 27.4 | 2.1 | 8.1 | 0.3 | 26.4 | 0.6 | 2.8 |
| 6 | 0.1 | 3.5 | 1.6 | 59.8 | 2.0 | 4.3 | 0.1 | 18.5 | 0.6 | 0.5 |
| 7 | 0.1 | 6.0 | 1.7 | 16.6 | 2.6 | 23.9 | 1.0 | 23.2 | 0.6 | 5.4 |
| 8 | 0.1 | 4.9 | 2.7 | 12.9 | 1.4 | 11.7 | 0.3 | 34.3 | 0.9 | 5.0 |
| 9 | 0.1 | 3.9 | 2.4 | 41.6 | 1.7 | 21.5 | 0.0 | 23.4 | 0.7 | 0.0 |
| 10 | 0.1 | 3.7 | 2.1 | 30.9 | 1.7 | 19.2 | 0.4 | 23.6 | 0.7 | 2.1 |
| 11 | 0.1 | 5.7 | 3.8 | 41.2 | 2.4 | 26.7 | 2.1 | 7.2 | 1.3 | 0.3 |
| 12 | 0.1 | 4.6 | 2.4 | 25.5 | 1.7 | 16.1 | 0.3 | 28.9 | 0.8 | 3.9 |
| 13 | 0.1 | 4.3 | 4.2 | 19.4 | 1.6 | 9.2 | 0.1 | 45.5 | 1.0 | 0.2 |

TABLE 6-continued

Fatty acid composition of lipid in germinating T1 transgenic *B. napus* seeds containing the T-DNA from the GA7-modB construct. The lipids also contained 0.1-0.3% of each of C16:1, C16:3, C24:0 and C24:1, and no C20:1Δ11.

| | | | | | | | | | | |
|---|---|---|---|---|---|---|---|---|---|---|
| 14 | 0.1 | 6.3 | 4.0 | 10.5 | 2.3 | 8.4 | 0.3 | 31.1 | 1.3 | 3.9 |
| 15 | 0.1 | 5.1 | 3.3 | 16.8 | 2.4 | 11.2 | 0.3 | 28.8 | 1.0 | 4.5 |
| 16 | 0.1 | 4.4 | 4.0 | 16.2 | 1.5 | 11.6 | 0.2 | 33.5 | 0.9 | 2.8 |
| 17 | 0.2 | 7.2 | 4.9 | 15.0 | 2.1 | 8.9 | 0.3 | 25.9 | 1.4 | 5.1 |
| 18 | 0.1 | 4.0 | 2.3 | 64.8 | 1.2 | 7.2 | 0.1 | 12.5 | 1.0 | 3.5 |

| Seed | C20:1Δ11 | C20:2ω6 | C20:3ω3 | C22:0 | C20:4ω3 | C20:5ω3 | C22:3n3 | 22:5n3 | C22:6n3 |
|---|---|---|---|---|---|---|---|---|---|
| 1 | 1.0 | 0.1 | 2.1 | 0.3 | 2.8 | 0.3 | 0.1 | 0.5 | 3.9 |
| 2 | 1.1 | 0.1 | 1.9 | 0.4 | 6.9 | 1.0 | 0.0 | 1.7 | 9.5 |
| 3 | 1.4 | 0.1 | 0.3 | 0.5 | 11.3 | 0.0 | 0.0 | 0.0 | 0.0 |
| 4 | 1.0 | 0.1 | 0.8 | 0.5 | 11.2 | 1.9 | 0.0 | 1.7 | 8.7 |
| 5 | 1.0 | 0.1 | 1.5 | 0.3 | 7.6 | 1.5 | 0.0 | 1.8 | 12.2 |
| 6 | 1.3 | 0.0 | 0.7 | 0.3 | 6.0 | 0.0 | 0.0 | 0.0 | 0.0 |
| 7 | 0.8 | 0.2 | 0.6 | 0.4 | 2.6 | 1.1 | 0.0 | 1.7 | 9.9 |
| 8 | 0.9 | 0.2 | 2.4 | 0.5 | 4.1 | 1.3 | 0.0 | 1.8 | 13.8 |
| 9 | 1.2 | 0.1 | 2.2 | 0.4 | 0.0 | 0.0 | 0.1 | 0.0 | 0.0 |
| 10 | 1.1 | 0.1 | 1.5 | 0.4 | 3.6 | 0.6 | 0.0 | 0.7 | 6.9 |
| 11 | 1.2 | 0.2 | 0.3 | 0.8 | 4.8 | 0.0 | 0.0 | 0.0 | 0.0 |
| 12 | 1.1 | 0.1 | 1.9 | 0.4 | 3.9 | 0.6 | 0.0 | 1.1 | 6.2 |
| 13 | 1.1 | 0.1 | 5.2 | 0.4 | 2.6 | 0.3 | 0.2 | 0.4 | 3.4 |
| 14 | 0.8 | 0.1 | 2.3 | 0.6 | 4.6 | 1.8 | 0.1 | 2.5 | 18.1 |
| 15 | 0.9 | 0.1 | 2.1 | 0.6 | 3.2 | 1.5 | 0.1 | 1.8 | 15.1 |
| 16 | 1.1 | 0.2 | 3.7 | 0.4 | 4.6 | 0.7 | 0.1 | 1.3 | 12.1 |
| 17 | 0.9 | 0.0 | 1.6 | 0.8 | 4.9 | 2.1 | 0.0 | 2.2 | 15.0 |
| 18 | 1.5 | 0.1 | 0.0 | 0.7 | 0.0 | 0.0 | 0.0 | 0.0 | 0.0 |

TABLE 7

Fatty acid composition of lipid in T2 transgenic *B. napus* seeds containing the T-DNA from the GA7-modB construct.

| Sample (T2 seed) | C16:0 | C18:0 | C18:1 | C18:1d11 | C18:2 | C18:3ω6 | C18:3ω3 | C18:4ω3 | C20:1Δ11 | C20:2ω6 |
|---|---|---|---|---|---|---|---|---|---|---|
| CT136-27-18-1 | 5.0 | 2.6 | 25.4 | 3.6 | 6.7 | 0.2 | 37.5 | 1.4 | 1.0 | 0.1 |
| CT136-27-18-2 | 7.1 | 2.8 | 16.9 | 4.3 | 5.5 | 0.4 | 29.1 | 5.4 | 0.8 | 0.1 |
| CT136-27-18-3 | 5.4 | 2.5 | 26.5 | 3.8 | 6.4 | 0.4 | 26.4 | 4.7 | 1.0 | 0.1 |
| CT136-27-18-4 | 5.3 | 2.4 | 34.7 | 4.0 | 5.9 | 0.3 | 30.3 | 1.3 | 1.1 | 0.1 |
| CT136-27-18-5 | 4.8 | 2.7 | 34.5 | 3.8 | 5.6 | 0.3 | 23.5 | 3.9 | 1.2 | 0.1 |
| CT136-27-18-6 | 5.0 | 2.1 | 54.3 | 3.8 | 5.7 | 0.2 | 18.2 | 0.6 | 1.5 | 0.1 |
| CT136-27-18-7 | 5.3 | 2.1 | 43.8 | 4.2 | 5.6 | 0.4 | 18.3 | 2.2 | 1.3 | 0.2 |
| CT136-27-18-8 | 5.4 | 2.7 | 25.8 | 4.1 | 6.7 | 0.4 | 26.6 | 5.7 | 1.0 | 0.1 |
| CT136-27-18-9 | 4.6 | 1.6 | 53.8 | 3.7 | 17.5 | 0.5 | 9.2 | 0.5 | 1.6 | 0.3 |
| CT136-27-18-10 | 4.8 | 2.4 | 44.1 | 3.7 | 5.4 | 0.4 | 19.1 | 2.3 | 1.1 | 0.1 |
| CT136-27-18-11 | 5.1 | 2.2 | 48.3 | 4.1 | 10.9 | 0.7 | 12.5 | 1.2 | 1.3 | 0.2 |
| CT136-27-18-12 | 5.3 | 2.7 | 23.3 | 3.7 | 6.0 | 0.4 | 27.9 | 4.9 | 0.9 | 0.1 |
| CT136-27-18-13 | 5.5 | 3.4 | 30.7 | 5.6 | 5.1 | 0.4 | 23.1 | 3.5 | 1.1 | 0.1 |
| CT136-27-18-14 | 5.4 | 2.3 | 23.9 | 3.5 | 6.0 | 0.4 | 30.1 | 3.7 | 1.0 | 0.1 |
| CT136-27-18-15 | 5.0 | 2.3 | 45.4 | 4.0 | 5.3 | 0.4 | 16.2 | 2.3 | 1.2 | 0.1 |
| CT136-27-18-18 | 5.1 | 2.3 | 29.0 | 3.6 | 5.7 | 0.4 | 26.5 | 3.8 | 1.1 | 0.2 |
| CT136-27-18-19 | 5.8 | 2.3 | 19.7 | 4.2 | 6.7 | 0.7 | 23.7 | 7.7 | 0.9 | 0.1 |
| CT136-27-18-20 | 5.7 | 2.9 | 23.2 | 4.0 | 5.6 | 0.3 | 35.8 | 2.4 | 1.0 | 0.1 |

| Sample (T2 seed) | C20:3ω3 | C20:4ω3 | C20:5ω3 | C22:5ω3 | C22:6ω3 | Total ω3 (%) | Total ω6 (%) | Ratio ω6 to ω3 | Total PUFA content (%) |
|---|---|---|---|---|---|---|---|---|---|
| CT136-27-18-1 | 2.1 | 0.8 | 0.4 | 0.9 | 10.2 | 53.4 | 7.1 | 0.13 | 60.5 |
| CT136-27-18-2 | 1.2 | 0.5 | 0.5 | 1.9 | 21.2 | 59.8 | 6.1 | 0.10 | 66.0 |
| CT136-27-18-3 | 0.7 | 1.1 | 0.6 | 1.2 | 17.3 | 52.0 | 6.9 | 0.13 | 58.9 |
| CT136-27-18-4 | 1.1 | 1.5 | 0.3 | 0.4 | 9.3 | 44.4 | 6.3 | 0.14 | 50.7 |
| CT136-27-18-5 | 0.7 | 1.1 | 0.5 | 1.1 | 14.2 | 45.1 | 6.0 | 0.13 | 51.1 |
| CT136-27-18-6 | 1.1 | 0.7 | 0.1 | 0.2 | 4.4 | 25.5 | 6.1 | 0.24 | 31.5 |
| CT136-27-18-7 | 0.6 | 1.5 | 0.4 | 0.5 | 11.6 | 35.2 | 6.2 | 0.18 | 41.4 |
| CT136-27-18-8 | 0.6 | 1.3 | 0.6 | 1.2 | 15.8 | 51.9 | 7.1 | 0.14 | 59.0 |
| CT136-27-18-9 | 0.6 | 0.4 | 0.1 | 0.1 | 3.7 | 14.5 | 18.3 | 1.26 | 32.8 |
| CT136-27-18-10 | 0.6 | 1.5 | 0.5 | 0.8 | 11.4 | 36.1 | 5.9 | 0.16 | 42.0 |
| CT136-27-18-11 | 0.5 | 1.5 | 0.3 | 0.3 | 9.1 | 25.3 | 11.8 | 0.47 | 37.1 |
| CT136-27-18-12 | 0.7 | 1.3 | 0.8 | 1.5 | 18.5 | 55.7 | 6.6 | 0.12 | 62.2 |
| CT136-27-18-13 | 1.2 | 1.1 | 0.6 | 1.2 | 14.9 | 45.8 | 5.5 | 0.12 | 51.3 |
| CT136-27-18-14 | 1.0 | 0.7 | 0.6 | 1.2 | 18.2 | 55.5 | 6.6 | 0.12 | 62.1 |
| CT136-27-18-15 | 0.5 | 1.9 | 0.6 | 0.7 | 12.3 | 34.4 | 5.8 | 0.17 | 40.3 |

TABLE 7-continued

Fatty acid composition of lipid in T2 transgenic *B. napus* seeds containing the T-DNA from the GA7-modB construct.

| | | | | | | | | | |
|---|---|---|---|---|---|---|---|---|---|
| CT136-27-18-18 | 0.8 | 0.8 | 0.6 | 1.0 | 17.4 | 50.8 | 6.3 | 0.12 | 57.1 |
| CT136-27-18-19 | 0.4 | 0.7 | 0.6 | 1.7 | 22.7 | 57.6 | 7.5 | 0.13 | 65.1 |
| CT136-27-18-20 | 1.3 | 1.1 | 0.5 | 1.0 | 13.0 | 55.1 | 6.1 | 0.11 | 61.2 |

ARA (C20:4ω6) and DPAω6 were not detected in any of the samples. The samples also contained 0.1% C14:0 about 0.2% or 0.3% C16:1, about 0.1 to 0.3% C16:3, between about 0.7% and 1.0% C20:0, about 0.3% C22:0, and some samples contained trace levels (<0.1%) of C20:1Δ13, C22:3ω3, C24:0 and C24:1

TABLE 8

Fatty acid composition of the lipid in T2 transgenic *B. napus* seeds transformed with the T-DNA of the GA7-modB construct, with a mutation in the Δ4-desaturase gene. The lipids also contained about 0.1% 14:0, 0.2% 16:3, 0.2-0.4% GLA, 0.1% 20:1Δ13, 0.3-0.4% 22:0, and ARA, DPAω6 (22:5ω6), 16:2 and 22:1 were not detected.

| | C16:0 | C16:1 | C18:0 | C18:1 | C18:1Δ11 | C18:2 | C18:3ω3 | C20:0 | C18:4ω3 | C20:1Δ11 | C20:2ω6 |
|---|---|---|---|---|---|---|---|---|---|---|---|
| CT-137-2-34 | 5.3 | 0.2 | 3.7 | 26.8 | 3.1 | 12.4 | 29.1 | 0.8 | 2.5 | 0.8 | 0.1 |
| CT-137-2-38 | 5.3 | 0.2 | 4.2 | 24.4 | 3.0 | 12.6 | 29.4 | 0.9 | 2.5 | 0.8 | 0.1 |
| CT-137-2-48 | 5.0 | 0.2 | 4.2 | 24.1 | 3.1 | 11.9 | 31.0 | 0.9 | 2.4 | 0.9 | 0.1 |
| CT-137-2-51 | 5.7 | 0.2 | 4.6 | 22.3 | 3.4 | 12.3 | 34.5 | 1.0 | 2.0 | 0.8 | 0.1 |
| CT-137-2-59 | 5.4 | 0.2 | 3.9 | 25.7 | 3.4 | 12.9 | 27.8 | 0.9 | 2.6 | 0.8 | 0.1 |

| | C20:3ω6 | C20:3ω3 | C20:4ω3 | C20:5ω3 | C22:2ω6 | C22:3ω3 | C24:0 | C24:1 | C22:5ω3 | C22:6ω3 |
|---|---|---|---|---|---|---|---|---|---|---|
| CT-137-2-34 | 0.0 | 1.1 | 1.7 | 0.8 | 0.0 | 0.1 | 0.1 | 0.1 | 10.0 | 0.0 |
| CT-137-2-38 | 0.0 | 1.3 | 2.2 | 0.9 | 0.0 | 0.1 | 0.2 | 0.1 | 10.8 | 0.0 |
| CT-137-2-48 | 0.0 | 1.5 | 2.0 | 1.0 | 0.0 | 0.1 | 0.1 | 0.1 | 10.5 | 0.0 |
| CT-137-2-51 | 0.0 | 1.9 | 1.2 | 0.5 | 0.0 | 0.1 | 0.2 | 0.2 | 7.9 | 0.0 |
| CT-137-2-59 | 0.0 | 1.0 | 1.9 | 0.9 | 0.0 | 0.1 | 0.2 | 0.1 | 11.0 | 0.0 |

TABLE 9

Fatty acid composition of seedoil from T2 seed of *B. napus* transformed with the T-DNA from GA7-modB.

| C16:0 | C18:0 | C18:1Δ9 | C18:1Δ7 | C18:2ω6 | C18:3ω6 | C18:3ω3 | C20:0 | C18:4ω3 |
|---|---|---|---|---|---|---|---|---|
| 6.3 | 2.4 | 8.4 | 3.1 | 6.9 | 1.1 | 21.9 | 0.7 | 7.5 |

| C20:1ω9c | C20:2ω6 + C21:0 | C20:3ω3 | C20:4ω3 | C20:5ω3 | C22:5ω6 | C22:5ω3 | C22:6ω3 |
|---|---|---|---|---|---|---|---|
| 0.7 | 0.1 | 0.5 | 0.5 | 0.6 | 0.2 | 1.5 | 34.3 |

The seedoil samples also contained 0.1% C14:0; 0.2% C16:1; 0.1% C20:3ω6; no C22:1 and C22:2ω6; 0.1% C24:0 and 0.2% C24:1, 2.6% other fatty acids.

Example 4. Analysis of TAG from Transgenic *A. thaliana* Seeds Producing DHA

The positional distribution of DHA on the TAG from the transformed *A. thaliana* seed was determined by NMR. Total lipid was extracted from approximately 200 mg of seed by first crushing them under hexane before transferring the crushed seed to a glass tube containing 10 mL hexane. The tube was warmed at approximately 55° C. in a water bath and then vortexed and centrifuged. The hexane solution was removed and the procedure repeated with a further 4×10 mL. The extracts were combined, concentrated by rotary evaporation and the TAG in the extracted lipid purified away from polar lipids by passage through a short silica column using 20 mL of 7% diethyl ether in hexane. Acyl group positional distributions on the purified TAG were determined quantitatively as previously described (Petrie et al., 2010a and b).

The analysis showed that the majority of the DHA in the total seed oil was located at the sn-1/3 positions of TAG with little found at the sn-2 position. This was in contrast to TAG from ARA producing seeds which demonstrated that 50% of the ARA ($20:4^{\Delta 5,8,11,14}$) was located at the sn-2 position of transgenic canola oil whereas only 33% would be expected in a random distribution (Petrie et al., 2012).

The total lipid from transgenic *A. thaliana* seeds was also analysed by triple quadrupole LC-MS to determine the major DHA-containing triacylglycerol (TAG) species. The most abundant DHA-containing TAG species was found to be DHA-18:3-18:3 (TAG 58:12; nomenclature not descriptive of positional distribution) with the second-most abundant being DHA-18:3-18:2 (TAG 58:11). Tri-DHA TAG (TAG 66:18) was observed in total seed oil, albeit at low but detectable levels. Other major DHA-containing TAG species included DHA-34:3 (TAG 56:9), DHA-36:3 (TAG 58:9), DHA-36:4 (TAG 58:10), DHA-36:7 (TAG 58:13) and DHA-38:4 (TAG 60:10). The identities of the two major DHA-containing TAG were further confirmed by Q-TOF MS/MS.

Example 5. Assaying Sterol Content and Composition in Oils

The phytosterols from 12 vegetable oil samples purchased from commercial sources in Australia were characterised by GC and GC-MS analysis as O-trimethylsilyl ether (OTMSi-ether) derivatives as described in Example 1. Sterols were identified by retention data, interpretation of mass spectra and comparison with literature and laboratory standard mass spectral data. The sterols were quantified by use of a 5β(H)-Cholan-24-ol internal standard. The basic phytosterol structure and the chemical structures of some of the identified sterols are shown in FIG. 3 and Table 10.

The vegetable oils analysed were from: sesame (*Sesamum indicum*), olive (*Olea europaea*), sunflower (*Helianthus annus*), castor (*Ricinus communis*), canola (*Brassica napus*), safflower (*Carthamus tinctorius*), peanut (*Arachis hypogaea*), flax (*Linum usitatissimum*) and soybean (*Glycine max*). In decreasing relative abundance, across all of the oil samples, the major phytosterols were: β-sitosterol (range 28-55% of total sterol content), Δ5-avenasterol (isofucosterol) (3-24%), campesterol (2-33%), Δ5-stigmasterol (0.7-18%), Δ7-stigmasterol (1-18%) and Δ7-avenasterol (0.1-5%). Several other minor sterols were identified, these were: cholesterol, brassicasterol, chalinasterol, campestanol and eburicol. Four C29:2 and two C30:2 sterols were also detected, but further research is required to complete identification of these minor components. In addition, several other unidentified sterols were present in some of the oils but due to their very low abundance, the mass spectra were not intense enough to enable identification of their structures.

TABLE 10

IUPAC/systematic names of identified sterols.

| Sterol No. | Common name(s) | IUPAC/Systematic name |
|---|---|---|
| 1 | cholesterol | cholest-5-en-3β-ol |
| 2 | brassicasterol | 24-methylcholesta-5,22E-dien-3β-ol |
| 3 | chalinasterol/24-methylene cholesterol | 24-methylcholesta-5,24(28)E-dien-3β-ol |
| 4 | campesterol/24-methylcholesterol | 24-methylcholest-5-en-3β-ol |
| 5 | campestanol/24-methylcholestanol | 24-methylcholestan-3β-ol |
| 7 | Δ5-stigmasterol | 24-ethylcholesta-5,22E-dien-3β-ol |
| 9 | ergost-7-en-3β-ol | 24-methylcholest-7-en-3β-ol |
| 11 | eburicol | 4,4,14-trimthylergosta-8,24(28)-dien-3β-ol |
| 12 | β-sitosterol/24-ethylcholesterol | 24-ethylcholest-5-en-3β-ol |
| 13 | D5-avenasterol/isofucosterol | 24-ethylcholesta-5,24(28)Z-dien-3β-ol |
| 19 | D7-stigmasterol/stigmast-7-en-3b-ol | 24-ethylcholest-7-en-3β-ol |
| 20 | D7-avenasterol | 24-ethylcholesta 7,24(28)-dien-3β-ol |

The sterol contents expressed as mg/g of oil in decreasing amount were: canola oil (6.8 mg/g), sesame oil (5.8 mg/g), flax oil (4.8-5.2 mg/g), sunflower oil (3.7-4.1 mg/g), peanut oil (3.2 mg/g), safflower oil (3.0 mg/g), soybean oil (3.0 mg/g), olive oil (2.4 mg/g), castor oil (1.9 mg/g). The % sterol compositions and total sterol content are presented in Table 11.

Among all the seed oil samples, the major phytosterol was generally β-sitosterol (range 30-57% of total sterol content). There was a wide range amongst the oils in the proportions of the other major sterols: campesterol (2-17%), Δ5-stigmasterol (0.7-18%), Δ5-avenasterol (4-23%), Δ7-stigmasterol (1-18%). Oils from different species had a different sterol profile with some having quite distinctive profiles. In the case of canola oil, it had the highest proportion of campesterol (33.6%), while the other species samples generally had lower levels, e.g. up to 17% in peanut oil. Safflower oil had a relatively high proportion of Δ7-stigmasterol (18%), while this sterol was usually low in the other species oils, up to 9% in sunflower oil. Because they were distinctive for each species, sterol profiles can therefore be used to help in the identification of specific vegetable or plant oils and to check their genuineness or adulteration with other oils.

Two samples each of sunflower and safflower were compared, in each case one was produced by cold pressing of seeds and unrefined, while the other was not cold-pressed and refined. Although some differences were observed, the two sources of oils had similar sterol compositions and total sterol contents, suggesting that processing and refining had little effect on these two parameters. The sterol content among the samples varied three-fold and ranged from 1.9 mg/g to 6.8 mg/g. Canola oil had the highest and castor oil the lowest sterol content.

Example 6. Increasing Accumulation of DHA and DPA at the sn-2 TAG Position

The present inventors considered that DHA and/or DPA accumulation at the sn-2 position in TAG could be increased by co-expressing an 1-acyl-glycerol-3-phosphate acyltransferase (LPAAT) together with the DHA or DPA biosynthesis pathway such as conferred by the GA7 construct or its variants. Preferred LPAATs are those which can act on polyunsaturated C22 fatty acyl-CoA as substrate, preferably DHA-CoA and/or DPA-CoA, especially those that can use both DHA-CoA and DPA-CoA as substrates, resulting in increased insertion of the polyunsaturated C22 chain at the sn-2 position of LPA to form PA, relative to the endogenous LPAAT. Cytoplasmic LPAAT enzymes often display varied substrate preferences, particularly where the species synthesises and accumulates unusual fatty acids in TAG. A LPAAT2 from *Limnanthes douglasii* was shown to use erucoyl-CoA (C22:1-CoA) as a substrate for PA synthesis, in contrast to an LPAAT1 from the same species that could not utilise the C22 substrate (Brown et al., 2002).

TABLE 11

| Sterol content and composition of assayed plant oils. | | | | | | | | | |
|---|---|---|---|---|---|---|---|---|---|
| Sterol common name | Sesame | Olive | Sunflower | Castor | Canola | Safflower | Peanut | Flax | Soybean |
| cholesterol | 0.2 | 0.8 | 0.2 | 0.1 | 0.3 | 0.2 | 0.2 | 0.4 | 0.2 |
| brassicasterol | 0.1 | 0.0 | 0.0 | 0.3 | 0.1 | 0.0 | 0.0 | 0.2 | 0.0 |
| chalinasterol/24-methylene cholesterol | 1.5 | 0.1 | 0.3 | 1.1 | 2.4 | 0.2 | 0.9 | 1.5 | 0.8 |
| campesterol/24-methylcholesterol | 16.2 | 2.4 | 7.4 | 8.4 | 33.6 | 12.1 | 17.4 | 15.7 | 16.9 |
| campestanol/24-methylcholestanol | 0.7 | 0.3 | 0.3 | 0.9 | 0.2 | 0.8 | 0.3 | 0.2 | 0.7 |
| C29:2* | 0.0 | 0.0 | 0.1 | 0.0 | 0.1 | 0.5 | 0.0 | 1.2 | 0.1 |
| Δ5-stigmasterol | 6.4 | 1.2 | 7.4 | 18.6 | 0.7 | 7.0 | 6.9 | 5.1 | 17.6 |
| unknown | 0.5 | 1.3 | 0.7 | 0.8 | 0.7 | 0.7 | 0.4 | 0.7 | 1.3 |
| ergost-7-en-3β-ol | 0.1 | 0.1 | 1.9 | 0.2 | 0.4 | 2.7 | 1.4 | 1.4 | 1.0 |
| unknown | 0.0 | 1.3 | 0.9 | 1.2 | 0.9 | 1.8 | 1.2 | 0.7 | 0.7 |
| eburicol | 1.6 | 1.8 | 4.1 | 1.5 | 1.0 | 1.9 | 1.2 | 3.5 | 0.9 |
| β-sitosterol/24-ethylcholesterol | 55.3 | 45.6 | 43.9 | 37.7 | 50.8 | 40.2 | 57.2 | 29.9 | 40.2 |
| Δ5-avenasterol/isofucosterol | 8.6 | 16.9 | 7.2 | 19.3 | 4.4 | 7.3 | 5.3 | 23.0 | 3.3 |
| triterpenoid alcohol | 0.0 | 2.4 | 0.9 | 0.0 | 0.0 | 1.6 | 0.0 | 0.0 | 0.9 |
| triterpenoid alcohol | 0.0 | 0.0 | 0.7 | 0.0 | 0.0 | 2.8 | 0.0 | 0.0 | 0.0 |
| Δ7-stigmasterol/stigmast-7-en-3β-ol | 2.2 | 7.1 | 9.3 | 2.3 | 0.9 | 10.5 | 1.1 | 7.9 | 5.6 |
| Δ7-avenasterol | 1.3 | 0.1 | 4.0 | 0.6 | 0.2 | 2.0 | 0.7 | 0.4 | 0.6 |
| Total sterol (mg/g oil) | 5.8 | 2.4 | 4.1 | 1.9 | 6.8 | 3.2 | 3.2 | 4.8 | 3.0 |

C29:2* denotes a C29 sterol with two double bonds

Known LPAATs were considered and a number were selected for testing, including some which were not expected to increase DHA incorporation at the sn-2 position, as controls. The known LPAATs included: *Arabidopsis thaliana* LPAAT2: (SEQ ID NO: 40, Accession No. ABG48392, Kim et al., 2005), *Limnanthes alba* LPAAT (SEQ ID NO: 41, Accession No. AAC49185, Lassner et al., 1995), *Saccharomyces cerevisiae* Slc1p (SEQ ID NO: 42, Accession No. NP_010231, Zou et al., 1997), *Mortierella alpina* LPAAT1 (SEQ ID NO: 44, Accession No. AED33305; U.S. Pat. No. 7,879,591) and *Brassica napus* LPAATs (SEQ ID NO: 45 and SEQ ID NO:46, Accession Nos ADC97479 and ADC97478 respectively).

The *Arabidopsis* LPAAT2 (also designated LPAT2) is an endoplasmic reticulum-localised enzyme shown to have activity on C16 and C18 substrates, however activity on C20 or C22 substrates was not tested (Kim et al., 2005). *Limnanthes alba* LPAAT2 was demonstrated to insert a C22:1 acyl chain into the sn-2 position of PA, although the ability to use DHA or DPA as a substrate was not tested (Lassner et al., 1995). The selected *S. cerevisiae* LPAAT Slc1p was shown to have activity using 22:1-CoA in addition to 18:1-CoA as substrates, indicating a broad substrate specificity with respect to chain length (Zou et al., 1997). Again, DHA-CoA, DPA-CoA and other LC-PUFAs were not tested as substrates. The *Mortierella* LPAAT had previously been shown to have activity on EPA and DHA fatty acid substrates in transgenic *Yarrowia lipolytica* (U.S. Pat. No. 7,879,591) but its activity in plant cells was unknown.

Additional LPAATs were identified by the inventors. *Micromonas pusilla* is a microalga that produces and accumulates DHA in its oil, although the positional distribution of the DHA on TAG in this species has not been confirmed. The *Micromonas pusilla* LPAAT (SEQ ID NO: 43, Accession No. XP_002501997) was identified by searching the *Micromonas pusilla* genomic sequence using the *Arabidopsis* LPAAT2 as a BLAST query sequence. Several candidate sequences emerged and the sequence XP_002501997 was synthesised for testing on C22 LC-PUFA. The *Ricinus communis* LPAAT was annotated as a putative LPAAT in the castor genome sequence (Chan et al., 2010). Four candidate LPAATs from the castor genome were synthesised and tested in crude leaf lysates of infiltrated *N. benthamiana* leaf tissue. The candidate sequence described here showed LPAAT activity.

A number of candidate LPAATs were aligned with known LPAATs on a phylogenetic tree. It was noted that the putative *Micromonas* LPAAT did not cluster with the putative C22 LPAATs but was a divergent sequence.

As an initial test of various LPAATs for their ability to use DHA-CoA and/or DPA-CoA as substrate, chimeric genetic constructs were made for constitutive expression of exogenous LPAATs in *N. benthamiana* leaves, each under the control of the 35S promoter, as follows: 35S:Arath-LPAAT2 (*Arabidopsis* ER LPAAT); 35S:Limal-LPAAT (*Limnanthes alba* LPAAT); 35S:Sacce-Slc1p (*S. cerevisiae* LPAAT); 35S:Micpu-LPAAT (*Micromonas pusilla* LPAAT); 35S:Moral-LPAAT1 (*Mortierella alpina* LPAAT); 35S:Brana-LPAAT1.13 (*Brassica napus* LPAAT1.13); 35S:Brana-LPAAT1.5 (*Brassica napus* LPAAT1.5). A 35S:p19 construct lacking an exogenous LPAAT was used as a control in the experiment; it was included in each *N. benthamiana* inoculation. Each of these constructs was introduced via *Agrobacterium* into *N. benthamiana* leaves as described in Example 1, and 5 days after infiltration, the treated leaf zones were excised and ground to make leaf lysates. Each lysate included the exogenous LPAAT as well as the endogenous enzymes for synthesizing LPA. In vitro reactions were set up by separately adding $^{14}$C-labelled-OA and -DHA to the lysates. Reactions were incubated at 25° C. and the level of incorporation of the $^{14}$C labelled fatty acids into PA determined by TLC. The ability of each LPAAT to use DHA relative to ARA and the C18 fatty acids were assessed. The meadowfoam (*Limnanthes alba*), *Mortierella* and *Saccharomyces* LPAATs were found to have activity on DHA substrate, with radiolabelled PA appearing for these but not the other LPAATs. All LPAATs were confirmed active by the oleic acid control feed.

To test LPAAT activity in seeds, several of the protein coding sequences or LPAATs were inserted into a binary vector under the control of a conlinin (pLuCn12) promoter. The resultant genetic constructs containing the chimeric genes, Cn12:Arath-LPAAT (negative control), Cn12:Limal-LPAAT, Cn2:Sacce-Slc 1p, and Cn12:Moral-LPAAT, respectively, are then used to transform *A. thaliana* plants producing DHA in their seed to generate stable transformants expressing the LPAATs and the transgenic DHA pathway in a seed-specific manner to test whether there would be an increased incorporation of DHA at the sn-2 position of TAG. The constructs are also used to transform *B. napus* and *C. sativa* plants that already contain the GA7 construct and variants thereof (Examples 2 and 3) to generate progeny carrying both the parental and LPAAT genetic constructs. Increased incorporation of DHA and/or DPA at the sn-2 position of TAG is tested relative to the incorporation in plants lacking the LPAAT encoding transgenes. Oil content is also improved in the seeds, particularly for seeds producing higher levels of DHA.

The seed-specific pCn12:Moral-LPAAT1 construct was used to transform an already transgenic *Arabidopsis thaliana* line which was homozygous for the T-DNA from the GA7 construct and whose seed contained approximately 15% DHA in seed lipids (Petrie et al., 2012). For this, use was made of the kanamycin selectable marker gene in the pCn12:Moral-LPAAT1 construct which was different to the bar selectable marker gene already present in the transgenic line. Transgenic seedlings were selected which were resistant to kanamycin and grown to maturity in a glasshouse. T2 seeds were harvested and the fatty acid composition of their total seed lipids analysed by GC (Table 12). Three phenotypes were observed amongst the 33 independently transformed lines. In a first group (6/33 lines), DPA increased significantly to a level substantially greater than the level of DHA, up to about 10.6% of total seed lipids. This came at the expense of DHA which was strongly decreased in this group of lines. In two of the lines in this first group, the sum of DPA+DHA was reduced, but not in the other 4 lines. In a second group (5/33), the levels of DPA and DHA were about equal, with the sum of DPA+DHA about the same as for the parental seed. In the third group, the levels of DPA and DHA were similar to those in the parental seeds. One possible explanation for the increased level of DPA in the first and second groups is that the LPAAT out-competes the Δ4-desaturase for DPA-CoA substrate and preferentially incorporates the DPA into PA and thence into TAG, relative to the Δ4-desaturation. A second possible explanation is that the Δ4-desaturation is partially inhibited.

Seed from the *Arabidopsis* plants transformed with the T-DNA of the GA7 construct which had been further transformed with the pCn12::Moral-LPAAT vector were harvested and oil extracted from the seed. The TAG fraction was then isolated from the extracted oil by TLC methods and recovered from the TLC plate. These TAG samples and samples of the seedoil prior to the fractionation were analysed by digestion with *Rhizopus* lipase to determine the positional distribution of the DHA. The lipase is specific for acyl groups esterified at the sn-1 or sn-3 position of TAG. This was performed by emulsifying each lipid sample in 5% gum arabic using an ultrasonicator, adding the *Rhizopus* lipase solution in 0.1M Tris-HCl pH 7.7 containing 5 mM $CaCl_2$ and incubating the mixtures at 30° C. with continuous shaking. Each reaction was stopped by adding chloroform: methanol (2/1, v/v) and one volume of 0.1M KCl to each mixture. The lipid was extracted into the chloroform fraction and the relative amounts determined of the sn-2 MAG, sn-1/3 FFA, DAG and TAG components of the resulting lipid by separation on 2.3% boric acid impregnated TLC using hexane/diethylether/acetic acid (50/50/1, v/v). Lipid bands were visualized by spraying 0.01% primuline in acetone/water (80/20, v/v) onto the TLC plate and visualisation under UV light. Individual lipid bands were identified on the basis of lipid standard spots, resolved on the same TLC plate. TLC lipid bands were collected into glass vials and their fatty acid methyl esters were prepared using 1N methanolic-HCl (Supelco) and incubating at 80° C. for 2 h. Fatty acid composition of individual lipids were analysed by GC.

This assay demonstrated that the DHA in the parental seeds transformed with the GA7 (lines 22-2-1-1 and 22-2-38-7) was preferentially esterified at the sn-1 or sn-3 position of the TAG. In contrast, the DHA in the NY11 and NY15 seed transformed with both the GA7 constructs and the transgene encoding LPAAT was enriched at the sn-2 position, with 35% of the DHA in one of the lines and 48% of the DHA in the other line being esterified at the sn-2 position of TAG i.e. after lipase digestion the DHA was present as sn-2-MAG (Table 13). Analogous results are obtained for *B. napus* and *B. juncea* seeds transformed with both the T-DNA from the GA7-modB construct and the LPAAT-encoding gene and producing DHA, and with *B. napus* and *B. juncea* seeds producing DPA.

In order to determine whether the *Mortierella* LPAAT or another LPAAT had preference for either DPA-CoA or DHA-CoA, in vitro reactions are set up by separately adding $^{14}C$-labelled-DPA-CoA or -DHA-CoA to lysates of *N. benthamiana* leaves transiently expressing the candidate LPAAT under control of a constitutive promoter as described above. Reactions are incubated at 25° C. and the level of incorporation of the $^{14}C$ labelled fatty acids into PA determined by TLC analysis of the lipids. The ability of each LPAAT to use DHA-CoA relative to DPA-CoA is assessed. Genes encoding LPAATs which are confirmed to have good DHA incorporating LPAAT activity are used to produced transformed DHA-producing canola plants and seed.

Genes encoding LPAATs which have strong activity using DPA-CoA are used to transform DPA-producing plants and seed, to increase the amount of DPA esterified at the sn-2 position of TAG.

TABLE 12

Fatty acid composition (% of total fatty acids) of transgenic *A. thaliana* seeds transformed with an LPAAT1 construct as well as the T-DNA from the GA7 construct for DHA production. C20:4ω6 was not detected in the seeds. The seeds also contained 0.3-0.9% C22:0 and 0.4-1.5% C22:1.

| | C16:0 | C18:0 | C18:1 | 18:1Δ11 | C18:2 | C18:3ω6 | C18:3ω3 | C20:0 | 18:4ω3 |
|---|---|---|---|---|---|---|---|---|---|
| NY-1 | 9.3 | 3.2 | 9.1 | 6.8 | 9.4 | 0.5 | 23.8 | 1.6 | 4.1 |
| NY-2 | 10.7 | 3.3 | 6.5 | 4.4 | 7.6 | 0.3 | 28.1 | 1.9 | 4.3 |
| NY-3 | 9.3 | 2.8 | 6.3 | 3.4 | 10.3 | 0.2 | 32.8 | 2.2 | 2.7 |
| NY-4 | 11.4 | 3.5 | 4.5 | 3.1 | 7.0 | 0.3 | 32.5 | 2.1 | 4.7 |
| NY-5 | 14.6 | 4.5 | 7.0 | 7.7 | 6.7 | 0.3 | 20.7 | 2.2 | 5.7 |
| NY-6 | 7.8 | 2.7 | 12.5 | 2.2 | 18.0 | 0.1 | 24.9 | 1.8 | 0.7 |
| NY-7 | 9.3 | 2.9 | 6.7 | 3.8 | 9.2 | 0.2 | 31.5 | 2.1 | 3.2 |
| NY-8 | 8.8 | 3.2 | 8.2 | 5.5 | 11.0 | 0.3 | 25.3 | 1.9 | 3.0 |
| NY-9 | 12.3 | 3.7 | 5.0 | 4.6 | 7.1 | 0.2 | 28.3 | 2.3 | 4.2 |
| NY-10 | 8.6 | 3.2 | 8.5 | 3.1 | 9.7 | 0.3 | 31.5 | 1.6 | 3.4 |

TABLE 12-continued

Fatty acid composition (% of total fatty acids) of transgenic *A. thaliana* seeds transformed with an LPAAT1 construct as well as the T-DNA from the GA7 construct for DHA production. C20:4ω6 was not detected in the seeds. The seeds also contained 0.3-0.9% C22:0 and 0.4-1.5% C22:1.

| | | | | | | | | | |
|---|---|---|---|---|---|---|---|---|---|
| NY-11 | 11.5 | 3.2 | 4.5 | 2.5 | 7.1 | 0.3 | 33.3 | 2.1 | 3.9 |
| NY-12 | 8.7 | 3.2 | 7.5 | 5.1 | 8.5 | 0.2 | 26.8 | 2.0 | 3.7 |
| NY-13 | 11.5 | 3.4 | 5.2 | 3.4 | 8.3 | 0.3 | 30.0 | 2.2 | 5.0 |
| NY-14 | 9.2 | 2.9 | 6.6 | 2.0 | 10.3 | 0.2 | 34.7 | 1.9 | 3.3 |
| NY-15 | 10.9 | 3.3 | 4.6 | 2.7 | 7.0 | 0.3 | 34.1 | 1.9 | 5.1 |
| NY-16 | 10.5 | 3.4 | 6.0 | 4.6 | 7.8 | 0.3 | 30.3 | 1.8 | 4.4 |
| NY-17 | 9.1 | 2.4 | 5.9 | 2.5 | 10.4 | 0.2 | 35.4 | 1.6 | 3.6 |
| NY-18 | 9.7 | 3.6 | 8.8 | 6.2 | 12.1 | 0.3 | 21.0 | 1.9 | 4.0 |
| NY-19 | 8.4 | 3.1 | 12.0 | 3.1 | 14.6 | 0.2 | 28.8 | 1.7 | 1.6 |
| NY-20 | 10.1 | 3.2 | 5.4 | 3.3 | 8.9 | 0.3 | 32.8 | 2.1 | 4.1 |
| NY-21 | 10.5 | 3.6 | 5.6 | 3.8 | 8.2 | 0.3 | 31.9 | 2.0 | 4.6 |
| NY-22 | 8.4 | 3.3 | 7.4 | 2.3 | 9.4 | 0.2 | 33.5 | 1.8 | 3.4 |

| | 20:1Δ11 | 20:1Δ13 | C20:2ω6 | C20:3ω3 | C20:4ω3 | C20:5ω3 | 22:5ω3 | C22:6ω3 |
|---|---|---|---|---|---|---|---|---|
| NY-1 | 7.9 | 5.1 | 0.6 | 0.9 | 0.6 | 1.2 | 7.9 | 4.5 |
| NY-2 | 8.5 | 3.7 | 0.7 | 1.1 | 1.1 | 1.4 | 1.1 | 11.6 |
| NY-3 | 6.2 | 3.6 | 1.1 | 1.9 | 1.4 | 0.7 | 1.0 | 10.7 |
| NY-4 | 5.5 | 2.3 | 1.0 | 1.9 | 0.8 | 1.1 | 0.9 | 14.3 |
| NY-5 | 5.4 | 4.8 | 0.4 | 0.9 | 0.8 | 1.2 | 1.0 | 11.7 |
| NY-6 | 15.5 | 3.1 | 1.4 | 1.2 | 0.5 | 0.3 | 3.0 | 0.8 |
| NY-7 | 7.5 | 3.7 | 0.9 | 1.6 | 1.3 | 0.8 | 1.1 | 10.9 |
| NY-8 | 8.3 | 5.4 | 1.0 | 1.2 | 0.8 | 0.8 | 6.1 | 6.0 |
| NY-9 | 5.6 | 3.8 | 0.8 | 1.6 | 0.7 | 1.1 | 1.2 | 13.8 |
| NY-10 | 8.7 | 2.8 | 1.0 | 1.3 | 0.9 | 1.1 | 10.6 | 1.0 |
| NY-11 | 5.7 | 1.9 | 0.9 | 2.0 | 0.7 | 0.8 | 1.0 | 15.6 |
| NY-12 | 8.7 | 5.1 | 0.9 | 1.2 | 1.1 | 1.2 | 10.0 | 2.6 |
| NY-13 | 6.2 | 3.2 | 0.9 | 1.7 | 1.5 | 1.1 | 1.0 | 11.6 |
| NY-14 | 7.7 | 1.6 | 1.2 | 1.8 | 1.2 | 0.9 | 0.8 | 11.1 |
| NY-15 | 5.5 | 2.0 | 0.9 | 1.8 | 0.8 | 1.0 | 1.0 | 14.7 |
| NY-16 | 5.4 | 2.9 | 0.7 | 1.5 | 0.9 | 1.1 | 1.3 | 14.2 |
| NY-17 | 6.4 | 2.1 | 1.1 | 1.9 | 1.2 | 1.0 | 0.9 | 11.7 |
| NY-18 | 8.3 | 5.9 | 0.8 | 0.9 | 0.6 | 1.0 | 5.7 | 5.1 |
| NY-19 | 11.3 | 3.2 | 1.0 | 1.4 | 0.6 | 0.6 | 3.9 | 1.2 |
| NY-20 | 5.5 | 2.8 | 1.0 | 1.9 | 1.1 | 0.9 | 1.1 | 12.1 |
| NY-21 | 5.9 | 2.8 | 0.9 | 1.7 | 0.8 | 1.0 | 0.9 | 12.5 |
| NY-22 | 8.8 | 2.2 | 1.2 | 1.7 | 1.3 | 1.0 | 5.5 | 6.1 |

TABLE 13

Presence of DHA at the sn-2 position of TAG or in the total oil from transgenic *A. thaliana* seeds transformed with the Cnl2::MoraI-LPAAT gene as well as the T-DNA of the GA7 construct, showing the positional distribution of DHA in TAG. The TAG and sn-2 MAG fatty acid compositions also contained 0-0.4% each of 14:0, 16:1ω13t, 16:2, 16:3, 22:0, and 24:0. The seeds contained no detected C20:3ω6, C20:4ω6.

| Sample | C16:0 | C16:1Δ9 | C18:0 | C18:1 | C18:1Δ11 | C18:2 | C18:3ω6 | C18:3ω3 | C20:0 | C18:4 | C20:1Δ11 |
|---|---|---|---|---|---|---|---|---|---|---|---|
| 22-2-1-1 TAG | 12.2 | 0.4 | 4.4 | 6.4 | 3.9 | 7.2 | 0.8 | 28.8 | 1.6 | 4.3 | 9.7 |
| 2-MAG | 0.6 | 0.1 | 0.3 | 8.3 | 2.5 | 10.1 | 0.7 | 53.9 | 0.2 | 6.5 | 0.3 |
| 22-2-38-7 oil | 10.0 | 0.2 | 3.7 | 6.0 | 2.7 | 6.4 | 0.4 | 33.8 | 1.6 | 3.7 | 11.3 |
| 2-MAG | 0.5 | 0.1 | 0.3 | 9.7 | 2.4 | 11.1 | 0.6 | 60.0 | 0.1 | 3.6 | 0.3 |
| Transformed additionally with gene encoding *Mortierella alpina* LPAAT: | | | | | | | | | | | |
| NY11-TAG | 11.0 | 0.2 | 3.4 | 6.0 | 2.8 | 9.2 | 0.3 | 34.8 | 1.6 | 3.6 | 6.3 |
| 2-MAG | 0.7 | 0.1 | 0.2 | 6.7 | 1.1 | 11.8 | 0.3 | 49.8 | 0.2 | 3.7 | 0.5 |
| NY-15-oiI | 11.0 | 0.0 | 3.3 | 4.6 | 2.8 | 6.9 | 0.3 | 33.6 | 2.0 | 5.1 | 5.5 |
| 2-MAG | 0.8 | 0.1 | 0.3 | 6.4 | 1.3 | 11.4 | 0.3 | 50.2 | 0.2 | 4.9 | 0.4 |

| Sample | C20:1Δ13 | C20:2ω6 | C20:3ω3 | C20:4ω3 | C22:1 | C20:5ω3 | C22:5ω6 | C22:4ω3 | C22:5ω3 | C22:6ω3 |
|---|---|---|---|---|---|---|---|---|---|---|
| 22-2-1-1 TAG | 2.3 | 0.7 | 1.3 | 1.0 | 0.6 | 2.1 | | 0.0 | 0.7 | 10.1 |
| 2-MAG | 0.1 | 0.1 | 0.3 | 0.2 | 0.0 | 3.8 | | 0.0 | 2.3 | 9.1 |
| | | | | | | | | DHA at sn-2 = 30% | | |
| 22-2-38-7 oil | 1.8 | 0.8 | 1.3 | 0.9 | 0.6 | 1.2 | | | 0.7 | 11.6 |
| 2-MAG | 0.1 | 0.1 | 0.4 | 0.2 | 0.0 | 2.1 | | 0.1 | 1.3 | 6.7 |
| | | | | | | | | DHA at sn-2 = 19% | | |
| Transformed additionally with gene encoding *Mortierella alpina* LPAAT: | | | | | | | | | | |
| NY11-TAG | 1.8 | 1.0 | 1.8 | 0.7 | 0.6 | 0.9 | 0.0 | 0.1 | 0.6 | 12.2 |
| 2-MAG | 1.5 | 0.3 | 1.6 | 0.6 | 0.1 | 0.8 | 0.1 | 0.2 | 1.6 | 17.8 |
| | | | | | | | | DHA at sn-2 = 48% | | |

TABLE 13-continued

Presence of DHA at the sn-2 position of TAG or in the total oil from transgenic *A. thaliana* seeds transformed with the Cnl2::Moral-LPAAT gene as well as the T-DNA of the GA7 construct, showing the positional distribution of DHA in TAG. The TAG and sn-2 MAG fatty acid compositions also contained 0-0.4% each of 14:0, 16:1ω13t, 16:2, 16:3, 22:0, and 24:0. The seeds contained no detected C20:3ω6, C20:4ω6.

| | | | | | | | | | | |
|---|---|---|---|---|---|---|---|---|---|---|
| NY-15-oil | 2.1 | 0.9 | 1.9 | 0.7 | 0.6 | 0.9 | 0.4 | | 0.9 | 14.9 |
| 2-MAG | 1.4 | 0.2 | 1.5 | 0.6 | 0.1 | 0.9 | 0.0 | 0.2 | 1.6 | 16.7 |
| | | | | | | | | DHA at sn-2 = 37% | | |

Example 7. Further Analysis of Transgenic *Camelina sativa* Seeds Total Lipid Content

*C. sativa* seed which was homozygous for the T-DNA from the GA7 construct and containing DHA in its total fatty acid content was analysed for its total lipid content and composition as follows. Two consecutive solvent extraction steps were performed on the seeds, firstly using hexane and secondly using chloroform/methanol. No antioxidants were added during the extractions or analysis. The Soxhlet extraction method which is commonly used to extract seed lipids by prolonged heating and refluxing of the lipid/solvent mixture was not used here because of the potential for degradation or oxidation of the ω3 PUFA such as DHA.

Hexane was used as the solvent in the first extraction since it is the industry standard for oilseeds. Also, it preferentially extracts TAG-containing oil due to its solvating properties and its relatively poor solubilization of polar lipids, particularly at room temperature. Transformed and control *Camelina* seeds (130 g and 30 g, respectively) were wetted with hexane and crushed using an electric agate mortar and pestle (Retsch Muhle, Germany). The mixtures were transferred to separatory funnels and extracted four times using a total of 800 mL hexane, including an overnight static extraction for the third extraction. For each extraction, extracts were filtered to remove fines through a GFC glass fiber filter under vacuum, and then rotary evaporated at 40° C. under vacuum. The extracts were pooled and constituted the TAG-rich hexane extracts.

Following extraction with hexane, the remaining seed meals were further extracted using chloroform-methanol (CM, 1:1 v/v) using the procedure as for the hexane extraction. The meal was then removed by filtration and the combined extracts rotary evaporated. The pooled CM total crude lipid extracts were then dissolved using a one-phase methanol-chloroform-water mix (2:1:0.8 v/v/v). The phases were separated by the addition of chloroform-water (final solvent ratio, 1:1:0.9 v/v/v methanol-chloroform-water). The purified lipid in each extract was partitioned in the lower chloroform phase, concentrated using rotary evaporation and constituted the polar lipid-rich CM extracts. The lipid content in each of these extracts was determined gravimetrically.

For fatty acid compositional analysis, aliquots of the hexane and CM extracts were trans-methylated according to the method of Christie et al. (1982) to produce fatty acid methyl esters (FAME) using methanol-chloroform-conc. hydrochloric acid (3 mL, 10:1:1, 80° C., 2 h). FAME were extracted into hexane-chloroform (4:1, 3×1.8 mL). Samples of the remaining seed meal (1-2 g) after the hexane and CM extractions were also trans-methylated to measure any residual lipid as FAME by gravimetry. The total lipid content of the seeds was calculated by adding the lipid contents of the hexane and CM extracts and the FAME content of the transmethylated meal after solvent extraction.

The transgenic seeds contained slightly less total lipid at 36.2% of seed weight compared to the wild-type *Camelina sativa* seeds at 40.9% of seed weight. For seeds including oilseeds, the total lipid was determined as the sum of solvent extractable lipid obtained by consecutive extractions with hexane, then chloroform-methanol, plus the residual lipid released by transmethylation of the extracted meal after the solvent extractions, as exemplified herein. This total lipid consisted mainly of fatty acid containing lipids such as triacylglycerols and polar lipids and small amounts of non-fatty acid lipids e.g. phytosterols and fatty alcohols which may be present in the free unesterified form or esterified with fatty acids. In addition, any sterol esters or wax esters and hydrocarbons such as carotenoids, for example β-carotene, were also included in the solvent extractable lipid if present. These were included in the overall gravimetric determination and were indicated in the TLC-FID analysis (Table 14).

Of the total lipid, 31%-38% of lipid per seed weight was extracted by hexane for the transgenic and control seeds, respectively, which accounted for 86% and 92% of the total lipid in the seeds. The CM extraction recovered a further 4.8% and 2.4% (of seed weight) mostly polar lipid-rich extract from the transgenic and control seeds, respectively. The residual lipid released by transmethylation of the remaining solvent extracted oilseed meal was 0.3% and 0.4% of seed weight, respectively. That is, the first and second solvent extractions together extracted 99% of the total lipid content of the seeds (i.e. of the 36.2% or 40.9% of the seed weight, which was mostly fatty acid containing lipid such as triglycerides and polar lipids consisting of glyco- and phospholipids (see next section—Lipid class analysis)).

Lipid Class Analysis

Lipid classes in the hexane and CM extracts were analyzed by thin-layer chromatography with flame-ionization detection (TLC-FID; Iatroscan Mark V, Iatron Laboratories, Tokyo, Japan) using hexane/diethyl ether/glacial acetic acid (70:10:0.1, v/v/v) as the developing solvent system in combination with Chromarod S-III silica on quartz rods. Suitable calibration curves were prepared using representative standards obtained from Nu-Chek Prep, Inc. (Elysian, Minn., USA). Data were processed using SIC-48011 software (SISC Version: 7.0-E). Phospholipid species were separated by applying the purified phospholipid fraction obtained from silica column chromatography and developing the rods in chloroform/methanol/glacial acetic acid/water (85:17:5:2, v/v/v) prior to FID detection.

To separate TAG, glycolipid and phospholipid fractions from the CM extracts, silica gel 60 (100-200 mesh) (0.3-1 g) in a short glass column or Pasteur pipette plugged with glass wool was used to purify 10 mg of the purified CM lipid extract. The residual TAG fraction in the CM extract was eluted using 20 mL of 10% diethyl ether in hexane, the glycolipids eluted with 20 mL of acetone and the phospholipids eluted in two steps, first 10 mL of methanol then 10 mL of methanol-chloroform-water (5:3:2). This second elution increased the recovery of phospholipids. The yield of each fraction was determined gravimetrically and the purity checked by TLC-FID. All extracts and fractions were stored in dichloromethane at −20° C. until further analysis by GC and GC-MS.

The TAG-rich hexane extracts from each of the transgenic and control seeds contained about 96% TAG. The CM extracts contained residual TAG amounting to 44% and 13% by weight of the CM extracts, respectively, for the transgenic and wild-type seeds. In contrast to the hexane extracts, the CM extracts were rich in polar lipids, namely phospholipids and glycolipids, amounting to 50% and 76% by weight of the CM extracts, respectively, for the transgenic and control seeds (Table 14). The main phospholipid was phosphatidyl choline (PC) and accounted for 70%-79% of the total phospholipids followed by phosphatidyl ethanolamine (PE, 7%-13%) with relatively low levels of phosphatidic acid (PA, 2%-5%) and phosphatidyl serine (PS, <2%). There are procedural advantages for filing a response to the final Office Action before 7 Jul. 2015.

Fatty Acid Composition

Generally for seeds producing DHA and/or DPA, the inventors observed that the fatty acid composition of the total lipids in the seeds as determined by direct transmethylation of all of the lipid in the seed was similar to that of the TAG fraction. This was because more than 90% of the total lipids present in the seed occurred in the form of TAG.

The fatty acid composition of the different lipid classes in the hexane and CM extracts was determined by gas chromatography (GC) and GC-MS analysis using an Agilent Technologies 6890A GC instrument (Palo Alto, Calif., USA) fitted with a Supelco Equity™-1 fused silica capillary column (15 m×0.1 mm i.d., 0.1 μm film thickness, Bellefont, Pa., USA), an FID, a split/splitless injector and an Agilent Technologies 7683B Series auto sampler and injector. Helium was the carrier gas. Samples were injected in split-less mode at an oven temperature of 120° C. After injection, the oven temperature was raised to 270° C. at 10° C. $min^{-1}$ and finally to 300° C. at 5° C. $min^{-1}$. Eluted compounds were quantified with Agilent Technologies ChemStation software (Palo Alto, Calif., USA). GC results were subject to an error of not more than ±5% of individual component areas.

TABLE 14

Lipid class composition (% of total lipid obtained for each extraction step) of hexane and CM extracts from transgenic and control *Camelina sativa* seeds. SE, WE and HC were not separated from each other.

| | Transgenic seeds | | Control seeds | |
|---|---|---|---|---|
| Lipid class | Hexane | CM | Hexane | CM |
| SE/WE/HC* | 1.0 | 1.4 | 1.0 | 1.4 |
| TAG | 95.6 | 44.2 | 96.0 | 13.1 |
| FFA | 0.9 | 1.3 | 0.8 | 1.4 |
| UN** | 0.9 | 1.1 | 0.8 | 1.2 |
| ST | 0.5 | 0.7 | 0.4 | 0.4 |
| MAG | 0.7 | 1.1 | 0.8 | 6.2 |
| PL | 0.3 | 50.3 | 0.3 | 76.3 |
| Total | 100.0 | 100.0 | 100.0 | 100.0 |

Abbreviations:
sterol esters (SE),
wax esters (WE).
hydrocarbons (HC),
triacylglycerols (TAG),
free fatty acids (FFA),
unknown (UN),
sterols (ST),
monoacylglycerols (MAG),
polar lipids (PL) consisting of glycolipids and phospholipids;
*SE, WE and HC co-elute with this system;
**May contain fatty alcohols and diacylglycerols (DAG).

GC-mass spectrometric (GC-MS) analyses were performed on a Finnigan Trace ultra Quadrupole GC-MS (model: ThermoQuest Trace DSQ, Thermo Electron Corporation). Data were processed with ThermoQuest Xcalibur software (Austin, Tex., USA). The GC was fitted with an on-column injector and a capillary HP-5 Ultra Agilient J & W column (50 m×0.32 mm i.d., 0.17 μm film thickness, Agilent Technologies, Santa Clara, Calif., USA) of similar polarity to that described above. Individual components were identified using mass spectral data and by comparing retention time data with those obtained for authentic and laboratory standards. A full procedural blank analysis was performed concurrent to the sample batch.

The data for the fatty acid composition in the different lipid classes in the extracts are shown in Table 15. In the DHA-producing *Cainelina* seed, the DHA was distributed in the major lipid fractions (TAG, phospholipids and glycolipids) at a proportion ranging between 1.6% and 6.8% with an inverse relationship between the proportions of DHA and ALA. The TAG-rich hexane extract from the transgenic seed contained 6.8% DHA and 41% ALA (Table 15). The polar lipid-rich CM extract contained 4.2% DHA and 50% ALA i.e. relatively less DHA and more ALA. Residual TAG from the polar lipid-rich CM extract contained 6% DHA and 40% ALA. The glycolipid fraction isolated from the CM extract contained 3% DHA and 39% ALA and the phospholipid fraction contained the lowest level of DHA (1.6%) and the highest levels of ALA (54%). The transgenic *Camelina* seed contained higher levels of ALA and lower levels of LA (linoleic acid, 18:2ω6) compared with the control seeds in the major lipid classes (TAG, glycolipids and phospholipids). The proportions of ALA and LA were: ALA 39%-54% and LA 4%-9% for transgenic seeds and ALA 12%-32% and LA 20%-29% for control seeds. The relative level of erucic acid (22:1(.09) was lower in all fractions in the transgenic seeds than in the control seeds, for example, in the hexane extracts 1.3% versus 2.7% (Table 15).

Sterol Composition in the Seeds

To determine the sterol content and composition in the extracted lipids, samples of approximately 10 mg total lipid from the TAG-rich hexane extract and the polar lipid-rich CM extract were saponified using 4 mL 5% KOH in 80%

MeOH and heated for 2 h at 80° C. in a Teflon-lined screw-capped glass test tube. After the reaction mixtures were cooled, 2 mL of Milli-Q water was added and the sterols and alcohols were extracted three times into 2 mL of hexane:dichloromethane (4:1, v/v) by shaking and vortexing. The mixtures were centrifuged and each extract in the organic phase was washed with 2 mL of Milli-Q water by shaking and centrifugation. After taking off the top sterol-containing organic layer, the solvent was evaporated using a stream of nitrogen gas and the sterols and alcohols silylated using 200 μL of Bis(trimethylsilyl)-trifluoroacetamide (BSTFA, Sigma-Aldrich) by heating for 2 h at 80° C. in a sealed GC vial. By this method, free hydroxyl groups were converted to their trimethylsilyl ethers. The sterol- and alcohol-OTMSi derivatives were dried under a stream of nitrogen gas on a heating block (40° C.) and re-dissolved in dichloromethane (DCM) immediately prior to GC/GC-MS analysis as described above.

profiles were similar between the transgenic and control seeds for both the hexane and CM extracts.

Fatty Alcohol Analysis

Fatty alcohols in the seeds were derivatised and analysed as for the sterols. A series of fatty alcohols from $C_{16}$-$C_{22}$, with accompanying iso-branched fatty alcohols, were identified in both the hexane and CM extracts. Similar profiles were observed for the transgenic and control seeds, with some variation in the proportions of individual components observed. Phytol, derived from chlorophyll, was the major aliphatic alcohol and accounted for 47% and 37% of the total fatty alcohols in the hexane fractions in the transgenic and control seeds, respectively. The odd-chain alcohols were present at higher levels in the CM extract (37%-38% of the total fatty alcohol content) than in the hexane extract (16%-23%). Iso-17:0 (16%-38%) predominated over 17:0 (0.3%-5.7%). Another odd-chain alcohol present was 19:0 (4.5%-6.5%). Other alcohols detected included iso-16:0, 16:0, iso-18:0, 18:1, 18:0, with minor levels of iso-20:0, 20:1, 20:0, iso-22:0, 22:1 and 22:0 also present.

TABLE 15

Fatty acid composition (% of total fatty acids) of lipid extracts and fractions of transgenic and control *C. sativa* seeds.

| | Transgenic seeds | | | | | | Control seeds | | | | | |
|---|---|---|---|---|---|---|---|---|---|---|---|---|
| | Hexane | CM | | | | Meal | Hexane | CM | | | | Meal |
| Fatty acid | TAG | Total | TAG | GL | PL | Residue | TAG | Total | TAG | GL | PL | Residue |
| 16:1ω7 | 0.1 | 0.2 | 0.1 | 0.2 | 0.1 | 0.2 | 0.1 | 0.2 | 0.2 | — | — | 0.3 |
| 16:0 | 6.2 | 12.8 | 6.8 | 21.3 | 19.4 | 10.4 | 6.7 | 12.8 | 7.8 | 29.6 | 13.7 | 10.3 |
| 18:4ω3 | 3.7 | 3.3 | 3.4 | 2.1 | 2.9 | 3.6 | — | — | — | — | — | — |
| 18:2ω6 | 7.1 | 3.9 | 8.8 | 7.2 | 3.7 | 8.8 | 22.2 | 28.4 | 29.4 | 20.8 | 29.3 | 27.9 |
| 18:3ω3 | 41.9 | 50.3 | 39.9 | 38.6 | 54.1 | 38.9 | 32.0 | 20.6 | 19.7 | 13.0 | 12.3 | 20.0 |
| 18:1ω9 | 11.1 | 4.7 | 9.6 | 7.2 | 2.8 | 8.1 | 14.0 | 25.4 | 13.3 | 14.7 | 35.7 | 14.3 |
| 18:1ω7 | 1.4 | 2.3 | 2.1 | 3.7 | 3.4 | 2.8 | 1.0 | 1.5 | 2.2 | 4.0 | 2.8 | 2.2 |
| 18:0 | 3.2 | 4.0 | 3.0 | 4.5 | 5.7 | 3.1 | 3.0 | 2.7 | 2.9 | 5.7 | 3.6 | 2.7 |
| 20:5ω3 | 0.4 | 0.2 | 0.3 | — | — | 0.3 | — | — | — | — | — | — |
| 20:4ω3 | 0.4 | 0.4 | 0.4 | — | 0.2 | 0.3 | — | — | — | — | — | — |
| 20:2ω6 | 0.7 | 0.7 | 0.8 | 0.6 | 0.4 | 0.7 | 1.8 | 0.8 | 2.1 | 1.2 | — | 1.8 |
| 20:3ω3 | 0.8 | 1.2 | 0.9 | 0.6 | 1.3 | 0.5 | 0.9 | 0.3 | — | — | — | 0.4 |
| 20:1ω9/11 | 11.6 | 6.1 | 10.9 | 5.1 | 1.3 | 8.4 | 12.5 | 3.0 | 11.1 | 4.2 | 1.7 | 9.4 |
| 20:1ω7 | 0.6 | 0.8 | 1.4 | 0.6 | 0.2 | 1.1 | 0.6 | 0.6 | 2.0 | 1.3 | — | 1.8 |
| 20:0 | 1.3 | 0.8 | 1.4 | 0.6 | 0.1 | 1.4 | 1.5 | 0.7 | 2.0 | 1.4 | — | 1.8 |
| 22:6ω3 | 6.8 | 4.2 | 6.1 | 3.0 | 1.6 | 5.4 | — | — | — | — | — | — |
| 22:5ω3 | 0.3 | 1.1 | 0.4 | 0.6 | 1.4 | 0.3 | — | — | — | — | — | — |
| 22:1ω9 | 1.3 | 1.0 | 1.8 | 0.6 | 0.1 | 1.5 | 2.7 | 0.7 | 3.6 | 0.9 | — | 2.9 |
| 22:0 | 0.3 | 0.2 | 0.3 | 0.6 | 0.1 | 0.7 | 0.3 | 0.2 | 0.7 | 0.8 | — | 0.8 |
| 24:1ω9 | 0.3 | 0.4 | 0.4 | 0.6 | 0.3 | 0.6 | 0.3 | 0.6 | 0.7 | 0.9 | 0.5 | 1.0 |
| 24:0 | 0.1 | 0.4 | 0.2 | 0.9 | 0.4 | 1.1 | 0.1 | 0.4 | 0.5 | 1.4 | 0.4 | 1.3 |
| others* | 0.4 | 1.0 | 1.0 | 1.4 | 0.5 | 1.8 | 0.3 | 1.1 | 0.9 | 0.1 | — | 1.1 |
| Total | 100 | 100 | 100 | 100 | 100 | 100 | 100 | 100 | 100 | 100 | 100 | 100 |

Abbreviations: triacylglycerols (TAG), glycolipids (GL), phospholipids (PL);
Total: polar lipid-rich extract containing GL and PL from CM extraction;
TAG, GL and PL were separated by silica column chromatography of the CM extracts;
*Sum of minor fatty acids The major sterols in both the transgenic and control seeds were 24-ethylcholesterol (sitosterol, 43%-54% of the total sterols), 24-methylcholesterol (campesterol, 20%-26%) with lower levels of cholesterol (5%-8%), brassicasterol (2%-7%), isofucosterol (Δ5-avenasterol, 4%-6%), stigmasterol (0.5%-3%), cholest-7-en-3β-ol, (0.2%-0.5%), 24-methylcholestanol (campestanol, 0.4%-1%) and 24-dehydrocholesterol (0.5%-2%) (Table 16). These nine sterols accounted for 86%-95% of the total sterols, with the remaining components being sterols only partially identified for the numbers of carbons and double bonds. The overall sterol Discussion The results indicated that crushing using a motorized mortar and pestle with multiple extractions with hexane at room temperature was effective in recovering most of the TAG-containing oil from the transgenic seeds. In addition to the oil from the transgenic seeds containing moderate levels of DHA, the transgenic seeds also had markedly higher levels of ALA in the major lipid classes (triacylglycerols, glycolipids and phospholipids) compared with the control seeds. This showed that the Δ15-desaturase activity was considerably enhanced in the transgenic seeds during seed development. Interestingly, there were some slight differences in the fatty acid composition and proportion of DHA in the various extracts and fractions with the DHA levels being higher in the TAG-rich hexane extract and TAG from CM extraction (6%-6.8%) and lower in the polar lipid fractions (3% in glycolipids and 1.6% in phospholipids). The level of 16:0 was higher in the polar lipid fractions of glycolipids and phospholipids in the CM extracts (19%-21%) compared with the TAG-rich hexane extract and TAG from CM extraction (6%-7%).

TABLE 16

Sterol composition (% of total sterols) of transgenic and control *Camelina* seeds.

| | Transgenic seeds | | Control seeds | |
|---|---|---|---|---|
| Sterols | Hexane | CM | Hexane | CM |
| 24-dehydrocholesterol | 0.8 | 1.8 | 0.5 | 1.4 |
| cholesterol | 5.7 | 7.6 | 4.7 | 7.2 |
| brassicasterol | 4.4 | 6.5 | 1.9 | 4.2 |
| cholest-7-en-3β-ol | 0.2 | 0.5 | 0.3 | 0.4 |
| campesterol | 24.5 | 20.8 | 25.7 | 21.7 |
| campestanol | 0.4 | 1.1 | 0.4 | 0.9 |
| stigmasterol | 1.0 | 2.6 | 0.5 | 1.6 |
| sitosterol | 54.3 | 43.7 | 53.8 | 42.9 |
| Δ5-avenasterol (isofucosterol) | 4.2 | 5.2 | 4.7 | 5.5 |
| Sum | 95.5 | 89.6 | 92.6 | 85.9 |
| Others | | | | |
| UN1 C28 1db | 0.6 | 1.2 | 0.7 | 1.2 |
| UN2 C29 1db | 1.2 | 2.0 | 1.2 | 2.4 |
| UN3 C29 2db | 0.9 | 1.8 | 1.3 | 2.4 |
| UN4 C28 1db | 0.3 | 0.9 | 0.6 | 1.1 |
| UN5 C30 2db | 1.2 | 1.8 | 1.4 | 1.8 |
| UN6 C29 1db + C30 2db | 0.3 | 2.7 | 2.2 | 5.2 |
| Sum of others | 4.5 | 10.4 | 7.4 | 14.1 |
| Total | 100 | 100 | 100 | 100 |

Abbreviations:
UN denotes unknown sterol, the number after C indicates the number of carbon atoms and db denotes number of double bonds The sterol composition of the transgenic seeds and control seeds were similar to that found in refined *Camelina* oil (Shukla et al., 2002) with the same major sterols present, indicating that the added genes did not affect sterol synthesis in the seeds. The level of cholesterol in *Camelina* oil was higher than occurred in most vegetable oils. Brassicasterol was present, which is a characteristic sterol found in the Brassicaceae family which includes *Camelina sativa.*

Example 8. Production of LC-PUFA in *Brassica juncea* Seeds

Transgenic *Brassica juncea* plants were produced using the GA7-modB construct (Example 3) for the production of DHA, as follows. *B. juncea* seeds of a long-daylength sensitive variety were sterilized using chlorine gas as described by Kereszt et al. (2007). Sterilized seeds were germinated on ½ strength MS media (Murashige and Skoog, 1962) solidified with 0.8% agar, adjusted to pH 5.8 and grown at 24° C. under fluorescent lighting (50 μE/m$^2$s) with a 16/8 hour (light/dark) photoperiod for 6-7 days. Cotyledonary petioles with 2-4 mm stalk were isolated aseptically from these seedlings and used as explants. *Agrobacterium tumefaciens* strain AGL1 was transformed with the binary construct GA7. *Agrobacterium* culture was initiated and processed for infection as described by Belide et al. (2013). For all transformations, about 50 freshly-isolated cotyledonary petioles were infected with 10 ml of *A. tumefaciens* culture for 6 minutes. The infected petioles were blotted on sterile filter paper to remove excess *A. tumefaciens* and transferred to co-cultivation media (MS containing 1.5 mg/L BA, 0.01 mg/L NAA and 100 μM acetosyringone, also supplemented with L-cysteine (50 mg/L), ascorbic acid (15 mg/L) and MES (250 mg/L). All plates were sealed with micropore tape and incubated in the dark at 24° C. for 48 hours of co-cultivation. The explants were then transferred to pre-selection medium (MS-agar containing 1.5 mg/L BA, 0.01 mg/L NAA, 3 mg/L $AgNO_3$, 250 mg/L cefotaxime and 50 mg/L timentin) and cultured for 4-5 days at 24° C. with a 16/8 hour photoperiod before the explants were transferred to selection medium (MS-agar containing 1.5 mg/L BA, 0.01 mg/L NAA, 3 mg/L $AgNO_3$, 250 mg/L cefotaxime, 50 mg/L timentin and 5 mg/L PPT) and cultured for 4 weeks at 24° C. with 16/8 hour photoperiod. Explants with green callus were transferred to shoot regeneration medium (MS-agar containing 2.0 mg/L BA, 3 mg/L $AgNO_3$, 250 mg/L cefotaxime, 50 mg/L timentin and 5 mg/L PPT) and cultured for another 2 weeks. Small regenerating shoot buds were transferred to hormone free MS medium (MS-agar containing 3 mg/L $AgNO_3$, 250 mg/L cefotaxime, 50 mg/L timentin and 5 mg/L PPT) and cultured for another 2-3 weeks.

Potential transgenic shoots of at least 1.5 cm in size were isolated and transferred to root induction medium (MS-agar containing 0.5 mg/L NAA, 3 mg/L $AgNO_3$, 250 mg/L cefotaxime and 50 mg/L timentin) and cultured for 2-3 weeks. Transgenic shoots confirmed by PCR and having prolific roots were transferred to soil in a greenhouse and grown under a photoperiod of 16/8 h (light/dark) at 22° C. Three confirmed transgenic plants were obtained. The transformed plants were grown in the greenhouse, allowed to self-fertilise, and T1 seed harvested. The fatty acid composition was analysed of the lipid from pools of T1 seeds from each T0 transformed plants, which showed the presence of 2.8% DPA and 7.2% DHA in one line designated JT1-4, whereas another line designated JT1-6 exhibited 2.6% DPA.

Seedoil from individual T1 seeds was analysed for fatty acid composition; some of the data is shown in Table 17. Several T1 seeds produced DHA at a level of 10% to about 21% of the total fatty acid content, including JT1-4-A-13, JT1-4-A-5, and JT1-4-B-13. Surprisingly and unexpectedly, some of the T1 seeds contained DPA at levels of 10% to about 18% of the total fatty acid content and no detectable DHA (<0.1%). The inventors concluded that the Δ4-desaturase gene in the T-DNA inserted in these plants was inactivated through a spontaneous mutation, similar to that described in Example 2. T1 seeds were germinated and one emerged cotyledon from each analysed for fatty acid composition in the remaining oil. The remainder of each seedling was maintained and grown to maturity to provide T2 seed.

Transgenic plants which were homozygous for single T-DNA insertions were identified and selected. Plants of one selected line designated JT1-4-17 had a single T-DNA insertion and produced DHA with only low levels of DPA, whereas those of a second selected line designated JT1-4-34 also had a single T-DNA insertion but produced DPA without producing DHA. The inventors concluded that the original transformant contained two separate T-DNAs, one which conferred production of DHA and the other which conferred production of DPA without DHA. The *B. juncea* plants producing DHA in their seeds were crossed with the plants producing DPA in their seeds. The F1 progeny included plants which were heterozygous for both of the T-DNA insertions. Seed from these progeny plants were observed to produce about 20% DHA and about 6% DPA, for a total DHA+DPA content of 26%. The F1 plants are self-fertilised and progeny which are homozygous for both of the T-DNA insertions are expected to produce up to 35% DHA and DPA.

About 18% DPA was observed in the lipid of pooled seed of the T3 progeny designated JT1-4-34-11. Similarly about 17.5% DHA was observed in the lipid from pooled seed in the progeny of T3 JT1-4-17-20. Fatty acid compositions of JT1-4 T1 pooled seed, T1 single seed, T2 pooled seed, T2 single seed, and T3 pooled seed, T3 single seed are in Tables 18 to 21. JT1-4 T3 segregant JT-1-4-34-11, had a pooled T3 seed DPA content of 18% and the single seed from this particular segregant had a DPA content of about 26%, each as a percentage of the total fatty acid content.

The following parameters were calculated for oil from a seed having 17.9% DPA: total saturated fatty acids, 6.8%; total monounsaturated fatty acids, 36.7%; total polyunsaturated fatty acids, 56.6%, total ω6 fatty acids, 7.1%; new ω6 fatty acids, 0.4% of which all was GLA; total ω3 fatty acids, 46.5%; new ω3 fatty acids, 24.0%; ratio of total ω6: total ω3 fatty acids, 6.5; ratio of new ω6: new ω3 fatty acids, 60; the efficiency of conversion of oleic acid to LA by Δ12-desaturase, 61%; the efficiency of conversion of ALA to SDA by Δ6-desaturase, 51%; the efficiency of conversion of SDA to ETA acid by Δ6-elongase, 90%; the efficiency of conversion of ETA to EPA by Δ5-desaturase, 87%; the efficiency of conversion of EPA to DPA by Δ5-elongase, 98%.

In order to produce more transgenic plants in *B. juncea* with the modB construct, the transformation was repeated five times and 16 presumed transgenic shoots/seedlings were regenerated. T1 seed analysis is carried out to determine DPA and DHA content.

In order to produce further seed containing DPA and no DHA, a genetic construct which was a variant of the modB construct was made, lacking a Δ4-desaturase gene, as follows. Two DNA fragments, EPA-DPA fragment 1 and EPA-DPA fragment 2, were synthesised (Geneart, Germany) with appropriate restriction sites. An intermediate cloning vector, pJP3660, was generated by cloning the AatII-MluI fragment of EPA-DPA fragment 1 into the AscI-AatII sites in a vector designated 11ABHZHC_GA7-frag_d6D_pMS, a vector earlier used in the construction of GA7-modB which contained a Δ6 desaturase cassette. pJP3661 was then generated by cloning the PmeI-PspOMI fragment of pJP3660 into the PmeI-PspOMI sites of modB. The DPA vector, pJP3662 (FIG. 4), was then assembled by cloning the BsiWI-PspOMI fragment of EPA-DPA fragment 2 into the BsiWI-PspOMI sites of pJP3661. This vector contained the fatty acid biosynthesis genes coding for enzymes which converted oleic acid to DPAco3 and the corresponding ω6 fatty acid. The resultant construct used to transform *B. juncea* and *B. napus*. Progeny seed with up to 35% DPA in the total fatty acid content of the seed lipid are produced.

When the oil extracted from the seeds of a plant producing DHA was examined by NMR, at least 95% of the DHA was observed to be present at the sn-1,3 position of the TAG molecules.

TABLE 17

Fatty acid composition of seedoil from T1 seeds of *B. juncea* transformed with the T-DNA from GA7.

| T1 seed No. | C16:0 | C16:1Δ9 | C18:0 | C18:1 | 18:1Δ11 | C18:2 | C18:3ω6 | C18:3ω3 | C20:0 |
|---|---|---|---|---|---|---|---|---|---|
| JT1-4-A-1 | 5.0 | 0.2 | 2.7 | 23.5 | 3.4 | 17.0 | 0.7 | 24.8 | 0.7 |
| JT1-4-A-2 | 4.3 | 0.3 | 2.6 | 37.2 | 3.2 | 11.0 | 0.3 | 22.1 | 0.7 |
| JT1-4-A-3 | 5.6 | 0.3 | 2.7 | 20.8 | 3.7 | 16.0 | 0.6 | 24.4 | 0.7 |
| JT1-4-A-4 | 4.6 | 0.4 | 2.8 | 36.2 | 3.4 | 10.6 | 0.3 | 24.5 | 0.8 |
| JT1-4-A-5 | 5.0 | 0.2 | 3.2 | 20.3 | 3.6 | 13.7 | 0.7 | 25.9 | 0.7 |
| JT1-4-A-6 | 4.8 | 0.4 | 3.4 | 37.9 | 3.7 | 7.4 | 0.4 | 19.9 | 0.9 |
| JT1-4-A-7 | 5.6 | 0.3 | 3.0 | 26.2 | 4.0 | 8.9 | 0.3 | 26.6 | 0.6 |
| JT1-4-A-8 | 4.8 | 0.4 | 2.9 | 40.3 | 3.4 | 7.8 | 0.3 | 22.2 | 0.8 |
| JT1-4-A-9 | 7.1 | 0.3 | 3.6 | 17.7 | 4.3 | 17.9 | 0.7 | 23.1 | 1.0 |
| JT1-4-A-10 | 5.1 | 0.2 | 4.2 | 22.3 | 3.4 | 19.5 | 0.7 | 21.7 | 0.8 |
| JT1-4-A-11 | 5.0 | 0.5 | 2.8 | 37.6 | 4.0 | 7.1 | 0.4 | 19.2 | 0.7 |
| JT1-4-A-12 | 5.2 | 0.3 | 3.0 | 28.2 | 4.0 | 9.2 | 0.3 | 27.4 | 0.6 |
| JT1-4-A-13 | 5.4 | 0.2 | 3.0 | 16.7 | 4.1 | 9.9 | 0.6 | 29.9 | 0.7 |
| JT1-4-A-14 | 5.1 | 0.4 | 3.1 | 30.0 | 4.0 | 11.5 | 0.3 | 27.7 | 0.7 |
| JT1-4-A-15 | 5.1 | 0.4 | 2.5 | 34.2 | 3.6 | 6.9 | 0.6 | 20.4 | 0.7 |
| JT1-4-B-1 | 5.5 | 0.2 | 2.7 | 18.9 | 4.0 | 17.6 | 0.8 | 24.1 | 0.8 |
| JT1-4-B-2 | 5.5 | 0.2 | 2.7 | 20.2 | 4.0 | 14.3 | 0.5 | 25.5 | 0.7 |
| JT1-4-B-3 | 5.3 | 0.3 | 3.6 | 34.1 | 3.5 | 35.0 | 0.6 | 9.3 | 0.8 |
| JT1-4-B-4 | 5.3 | 0.3 | 3.1 | 25.2 | 3.6 | 17.0 | 0.7 | 24.1 | 0.7 |
| JT1-4-B-5 | 5.5 | 0.5 | 2.2 | 30.1 | 4.6 | 10.2 | 0.5 | 21.7 | 0.6 |
| JT1-4-B-8 | 6.2 | 0.5 | 1.9 | 33.1 | 4.0 | 30.0 | 0.5 | 12.7 | 0.6 |
| JT1-4-B-13 | 5.6 | 0.3 | 2.8 | 20.9 | 3.9 | 11.9 | 0.4 | 27.0 | 0.7 |

| T1 seed No. | C18:4ω3 | 20:1Δ11 | C20:2ω6 | C20:3ω3 | C20:4ω3 | C20:5ω3 | C22:5ω3 | C22:6ω3 |
|---|---|---|---|---|---|---|---|---|
| JT1-4-A-1 | 2.0 | 1.1 | 0.2 | 0.8 | 4.0 | 0.6 | 2.4 | 9.9 |
| JT1-4-A-2 | 0.9 | 1.3 | 0.2 | 1.4 | 3.2 | 0.3 | 9.4 | 0.0 |
| JT1-4-A-3 | 2.0 | 0.9 | 0.2 | 1.1 | 4.5 | 0.7 | 3.1 | 11.4 |
| JT1-4-A-4 | 9.9 | 1.7 | 0.2 | 0.3 | 0.5 | 0.0 | 2.5 | 0.0 |
| JT1-4-A-5 | 2.0 | 0.9 | 0.2 | 1.3 | 4.4 | 1.5 | 1.6 | 13.5 |
| JT1-4-A-6 | 1.4 | 1.4 | 0.1 | 0.8 | 1.9 | 0.4 | 13.9 | 0.0 |
| JT1-4-A-7 | 1.8 | 1.0 | 0.1 | 1.8 | 3.7 | 1.3 | 2.2 | 11.3 |
| JT1-4-A-8 | 1.4 | 1.3 | 0.1 | 0.8 | 2.4 | 0.4 | 9.6 | 0.0 |
| JT1-4-A-9 | 2.1 | 0.8 | 0.2 | 1.5 | 3.6 | 0.8 | 2.0 | 11.9 |
| JT1-4-A-10 | 1.5 | 0.9 | 0.2 | 1.7 | 7.8 | 0.9 | 1.0 | 6.5 |
| JT1-4-A-11 | 1.9 | 1.4 | 0.2 | 0.5 | 1.6 | 0.3 | 15.5 | 0.0 |
| JT1-4-A-12 | 1.9 | 0.9 | 0.1 | 1.5 | 3.2 | 1.1 | 1.8 | 10.2 |
| JT1-4-A-13 | 2.2 | 1.0 | 0.2 | 1.7 | 2.0 | 1.1 | 2.0 | 17.9 |

TABLE 17-continued

Fatty acid composition of seedoil from T1 seeds of *B. juncea* transformed with the T-DNA from GA7.

| | | | | | | | | |
|---|---|---|---|---|---|---|---|---|
| JT1-4-A-14 | 2.2 | 1.0 | 0.1 | 0.6 | 2.4 | 0.8 | 1.3 | 7.8 |
| JT1-4-A-15 | 1.6 | 1.1 | 0.2 | 0.6 | 4.7 | 0.9 | 15.2 | 0.0 |
| JT1-4-B-1 | 2.2 | 1.0 | 0.2 | 1.2 | 4.6 | 0.9 | 2.2 | 11.5 |
| JT1-4-B-2 | 1.7 | 0.9 | 0.2 | 1.6 | 8.7 | 1.3 | 2.2 | 8.5 |
| JT1-4-B-3 | 0.2 | 1.4 | 0.4 | 0.6 | 0.9 | 0.1 | 0.3 | 2.1 |
| JT1-4-B-4 | 1.9 | 1.0 | 0.2 | 0.8 | 4.3 | 0.5 | 2.3 | 7.8 |
| JT1-4-B-5 | 1.4 | 1.1 | 0.2 | 0.9 | 2.4 | 0.5 | 16.1 | 0.0 |
| JT1-4-B-8 | 0.3 | 1.3 | 0.4 | 1.4 | 0.9 | 0.1 | 4.4 | 0.0 |
| JT1-4-B-13 | 2.0 | 1.0 | 0.2 | 1.7 | 2.3 | 0.7 | 4.1 | 13.5 |

The seedoil samples also contained 0.1% C14:0; 0.1-0.2% C16:3; 0.0-0.1% of each of C20:1Δ13, C20:3ω6 and C20:4ω6; 0.3-0.4% C22:0; no C22:1 and C22:2ω6; 0.2% C24:0 and 0.2-0.4% C24:1.

TABLE 18

Fatty acid composition of lipid from T1 seeds (pooled) of *B. juncea* transformed with the T-DNA from GA7-modB. The lipids also contained about 0.1% of each of 14:0, 16:3, 20:1d13, and 16:2, 22:1 were not detected.

| Seed | C16:0 | C16:1 | C18:0 | C18:1 | C18:1Δ11 | C18:2 | C18:3ω6 | C18:3ω3 | C20:0 | C18:4ω3 | C20:1Δ11 | C20:2ω6 | C20:3ω6 |
|---|---|---|---|---|---|---|---|---|---|---|---|---|---|
| JT1-2 | 4.2 | 0.3 | 2.5 | 42.4 | 3.2 | 27.7 | 0.1 | 16.4 | 0.6 | 0.0 | 1.2 | 0.1 | 0.0 |
| JT1-3 | 4.5 | 0.3 | 2.7 | 44.6 | 3.1 | 26.8 | 0.1 | 14.8 | 0.7 | 0.0 | 1.2 | 0.1 | 0.0 |
| JT1-4 | 5.1 | 0.3 | 3.2 | 26.8 | 3.5 | 17.4 | 0.5 | 22.8 | 0.7 | 2.5 | 1.1 | 0.2 | 0.0 |
| JT1-5 | 4.7 | 0.4 | 2.4 | 41.6 | 3.4 | 28.4 | 0.1 | 15.8 | 0.7 | 0.0 | 1.2 | 0.1 | 0.0 |
| JT1-6 | 4.8 | 0.4 | 2.3 | 37.3 | 3.3 | 30.2 | 0.4 | 13.2 | 0.7 | 0.2 | 1.4 | 0.3 | 0.0 |

| Seed | C20:4ω6 | C20:3ω3 | C22:0 | C20:4ω3 | C20:5ω3 | C22:2ω6 | C22:3ω3 | C24:0 | C24:1 | C22:5ω3 | C22:6ω3 |
|---|---|---|---|---|---|---|---|---|---|---|---|
| JT1-2 | 0.0 | 0.0 | 0.3 | 0.0 | 0.0 | 0.0 | 0.0 | 0.2 | 0.4 | 0.0 | 0.0 |
| JT1-3 | 0.0 | 0.0 | 0.3 | 0.0 | 0.0 | 0.0 | 0.0 | 0.2 | 0.4 | 0.0 | 0.0 |
| JT1-4 | 0.0 | 1.2 | 0.3 | 2.9 | 0.7 | 0.0 | 0.1 | 0.2 | 0.3 | 2.8 | 7.2 |
| JT1-5 | 0.0 | 0.0 | 0.3 | 0.0 | 0.0 | 0.0 | 0.0 | 0.2 | 0.4 | 0.0 | 0.0 |
| JT1-6 | 0.0 | 0.7 | 0.3 | 0.6 | 0.1 | 0.0 | 0.3 | 0.2 | 0.5 | 2.6 | 0.0 |

TABLE 19

Fatty acid composition of seed oil from T1(single) seeds of *B. juncea* transformed with the T-DNA from GA7-modB.

| T1 Seed No. | C16:0 | C16:1Δ9 | C18:0 | C18:1 | 18:1Δ11 | C18:2 | C18:3ω6 | C18:3ω3 | C20:0 |
|---|---|---|---|---|---|---|---|---|---|
| JT1-4-A-1 | 5.0 | 0.2 | 2.7 | 23.5 | 3.4 | 17.0 | 0.7 | 24.8 | 0.7 |
| JT1-4-A-2 | 4.3 | 0.3 | 2.6 | 37.2 | 3.2 | 11.0 | 0.3 | 22.1 | 0.7 |
| JT1-4-A-3 | 5.6 | 0.3 | 2.7 | 20.8 | 3.7 | 16.0 | 0.6 | 24.4 | 0.7 |
| JT1-4-A-4 | 4.6 | 0.4 | 2.8 | 36.2 | 3.4 | 10.6 | 0.3 | 24.5 | 0.8 |
| JT1-4-A-5 | 5.0 | 0.2 | 3.2 | 20.3 | 3.6 | 13.7 | 0.7 | 25.9 | 0.7 |
| JT1-4-A-6 | 4.8 | 0.4 | 3.4 | 37.9 | 3.7 | 7.4 | 0.4 | 19.9 | 0.9 |
| JT1-4-A-7 | 5.6 | 0.3 | 3.0 | 26.2 | 4.0 | 8.9 | 0.3 | 26.6 | 0.6 |
| JT1-4-A-8 | 4.8 | 0.4 | 2.9 | 40.3 | 3.4 | 7.8 | 0.3 | 22.2 | 0.8 |
| JT1-4-A-9 | 7.1 | 0.3 | 3.6 | 17.7 | 4.3 | 17.9 | 0.7 | 23.1 | 1.0 |
| JT1-4-A-10 | 5.1 | 0.2 | 4.2 | 22.3 | 3.4 | 19.5 | 0.7 | 21.7 | 0.8 |
| JT1-4-A-11 | 5.0 | 0.5 | 2.8 | 37.6 | 4.0 | 7.1 | 0.4 | 19.2 | 0.7 |
| JT1-4-A-12 | 5.2 | 0.3 | 3.0 | 28.2 | 4.0 | 9.2 | 0.3 | 27.4 | 0.6 |
| JT1-4-A-13 | 5.4 | 0.2 | 3.0 | 16.7 | 4.1 | 9.9 | 0.6 | 29.9 | 0.7 |
| JT1-4-A-14 | 5.1 | 0.4 | 3.1 | 30.0 | 4.0 | 11.5 | 0.3 | 27.7 | 0.7 |
| JT1-4-A-15 | 5.1 | 0.4 | 2.5 | 34.2 | 3.6 | 6.9 | 0.6 | 20.4 | 0.7 |
| JT1-4-B-1 | 5.5 | 0.2 | 2.7 | 18.9 | 4.0 | 17.6 | 0.8 | 24.1 | 0.8 |
| JT1-4-B-2 | 5.5 | 0.2 | 2.7 | 20.2 | 4.0 | 14.3 | 0.5 | 25.5 | 0.7 |
| JT1-4-B-3 | 5.3 | 0.3 | 3.6 | 34.1 | 3.5 | 35.0 | 0.6 | 9.3 | 0.8 |
| JT1-4-B-4 | 5.3 | 0.3 | 3.1 | 25.2 | 3.6 | 17.0 | 0.7 | 24.1 | 0.7 |
| JT1-4-B-5 | 5.5 | 0.5 | 2.2 | 30.1 | 4.6 | 10.2 | 0.5 | 21.7 | 0.6 |
| JT1-4-B-6 | 5.6 | 0.3 | 2.5 | 19.5 | 3.8 | 15.2 | 0.5 | 27.7 | 0.6 |
| JT1-4-B-7 | 5.9 | 0.5 | 2.0 | 29.9 | 4.0 | 11.2 | 0.3 | 26.2 | 0.6 |
| JT1-4-B-8 | 6.2 | 0.5 | 1.9 | 33.1 | 4.0 | 30.0 | 0.5 | 12.7 | 0.6 |
| JT1-4-B-9 | 4.9 | 0.2 | 3.4 | 24.6 | 3.0 | 18.5 | 0.3 | 26.2 | 0.8 |
| JT1-4-B-10 | 5.2 | 0.3 | 2.7 | 19.0 | 4.0 | 12.0 | 0.6 | 30.5 | 0.7 |
| JT1-4-B-11 | 4.8 | 0.2 | 3.0 | 23.7 | 3.1 | 18.1 | 0.6 | 23.5 | 0.7 |
| JT1-4-B-12 | 5.0 | 0.2 | 2.6 | 19.6 | 3.4 | 12.5 | 0.6 | 26.9 | 0.8 |

TABLE 19-continued

Fatty acid composition of seed oil from T1(single) seeds of *B. juncea* transformed with the T-DNA from GA7-modB.

| | | | | | | | | |
|---|---|---|---|---|---|---|---|---|
| JT1-4-B-13 | 5.6 | 0.3 | 2.8 | 20.9 | 3.9 | 11.9 | 0.4 | 27.0 | 0.7 |
| JT1-4-B-14 | 5.1 | 0.3 | 3.1 | 25.5 | 3.3 | 16.7 | 0.7 | 23.9 | 0.8 |
| JT1-4-B-15 | 5.6 | 0.3 | 2.7 | 19.5 | 4.1 | 14.0 | 0.8 | 24.6 | 0.7 |

| T1 Seed No. | C18:4ω3 | 20:1Δ11 | C20:2ω6 | C20:3ω3 | C20:4ω3 | C20:5ω3 | C22:5ω3 | C22:6ω3 |
|---|---|---|---|---|---|---|---|---|
| JT1-4-A-1 | 2.0 | 1.1 | 0.2 | 0.8 | 4.0 | 0.6 | 2.4 | 9.9 |
| JT1-4-A-2 | 0.9 | 1.3 | 0.2 | 1.4 | 3.2 | 0.3 | 9.4 | 0.0 |
| JT1-4-A-3 | 2.0 | 0.9 | 0.2 | 1.1 | 4.5 | 0.7 | 3.1 | 11.4 |
| JT1-4-A-4 | 9.9 | 1.7 | 0.2 | 0.3 | 0.5 | 0.0 | 2.5 | 0.0 |
| JT1-4-A-5 | 2.0 | 0.9 | 0.2 | 1.3 | 4.4 | 1.5 | 1.6 | 13.5 |
| JT1-4-A-6 | 1.4 | 1.4 | 0.1 | 0.8 | 1.9 | 0.4 | 13.9 | 0.0 |
| JT1-4-A-7 | 1.8 | 1.0 | 0.1 | 1.8 | 3.7 | 1.3 | 2.2 | 11.3 |
| JT1-4-A-8 | 1.4 | 1.3 | 0.1 | 0.8 | 2.4 | 0.4 | 9.6 | 0.0 |
| JT1-4-A-9 | 2.1 | 0.8 | 0.2 | 1.5 | 3.6 | 0.8 | 2.0 | 11.9 |
| JT1-4-A-10 | 1.5 | 0.9 | 0.2 | 1.7 | 7.8 | 0.9 | 1.0 | 6.5 |
| JT1-4-A-11 | 1.9 | 1.4 | 0.2 | 0.5 | 1.6 | 0.3 | 15.5 | 0.0 |
| JT1-4-A-12 | 1.9 | 0.9 | 0.1 | 1.5 | 3.2 | 1.1 | 1.8 | 10.2 |
| JT1-4-A-13 | 2.2 | 1.0 | 0.2 | 1.7 | 2.0 | 1.1 | 2.0 | 17.9 |
| JT1-4-A-14 | 2.2 | 1.0 | 0.1 | 0.6 | 2.4 | 0.8 | 1.3 | 7.8 |
| JT1-4-A-15 | 1.6 | 1.1 | 0.2 | 0.6 | 4.7 | 0.9 | 15.2 | 0.0 |
| JT1-4-B-1 | 2.2 | 1.0 | 0.2 | 1.2 | 4.6 | 0.9 | 2.2 | 11.5 |
| JT1-4-B-2 | 1.7 | 0.9 | 0.2 | 1.6 | 8.7 | 1.3 | 2.2 | 8.5 |
| JT1-4-B-3 | 0.2 | 1.4 | 0.4 | 0.6 | 0.9 | 0.1 | 0.3 | 2.1 |
| JT1-4-B-4 | 1.9 | 1.0 | 0.2 | 0.8 | 4.3 | 0.5 | 2.3 | 7.8 |
| JT1-4-B-5 | 1.4 | 1.1 | 0.2 | 0.9 | 2.4 | 0.5 | 16.1 | 0.0 |
| JT1-4-B-6 | 2.1 | 0.9 | 0.2 | 1.1 | 3.7 | 0.6 | 3.3 | 11.1 |
| JT1-4-B-7 | 11.5 | 1.4 | 0.2 | 0.3 | 0.4 | 0.0 | 4.1 | 0.1 |
| JT1-4-B-8 | 0.3 | 1.3 | 0.4 | 1.4 | 0.9 | 0.1 | 4.4 | 0.0 |
| JT1-4-B-9 | 1.3 | 1.1 | 0.2 | 2.0 | 5.5 | 0.6 | 0.8 | 5.2 |
| JT1-4-B-10 | 1.6 | 1.0 | 0.2 | 1.7 | 4.9 | 1.1 | 3.0 | 10.2 |
| JT1-4-B-11 | 1.6 | 1.2 | 0.2 | 1.5 | 4.5 | 0.8 | 1.6 | 9.6 |
| JT1-4-B-12 | 3.1 | 1.1 | 0.2 | 0.9 | 5.6 | 0.9 | 3.5 | 11.7 |
| JT1-4-B-13 | 2.0 | 1.0 | 0.2 | 1.7 | 2.3 | 0.7 | 4.1 | 13.5 |
| JT1-4-B-14 | 1.8 | 1.2 | 0.2 | 0.9 | 2.6 | 0.4 | 2.9 | 9.2 |
| JT1-4-B-15 | 2.7 | 0.9 | 0.2 | 0.7 | 9.4 | 1.3 | 2.5 | 8.5 |

The seed oil samples also contained 0.1% C14:0; 0.1-0.2% C16:3; 0.0-0.1% of each of C20:1Δ13, C20:3ω6 and C20:4ω6; 0.3-0.4% C22:0; no C22:1 and C22:2ω6; 0.2% C24:0 and 0.2-0.4% C24:1.

TABLE 20

Fatty acid composition of seed oil from T2 single seeds of *B. juncea* transformed with the T-DNA from GA7-modB. The lipids also contained 0.1-0.2% C16:1Δ9, C16:3 and C20:2ω6, 0.5-0.6% C20:0, no C20:3ω6, C20:4ω6 and C22:2ω6

| Seed No. | C16:0 | C18:0 | C18:1 | C18:1Δ11 | C18:2 | C18:3ω6 | C18:3ω3 | C18:4 | C20:1Δ11 | C20:3ω3 | C22:0 |
|---|---|---|---|---|---|---|---|---|---|---|---|
| 1 | 4.4 | 1.7 | 36.3 | 2.9 | 8.3 | 0.5 | 22.0 | 1.4 | 1.2 | 0.4 | 0.3 |
| 2 | 5.6 | 1.9 | 39.1 | 3.1 | 8.4 | 0.4 | 18.9 | 1.2 | 1.3 | 0.5 | 0.3 |
| 3 | 5.5 | 1.8 | 42.3 | 3.2 | 9.9 | 0.3 | 24.0 | 5.9 | 1.5 | 0.2 | 0.4 |
| 4 | 5.6 | 1.5 | 36.8 | 3.7 | 9.4 | 0.3 | 19.6 | 0.6 | 1.4 | 1.4 | 0.3 |
| 5 | 4.6 | 1.7 | 36.3 | 2.7 | 7.2 | 0.3 | 22.6 | 1.0 | 1.5 | 0.7 | 0.3 |
| 6 | 4.9 | 1.8 | 38.3 | 3.1 | 7.4 | 0.3 | 20.2 | 0.8 | 1.3 | 0.8 | 0.3 |
| 7 | 4.7 | 1.7 | 36.2 | 3.0 | 8.2 | 0.4 | 20.9 | 0.7 | 1.3 | 0.9 | 0.3 |
| 8 | 4.8 | 2.2 | 41.0 | 3.0 | 9.8 | 0.2 | 27.0 | 4.2 | 1.8 | 0.3 | 0.3 |
| 9 | 5.8 | 1.7 | 36.6 | 3.7 | 9.1 | 0.3 | 21.3 | 0.9 | 1.4 | 0.8 | 0.3 |
| 10 | 4.8 | 2.1 | 47.1 | 2.9 | 7.4 | 0.2 | 23.9 | 4.8 | 1.7 | 0.2 | 0.3 |
| 11 | 5.1 | 1.7 | 37.4 | 3.3 | 7.7 | 0.3 | 20.7 | 0.9 | 1.4 | 0.8 | 0.3 |
| 12 | 4.7 | 1.8 | 37.3 | 2.7 | 7.9 | 0.4 | 20.6 | 1.1 | 1.3 | 0.5 | 0.3 |
| 13 | 4.9 | 2.0 | 37.9 | 3.0 | 7.1 | 0.4 | 20.1 | 1.1 | 1.3 | 0.6 | 0.3 |
| 14 | 4.7 | 1.6 | 35.7 | 3.2 | 6.9 | 0.3 | 22.4 | 0.7 | 1.4 | 1.3 | 0.3 |
| 15 | 4.7 | 1.8 | 37.6 | 3.4 | 7.8 | 0.3 | 23.7 | 0.6 | 1.5 | 1.2 | 0.2 |
| 16 | 5.3 | 1.6 | 35.3 | 3.5 | 8.1 | 0.5 | 21.1 | 0.8 | 1.2 | 0.7 | 0.3 |
| 17 | 4.9 | 1.7 | 39.4 | 3.3 | 7.7 | 0.3 | 21.1 | 0.7 | 1.4 | 0.8 | 0.3 |
| 18 | 5.0 | 1.8 | 38.5 | 3.1 | 7.8 | 0.4 | 20.5 | 0.8 | 1.3 | 0.8 | 0.2 |
| 19 | 5.1 | 1.8 | 39.5 | 2.9 | 9.0 | 0.2 | 22.2 | 0.6 | 1.5 | 1.0 | 0.3 |
| 20 | 4.8 | 1.8 | 38.2 | 3.2 | 7.8 | 0.4 | 21.1 | 0.7 | 1.4 | 0.7 | 0.3 |
| 21 | 5.0 | 2.0 | 39.7 | 2.9 | 7.9 | 0.4 | 20.2 | 0.7 | 1.3 | 0.7 | 0.3 |

TABLE 20-continued

Fatty acid composition of seed oil from T2 single seeds of *B. juncea* transformed with the T-DNA from GA7-modB. The lipids also contained 0.1-0.2% C16:1Δ9, C16:3 and C20:2ω6, 0.5-0.6% C20:0, no C20:3ω6, C20:4ω6 and C22:2ω6

| | | | | | | | | | | | |
|---|---|---|---|---|---|---|---|---|---|---|---|
| 22 | 4.7 | 1.6 | 36.0 | 3.3 | 8.3 | 0.3 | 23.7 | 0.6 | 1.5 | 1.2 | 0.3 |
| 23 | 6.2 | 2.1 | 32.0 | 4.4 | 7.2 | 0.6 | 19.4 | 1.2 | 1.2 | 0.6 | 0.4 |

| Seed No. | C20:4ω3 | C20:5ω3 | C22:3ω3 | C24:0 | C22:5ω6 | C22:4ω3 | C24:1 | 22:5ω3 | C22:6ω3 |
|---|---|---|---|---|---|---|---|---|---|
| 1 | 4.2 | 0.6 | 0.1 | 0.1 | 0.0 | 1.8 | 0.3 | 12.1 | 0.0 |
| 2 | 2.5 | 0.4 | 0.1 | 0.2 | 0.0 | 1.5 | 0.4 | 12.6 | 0.0 |
| 3 | 0.5 | 0.0 | 0.0 | 0.2 | 0.0 | 0.4 | 0.4 | 1.5 | 0.0 |
| 4 | 1.9 | 0.3 | 0.2 | 0.2 | 0.0 | 1.6 | 0.4 | 13.1 | 0.0 |
| 5 | 2.1 | 0.3 | 0.1 | 0.2 | 0.0 | 2.2 | 0.3 | 14.4 | 0.0 |
| 6 | 2.7 | 0.5 | 0.2 | 0.2 | 0.0 | 1.7 | 0.3 | 13.7 | 0.0 |
| 7 | 2.9 | 0.5 | 0.2 | 0.2 | 0.0 | 2.0 | 0.3 | 14.2 | 0.0 |
| 8 | 0.5 | 0.0 | 0.1 | 0.2 | 0.0 | 0.7 | 0.3 | 2.2 | 0.0 |
| 9 | 1.5 | 0.3 | 0.1 | 0.2 | 0.0 | 1.2 | 0.4 | 12.7 | 0.0 |
| 10 | 0.5 | 0.0 | 0.0 | 0.2 | 0.0 | 0.5 | 0.3 | 1.5 | 0.0 |
| 11 | 2.5 | 0.4 | 0.1 | 0.2 | 0.0 | 1.6 | 0.4 | 13.6 | 0.0 |
| 12 | 4.3 | 0.6 | 0.1 | 0.1 | 0.0 | 2.2 | 0.3 | 12.3 | 0.0 |
| 13 | 4.1 | 0.5 | 0.1 | 0.1 | 0.0 | 2.1 | 0.3 | 12.6 | 0.0 |
| 14 | 3.0 | 0.5 | 0.2 | 0.1 | 0.0 | 1.9 | 0.3 | 14.0 | 0.0 |
| 15 | 1.7 | 0.3 | 0.2 | 0.1 | 0.0 | 1.8 | 0.3 | 11.4 | 0.0 |
| 16 | 3.1 | 0.5 | 0.2 | 0.1 | 0.0 | 1.9 | 0.3 | 13.9 | 0.0 |
| 17 | 2.0 | 0.3 | 0.2 | 0.1 | 0.0 | 1.7 | 0.3 | 12.3 | 0.0 |
| 18 | 2.3 | 0.3 | 0.2 | 0.1 | 0.0 | 2.0 | 0.3 | 13.1 | 0.0 |
| 19 | 1.7 | 0.2 | 0.1 | 0.2 | 0.0 | 1.6 | 0.3 | 10.2 | 0.0 |
| 20 | 2.1 | 0.4 | 0.2 | 0.1 | 0.0 | 1.7 | 0.3 | 13.3 | 0.0 |
| 21 | 2.3 | 0.3 | 0.2 | 0.1 | 0.0 | 1.9 | 0.3 | 12.2 | 0.0 |
| 22 | 1.7 | 0.3 | 0.2 | 0.1 | 0.0 | 1.8 | 0.3 | 12.7 | 0.0 |
| 23 | 2.2 | 0.5 | 0.3 | 0.2 | 0.0 | 1.6 | 0.4 | 17.6 | 0.0 |

TABLE 21

Fatty acid composition of seed oil from T3 single seeds of *B. juncea* transformed with the T-DNA from GA7-modB. The seeds also contained 0.1-0.2% of each of C16:3, C20:1Δ13, C20:2ω6. No C20:3ω6, C20:4ω6, C22:2ω6, C22:5ω6 and C22:6ω3 were detected.

| Seed | C16:0 | C16:1Δ9 | C18:0 | C18:1 | C18:1Δ11 | C18:2 | C18:3ω6 | C18:3ω3 | C20:0 | C18:4 | C20:1Δ11 |
|---|---|---|---|---|---|---|---|---|---|---|---|
| 1 | 4.8 | 0.4 | 2.8 | 38.4 | 3.7 | 5.7 | 0.4 | 18.0 | 0.7 | 1.0 | 1.5 |
| 2 | 4.3 | 0.4 | 3.0 | 43.3 | 3.6 | 5.2 | 0.2 | 18.5 | 0.7 | 0.8 | 1.7 |
| 3 | 4.6 | 0.4 | 2.8 | 33.1 | 4.1 | 5.1 | 0.4 | 18.5 | 0.7 | 1.2 | 1.4 |
| 4 | 4.5 | 0.4 | 2.9 | 39.5 | 3.3 | 6.3 | 0.4 | 18.5 | 0.8 | 1.2 | 1.5 |
| 5 | 4.9 | 0.5 | 2.8 | 32.2 | 3.9 | 4.7 | 0.3 | 20.7 | 0.8 | 1.2 | 1.4 |
| 6 | 4.3 | 0.3 | 3.0 | 38.1 | 3.2 | 5.8 | 0.3 | 19.4 | 0.7 | 1.1 | 1.5 |
| 7 | 5.4 | 0.5 | 3.2 | 29.3 | 4.0 | 4.6 | 0.4 | 18.6 | 0.9 | 1.7 | 1.3 |
| 8 | 5.2 | 0.5 | 3.7 | 34.5 | 4.1 | 4.5 | 0.3 | 17.2 | 1.0 | 1.4 | 1.4 |
| 9 | 5.3 | 0.5 | 3.4 | 33.4 | 3.7 | 4.6 | 0.3 | 17.6 | 0.9 | 1.7 | 1.2 |
| 10 | 4.6 | 0.4 | 3.0 | 39.5 | 3.5 | 5.1 | 0.3 | 17.8 | 0.8 | 0.8 | 1.6 |
| 11 | 4.3 | 0.4 | 3.1 | 41.7 | 3.5 | 5.6 | 0.2 | 19.0 | 0.7 | 0.9 | 1.6 |
| 12 | 4.8 | 0.5 | 2.8 | 33.8 | 4.0 | 5.3 | 0.4 | 18.2 | 0.7 | 1.4 | 1.3 |
| 13 | 4.4 | 0.4 | 3.5 | 40.3 | 3.5 | 5.2 | 0.2 | 19.1 | 0.7 | 1.0 | 1.5 |
| 14 | 4.8 | 0.4 | 3.2 | 36.1 | 3.7 | 5.9 | 0.3 | 19.9 | 0.7 | 1.4 | 1.3 |
| 15 | 4.0 | 0.3 | 2.8 | 37.2 | 3.2 | 4.9 | 0.3 | 19.6 | 0.8 | 0.9 | 1.6 |
| 16 | 4.5 | 0.4 | 3.8 | 36.7 | 3.2 | 4.5 | 0.2 | 19.0 | 0.9 | 1.1 | 1.4 |
| 17 | 5.2 | 0.4 | 2.8 | 27.8 | 3.7 | 5.3 | 0.5 | 18.3 | 0.8 | 1.7 | 1.3 |
| 18 | 5.4 | 0.6 | 2.8 | 31.7 | 4.1 | 4.6 | 0.3 | 18.5 | 0.8 | 1.3 | 1.3 |
| 19 | 6.4 | 0.6 | 2.7 | 30.3 | 3.5 | 4.1 | 0.4 | 16.1 | 0.8 | 2.1 | 1.1 |
| 20 | 4.3 | 0.3 | 3.2 | 39.2 | 3.3 | 5.7 | 0.2 | 20.1 | 0.7 | 0.9 | 1.6 |

| Seed | C20:3ω3 | C22:0 | C20:4ω3 | C20:5ω3 | C22:3ω3 | C22:4ω3 | C24:1 | C22:5ω3 |
|---|---|---|---|---|---|---|---|---|
| 1 | 1.1 | 0.3 | 1.4 | 0.4 | 0.3 | 1.4 | 0.5 | 16.3 |
| 2 | 1.4 | 0.3 | 1.2 | 0.3 | 0.2 | 1.2 | 0.3 | 12.4 |
| 3 | 1.1 | 0.3 | 1.6 | 0.5 | 0.3 | 1.4 | 0.4 | 20.8 |
| 4 | 1.0 | 0.3 | 1.7 | 0.3 | 0.2 | 1.8 | 0.3 | 14.2 |
| 5 | 2.0 | 0.3 | 1.4 | 0.5 | 0.3 | 1.2 | 0.4 | 19.4 |
| 6 | 1.2 | 0.3 | 1.5 | 0.4 | 0.2 | 1.3 | 0.4 | 16.0 |
| 7 | 1.2 | 0.4 | 1.6 | 0.7 | 0.3 | 1.4 | 0.5 | 22.9 |
| 8 | 1.5 | 0.4 | 1.4 | 0.6 | 0.3 | 1.2 | 0.5 | 19.4 |
| 9 | 1.1 | 0.4 | 1.5 | 0.6 | 0.2 | 1.2 | 0.5 | 20.7 |
| 10 | 1.4 | 0.4 | 1.3 | 0.4 | 0.3 | 1.3 | 0.4 | 16.1 |
| 11 | 1.3 | 0.3 | 1.4 | 0.3 | 0.2 | 1.5 | 0.3 | 12.7 |
| 12 | 1.2 | 0.3 | 1.6 | 0.6 | 0.3 | 1.3 | 0.4 | 20.1 |
| 13 | 1.6 | 0.3 | 1.4 | 0.4 | 0.2 | 1.4 | 0.3 | 13.8 |

TABLE 21-continued

Fatty acid composition of seed oil from T3 single seeds of *B. juncea* transformed with the T-DNA from GA7-modB. The seeds also contained 0.1-0.2% of each of C16:3, C20:1Δ13, C20:2ω6. No C20:3ω6, C20:4ω6, C22:2ω6, C22:5ω6 and C22:6ω3 were detected.

| | | | | | | | | |
|---|---|---|---|---|---|---|---|---|
| 14 | 1.1 | 0.3 | 1.9 | 0.5 | 0.2 | 1.7 | 0.3 | 15.4 |
| 15 | 1.5 | 0.4 | 1.3 | 0.5 | 0.3 | 1.1 | 0.4 | 17.9 |
| 16 | 1.8 | 0.4 | 1.2 | 0.5 | 0.2 | 1.0 | 0.5 | 17.8 |
| 17 | 1.0 | 0.4 | 1.9 | 0.7 | 0.3 | 1.7 | 0.5 | 24.7 |
| 18 | 1.4 | 0.4 | 1.4 | 0.6 | 0.2 | 1.3 | 0.4 | 21.8 |
| 19 | 0.9 | 0.4 | 1.4 | 0.7 | 0.2 | 1.1 | 0.5 | 25.8 |
| 20 | 1.7 | 0.3 | 1.3 | 0.3 | 0.2 | 1.3 | 0.3 | 14.1 |

Example 9. Further Analysis of Transformed Plants and Field Trials

Southern blot hybridisation analysis was carried out on selected T2 *B. napus* plants transformed with the T-DNA from the GA7-modB construct. DNA extracted from samples of plant tissue were digested with several restriction enzymes for the Southern blot hybridisation analysis. A radioactive probe corresponding to part of the T-DNA was hybridised to the blots, which were washed under stringent conditions, and the blots exposed to film to detect hybridising bands. Some of the samples exhibited single hybridising bands for each of the restriction digests, corresponding to single T-DNA insertions in the plants, while others showed two bands and others again showed multiple T-DNA bands, corresponding to 4 to 6 insertions. The number of hybridising bands observed by Southern Blot analysis correlated well with the T-DNA copy number in the transgenic plants as determined by the digital PCR method, up to a copy number of about 3 or 4. At higher copy numbers than about 5, the digital PCR method was less reliable.

Some of the selected lines were used as pollen donors in crosses with a series of about 30 different *B. napus* varieities of different genetic backgrounds. Further back-crosses are carried out to demonstrate whether the multiple T-DNA insertions are genetic linked or not, and allowing segregation of genetically-unlinked transgenic loci. Thereby, lines containing single transgenic loci are selected.

Single-primer PCR reactions are carried out on the transgenic lines, using primers adjacent to the left- and right-borders of the T-DNA, and any lines that show the presence of inverted repeats of the T-DNAs are discarded.

Several of the transgenic lines showed delayed flowering, while others had reduced seed-set and therefore reduced seed yield per plant after growth in the glasshouse, consistent with a reduced male or female fertility. Flower morphology was examined in these plants and it was observed that in some cases, dehiscence and release of pollen from the anthers was delayed so that styles had elongated before dehiscence occurred, thereby distancing the anthers from the stigmas. Full fertility could be restored by artificial pollination. Furthermore, pollen viability at dehiscence was determined by staining with the vital stains FDA and PI (Example 1) and was shown to be reduced in some of the lines, whereas in most of the transgenic lines, pollen viability was about 100% as in the wild-type controls. As a further test for a possible cause of the reduced seed yield in some plants, the fatty acid content and composition of flower buds including the anthers and stigmas/styles of some T3 and T4 plants was tested. No DHA was detected in the extracted lipids, indicating that the genes in the genetic construct were not expressed in the flower buds during plant development, and ruling this out as a cause of the reduced seed yield.

The oil content was measured by NMR and the DHA level in the total fatty acid content was determined for T2 seeds. Trangenic lines having less than 6% DHA were discarded. T-DNA copy number in leaf samples from plants of the T1, T2 and T3 generations were determined by the digital PCR method (Example 1).

Selected T3 and T4 seed lots were sown in the field at two sites in Victoria, Australia, each in 10 m rows at a sowing density of about 10 seeds/m. The selected seed lots included a B003-5-14 derived line which showed pooled seed DHA levels of about 8-11% and individual T2 seed DHA levels of up to about 19%, with a T0 plant T-DNA copy number of 3. The selected seed lots also included B0050-27 derived lines which had shown T2 seed DHA levels in excess of 20%, and a T2 plant T-DNA copy number of 1 or 2. Seeds sown in the field germinated and plantlets emerged at the same rate as the wild-type seeds. Plants grown from most, but not all, of the sown seed lots were phenotypically normal, for example had morphology, growth rate, plant height, male and female fertility, pollen viability (100%), seed set, silique size and morphology that was essentially the same as the wild-type control plants grown under the same conditions. Seed yield per plant was similar to that of wild-type controls grown under the same conditions. Other seed samples were sown in larger areas to bulk-up the selected transgenic lines. The total DHA content in harvested seeds was at least 30 mg/g seed.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abbadi et al. (2004) Plant Cell 16: 2734-2748.
Abbott et al. (1998) Science 282:2012-2018.
Agaba et al. (2004) Marine Biotechnol. (NY) 6:251-261.
Alvarez et al. (2000) Theor Appl Genet 100:319-327.
Armbrust et al. (2004) Science 306:79-86.
Baumlein et al. (1991) Mol. Gen. Genet. 225:459-467.
Baumlein et al. (1992) Plant J. 2:233-239.
Beaudoin et al. (2000) Proc. Natl. Acad. Sci. U.S.A. 97:6421-6426.
Belide et al. (2013) Plant Cell Tiss Organ Cult. 113:543-553.

Berberich. et al. (1998) Plant Mol. Biol. 36:297-306.
Broun et al. (1998) Plant J. 13:201-210.
Brown et al. (2002) Biochem J. 364:795-805.
Chan et al. (2006) Nature Biotechnology 28:951-956.
Chapman et al. (2004) Gen. Dev. 18:1179-1186.
Chen et al. (2004) The Plant Cell 16:1302-1313.
Cheng et al. (1996) Plant Cell Rep. 15:653-657.
Cheng et al. (2010) Transgenic Res 19: 221-229.
Cho et al. (1999a) J. Biol. Chem. 274:471-477.
Cho et al. (1999b) J. Biol. Chem. 274:37335-37339.
Christie (1982) J. Lipid Res. 23:1072-1075.
Damude et al. (2006). Proc Natl Acad Sci USA 103: 9446-9451.
Denic and Weissman (2007) Cell 130:663-677.
Domergue et al. (2002) Eur. J. Biochem. 269:4105-4113.
Domergue et al. (2003) J. Biol. Chem. 278: 35115-35126.
Domergue et al. (2005) Biochem. J. 1 389: 483-490.
Dunoyer et al. (2004) The Plant Cell 16:1235-1250.
Ellerstrom et al. (1996) Plant Mol. Biol. 32:1019-1027.
Gamez et al. (2003) Food Res International 36: 721-727.
Garcia-Maroto et al. (2002) Lipids 37:417-426.
Girke et al. (1998) Plant J. 15:39-48.
Harayama (1998). Trends Biotechnol. 16: 76-82.
Hastings et al. (2001) Proc. Natl. Acad. Sci. U.S.A. 98:14304-14309.
Hinchee et al. (1988) Biotechnology 6:915-922.
Hoffmann et al. (2008) J Biol. Chem. 283:22352-22362.
Hong et al. (2002a) Lipids 37:863-868.
Horiguchi et al. (1998) Plant Cell Physiol. 39:540-544.
Huang et al. (1999) Lipids 34:649-659.
Inagaki et al. (2002) Biosci. Biotechnol. Biochem. 66:613-621.
Kajikawa et al. (2004) Plant Mol. Biol. 54:335-52.
Kajikawa et al. (2006) FEBS Lett 580:149-154.
Kereszt et al. (2007) Nature Protoc 2:948-952.
Kim et al. (2005) Plant Cell. 2005 1073-89.
Knutzon et al. (1998) J. Biol Chem. 273:29360-6.
Koletzko et al. (1988) Am. J. Clin. Nutr. 47:954-959.
Koziel et al. (1996) Plant Mol. Biol. 32:393-405.
Lassner (1995) Plant Physiol. 109:1389-94.
Leonard et al. (2000) Biochem. J. 347:719-724.
Leonard et al. (2000b) Biochem. J. 350:765-770.
Leonard et al. (2002) Lipids 37:733-740.
Lewsey et al. (2007) Plant J. 50:240-252.
Lo et al. (2003) Genome Res. 13:455-466.
Lu and Kang (2008) Plant Cell Rep. 27:273-8.
Mallory et al. (2002) Nat. Biotech. 20:622-625.
Marangoni et al. (1995) Trends in Food Sci. Technol. 6: 329-335.
Meesapyodsuk et al. (2007) J Biol Chem 282: 20191-20199.
Meng et al. (2008) J. Gen. Virol. 89:2349-2358.
Meyer et al. (2003) Biochem. 42:9779-9788.
Meyer et al. (2004) Lipid Res 45:1899-1909.
Michaelson et al. (1998a) J. Biol. Chem. 273:19055-19059.
Michaelson et al. (1998b) FEBS Lett. 439:215-218.
Murashige and Skoog (1962) Physiologia Plantarum 15:473-497.
Napier et al. (1998) Biochem. J. 330:611-614.
Needleman and Wunsch (1970) J. Mol. Biol. 48:443-453.
Parker-Barnes et al. (2000) Proc. Natl. Acad. Sci. USA 97:8284-8289.
Pereira et al. (2004a) Biochem. J. 378:665-671.
Pereira et al. (2004b) Biochem. J. 384:357-366.
Perrin et al. (2000) Mol Breed 6:345-352.
Petrie et al. (2010a) Metab. Eng. 12:233-240.
Petrie et al. (2010b) Plant Methods 11:6:8.
Petrie et al. (2012) Transgenic Res. 21:139-147.
Potenza et al. (2004) In Vitro Cell Dev Biol-Plant 40:1-22.
Qi et al. (2002) FEBS Lett. 510:159-165.
Qi et al. (2004) Nat. Biotech. 22: 739-745.
Qiu et al. (2001) J. Biol. Chem. 276:31561-31566.
Reddy and Thomas (1996) Nat. Biotech. 14:639-642.
Reddy et al. (1993) Plant Mol. Biol. 22:293-300.
Robert et al. (2005) Func. Plant Biol. 32:473-479.
Robert et al. (2009) Marine Biotech 11:410-418.
Ruiz-Lopez et al. (2012) Transgenic Res. 21:139-147.
Saha et al. (2006) Plant Physiol. 141:1533-1543.
Saito et al. (2000) Eur. J. Biochem. 267:1813-1818.
Sakuradani et al. (1999) Gene 238:445-453.
Sato et al. (2004) Crop Sci. 44: 646-652.
Sakuradani et al. (2005) Appl. Microbiol. Biotechnol. 66:648-654.
Sayanova et al. (2006) J Biol Chem 281: 36533-36541.
Sayanova et al. (1997) Proc. Natl. Acad. Sci. U.S.A. 94:4211-4216.
Sayanova et al. (2003) FEBS Lett. 542:100-104.
Sayanova et al. (2006) Planta 224:1269-1277.
Sayanova et al. (2007) Plant Physiol 144:455-467.
Shukla et al. (2002) J. Amer. Oil Chem. Soc. 79:965-969.
Singh et al. (2005) Curr. Opin. in Plant Biol. 8:197-203.
Speranza et al. (2012) Process Biochemistry (In Press).
Sperling et al. (2000) Eur. J. Biochem. 267:3801-3811.
Sperling et al. (2001) Arch. Biochm. Biophys. 388:293-8.
Sprecher et al. (1995) J. Lipid Res. 36:2471-2477.
Spychalla et al. (1997) Proc. Natl. Acad. Sci. U.S.A. 94:1142-1147.
Tonon et al. (2003) FEBS Lett. 553:440-444.
Trautwein (2001) European J. Lipid Sci. and Tech. 103:45-55.
Tvrdik (2000) J. Cell Biol. 149:707-718.
Venegas-Caleron et al. (2010) Prog. Lipid Res. 49:108-119.
Voinnet et al. (2003) Plant J. 33:949-956.
Wallis and Browse (1999) Arch. Biochem. Biophys. 365: 307-316.
Watts and Browse (1999b) Arch. Biochem. Biophys. 362: 175-182.
Weiss et al. (2003) Int. J. Med. Microbiol. 293:95:106.
Weng et al., (2004) Plant Molecular Biology Reporter 22:289-300.
Whitney et al. (2003) Planta 217:983-992.
Wood (2009) Plant Biotechnol J. 7:914-24.
Wu et al. (2005) Nat. Biotech. 23:1013-1017.
Yang et al. (2003) Planta 216:597-603.
Zank et al. (2002) Plant J. 31:255-268.
Zank et al. (2005) WO 2005/012316
Zhang et al. (2004) FEBS Lett. 556:81-85.
Zhang et al. (2006) 20:3255-3268.
Zhang et al. (2007) FEBS Letters 581: 315-319.
Zhang et al. (2008) Yeast 25: 21-27.
Zhou et al. (2007) Phytochem. 68:785-796.
Zhou et al. (2008) Insect Mol Biol 17: 667-676.
Zou et al. (1997) Plant Cell. 9:909-23.

The invention claimed is:

1. *Brassica napus* seedoil, comprising fatty acids in an esterified form, the fatty acids comprising oleic acid, palmitic acid, ω6 polyunsaturated fatty acids which comprise linoleic acid (LA), ω3 polyunsaturated fatty acids which comprise α-linolenic acid (ALA), eicosapentaenoic acid (EPA), docosapentaenoic acid (DPA), docosahexaenoic acid (DHA), stearidonic acid (SDA) and eicosatetraenoic acid (ETA), wherein the level of palmitic acid in the total fatty acid content of the seedoil is between 2% and 16% by weight, wherein myristic acid (C14:0) is either absent or is present in the seedoil at a level of less than 1% by weight of the total fatty acid content of the seedoil, and wherein the level of EPA in the total fatty acid content of the seedoil is between 4% and 15% by weight.

2. The seedoil of claim 1, wherein a level of γ-linolenic acid (GLA) of less than 4% by weight is present in the total fatty acid content of the seedoil.

3. The seedoil of claim 2, wherein at least 70% of the DPA esterified in the form of triacylglycerols (TAG) in the seedoil is in the sn-1 or sn-3 position of the TAG.

4. The seedoil of claim 2, wherein at least 80% of the DPA esterified in the form of TAG in the seedoil is in the sn-1 or sn-3 position of the TAG.

5. The seedoil of claim 2, wherein the level of docosahexaenoic acid (DHA) in the total fatty acid content of the seedoil is less than 0.5% by weight.

6. The seedoil of claim 2, wherein the level of docosahexaenoic acid (DHA) in the total fatty acid content of the seedoil is less than 2% by weight.

7. The seedoil of claim 2, wherein the level of docosahexaenoic acid (DHA) in the total fatty acid content of the seedoil is between 0.5% and 2.0% by weight.

8. The seedoil of claim 7, wherein at least 70% of the DHA esterified in the form of triacylglycerols (TAG) in the seedoil is in the sn-1 or sn-3 position of the TAG.

9. The seedoil of claim 2, wherein the level of docosapentaenoic acid (DPA) in the total fatty acid content of the seedoil is between 0.05% and 8% by weight.

10. The seedoil of claim 9, wherein at least 70% of the DPA esterified in the form of triacylglycerols (TAG) in the seedoil is in the sn-1 or sn-3 position of the TAG.

11. The seedoil of claim 3, which has the following features i) the level of oleic acid in the total fatty acid content of the seedoil is between 1% and 60% by weight, ii) the level of linoleic acid (LA) in the total fatty acid content of the seedoil is between 4% and 35% by weight, iii) a level of γ-linolenic acid (GLA) of less than 4% by weight is present in the total fatty acid content of the seedoil, and iv) a level of total saturated fatty acids of between 4% and 25% by weight is present in the total fatty acid content of the seedoil.

12. The seedoil of claim 10, wherein the level of docosahexaenoic acid (DHA) in the total fatty acid content of the seedoil is between 0.5% and 2.0% by weight.

13. *Brassica napus* seedoil, comprising fatty acids in an esterified form, the fatty acids comprising oleic acid, palmitic acid, ω6 polyunsaturated fatty acids which comprise linoleic acid (LA), ω3 polyunsaturated fatty acids which comprise α-linolenic acid (ALA), eicosapentaenoic acid (EPA), docosapentaenoic acid (DPA), docosahexaenoic acid (DHA), stearidonic acid (SDA) and eicosatetraenoic acid (ETA), wherein the level of palmitic acid in the total fatty acid content of the seedoil is between 2% and 16% by weight, wherein the level of myristic acid (C14:0) is either absent or is present in the seedoil at a level of less than 1% by weight of the total fatty acid content of the seedoil, and wherein the level of DPA in the total fatty acid content of the seedoil is greater than the level of DHA.

14. The seedoil of claim 13, wherein the level of DPA in the total fatty acid content of the seedoil is about 2.5% by weight.

15. The seedoil of claim 13, wherein the level of DPA in the total fatty acid content of the seedoil is about 3.9% by weight and the level of DHA is about 1.2% by weight.

16. The seedoil of claim 13, wherein the level of DPA in the total fatty acid content of the seedoil is about 3.0% by weight and the level of DHA is about 0.8% by weight.

17. The seedoil of claim 13, wherein a level of γ-linolenic acid (GLA) of less than 4% by weight is present in the total fatty acid content of the seedoil.

18. The seedoil of claim 17, wherein at least 70% of the DPA esterified in the form of triacylglycerols (TAG) in the seedoil is in the sn-1 or sn-3 position of the TAG.

19. The seedoil of claim 17, wherein at least 80% of the DPA esterified in the form of TAG in the seedoil is in the sn-1 or sn-3 position of the TAG.

20. The seedoil of claim 17, wherein the level of docosahexaenoic acid (DHA) in the total fatty acid content of the seedoil is less than 0.5% by weight.

21. The seedoil of claim 17, wherein the level of docosahexaenoic acid (DHA) in the total fatty acid content of the seedoil is less than 2% by weight.

22. The seedoil of claim 17, wherein the level of docosahexaenoic acid (DHA) in the total fatty acid content of the seedoil is between 0.5% and 2.0% by weight.

23. The seedoil of claim 22, wherein at least 70% of the DHA esterified in the form of triacylglycerols (TAG) in the seedoil is in the sn-1 or sn-3 position of the TAG.

24. The seedoil of claim 17, wherein the level of docosapentaenoic acid (DPA) in the total fatty acid content of the seedoil is between 0.05% and 8% by weight.

25. The seedoil of claim 24, wherein at least 70% of the DPA esterified in the form of triacylglycerols (TAG) in the seedoil is in the sn-1 or sn-3 position of the TAG.

26. The seedoil of claim 18, which has the following features i) the level of oleic acid in the total fatty acid content of the seedoil is between 1% and 60% by weight, ii) the level of linoleic acid (LA) in the total fatty acid content of the seedoil is between 4% and 35% by weight, iii) a level of γ-linolenic acid (GLA) of less than 4% by weight is present in the total fatty acid content of the seedoil, and iv) a level of total saturated fatty acids of between 4% and 25% by weight is present in the total fatty acid content of the seedoil.

27. The seedoil of claim 25, wherein the level of docosahexaenoic acid (DHA) in the total fatty acid content of the seedoil is between 0.5% and 2.0% by weight.

28. *Brassica napus* seedoil, comprising a total fatty acid content which comprises fatty acids in an esterified polyunsaturated fatty acids which comprise linoleic acid (LA), ω3 polyunsaturated fatty acids which comprise α-linolenic acid (ALA), eicosapentaenoic acid (EPA), docosapentaenoic acid (DPA), docosahexaenoic acid (DHA), stearidonic acid (SDA) and eicosatetraenoic acid (ETA), wherein the level of palmitic acid in the total fatty acid content of the seedoil is between 2% and 16% by weight, wherein myristic acid (C14:0) is either absent or is present in the seedoil at a level of less than 1% by weight of the total fatty acid content of the seedoil, wherein at least 70% of the DPA esterified in the form of triacylglycerols (TAG) in the seedoil is in the sn-1 or sn-3 position of the TAG, and wherein ALA, SDA, ETA, EPA, DPA, DHA and eicosatrienoic acid (ETrA) are each present at a level in the total fatty acid content, each level being expressed as a percentage of the total fatty acid content, whereby the sum of the percentages for DPA and DHA divided by the sum of the percentages for ALA, SDA, ETA, EPA, DPA, DHA and ETrA, expressed as a percentage, is between 15.3% and 60.5%.

29. The seedoil of claim 28, wherein the sum of the percentages for DPA and DHA divided by the sum of the percentages for ALA, SDA, ETA, EPA, DPA, DHA and ETrA, expressed as a percentage, is between 17% and 55%.

30. The seedoil of claim 28, wherein the sum of the percentages for DPA and DHA divided by the sum of the percentages for ALA, SDA, ETA, EPA, DPA, DHA and ETrA, expressed as a percentage, is between 15.3% and 18.7%.

31. The seedoil of claim 28, wherein a level of γ-linolenic acid (GLA) of less than 4% by weight is present in the total fatty acid content of the seedoil.

32. The seedoil of claim 28, wherein at least 80% of the DPA esterified in the form of TAG in the seedoil is in the sn-1 or sn-3 position of the TAG.

33. The seedoil of claim 28, which has the following features i) the level of oleic acid in the total fatty acid content of the seedoil is between 1% and 60% by weight, ii) the level of linoleic acid (LA) in the total fatty acid content of the seedoil is between 4% and 35% by weight, iii) a level of γ-linolenic acid (GLA) of less than 4% by weight is present in the total fatty acid content of the seedoil, and iv) a level of total saturated fatty acids of between 4% and 25% by weight is present in the total fatty acid content of the seedoil.

34. The seedoil of claim 28, wherein the seedoil was obtained from *Brassica napus* seed harvested from a population of at least 1,000 *Brassica napus* plants grown in a field.

35. The seedoil of claim 28, wherein the level of EPA in the total fatty acid content of the seedoil is between 0.05% and 10% by weight.

36. The seedoil of claim 28, wherein the level of DPA in the total fatty acid content of the seedoil is about 2.5% by weight.

37. The seedoil of claim 28, wherein the level of DPA in the total fatty acid content of the seedoil is about 3.9% by weight and the level of DHA is about 1.2% by weight.

38. The seedoil of claim 28, wherein the level of DPA in the total fatty acid content of the seedoil is about 3.0% by weight and the level of DHA is about 0.8% by weight.

* * * * *

SEQUENCE LISTING

<160> NUMBER OF SEQ ID NOS: 58

<210> SEQ ID NO 1
<211> LENGTH: 21527
<212> TYPE: DNA
<213> ORGANISM: Artificial Sequence
<220> FEATURE:
<223> OTHER INFORMATION: pJP3416-GA7 nucleotide sequence.

<400> SEQUENCE: 1
tcctgtggtt ggcatgcaca tacaaatgga cgaacggata aacctttca cgcccttta 60 aatatccgat tattctaata aacgctcttt tctcttaggt ttacccgcca atatatcctg 120
tcaaacactg atagtttaaa ctgaaggcgg gaaacgacaa tctgctagtg gatctcccag 180
tcacgacgtt gtaaaacggg cgccccgcgg aaagcttgcg gccgcccgat ctagtaacat 240
agatgacacc gcgcgcgata atttatccta gtttgcgcgc tatattttgt tttctatcgc 300
gtattaaatg tataattgcg ggactctaat cataaaaacc catctcataa ataacgtcat 360
gcattacatg ttaattatta cgtgcttaac gtaattcaac agaaattata tgataatcat 420
cgcaagaccg gcaacaggat tcaatcttaa gaaactttat tgccaaatgt ttgaacgatc 480
ggcgcgcctc attagtgagc cttctcagcc tttccgttaa cgtagtagtg ctgtcccacc 540
ttatcaaggt tagagaaagt agccttccaa gcaccgtagt aagagagcac cttgtagttg 600
agtccccact tcttagcgaa aggaacgaat cttctgctaa cctcaggctg tctgaattga 660
ggcatatcag ggaagaggtg gtggataacc tgacagttaa ggtatcccat aagccagttc 720
acgtatcctc tagaaggatc gatatcaacg gtgtgatcaa cagcgtagtt aacccaagaa 780
aggtgcttat cagatggaac aacagggagg tgagtatgag aagtagagaa gtgagcgaaa 840
aggtacatgt aagcgatcca gtttccgaaa gtgaaccacc agtaagcaac aggccaagag 900
tatccagtag caagcttgat aacagcggtt ctaacaacat gagaaacgag catccaagaa 960
gcctcttcgt agttcttctt acggagaact tgtctagggt ggagaacgta gatccagaaa 1020
gcttgaacaa gaagtccaga ggtaacagga acgaaagtcc aagcttgaag tctagcccaa 1080
gctctagaga atcctctagg tctgttatcc tcaacagcag tgttgaagaa agccacagca 1140
ggagtggtat caagatccat atcgtgtcta accttttgag ggtagcatg gtgcttgtta 1200 tgcatctggt tccacatctc accagaagta gaaagtccga atccacaagt catagcctga 1260
agtctcttgt ccacgtaaac agatccggta agagagttat gtccaccctc atgttgaacc 1320
catccacatc tagctccgaa gaaagcaccg taaacaacag aagcaatgat agggtatcca 1380
gcgtacataa gagcagttcc aagagcgaat gtagcaagaa gctcgagaag tctgtaagcc 1440
acatgggtga tagaaggctt gaagaatcca tctctctcaa gctcagcacg ccatctagcg 1500
aaatcctcaa gcataggagc atcctcagac tcagatctct tgatctcagc aggtctagaa 1560
ggcaaagctc taagcatctt ccaagccttg agagaacgca tgtggaattc tttgaaagcc 1620
tcagtagcat cagcaccagt gttagcaagc atgtagaaga tcacagatcc accagggtgc 1680
ttgaagttag tcacatcgta ctcaacgtcc tcaactctaa cccatctagt ctcgaaagta 1740
gcagcaagct catgaggctc aagagtctta agatcaacag gagcagtaga agcatcctta 1800
gcatcaagag cctcagcaga agatttagac ctggtaagtg gagatctagg agaagatctt 1860
ccatcagtct taggagggca catggtatgg taattgtaaa tgtaattgta atgttgtttg 1920
ttgtttgttg ttgttggtaa ttgttgtaaa agatcctcgt gtatgttttt aatcttgttt 1980
gtatcgatga gttttggttt gagtaaagag tgaagcggat gagttaattt ataggctata 2040

-continued

```
aaggagattt gcatggcgat cacgtgtaat aatgcatgca cgcatgtgat tgtatgtgtg   2100
tgctgtgaga gagaagctct taggtgtttg aagggagtga caagtggcga agaaaaacaa   2160
ttctccgcgg ctgcatgcta tgtgtaacgt gtagctaatg ttctggcatg gcatcttatg   2220
aacgattctt tttaaaaaca aggtaaaaac ttaacttcat aaaattaaaa aaaaaaacgt   2280
ttactaagtt ggtttaaaag gggatgagac tagtagattg gttggttggt ttccatgtac   2340
cagaaggctt accctattag ttgaaagttg aaactttgtt ccctactcaa ttcctagttg   2400
tgtaaatgta tgtatatgta atgtgtataa aacgtagtac ttaaatgact aggagtggtt   2460
cttgagaccg atgagagatg ggagcagaac taaagatgat gacataatta agaacgaatt   2520
tgaaaggctc ttaggtttga atcctattcg agaatgtttt tgtcaaagat agtggcgatt   2580
ttgaaccaaa gaaaacattt aaaaaatcag tatccggtta cgttcatgca aatagaaagt   2640
ggtctaggat ctgattgtaa ttttagactt aaagagtctc ttaagattca atcctggctg   2700
tgtacaaaac tacaaataat atattttaga ctatttggcc ttaactaaac ttccactcat   2760
tatttactga ggttagagaa tagacttgcg aataaacaca ttcccgagaa atactcatga   2820
tcccataatt agtcagaggg tatgccaatc agatctaaga acacacattc cctcaaattt   2880
taatgcacat gtaatcatag tttagcacaa ttcaaaaata atgtagtatt aaagacagaa   2940
atttgtagac ttttttttgg cgttaaaaga agactaagtt tatacgtaca ttttatttta   3000
agtggaaaac cgaaattttc catcgaaata tatgaattta gtatatatat ttctgcaatg   3060
tactattttg ctattttggc aactttcagt ggactactac tttattacaa tgtgtatgga   3120
tgcatgagtt tgagtataca catgtctaaa tgcatgcttt gtaaaacgta acggaccaca   3180
aaagaggatc catacaaata catctcatag cttcctccat tattttccga cacaaacaga   3240
gcattttaca acaattacca acaacaacaa acaacaaaca acattacaat tacatttaca   3300
attaccatac catggaattc gcccagcctc ttgttgctat ggctcaagag caatacgctg   3360
ctatcgatgc tgttgttgct cctgctatct tctctgctac tgattctatc ggatggggac   3420
ttaagcctat ctcttctgct actaaggact tgcctcttgt tgagtctcct acacctctca   3480
tcctttcttt gcttgcttac ttcgctatcg ttggatctgg actcgtttac agaaaggttt   3540
tccctagaac cgtgaaggga caagatccat tccttttgaa ggctcttatg cttgctcaca   3600
acgtgttcct tatcggactt tctctttaca tgtgcctcaa gcttgtgtac gaggcttacg   3660
ttaacaagta ctctttctgg ggaaacgctt acaaccctgc tcaaactgag atggctaagg   3720
ttatctggat cttctacgtg agcaagatct acgagttcat ggataccttc atcatgctcc   3780
tcaagggaaa tgttaaccag gttagcttcc ttcacgttta ccatcacgga tctatctctg   3840
gaatctggtg gatgattact tacgctgctc ctggtggtga tgcttacttc tctgctgctc   3900
ttaactcttg ggttcacgtg tgtatgtaca cctactattt tatggctgcc gtgcttccta   3960
aggacgagaa aactaagaga aagtacctct ggtggggaag ataccttact caaatgcaga   4020
tgttccagtt cttcatgaac cttctccagg ctgtttacct tctctactct tcatctcctt   4080
accctaagtt tatcgctcag ctcctcgtgg tgtacatggt tactcttctc atgcttttcg   4140
gaaacttcta ctacatgaag caccacgcta gcaagtgatg aggcgcgccg ggccgccgcc   4200
atgtgacaga tcgaaggaag aaagtgtaat aagacgactc tcactactcg atcgctagtg   4260
attgtcattg ttatatataa taatgttatc tttcacaact tatcgtaatg catgtgaaac   4320
tataacacat taatcctact tgtcatatga taacactctc cccatttaaa actcttgtca   4380
```

atttaaagat ataagattct ttaaatgatt aaaaaaaata tattataaat tcaatcactc 4440
ctactaataa attattaatt attatttatt gattaaaaaa atacttatac taatttagtc 4500
tgaatagaat aattagattc tagtctcatc ccctttttaaa ccaacttagt aaacgttttt 4560
tttttaatt ttatgaagtt aagtttttac cttgttttta aaaagaatcg ttcataagat 4620
gccatgccag aacattagct acacgttaca catagcatgc agccgcggag aattgttttt 4680
cttcgccact tgtcactccc ttcaaacacc taagagcttc tctctcacag cacacacata 4740
caatcacatg cgtgcatgca ttattacacg tgatcgccat gcaaatctcc tttatagcct 4800
ataaattaac tcatccgctt cactctttac tcaaaccaaa actcatcgat acaaacaaga 4860
ttaaaaacat acacgaggat cttttacaac aattaccaac aacaacaaac aacaaacaac 4920
attacaatta catttacaat taccatacca tgcctccaag ggactcttac tcttatgctg 4980
ctcctccttc tgctcaactt cacgaagttg atactcctca agagcacgac aagaaagagc 5040
ttgttatcgg agatagggct tacgatgtta ccaacttcgt taagagacac cctggtggaa 5100
agatcattgc ttaccaagtt ggaactgatg ctaccgatgc ttacaagcag ttccatgtta 5160
gatctgctaa ggctgacaag atgcttaagt ctcttccttc tcgtcctgtt cacaagggat 5220
actctccaag aagggctgat cttatcgctg atttccaaga gttcaccaag caacttgagg 5280
ctgagggaat gttcgagcct tctcttcctc atgttgctta cagacttgct gaggttatcg 5340
ctatgcatgt tgctggtgct gctcttatct ggcatggata cactttcgct ggaatcgcta 5400
tgcttggagt tgttcaggga agatgtggat ggcttatgca tgagggtgga cattactctc 5460
tcactggaaa cattgctttc gacagagcta tccaagttgc ttgttacgga cttggatgtg 5520
gaatgtctgg tgcttggtgg cgtaaccagc ataacaagca ccatgctact cctcaaaagc 5580
ttcagcacga tgttgatctt gatacccttc ctctcgttgc tttccatgag agaatcgctg 5640
ctaaggttaa gtctcctgct atgaaggctt ggctttctat gcaagctaag cttttcgctc 5700
ctgttaccac tcttcttgtt gctcttggat ggcagcttta ccttcatcct agacacatgc 5760
tcaggactaa gcactacgat gagcttgcta tgctcggaat cagatacgga cttgttggat 5820
accttgctgc taactacggt gctggatacg ttctcgcttg ttaccttctt tacgttcagc 5880
ttggagctat gtacatcttc tgcaacttcg ctgtttctca tactcacctc cctgttgttg 5940
agcctaacga gcatgctact tgggttgagt acgctgctaa ccacactact aactgttctc 6000
catcttggtg gtgtgattgg tggatgtctt accttaacta ccagatcgag caccaccttt 6060
acccttctat gcctcaattc agacacccta agatcgctcc tagagttaag cagcttttcg 6120
agaagcacgg acttcactac gatgttagag gatacttcga ggctatggct gatactttcg 6180
ctaaccttga taacgttgcc catgctcctg agaagaaaat gcagtaatga gatcgttcaa 6240
acatttggca ataaagtttc ttaagattga atcctgttgc cggtcttgcg atgattatca 6300
tataatttct gttgaattac gttaagcacg taataattaa catgtaatgc atgacgttat 6360
ttatgagatg ggtttttatg attagagtcc cgcaattata catttaatac gcgatagaaa 6420
acaaaatata gcgcgcaaac taggataaat tatcgcgcgc ggtgtcatct atgttactag 6480
atcggtcgat taaaaatccc aattatattt ggtctaattt agtttggtat tgagtaaaac 6540
aaattcgaac caaaccaaaa tataaatata tagtttttat atatatgcct ttaagacttt 6600
ttatagaatt ttctttaaaa aatatctaga aatatttgcg actcttctgg catgtaatat 6660
ttcgttaaat atgaagtgct ccatttttat taactttaaa taattggttg tacgatcact 6720
ttcttatcaa gtgttactaa aatgcgtcaa tctctttgtt cttccatatt catatgtcaa 6780
aatctatcaa aattcttata tatctttttc gaatttgaag tgaaatttcg ataatttaaa 6840
attaaataga acatatcatt atttaggtat catattgatt tttatactta attactaaat 6900
ttggttaact ttgaaagtgt acatcaacga aaaattagtc aaacgactaa aataaataaa 6960
tatcatgtgt tattaagaaa attctcctat aagaatattt taatagatca tatgtttgta 7020
aaaaaaatta atttttacta acacatatat ttacttatca aaaatttgac aaagtaagat 7080
taaaataata ttcatctaac aaaaaaaaaa ccagaaaatg ctgaaaaccc ggcaaaaccg 7140
aaccaatcca aaccgatata gttggtttgg tttgattttg atataaaccg aaccaactcg 7200
gtccatttgc acccctaatc ataatagctt taatatttca agatattatt aagttaacgt 7260
tgtcaatatc ctggaaattt tgcaaaatga atcaagccta tatggctgta atatgaattt 7320
aaaagcagct cgatgtggtg gtaatatgta atttacttga ttctaaaaaa atatcccaag 7380
tattaataat ttctgctagg aagaaggtta gctacgattt acagcaaagc cagaatacaa 7440
agaaccataa agtgattgaa gctcgaaata tacgaaggaa caaatatttt taaaaaaata 7500
cgcaatgact tggaacaaaa gaaagtgata tattttttgt tcttaaacaa gcatcccctc 7560
taaagaatgg cagttttcct ttgcatgtaa ctattatgct cccttcgtta caaaaatttt 7620
ggactactat tgggaacttc ttctgaaaat agtgatagaa cccacacgag catgtgcttt 7680
ccatttaatt ttaaaaacca agaaacatac atacataaca ttccatcagc ctctctctct 7740
ttttattacg gttaatgact taaaacacat cttattatcc catccttaac acctagcagt 7800
gtctttatac gatctcatcg atcaccactt caaaaccatg cagactgctg ctgcccctgg 7860
agctggcatc ggctaggctg ggtgccgcac tgtcccggaa ggtccctagc gacttgttta 7920
gattgatggg accacctctc aacttcctgc tgctgtccct gctgctggat gtcctgcctc 7980
atctggccga ttgcacgctc cagtcccctg catgtgcact cgctcctcaa ttgcttaaga 8040
tcatcgcagc agctatcgaa gtgctggctc tgttgccctc ctccacggcc ttggttgtag 8100
tagtagctgc cgccgccctt ctggactttt tcccacagga accgccgaat aattcgatag 8160
aaccacacga gcatgtgctt tcatttattt taaaaaccaa gaaacataca taacatttca 8220
tcagcctctc tctctctctc tctctctctc tctctctctc tctctctctc tctctcttta 8280
ttacagctgt tacactaact taaaacacat tcatctcatt attattatta ttatccatcc 8340
ttaacaccta gcagtgtctt tgtacgatct cataatcgat cacccccttca tcaggtatcc 8400
ttaggcttca ctccaacgtt gttgcagtta cggaacatgt acacaccatc atggttctca 8460
acgaactggc aagatctcca agttttccaa aggctaaccc acatgttctc atcggtgtgt 8520
ctgtagtgct ctcccataac tttcttgatg cactcggtag cttctctagc atggtagaat 8580
gggatccttg aaacgtagtg atggagcaca tgagtctcga tgatgtcatg gaagatgatt 8640
ccgaggattc cgaactctct atcgatagta gcagcagcac ccttagcgaa agtccactct 8700
tgagcatcgt aatgaggcat agaagaatcg gtgtgctgaa ggaaggtaac gaaaacaagc 8760
cagtggttaa caaggatcca aggacagaac catgtgatga aagtaggcca gaatccgaaa 8820
accttgtaag cggtgtaaac agaagtgagg gtagcaagga ttccaagatc agaaagaacg 8880
atgtaccagt agtccttctt atcgaaaaca gggctagaag gccagtagtg agacttgaag 8940
aacttagaaa caccagggta aggttgtcca gtagcgttag tagcaaggta aagagaaagt 9000
cctccaagct gttggaacaa gagagcgaaa acagagtaga taggagtttc ctcagcgata 9060
tcgtgaaggc tggtaacttg gtgcttctct ttgaattcct cggcggtgta aggaacgaaa 9120

-continued

```
accatatctc tggtcatgtg tccagtagcc ttatggtgct tagcatgaga gaacttccag   9180
ctgaagtaag gaaccataac aagagagtgg agaacccatc caacggtatc gttaacccat   9240
ccgtagttag agaaagcaga atgtccacac tcatgtccaa ggatccagat tccgaatccg   9300
aaacaagaga tagagaacac gtaagcagac caagcagcga atctaaggaa ttcgttaggg   9360
agaagaggga tgtaggtaag tccaacgtaa gcgatagcag agatagccac gatatctctc   9420
accacgtaag acatagactt cacgagagat ctctcgtaac agtgcttagg gatagcgtca   9480
aggatatcct tgatggtgta atctggcacc ttgaaaacgt ttccgaaggt atcgatagcg   9540
gtcttttgct gcttgaaaga tgcaacgttt ccagaacgcc taacggtctt agtagatccc   9600
tcaaggatct cagatccaga cacggtaacc ttagacatgg tatggtaatt gtaaatgtaa   9660
ttgtaatgtt gtttgttgtt tgttgttgtt ggtaattgtt gtaaaatttt tggtggtgat   9720
tggttcttta aggtgtgaga gtgagttgtg agttgtgtgg tgggtttggt gagattgggg   9780
atggtgggtt tatatagtgg agactgagga atggggtcgt gagtgttaac tttgcatggg   9840
ctacacgtgg gttcttttgg gcttacacgt agtattattc atgcaaatgc agccaataca   9900
tatacggtat tttaataatg tgtgggaata caatatgccg agtattttac taattttggc   9960
aatgacaagt gtacatttgg attatcttac ttggcctctc ttgctttaat ttggattatt  10020
tttattctct taccttggcc gttcatattc acatccctaa aggcaagaca gaattgaatg  10080
gtggccaaaa attaaaacga tggatatgac ctacatagtg taggatcaat taacgtcgaa  10140
ggaaaatact gattctctca agcatacgga caagggtaaa taacatagtc accagaacat  10200
aataaacaaa aagtgcagaa gcaagactaa aaaaattagc tatggacatt caggttcata  10260
ttggaaacat cattatccta gtcttgtgac catccttcct cctgctctag ttgagaggcc  10320
ttgggactaa cgagaggtca gttgggatag cagatcctta tcctggacta gcctttctgg  10380
tgtttcagag tcttcgtgcc gccgtctaca tctatctcca ttaggtctga agatgactct  10440
tcacaccaac gacgtttaag gtctctatcc tactcctagc ttgcaatacc tggcttgcaa  10500
tacctggagc atcgtgcacg atgattggat actgtggagg aggagtgttt gctgatttag  10560
agctcccggt tgggtgattt gacttcgatt tcagtttagg cttgttgaaa tttttcaggt  10620
tccattgtga agcctttaga gcttgagctt ccttccatgt taatgccttg atcgaatact  10680
cctagagaaa agggaagtcg atctctgagt attgaaatcg aagtgcacat ttttttcaa   10740
cgtgtccaat caatccacaa acaaagcaga agacaggtaa tctttcatac ttatactgac  10800
aagtaatagt cttaccgtca tgcataataa cgtctcgttc cttcaagagg ggttttccga  10860
catccataac gacccgaagc ctcatgaaag cattagggaa gaacttttgg ttcttcttgt  10920
catggccttt ataggtgtca gccgagctcg ccaattcccg tccgactggc tccgcaaaat  10980
attcgaacgg caagttatgg acttgcaacc ataactccac ggtattgagc aggacctatt  11040
gtgaagactc atctcatgga gcttcagaat gtggttgtca gcaaaccaat gaccgaaatc  11100
catcacatga cggacgtcca gtgggtgagc gaaacgaaac aggaagcgcc tatctttcag  11160
agtcgtgagc tccacaccgg attccggcaa ctacgtgttg ggcaggcttc gccgtattag  11220
agatatgttg aggcagaccc atctgtgcca ctcgtacaat tacgagagtt gtttttttg   11280
tgattttcct agtttctcgt tgatggtgag ctcatattct acatcgtatg gtctctcaac  11340
gtcgtttcct gtcatctgat atcccgtcat ttgcatccac gtgcgccgcc tcccgtgcca  11400
agtccctagg tgtcatgcac gccaaattgg tggtggtgcg ggctgccctg tgcttcttac  11460
cgatgggtgg aggttgagtt tgggggtctc cgcggcgatg gtagtgggtt gacggtttgg  11520
```

tgtgggttga cggcattgat caatttactt cttgcttcaa attctttggc agaaaacaat 11580
tcattagatt agaactggaa accagagtga tgagacggat taagtcagat tccaacagag 11640
ttacatctct taagaaataa tgtaacccct ttagacttta tatatttgca attaaaaaaa 11700
taatttaact tttagacttt atatatagtt ttaataacta agtttaacca ctctattatt 11760
tatatcgaaa ctatttgtat gtctcccctc taaataaact tggtattgtg tttacagaac 11820
ctataatcaa ataatcaata ctcaactgaa gtttgtgcag ttaattgaag ggattaacgg 11880
ccaaaatgca ctagtattat caaccgaata gattcacact agatggccat ttccatcaat 11940
atcatcgccg ttcttcttct gtccacatat cccctctgaa acttgagaga cacctgcact 12000
tcattgtcct tattacgtgt tacaaaatga aacccatgca tccatgcaaa ctgaagaatg 12060
gcgcaagaac ccttcccctc catttcttat gtggcgacca tccatttcac catctcccgc 12120
tataaaacac ccccatcact tcacctagaa catcatcact acttgcttat ccatccaaaa 12180
gatacccact tttacaacaa ttaccaacaa caacaaacaa caaacaacat tacaattaca 12240
tttacaatta ccataccatg ccacctagcg ctgctaagca aatgggagct tctactggtg 12300
ttcatgctgg tgttactgac tcttctgctt tcaccagaaa ggatgttgct gatagacctg 12360
atctcaccat cgttggagat tctgtttacg atgctaaggc tttcagatct gagcatcctg 12420
gtggtgctca tttcgtttct ttgttcggag gaagagatgc tactgaggct ttcatggaat 12480
accatagaag ggcttggcct aagtctagaa tgtctagatt ccacgttgga tctcttgctt 12540
ctactgagga acctgttgct gctgatgagg gataccttca actttgtgct aggatcgcta 12600
agatggtgcc ttctgtttct tctggattcg ctcctgcttc ttactgggtt aaggctggac 12660
ttatccttgg atctgctatc gctcttgagg cttacatgct ttacgctgga aagagacttc 12720
tcccttctat cgttcttgga tggcttttcg ctcttatcgg tcttaacatc cagcatgatg 12780
ctaaccatgg tgctttgtct aagtctgctt ctgttaacct tgctcttgga ctttgtcagg 12840
attggatcgg aggatctatg atcctttggc ttcaagagca tgttgttatg caccacctcc 12900
acactaacga tgttgataag gatcctgatc aaaaggctca cggtgctctt agactcaagc 12960
ctactgatgc ttggtcacct atgcattggc ttcagcatct ttacctttg cctggtgaga 13020
ctatgtacgc tttcaagctt ttgttcctcg acatctctga gcttgttatg tggcgttggg 13080
agggtgagcc tatctctaag cttgctggat acctctttat gccttctttg cttctcaagc 13140
ttaccttctg ggctagattc gttgctttgc ctctttacct tgctccttct gttcatactg 13200
ctgtgtgtat cgctgctact gttatgactg gatctttcta cctcgctttc ttcttcttca 13260
tctcccacaa cttcgagggt gttgcttctg ttggacctga tggatctatc acttctatga 13320
ctagaggtgc tagcttcctt aagagacaag ctgagacttc ttctaacgtt ggaggacctc 13380
ttcttgctac tcttaacggt ggactcaact accaaattga gcatcacttg ttccctagag 13440
ttcaccatgg attctaccct agacttgctc ctcttgttaa ggctgagctt gaggctagag 13500
gaatcgagta caagcactac cctactatct ggtctaacct tgcttctacc ctcagacata 13560
tgtacgctct tggaagaagg cctagatcta aggctgagta atgacaagct tatgtgacgt 13620
gaaataataa cggtaaaata tatgtaataa taataataat aaagccacaa agtgagaatg 13680
aggggaaggg gaaatgtgta atgagccagt agccggtggt gctaattttg tatcgtattg 13740
tcaataaatc atgaatttg tggtttttat gtgttttttt aaatcatgaa ttttaaattt 13800
tataaaataa tctccaatcg gaagaacaac attccatatc catgcatgga tgtttcttta 13860
cccaaatcta gttcttgaga ggatgaagca tcaccgaaca gttctgcaac tatccctcaa 13920
aagctttaaa atgaacaaca aggaacagag caacgttcca aagatcccaa acgaaacata 13980
ttatctatac taatactata ttattaatta ctactgcccg gaatcacaat ccctgaatga 14040
ttcctattaa ctacaagcct tgttggcggc ggagaagtga tcggcgcggc gagaagcagc 14100
ggactcggag acgaggcctt ggaagatctg agtcgaacgg gcagaatcag tattttcctt 14160
cgacgttaat tgatcctaca ctatgtaggt catatccatc gttttaattt ttggccacca 14220
ttcaattctg tcttgccttt agggatgtga atatgaacgg ccaaggtaag agaataaaaa 14280
taatccaaat taaagcaaga gaggccaagt aagataatcc aaatgtacac ttgtcattgc 14340
caaaattagt aaaatactcg gcatattgta ttcccacaca ttattaaaat accgtatatg 14400
tattggctgc atttgcatga ataatactac gtgtaagccc aaaagaaccc acgtgtagcc 14460
catgcaaagt taacactcac gaccccattc ctcagtctcc actatataaa cccaccatcc 14520
ccaatctcac caaacccacc acacaactca caactcactc tcacacctta aagaaccaat 14580
caccaccaaa aattttacaa caattaccaa caacaacaaa caacaaacaa cattacaatt 14640
acatttacaa ttaccatacc atgagcgctg ttaccgttac tggatctgat cctaagaaca 14700
gaggatcttc tagcaacacc gagcaagagg ttccaaaagt tgctatcgat accaacggaa 14760
acgtgttctc tgttcctgat ttcaccatca aggacatcct tggagctatc cctcatgagt 14820
gttacgagag aagattggct acctctctct actacgtgtt cagagatatc ttctgcatgc 14880
ttaccaccgg ataccttacc cataagatcc tttaccctct cctcatctct tacacctcta 14940
acagcatcat caagttcact ttctgggccc tttacactta cgttcaagga cttttcggaa 15000
ccggaatctg ggttctcgct catgagtgtg gacatcaagc tttctctgat tacggaatcg 15060
tgaacgattt cgttggatgg acccttcact cttaccttat ggttccttac ttcagctgga 15120
agtactctca tggaaagcac cataaggcta ctggacacat gaccagagat atggttttcg 15180
ttcctgccac caaagaggaa ttcaagaagt ctaggaactt cttcggtaac ctcgctgagt 15240
actctgagga ttctccactt agaacccttt acgagcttct tgttcaacaa cttggaggat 15300
ggatcgctta cctcttcgtt aacgttacag gacaacctta ccctgatgtt ccttcttgga 15360
aatggaacca cttctggctt acctctccac ttttcgagca aagagatgct ctctacatct 15420
tcctttctga tcttggaatc ctcacccagg gaatcgttct tactctttgg tacaagaaat 15480
tcggaggatg gtccctttc atcaactggt tcgttcctta catctgggtt aaccactggc 15540
tcgttttcat cacattcctt cagcacactg atcctactat gcctcattac aacgctgagg 15600
aatggacttt cgctaagggt gctgctgcta ctatcgatag aaagttcgga ttcatcggac 15660
ctcacatctt ccatgatatc atcgagactc atgtgcttca ccactactgt tctaggatcc 15720
cattctacaa cgctagacct gcttctgagg ctatcaagaa agttatggga aagcactaca 15780
ggtctagcga cgagaacatg tggaagtcac tttggaagtc tttcaggtct tgccaatacg 15840
ttgacggtga taacggtgtt ctcatgttcc gtaacatcaa caactgcgga gttggagctg 15900
ctgagaagta atgaaggggt gatcgattat gagatcgtac aaagacactg ctaggtgtta 15960
aggatggata ataataataa taatgagatg aatgtgtttt aagttagtgt aacagctgta 16020
ataaagagag agagagagag agagagagag agagagagag agagagagag agagaggctg 16080
atgaaatgtt atgtatgttt cttggttttt aaaataaatg aaagcacatg ctcgtgtggt 16140
tctatcgaat tattcggcgg ttcctgtggg aaaaagtcca gaagggccgc cgcagctact 16200
actacaacca aggccgtgga ggagggcaac agagccagca cttcgatagc tgctgcgatg 16260
atcttaagca attgaggagc gagtgcacat gcaggggact ggagcgtgca atcggccaga 16320
tgaggcagga catccagcag cagggacagc agcaggaagt tgagaggtgg tcccatcaat 16380
ctaaacaagt cgctagggac cttccgggac agtgcggcac ccagcctagc cgatgccagc 16440
tccaggggca gcagcagtct gcatggtttt gaagtggtga tcgatgagat cgtataaaga 16500
cactgctagg tgttaaggat gggataataa gatgtgtttt aagtcattaa ccgtaataaa 16560
aagagagaga ggctgatgga atgttatgta tgtatgtttc ttggttttta aaattaaatg 16620
gaaagcacat gctcgtgtgg gttctatctc gattaaaaat cccaattata tttggtctaa 16680
tttagtttgg tattgagtaa aacaaattcg aaccaaacca aaatataaat atatagtttt 16740
tatatatatg cctttaagac tttttataga attttcttta aaaaatatct agaaatattt 16800
gcgactcttc tggcatgtaa tatttcgtta aatatgaagt gctccatttt tattaacttt 16860
aaataattgg ttgtacgatc actttcttat caagtgttac taaaatgcgt caatctcttt 16920
gttcttccat attcatatgt caaaatctat caaaattctt atatatcttt ttcgaatttg 16980
aagtgaaatt tcgataattt aaaattaaat agaacatatc attatttagg tatcatattg 17040
atttttatac ttaattacta aatttggtta actttgaaag tgtacatcaa cgaaaaatta 17100
gtcaaacgac taaaataaat aaatatcatg tgttattaag aaaattctcc tataagaata 17160
ttttaataga tcatatgttt gtaaaaaaaa ttaattttta ctaacacata tatttactta 17220
tcaaaaattt gacaaagtaa gattaaaata atattcatct aacaaaaaaa aaaccagaaa 17280
atgctgaaaa cccggcaaaa ccgaaccaat ccaaaccgat atagttggtt tggtttgatt 17340
ttgatataaa ccgaaccaac tcggtccatt tgcaccccta atcataatag ctttaatatt 17400
tcaagatatt attaagttaa cgttgtcaat atcctggaaa ttttgcaaaa tgaatcaagc 17460
ctatatggct gtaatatgaa tttaaaagca gctcgatgtg gtggtaatat gtaatttact 17520
tgattctaaa aaaatatccc aagtattaat aatttctgct aggaagaagg ttagctacga 17580
tttacagcaa agccagaata caaagaacca taaagtgatt gaagctcgaa atatacgaag 17640
gaacaaatat ttttaaaaaa atacgcaatg acttggaaca aaagaaagtg atatattttt 17700
tgttcttaaa caagcatccc ctctaaagaa tggcagtttt cctttgcatg taactattat 17760
gctcccttcg ttacaaaaat tttggactac tattgggaac ttcttctgaa aatagtcctg 17820
caggctagta gattggttgg ttggtttcca tgtaccagaa ggcttaccct attagttgaa 17880
agttgaaact ttgttcccta ctcaattcct agttgtgtaa atgtatgtat atgtaatgtg 17940
tataaaacgt agtacttaaa tgactaggag tggttcttga gaccgatgag agatgggagc 18000
agaactaaag atgatgacat aattaagaac gaatttgaaa ggctcttagg tttgaatcct 18060
attcgagaat gtttttgtca aagatagtgg cgattttgaa ccaaagaaaa catttaaaaa 18120
atcagtatcc ggttacgttc atgcaaatag aaagtggtct aggatctgat tgtaatttta 18180
gacttaaaga gtctcttaag attcaatcct ggctgtgtac aaaactacaa ataatatatt 18240
ttagactatt tggccttaac taaacttcca ctcattattt actgaggtta gagaatagac 18300
ttgcgaataa acacattccc gagaaatact catgatccca taattagtca gagggtatgc 18360
caatcagatc taagaacaca cattccctca aattttaatg cacatgtaat catagtttag 18420
cacaattcaa aaataatgta gtattaaaga cagaaatttg tagacttttt tttggcgtta 18480
aaagaagact aagtttatac gtacatttta ttttaagtgg aaaaccgaaa ttttccatcg 18540
aaatatatga atttagtata tatatttctg caatgtacta ttttgctatt ttggcaactt 18600

-continued

```
tcagtggact actactttat tacaatgtgt atggatgcat gagtttgagt atacacatgt  18660
ctaaatgcat gctttgtaaa acgtaacgga ccacaaaaga ggatccatac aaatacatct  18720
catagcttcc tccattattt tccgacacaa acagagcatt ttacaacaat taccaacaac  18780
aacaaacaac aaacaacatt acaattacat ttacaattac cataccatgg cctctatcgc  18840
tatccctgct gctcttgctg gaactcttgg atacgttacc tacaatgtgg ctaaccctga  18900
tatcccagct tctgagaaag ttcctgctta cttcatgcag gttgagtact ggggacctac  18960
tatcggaact attggatacc tcctcttcat ctacttcgga aagcgtatca tgcagaacag  19020
atctcaacct ttcggactca agaacgctat gctcgtttac aacttctacc agaccttctt  19080
caacagctac tgcatctacc ttttcgttac ttctcatagg gctcagggac ttaaggtttg  19140
gggaaacatc cctgatatga ctgctaactc ttggggaatc tctcaggtta tctggcttca  19200
ctacaacaac aagtacgttg agcttctcga caccttcttc atggtgatga ggaagaagtt  19260
cgaccagctt tctttccttc acatctacca ccacactctt ctcatctggt catggttcgt  19320
tgttatgaag cttgagcctg ttggagattg ctacttcgga tcttctgtta acaccttcgt  19380
gcacgtgatc atgtactctt actacggact tgctgctctt ggagttaact gtttctggaa  19440
gaagtacatc acccagatcc agatgcttca gttctgtatc tgtgcttctc actctatcta  19500
caccgcttac gttcagaata ccgctttctg gcttccttac cttcaactct gggttatggt  19560
gaacatgttc gttctcttcg ccaacttcta ccgtaagagg tacaagtcta agggtgctaa  19620
gaagcagtga taagggccgc cgccatgtga cagatcgaag gaagaaagtg taataagacg  19680
actctcacta ctcgatcgct agtgattgtc attgttatat ataataatgt tatctttcac  19740
aacttatcgt aatgcatgtg aaactataac acattaatcc tacttgtcat atgataacac  19800
tctccccatt taaaactctt gtcaatttaa agatataaga ttctttaaat gattaaaaaa  19860
aatatattat aaattcaatc actcctacta ataaattatt aattattatt tattgattaa  19920
aaaaatactt atactaattt agtctgaata gaataattag attctagcct gcagggcggc  19980
cgcggatccc atggagtcaa agattcaaat agaggaccta acagaactcg ccgtaaagac  20040
tggcgaacag ttcatacaga gtctcttacg actcaatgac aagaagaaaa tcttcgtcaa  20100
catggtggag cacgacacac ttgtctactc caaaaatatc aaagatacag tctcagaaga  20160
ccaaagggca attgagactt ttcaacaaag ggtaatatcc ggaaacctcc tcggattcca  20220
ttgcccagct atctgtcact ttattgtgaa gatagtggaa aaggaaggtg gctcctacaa  20280
atgccatcat tgcgataaag gaaaggccat cgttgaagat gcctctgccg acagtggtcc  20340
caaagatgga cccccaccca cgaggagcat cgtggaaaaa gaagacgttc caaccacgtc  20400
ttcaaagcaa gtggattgat gtgatatctc cactgacgta agggatgacg cacaatccca  20460
ctatccttcg caagaccctt cctctatata aggaagttca tttcatttgg agagaacacg  20520
ggggactgaa ttaaatatga gccctgagag gcgtcctgtt gaaatcagac ctgctactgc  20580
tgctgatatg gctgctgttt gtgatatcgt gaaccactac atcgagactt ctaccgttaa  20640
cttcagaact gagcctcaaa ctcctcaaga gtggatcgat gatcttgaga gactccaaga  20700
tagataccct tggcttgttg ctgaggttga gggtgttgtt gctggaatcg cttacgctgg  20760
accttggaag gctagaaacg cttacgattg gactgttgag tctaccgttt acgtttcaca  20820
cagacatcag agacttggac ttggatctac cctttacact caccttctca agtctatgga  20880
agctcaggga ttcaagtctg ttgttgctgt tatcggactc cctaacgatc cttctgttag  20940
acttcatgag gctcttggat acactgctag aggaactctt agagctgctg gatacaagca  21000
```

cggtggatgg catgatgttg gattctggca aagagatttc gagcttcctg ctcctcctag 21060
acctgttaga ccagttactc agatctgaat ttgcgtgatc gttcaaacat ttggcaataa 21120
agtttcttaa gattgaatcc tgttgccggt cttgcgatga ttatcatata atttctgttg 21180
aattacgtta agcatgtaat aattaacatg taatgcatga cgttatttat gagatgggtt 21240
tttatgatta gagtcccgca attatacatt taatacgcga tagaaaacaa aatatagcgc 21300
gcaaactagg ataaattatc gcgcgcggtg tcatctatgt tactagatca ctagtgatgt 21360
acggttaaaa ccaccccagt acattaaaaa cgtccgcaat gtgttattaa gttgtctaag 21420
cgtcaatttg tttacaccac aatatatcct gccaccagcc agccaacagc tccccgaccg 21480
gcagctcggc acaaaatcac cactcgatac aggcagccca tcagtcc 21527

<210> SEQ ID NO 2
<211> LENGTH: 23512
<212> TYPE: DNA
<213> ORGANISM: Artificial Sequence
<220> FEATURE:
<223> OTHER INFORMATION: pGA7- mod_B nucleotide sequence

<400> SEQUENCE: 2
tcctgtggtt ggcatgcaca tacaaatgga cgaacggata aaccttttca cgccctttta 60
aatatccgat tattctaata aacgctcttt tctcttaggt ttacccgcca atatatcctg 120
tcaaacactg atagtttaaa ctgaaggcgg gaaacgacaa tctgctagtg gatctcccag 180
tcacgacgtt gtaaaacggg cgccccgcgg aaagcttgcg gccgcggtac cgcccgttcg 240
actcagatct tccaaggcct cgtctccgag tccgctgctt ctcgccgcgc cgatcacttc 300
tccgccgcca acaaggcttg tagttaatag gaatcattca gggattgtga ttccgggcag 360
tagtaattaa taatatagta ttagtataga taatatgttt cgtttgggat ctttggaacg 420
ttgctctgtt ccttgttgtt cattttaaag cttttgaggg atagttgcag aactgttcgg 480
tgatgcttca tcctctcaag aactagattt gggtaaagaa acatccatgc atggatatgg 540
aatgttgttc ttccgattgg agattatttt ataaaattta aaattcatga tttaaaaaaa 600
cacataaaaa ccacaaaatt catgatttat tgacaatacg atacaaaatt agcaccaccg 660
gctactggct cattacacat ttccccttcc cctcattctc actttgtggc tttattatta 720
ttattattac atatatttta ccgttattat ttcacgtcac ataagcttgt taattaatca 780
ttagtgagcc ttctcagcct ttccgttaac gtagtagtgc tgtcccacct tatcaaggtt 840
agagaaagta gccttccaag caccgtagta agagagcacc ttgtagttga gtccccactt 900
cttagcgaaa ggaacgaatc ttctgctaac ctcaggctgt ctgaattgag gcatatcagg 960
gaagaggtgg tggataacct gacagttaag gtatcccata agccagttca cgtatcctct 1020
agaaggatcg atatcaacgg tgtgatcaac agcgtagtta acccaagaaa ggtgcttatc 1080
agatggaaca acagggaggt gagtatgaga agtagagaag tgagcgaaaa ggtacatgta 1140
agcgatccag tttccgaaag tgaaccacca gtaagcaaca ggccaagagt atccagtagc 1200
aagcttgata acagcggttc taacaacatg agaaacgagc atccaagaag cctcttcgta 1260
gttcttctta cggagaactt gtctagggtg gagaacgtag atccagaaag cttgaacaag 1320
aagtccagag gtaacaggaa cgaaagtcca agcttgaagt ctagcccaag ctctagagaa 1380
tcctctaggt ctgttatcct caacagcagt gttgaagaaa gccacagcag gagtggtatc 1440
aagatccata tcgtgtctaa ccttttgagg ggtagcatgg tgcttgttat gcatctggtt 1500

-continued

```
ccacatctca ccagaagtag aaagtccgaa tccacaagtc atagcctgaa gtctcttgtc   1560
cacgtaaaca gatccggtaa gagagttatg tccaccctca tgttgaaccc atccacatct   1620
agctccgaag aaagcaccgt aaacaacaga agcaatgata gggtatccag cgtacataag   1680
agcagttcca agagcgaatg tagcaagaag ctcgagaagt ctgtaagcca catgggtgat   1740
agaaggcttg aagaatccat ctctctcaag ctcagcacgc catctagcga aatcctcaag   1800
cataggagca tcctcagact cagatctctt gatctcagca ggtctagaag gcaaagctct   1860
aagcatcttc caagccttga gagaacgcat gtggaattct ttgaaagcct cagtagcatc   1920
agcaccagtg ttagcaagca tgtagaagat cacagatcca ccagggtgct tgaagttagt   1980
cacatcgtac tcaacgtcct caactctaac ccatctagtc tcgaaagtag cagcaagctc   2040
atgaggctca agagtcttaa gatcaacagg agcagtagaa gcatccttag catcaagagc   2100
ctcagcagaa gatttagacc tggtaagtgg agatctagga gaagatcttc catcagtctt   2160
aggagggcac atggtatggt aattgtaaat gtaattgtaa tgttgtttgt tgtttgttgt   2220
tgttggtaat tgttgtaaaa ttaattaagt gggtatcttt tggatggata agcaagtagt   2280
gatgatgttc taggtgaagt gatgggggtg ttttatagcg ggagatggtg aaatggatgg   2340
tcgccacata agaaatggag gggaagggtt cttgcgccat tcttcagttt gcatggatgc   2400
atgggtttca ttttgtaaca cgtaataagg acaatgaagt gcaggtgtct ctcaagtttc   2460
agaggggata tgtggacaga agaagaacgg cgatgatatt gatggaaatg gccatctagt   2520
gtgaatctat tcggttgata atactagtgc attttggccg ttaatccctt caattaactg   2580
cacaaacttc agttgagtat tgattatttg attataggtt ctgtaaacac aataccaagt   2640
ttatttagag ggagagacata caaatagttt cgatataaat aatagagtgg ttaaacttag   2700
ttattaaaac tatatataaa gtctaaaagt taaattattt ttttaattgc aaatatataa   2760
agtctaaagg ggttacatta tttcttaaga gatgtaactc tgttggaatc tgacttaatc   2820
cgtctcatca ctctggtttc cagttctaat ctaatgaatt gttttctgcc aaagaatttg   2880
aagcaagaag taaattgatc aatgccgtca acccacacca aaccgtcaac ccactaccat   2940
cgccgcggag acccccaaac tcaacctcca cccatcggta agaagcacag ggcagcccgc   3000
accaccacca atttggcgtg catgacacct agggacttgg cacgggaggc ggcgcacgtg   3060
gatgcaaatg acgggatatc agatgacagg aaacgacgtt gagagaccat acgatgtaga   3120
atatgagctc accatcaacg agaaactagg aaaatcacaa aaaaaacaac tctcgtaatt   3180
gtacgagtgg cacagatggg tctgcctcaa catatctcta atacggcgaa gcctgcccaa   3240
cacgtagttg ccggaatccg gtgtggagct cacgactctg aaagataggc gcttcctgtt   3300
tcgtttcgct cacccactgg acgtccgtca tgtgatggat ttcggtcatt ggtttgctga   3360
caaccacatt ctgaagctcc atgagatgag tcttcacaat aggtcctgct caataccgtg   3420
gagttatggt tgcaagtcca taacttgccg ttcgaatatt ttgcggagcc agtcggacgg   3480
gaattggcga gctcggctga cacctataaa ggccatgaca agaagaacca aaagttcttc   3540
cctaatgctt tcatgaggct tcgggtcgtt atggatgtcg gaaaacccct cttgaaggaa   3600
cgagacgtta ttatgcatga cggtaagact attacttgtc agtataagta tgaaagatta   3660
cctgtcttct gctttgtttg tggattgatt ggacacgttg aaaaaaaatg tgcacttcga   3720
tttcaatact cagagatcga cttccctttt ctctaggagt attcgatcaa ggcattaaca   3780
tggaaggaag ctcaagctct aaaggcttca caatggaacc tgaaaaattt caacaagcct   3840
aaactgaaat cgaagtcaaa tcacccaacc gggagctcta aatcagcaaa cactcctcct   3900
```

```
ccacagtatc caatcatcgt gcacgatgct ccaggtattg caagccaggt attgcaagct   3960
aggagtagga tagagacctt aaacgtcgtt ggtgtgaaga gtcatcttca gacctaatgg   4020
agatagatgt agacggcggc acgaagactc tgaaacacca gaaaggctag tccaggataa   4080
ggatctgcta tcccaactga cctctcgtta gtcccaaggc ctctcaacta gagcaggagg   4140
aaggatggtc acaagactag gataatgatg tttccaatat gaacctgaat gtccatagct   4200
aatttttttta gtcttgcttc tgcacttttt gtttattatg ttctggtgac tatgttattt   4260
acccttgtcc gtatgcttga gggtacccta gtagattggt tggttggttt ccatgtacca   4320
gaaggcttac cctattagtt gaaagttgaa actttgttcc ctactcaatt cctagttgtg   4380
taaatgtatg tatatgtaat gtgtataaaa cgtagtactt aaatgactag gagtggttct   4440
tgagaccgat gagagatggg agcagaacta aagatgatga cataattaag aacgaatttg   4500
aaaggctctt aggtttgaat cctattcgag aatgtttttg tcaaagatag tggcgatttt   4560
gaaccaaaga aaacatttaa aaaatcagta tccggttacg ttcatgcaaa tagaaagtgg   4620
tctaggatct gattgtaatt ttagacttaa agagtctctt aagattcaat cctggctgtg   4680
tacaaaacta caaataatat attttagact atttggcctt aactaaactt ccactcatta   4740
tttactgagg ttagagaata gacttgcgaa taaacacatt cccgagaaat actcatgatc   4800
ccataattag tcagagggta tgccaatcag atctaagaac acacattccc tcaaatttta   4860
atgcacatgt aatcatagtt tagcacaatt caaaaataat gtagtattaa agacagaaat   4920
ttgtagactt tttttggcg ttaaaagaag actaagttta tacgtacatt ttattttaag   4980
tggaaaaccg aaattttcca tcgaaatata tgaatttagt atatatattt ctgcaatgta   5040
ctattttgct attttggcaa ctttcagtgg actactactt tattacaatg tgtatggatg   5100
catgagtttg agtatacaca tgtctaaatg catgctttgt aaaacgtaac ggaccacaaa   5160
agaggatcca tacaaataca tctcatagct tcctccatta ttttccgaca caaacagagc   5220
attttacaac aattaccaac aacaacaaac aacaaacaac attacaatta catttacaat   5280
taccatacca tggcctctat cgctatccct gctgctcttg ctggaactct tggatacgtt   5340
acctacaatg tggctaaccc tgatatccca gcttctgaga aagttcctgc ttacttcatg   5400
caggttgagt actggggacc tactatcgga actattggat acctcctctt catctacttc   5460
ggaaagcgta tcatgcagaa cagatctcaa cctttcggac tcaagaacgc tatgctcgtt   5520
tacaacttct accagacctt cttcaacagc tactgcatct accttttcgt tacttctcat   5580
agggctcagg gacttaaggt ttggggaaac atccctgata tgactgctaa ctcttgggga   5640
atctctcagg ttatctggct tcactacaac aacaagtacg ttgagcttct cgacaccttc   5700
ttcatggtga tgaggaagaa gttcgaccag ctttctttcc ttcacatcta ccaccacact   5760
cttctcatct ggtcatggtt cgttgttatg aagcttgagc ctgttggaga ttgctacttc   5820
ggatcttctg ttaacacctt cgtgcacgtg atcatgtact cttactacgg acttgctgct   5880
cttggagtta actgtttctg gaagaagtac atcacccaga tccagatgct tcagttctgt   5940
atctgtgctt ctcactctat ctacaccgct tacgttcaga ataccgcttt ctggcttcct   6000
taccttcaac tctgggttat ggtgaacatg ttcgttctct tcgccaactt ctaccgtaag   6060
aggtacaagt ctaagggtgc taagaagcag tgataaggcg cgcggcgcgc cgggccgccg   6120
ccatgtgaca gatcgaagga agaaagtgta ataagacgac tctcactact cgatcgctag   6180
tgattgtcat tgttatatat aataatgtta tctttcacaa cttatcgtaa tgcatgtgaa   6240
```

-continued

```
actataacac attaatccta cttgtcatat gataacactc tccccattta aaactcttgt   6300
caatttaaag atataagatt ctttaaatga ttaaaaaaaa tatattataa attcaatcac   6360
tcctactaat aaattattaa ttattattta ttgattaaaa aaatacttat actaatttag   6420
tctgaataga ataattagat tctagtctca tccccttttta aaccaactta gtaaacgttt   6480
tttttttaa ttttatgaag ttaagttttt accttgtttt taaaaagaat cgttcataag   6540
atgccatgcc agaacattag ctacacgtta cacatagcat gcagccgcgg agaattgttt   6600
ttcttcgcca cttgtcactc ccttcaaaca cctaagagct tctctctcac agcacacaca   6660
tacaatcaca tgcgtgcatg cattattaca cgtgatcgcc atgcaaatct cctttatagc   6720
ctataaatta actcatccgc ttcactcttt actcaaacca aaactcatcg atacaaacaa   6780
gattaaaaac atacacgagg atcttttaca acaattacca acaacaacaa acaacaaaca   6840
acattacaat tacatttaca attaccatac catgcctcca agggactctt actcttatgc   6900
tgctcctcct tctgctcaac ttcacgaagt tgatactcct caagagcacg acaagaaaga   6960
gcttgttatc ggagataggg cttacgatgt taccaacttc gttaagagac accctggtgg   7020
aaagatcatt gcttaccaag ttggaactga tgctaccgat gcttacaagc agttccatgt   7080
tagatctgct aaggctgaca agatgcttaa gtctcttcct tctcgtcctg ttcacaaggg   7140
atactctcca agaagggctg atcttatcgc tgatttccaa gagttcacca agcaacttga   7200
ggctgaggga atgttcgagc cttctcttcc tcatgttgct tacagacttg ctgaggttat   7260
cgctatgcat gttgctggtg ctgctcttat ctggcatgga tacactttcg ctggaatcgc   7320
tatgcttgga gttgttcagg gaagatgtgg atggcttatg catgagggtg gacattactc   7380
tctcactgga aacattgctt tcgacagagc tatccaagtt gcttgttacg gacttggatg   7440
tggaatgtct ggtgcttggt ggcgtaacca gcataacaag caccatgcta ctcctcaaaa   7500
gcttcagcac gatgttgatc ttgataccct tcctctcgtt gctttccatg agagaatcgc   7560
tgctaaggtt aagtctcctg ctatgaaggc ttggctttct atgcaagcta agcttttcgc   7620
tcctgttacc actcttcttg ttgctcttgg atggcagctt taccttcatc ctagacacat   7680
gctcaggact aagcactacg atgagcttgc tatgctcgga atcagatacg gacttgttgg   7740
ataccttgct gctaactacg gtgctggata cgttctcgct tgttaccttc tttacgttca   7800
gcttggagct atgtacatct tctgcaactt cgctgtttct catactcacc tccctgttgt   7860
tgagcctaac gagcatgcta cttgggttga gtacgctgct aaccacacta ctaactgttc   7920
tccatcttgg tggtgtgatt ggtggatgtc ttaccttaac taccagatcg agcaccacct   7980
ttacccttct atgcctcaat tcagacaccc taagatcgct cctagagtta agcagctttt   8040
cgagaagcac ggacttcact acgatgttag aggatacttc gaggctatgg ctgatacttt   8100
cgctaacctt gataacgttg cccatgctcc tgagaagaaa atgcagtaat gagatcgttc   8160
aaacatttgg caataaagtt tcttaagatt gaatcctgtt gccggtcttg cgatgattat   8220
catataattt ctgttgaatt acgttaagca cgtaataatt aacatgtaat gcatgacgtt   8280
atttatgaga tgggttttta tgattagagt cccgcaatta tacatttaat acgcgataga   8340
aaacaaaata tagcgcgcaa actaggataa attatcgcgc gcggtgtcat ctatgttact   8400
agatcggtcg attaaaaatc ccaattatat ttggtctaat ttagtttggt attgagtaaa   8460
acaaattcga accaaaccaa aatataaata tatagttttt atatatatgc ctttaagact   8520
ttttatagaa ttttctttaa aaaatatcta gaaatatttg cgactcttct ggcatgtaat   8580
atttcgttaa atatgaagtg ctccattttt attaacttta aataattggt tgtacgatca   8640
```

```
ctttcttatc aagtgttact aaaatgcgtc aatctctttg ttcttccata ttcatatgtc   8700
aaaatctatc aaaattctta tatatctttt tcgaatttga agtgaaattt cgataattta   8760
aaattaaata gaacatatca ttatttaggt atcatattga tttttatact taattactaa   8820
atttggttaa ctttgaaagt gtacatcaac gaaaaattag tcaaacgact aaaataaata   8880
aatatcatgt gttattaaga aaattctcct ataagaatat tttaatagat catatgtttg   8940
taaaaaaaat taatttttac taacacatat atttacttat caaaaatttg acaaagtaag   9000
attaaaataa tattcatcta acaaaaaaaa aaccagaaaa tgctgaaaac ccggcaaaac   9060
cgaaccaatc caaaccgata tagttggttt ggtttgattt tgatataaac cgaaccaact   9120
cggtccattt gcacccctaa tcataatagc tttaatattt caagatatta ttaagttaac   9180
gttgtcaata tcctggaaat tttgcaaaat gaatcaagcc tatatggctg taatatgaat   9240
ttaaaagcag ctcgatgtgg tggtaatatg taatttactt gattctaaaa aaatatccca   9300
agtattaata atttctgcta ggaagaaggt tagctacgat ttacagcaaa gccagaatac   9360
aaagaaccat aaagtgattg aagctcgaaa tatacgaagg aacaaatatt tttaaaaaaa   9420
tacgcaatga cttggaacaa aagaaagtga tatatttttt gttcttaaac aagcatcccc   9480
tctaaagaat ggcagttttc ctttgcatgt aactattatg ctcccttcgt tacaaaaatt   9540
ttggactact attgggaact tcttctgaaa atagtgatag aacccacacg agcatgtgct   9600
ttccatttaa ttttaaaaac caagaaacat acatacataa cattccatca gcctctctct   9660
ctttttatta cggttaatga cttaaaacac atcttattat cccatcctta acacctagca   9720
gtgtctttat acgatctcat cgatcaccac ttcaaaacca tgcagactgc tgctgcccct   9780
ggagctggca tcggctaggc tgggtgccgc actgtcccgg aaggtcccta gcgacttgtt   9840
tagattgatg ggaccacctc tcaacttcct gctgctgtcc ctgctgctgg atgtcctgcc   9900
tcatctggcc gattgcacgc tccagtcccc tgcatgtgca ctcgctcctc aattgcttaa   9960
gatcatcgca gcagctatcg aagtgctggc tctgttgccc tcctccacgg ccttggttgt  10020
agtagtagct gccgccgccc ttctggactt tttcccacag gaaccgccga ataattcgat  10080
agaaccacac gagcatgtgc tttcatttat tttaaaaacc aagaaacata cataacattt  10140
catcagcctc tctctctctc tctctctctc tctctctctc tctctctctc tctctctctt  10200
tattacagct gttacactaa cttaaaacac attcatctca ttattattat tattatccat  10260
ccttaacacc tagcagtgtc tttgtacgat ctcataatcg atcacccctt catcaggtat  10320
ccttaggctt cactccaacg ttgttgcagt tacggaacat gtacacacca tcatggttct  10380
caacgaactg gcaagatctc caagttttcc aaaggctaac ccacatgttc tcatcggtgt  10440
gtctgtagtg ctctcccata actttcttga tgcactcggt agcttctcta gcatggtaga  10500
atgggatcct tgaaacgtag tgatggagca catgagtctc gatgatgtca tggaagatga  10560
ttccgaggat tccgaactct ctatcgatag tagcagcagc acccttagcg aaagtccact  10620
cttgagcatc gtaatgaggc atagaagaat cggtgtgctg aaggaaggta acgaaaacaa  10680
gccagtggtt aacaaggatc caaggacaga accatgtgat gaaagtaggc cagaatccga  10740
aaaccttgta agcggtgtaa acagaagtga gggtagcaag gattccaaga tcagaaagaa  10800
cgatgtacca gtagtccttc ttatcgaaaa cagggctaga aggccagtag tgagacttga  10860
agaacttaga aacaccaggg taaggttgtc cagtagcgtt agtagcaagg taaagagaaa  10920
gtcctccaag ctgttggaac aagagagcga aaacagagta gataggagtt tcctcagcga  10980
```

-continued

```
tatcgtgaag gctggtaact tggtgcttct ctttgaattc ctcggcggtg taaggaacga  11040
aaaccatatc tctggtcatg tgtccagtag ccttatggtg cttagcatga gagaacttcc  11100
agctgaagta aggaaccata acaagagagt ggagaaccca tccaacggta tcgttaaccc  11160
atccgtagtt agagaaagca gaatgtccac actcatgtcc aaggatccag attccgaatc  11220
cgaaacaaga gatagagaac acgtaagcag accaagcagc gaatctaagg aattcgttag  11280
ggagaagagg gatgtaggta agtccaacgt aagcgatagc agagatagcc acgatatctc  11340
tcaccacgta agacatagac ttcacgagag atctctcgta acagtgctta gggatagcgt  11400
caaggatatc cttgatggtg taatctggca ccttgaaaac gtttccgaag gtatcgatag  11460
cggtcttttg ctgcttgaaa gatgcaacgt ttccagaacg cctaacggtc ttagtagatc  11520
cctcaaggat ctcagatcca gacacggtaa ccttagacat ggtatggtaa ttgtaaatgt  11580
aattgtaatg ttgtttgttg tttgttgttg ttggtaattg ttgtaaaatt tttggtggtg  11640
attggttctt taaggtgtga gagtgagttg tgagttgtgt ggtgggtttg gtgagattgg  11700
ggatggtggg tttatatagt ggagactgag gaatggggtc gtgagtgtta actttgcatg  11760
ggctacacgt gggttctttt gggcttacac gtagtattat tcatgcaaat gcagccaata  11820
catatacggt attttaataa tgtgtgggaa tacaatatgc cgagtatttt actaattttg  11880
gcaatgacaa gtgtacattt ggattatctt acttggcctc tcttgcttta atttggatta  11940
tttttattct cttaccttgg ccgttcatat tcacatccct aaaggcaaga cagaattgaa  12000
tggtggccaa aaattaaaac gatggatatg acctacatag tgtaggatca attaacgtcg  12060
aaggaaaata ctgattctct caagcatacg gacaagggta aataacatag tcaccagaac  12120
ataataaaca aaaagtgcag aagcaagact aaaaaaatta gctatggaca ttcaggttca  12180
tattggaaac atcattatcc tagtcttgtg accatccttc ctcctgctct agttgagagg  12240
ccttgggact aacgagaggt cagttgggat agcagatcct tatcctggac tagcctttct  12300
ggtgtttcag agtcttcgtg ccgccgtcta catctatctc cattaggtct gaagatgact  12360
cttcacacca acgacgttta aggtctctat cctactccta gcttgcaata cctggcttgc  12420
aatacctgga gcatcgtgca cgatgattgg atactgtgga ggaggagtgt ttgctgattt  12480
agagctcccg gttgggtgat ttgacttcga tttcagttta ggcttgttga aatttttcag  12540
gttccattgt gaagccttta gagcttgagc ttccttccat gttaatgcct tgatcgaata  12600
ctcctagaga aaagggaagt cgatctctga gtattgaaat cgaagtgcac atttttttc  12660
aacgtgtcca atcaatccac aaacaaagca gaagacaggt aatctttcat acttatactg  12720
acaagtaata gtcttaccgt catgcataat aacgtctcgt tccttcaaga ggggttttcc  12780
gacatccata acgacccgaa gcctcatgaa agcattaggg aagaactttt ggttcttctt  12840
gtcatggcct ttataggtgt cagccgagct cgccaattcc cgtccgactg gctccgcaaa  12900
atattcgaac ggcaagttat ggacttgcaa ccataactcc acggtattga gcaggaccta  12960
ttgtgaagac tcatctcatg gagcttcaga atgtggttgt cagcaaacca atgaccgaaa  13020
tccatcacat gacggacgtc cagtgggtga gcgaaacgaa acaggaagcg cctatctttc  13080
agagtcgtga gctccacacc ggattccggc aactacgtgt tgggcaggct tcgccgtatt  13140
agagatatgt tgaggcagac ccatctgtgc cactcgtaca attacgagag ttgtttttt  13200
tgtgattttc ctagtttctc gttgatggtg agctcatatt ctacatcgta tggtctctca  13260
acgtcgtttc ctgtcatctg atatcccgtc atttgcatcc acgtgcgccg cctcccgtgc  13320
caagtcccta ggtgtcatgc acgccaaatt ggtggtggtg cgggctgccc tgtgcttctt  13380
```

accgatgggt ggaggttgag tttgggggtc tccgcggcga tggtagtggg ttgacggttt 13440
ggtgtgggtt gacggcattg atcaatttac ttcttgcttc aaattctttg gcagaaaaca 13500
attcattaga ttagaactgg aaaccagagt gatgagacgg attaagtcag attccaacag 13560
agttacatct cttaagaaat aatgtaaccc ctttagactt tatatatttg caattaaaaa 13620
aataatttaa cttttagact ttatatatag ttttaataac taagtttaac cactctatta 13680
tttatatcga aactatttgt atgtctcccc tctaaataaa cttggtattg tgtttacaga 13740
acctataatc aaataatcaa tactcaactg aagtttgtgc agttaattga agggattaac 13800
ggccaaaatg cactagtatt atcaaccgaa tagattcaca ctagatggcc atttccatca 13860
atatcatcgc cgttcttctt ctgtccacat atcccctctg aaacttgaga gacacctgca 13920
cttcattgtc cttattacgt gttacaaaat gaaacccatg catccatgca aactgaagaa 13980
tggcgcaaga acccttcccc tccatttctt atgtggcgac catccatttc accatctccc 14040
gctataaaac acccccatca cttcacctag aacatcatca ctacttgctt atccatccaa 14100
aagataccca cttttacaac aattaccaac aacaacaaac aacaaacaac attacaatta 14160
catttacaat taccatacca tgccacctag cgctgctaag caaatgggag cttctactgg 14220
tgttcatgct ggtgttactg actcttctgc tttcaccaga aaggatgttg ctgatagacc 14280
tgatctcacc atcgttggag attctgttta cgatgctaag gctttcagat ctgagcatcc 14340
tggtggtgct catttcgttt ctttgttcgg aggaagagat gctactgagg ctttcatgga 14400
ataccataga agggcttggc ctaagtctag aatgtctaga ttccacgttg gatctcttgc 14460
ttctactgag gaacctgttg ctgctgatga gggatacctt caactttgtg ctaggatcgc 14520
taagatggtg ccttctgttt cttctggatt cgctcctgct tcttactggg ttaaggctgg 14580
acttatcctt ggatctgcta tcgctcttga ggcttacatg ctttacgctg gaaagagact 14640
tctcccttct atcgttcttg gatggctttt cgctcttatc ggtcttaaca tccagcatga 14700
tgctaaccat ggtgctttgt ctaagtctgc ttctgttaac cttgctcttg gactttgtca 14760
ggattggatc ggaggatcta tgatcctttg gcttcaagag catgttgtta tgcaccacct 14820
ccacactaac gatgttgata aggatcctga tcaaaaggct cacggtgctc ttagactcaa 14880
gcctactgat gcttggtcac ctatgcattg gcttcagcat ctttaccttt tgcctggtga 14940
gactatgtac gctttcaagc ttttgttcct cgacatctct gagcttgtta tgtggcgttg 15000
ggagggtgag cctatctcta agcttgctgg atacctcttt atgccttctt tgcttctcaa 15060
gcttaccttc tgggctagat tcgttgcttt gcctctttac cttgctcctt ctgttcatac 15120
tgctgtgtgt atcgctgcta ctgttatgac tggatctttc tacctcgctt tcttcttctt 15180
catctcccac aacttcgagg gtgttgcttc tgttggacct gatggatcta tcacttctat 15240
gactagaggt gctagcttcc ttaagagaca agctgagact tcttctaacg ttggaggacc 15300
tcttcttgct actcttaacg gtggactcaa ctaccaaatt gagcatcact tgttccctag 15360
agttcaccat ggattctacc ctagacttgc tcctcttgtt aaggctgagc ttgaggctag 15420
aggaatcgag tacaagcact accctactat ctggtctaac cttgcttcta ccctcagaca 15480
tatgtacgct cttggaagaa ggcctagatc taaggctgag taatgacaag cttatgtgac 15540
gtgaaataat aacggtaaaa tatatgtaat aataataata ataaagccac aaagtgagaa 15600
tgaggggaag gggaaatgtg taatgagcca gtagccggtg gtgctaattt tgtatcgtat 15660
tgtcaataaa tcatgaattt tgtggttttt atgtgttttt ttaaatcatg aattttaaat 15720

-continued

```
tttataaaat aatctccaat cggaagaaca acattccata tccatgcatg gatgtttctt  15780
tacccaaatc tagttcttga gaggatgaag catcaccgaa cagttctgca actatccctc  15840
aaaagcttta aaatgaacaa caaggaacag agcaacgttc caaagatccc aaacgaaaca  15900
tattatctat actaatacta tattattaat tactactgcc cggaatcaca atccctgaat  15960
gattcctatt aactacaagc cttgttggcg gcggagaagt gatcggcgcg gcgagaagca  16020
gcggactcgg agacgaggcc ttggaagatc tgagtcgaac gggcagaatc agtattttcc  16080
ttcgacgtta attgatccta cactatgtag gtcatatcca tcgttttaat ttttggccac  16140
cattcaattc tgtcttgcct ttagggatgt gaatatgaac ggccaaggta agagaataaa  16200
aataatccaa attaaagcaa gagaggccaa gtaagataat ccaaatgtac acttgtcatt  16260
gccaaaatta gtaaaatact cggcatattg tattcccaca cattattaaa ataccgtata  16320
tgtattggct gcatttgcat gaataatact acgtgtaagc ccaaaagaac ccacgtgtag  16380
cccatgcaaa gttaacactc acgaccccat tcctcagtct ccactatata aacccaccat  16440
ccccaatctc accaaaccca ccacacaact cacaactcac tctcacacct taaagaacca  16500
atcaccacca aaaattttac aacaattacc aacaacaaca aacaacaaac aacattacaa  16560
ttacatttac aattaccata ccatgagcgc tgttaccgtt actggatctg atcctaagaa  16620
cagaggatct tctagcaaca ccgagcaaga ggttccaaaa gttgctatcg ataccaacgg  16680
aaacgtgttc tctgttcctg atttcaccat caaggacatc cttggagcta tccctcatga  16740
gtgttacgag agaagattgg ctacctctct ctactacgtg ttcagagata tcttctgcat  16800
gcttaccacc ggatacctta cccataagat cctttaccct ctcctcatct cttacacctc  16860
taacagcatc atcaagttca ctttctgggc cctttacact tacgttcaag gacttttcgg  16920
aaccggaatc tgggttctcg ctcatgagtg tggacatcaa gctttctctg attacggaat  16980
cgtgaacgat ttcgttggat ggacccttca ctcttacctt atggttcctt acttcagctg  17040
gaagtactct catggaaagc accataaggc tactggacac atgaccagag atatggtttt  17100
cgttcctgcc accaaagagg aattcaagaa gtctaggaac ttcttcggta acctcgctga  17160
gtactctgag gattctccac ttagaaccct ttacgagctt cttgttcaac aacttggagg  17220
atggatcgct tacctcttcg ttaacgttac aggacaacct taccctgatg ttccttcttg  17280
gaaatggaac cacttctggc ttacctctcc actttcgag caaagagatg ctctctacat  17340
cttcctttct gatcttggaa tcctcaccca gggaatcgtt cttactcttt ggtacaagaa  17400
attcggagga tggtcccttt tcatcaactg gttcgttcct tacatctggg ttaaccactg  17460
gctcgttttc atcacattcc ttcagcacac tgatcctact atgcctcatt acaacgctga  17520
ggaatggact ttcgctaagg gtgctgctgc tactatcgat agaaagttcg gattcatcgg  17580
acctcacatc ttccatgata tcatcgagac tcatgtgctt caccactact gttctaggat  17640
cccattctac aacgctagac ctgcttctga ggctatcaag aaagttatgg gaaagcacta  17700
caggtctagc gacgagaaca tgtggaagtc actttggaag tctttcaggt cttgccaata  17760
cgttgacggt gataacggtg ttctcatgtt ccgtaacatc aacaactgcg gagttggagc  17820
tgctgagaag taatgaaggg gtgatcgatt atgagatcgt acaaagacac tgctaggtgt  17880
taaggatgga taataataat aataatgaga tgaatgtgtt ttaagttagt gtaacagctg  17940
taataaagag agagagagag agagagagag agagagagag agagagagag agagagaggc  18000
tgatgaaatg ttatgtatgt ttcttggttt ttaaaataaa tgaaagcaca tgctcgtgtg  18060
gttctatcga attattcggc ggttcctgtg ggaaaaagtc cagaagggcc gccgcagcta  18120
```

ctactacaac caaggccgtg gaggagggca acagagccag cacttcgata gctgctgcga 18180
tgatcttaag caattgagga gcgagtgcac atgcagggga ctggagcgtg caatcggcca 18240
gatgaggcag gacatccagc agcagggaca gcagcaggaa gttgagaggt ggtcccatca 18300
atctaaacaa gtcgctaggg accttccggg acagtgcggc acccagccta gccgatgcca 18360
gctccagggg cagcagcagt ctgcatggtt ttgaagtggt gatcgatgag atcgtataaa 18420
gacactgcta ggtgttaagg atgggataat aagatgtgtt ttaagtcatt aaccgtaata 18480
aaaagagaga gaggctgatg gaatgttatg tatgtatgtt tcttggtttt taaaattaaa 18540
tggaaagcac atgctcgtgt gggttctatc tcgattaaaa atcccaatta tatttggtct 18600
aatttagttt ggtattgagt aaaacaaatt cgaaccaaac caaaatataa atatatagtt 18660
tttatatata tgcctttaag actttttata gaattttctt taaaaaatat ctagaaatat 18720
ttgcgactct tctggcatgt aatatttcgt taaatatgaa gtgctccatt tttattaact 18780
ttaaataatt ggttgtacga tcactttctt atcaagtgtt actaaaatgc gtcaatctct 18840
ttgttcttcc atattcatat gtcaaaatct atcaaaattc ttatatatct ttttcgaatt 18900
tgaagtgaaa tttcgataat ttaaaattaa atagaacata tcattattta ggtatcatat 18960
tgatttttat acttaattac taaatttggt taactttgaa agtgtacatc aacgaaaaat 19020
tagtcaaacg actaaaataa ataaatatca tgtgttatta agaaaattct cctataagaa 19080
tattttaata gatcatatgt ttgtaaaaaa aattaatttt tactaacaca tatatttact 19140
tatcaaaaat ttgacaaagt aagattaaaa taatattcat ctaacaaaaa aaaaaccaga 19200
aaatgctgaa aacccggcaa aaccgaacca atccaaaccg atatagttgg tttggtttga 19260
ttttgatata aaccgaacca actcggtcca tttgcacccc taatcataat agctttaata 19320
tttcaagata ttattaagtt aacgttgtca atatcctgga aattttgcaa aatgaatcaa 19380
gcctatatgg ctgtaatatg aatttaaaag cagctcgatg tggtggtaat atgtaattta 19440
cttgattcta aaaaaatatc ccaagtatta ataatttctg ctaggaagaa ggttagctac 19500
gatttacagc aaagccagaa tacaaagaac cataaagtga ttgaagctcg aaatatacga 19560
aggaacaaat atttttaaaa aaatacgcaa tgacttggaa caaaagaaag tgatatattt 19620
tttgttctta aacaagcatc ccctctaaag aatggcagtt ttcctttgca tgtaactatt 19680
atgctccctt cgttacaaaa attttggact actattggga acttcttctg aaaatagtcc 19740
tgcaggctag tagattggtt ggttggtttc catgtaccag aaggcttacc ctattagttg 19800
aaagttgaaa ctttgttccc tactcaattc ctagttgtgt aaatgtatgt atatgtaatg 19860
tgtataaaac gtagtactta aatgactagg agtggttctt gagaccgatg agagatggga 19920
gcagaactaa agatgatgac ataattaaga acgaatttga aaggctctta ggtttgaatc 19980
ctattcgaga atgtttttgt caaagatagt ggcgattttg aaccaaagaa aacatttaaa 20040
aaatcagtat ccggttacgt tcatgcaaat agaaagtggt ctaggatctg attgtaattt 20100
tagacttaaa gagtctctta agattcaatc ctggctgtgt acaaaactac aaataatata 20160
ttttagacta tttggcctta actaaacttc cactcattat ttactgaggt tagagaatag 20220
acttgcgaat aaacacattc ccgagaaata ctcatgatcc cataattagt cagagggtat 20280
gccaatcaga tctaagaaca cacattccct caaattttaa tgcacatgta atcatagttt 20340
agcacaattc aaaaataatg tagtattaaa gacagaaatt tgtagacttt tttttggcgt 20400
taaaagaaga ctaagtttat acgtacattt tattttaagt ggaaaaccga aattttccat 20460

```
cgaaatatat gaatttagta tatatatttc tgcaatgtac tattttgcta ttttggcaac  20520
tttcagtgga ctactacttt attacaatgt gtatggatgc atgagtttga gtatacacat  20580
gtctaaatgc atgctttgta aaacgtaacg gaccacaaaa gaggatccat acaaatacat  20640
ctcatagctt cctccattat tttccgacac aaacagagca ttttacaaca attaccaaca  20700
acaacaaaca acaaacaaca ttacaattac atttacaatt accataccat ggaatttgct  20760
caacctctcg ttgctatggc tcaagagcag tacgctgcta tcgatgctgt tgttgctcct  20820
gctatcttct ctgctaccga ctctattgga tggggactca agcctatctc ttctgctact  20880
aaggatctcc ctctcgttga atctcctacc cctcttatcc tttctctcct cgcttacttc  20940
gctatcgttg gttctggact cgtttaccgt aaagtgttcc ctagaaccgt taagggacag  21000
gatcctttcc ttctcaaggc tcttatgctc gctcacaacg ttttccttat cggactcagc  21060
ctttacatgt gcctcaagct cgtttacgag gcttacgtga acaagtactc cttctgggga  21120
aacgcttaca accctgctca aaccgagatg gctaaggtga tctggatctt ctacgtgtcc  21180
aagatctacg agttcatgga caccttcatc atgcttctca agggaaacgt taaccaggtt  21240
tccttcctcc atgtttacca ccacggatct atctctggaa tctggtggat gatcacttat  21300
gctgctccag gtggagatgc ttacttctct gctgctctca actcttgggt tcatgtgtgc  21360
atgtacacct actacttcat ggctgctgtt cttcctaagg acgaaaagac caagagaaag  21420
tacctttggt ggggaagata ccttacccag atgcaaatgt tccagttctt catgaacctt  21480
ctccaggctg tttacctcct ctactcttct tctccttacc ctaagttcat tgctcaactc  21540
ctcgttgttt acatggttac cctcctcatg cttttcggaa acttctacta catgaagcac  21600
cacgcttcta agtgataagg gccgccgcca tgtgacagat cgaaggaaga aagtgtaata  21660
agacgactct cactactcga tcgctagtga ttgtcattgt tatatataat aatgttatct  21720
ttcacaactt atcgtaatgc atgtgaaact ataacacatt aatcctactt gtcatatgat  21780
aacactctcc ccatttaaaa ctcttgtcaa tttaaagata taagattctt taaatgatta  21840
aaaaaaatat attataaatt caatcactcc tactaataaa ttattaatta ttatttattg  21900
attaaaaaaa tacttatact aatttagtct gaatagaata attagattct agcctgcagg  21960
gcggccgcgg atcccatgga gtcaaagatt caaatagagg acctaacaga actcgccgta  22020
aagactggcg aacagttcat acagagtctc ttacgactca atgacaagaa gaaaatcttc  22080
gtcaacatgg tggagcacga cacacttgtc tactccaaaa atatcaaaga tacagtctca  22140
gaagaccaaa gggcaattga gacttttcaa caaagggtaa tatccggaaa cctcctcgga  22200
ttccattgcc cagctatctg tcactttatt gtgaagatag tggaaaagga aggtggctcc  22260
tacaaatgcc atcattgcga taaaggaaag gccatcgttg aagatgcctc tgccgacagt  22320
ggtcccaaag atggaccccc acccacgagg agcatcgtgg aaaaagaaga cgttccaacc  22380
acgtcttcaa agcaagtgga ttgatgtgat atctccactg acgtaaggga tgacgcacaa  22440
tcccactatc cttcgcaaga cccttcctct atataaggaa gttcatttca tttggagaga  22500
acacggggga ctgaattaaa tatgagccct gagaggcgtc ctgttgaaat cagacctgct  22560
actgctgctg atatggctgc tgtttgtgat atcgtgaacc actacatcga gacttctacc  22620
gttaacttca gaactgagcc tcaaactcct caagagtgga tcgatgatct tgagagactc  22680
caagatagat acccttggct tgttgctgag gttgagggtg ttgttgctgg aatcgcttac  22740
gctggacctt ggaaggctag aaacgcttac gattggactg ttgagtctac cgtttacgtt  22800
tcacacagac atcagagact tggacttgga tctacccttt acactcacct tctcaagtct  22860
```

-continued

```
atggaagctc agggattcaa gtctgttgtt gctgttatcg gactccctaa cgatccttct  22920

gttagacttc atgaggctct tggatacact gctagaggaa ctcttagagc tgctggatac  22980

aagcacggtg gatggcatga tgttggattc tggcaaagag atttcgagct tcctgctcct  23040

cctagacctg ttagaccagt tactcagatc tgaatttgcg tgatcgttca aacatttggc  23100

aataaagttt cttaagattg aatcctgttg ccggtcttgc gatgattatc atataatttc  23160

tgttgaatta cgttaagcat gtaataatta acatgtaatg catgacgtta tttatgagat  23220

gggtttttat gattagagtc ccgcaattat acatttaata cgcgatagaa aacaaaatat  23280

agcgcgcaaa ctaggataaa ttatcgcgcg cggtgtcatc tatgttacta gatcactagt  23340

gatgtacggt taaaaccacc ccagtacatt aaaaacgtcc gcaatgtgtt attaagttgt  23400

ctaagcgtca atttgtttac accacaatat atcctgccac cagccagcca acagctcccc  23460

gaccggcagc tcggcacaaa atcaccactc gatacaggca gcccatcagt cc          23512
```

<210> SEQ ID NO 3
<211> LENGTH: 1254
<212> TYPE: DNA
<213> ORGANISM: Artificial Sequence
<220> FEATURE:
<223> OTHER INFORMATION: Codon-optimized open reading frame for
      expression of Lachancea kluyveri  12 desaturase in plants

<400> SEQUENCE: 3

```
atgagcgctg ttaccgttac tggatctgat cctaagaaca gaggatcttc tagcaacacc    60

gagcaagagg ttccaaaagt tgctatcgat accaacggaa acgtgttctc tgttcctgat   120

ttcaccatca aggacatcct tggagctatc cctcatgagt gttacgagag aagattggct   180

acctctctct actacgtgtt cagagatatc ttctgcatgc ttaccaccgg ataccttacc   240

cataagatcc tttaccctct cctcatctct tacacctcta acagcatcat caagttcact   300

ttctgggccc tttacactta cgttcaagga cttttcggaa ccggaatctg ggttctcgct   360

catgagtgtg gacatcaagc tttctctgat tacggaatcg tgaacgattt cgttggatgg   420

acccttcact cttaccttat ggttccttac ttcagctgga agtactctca tggaaagcac   480

cataaggcta ctggacacat gaccagagat atggttttcg ttcctgccac caaagaggaa   540

ttcaagaagt ctaggaactt cttcggtaac ctcgctgagt actctgagga ttctccactt   600

agaacccttt acgagcttct tgttcaacaa cttggaggat ggatcgctta cctcttcgtt   660

aacgttacag gacaacctta ccctgatgtt ccttcttgga aatggaacca cttctggctt   720

acctctccac ttttcgagca aagagatgct ctctacatct tcctttctga tcttggaatc   780

ctcacccagg gaatcgttct tactctttgg tacaagaaat tcggaggatg gtcccttttc   840

atcaactggt tcgttcctta catctgggtt aaccactggc tcgttttcat cacattcctt   900

cagcacactg atcctactat gcctcattac aacgctgagg aatggacttt cgctaagggt   960

gctgctgcta ctatcgatag aaagttcgga ttcatcggac ctcacatctt ccatgatatc  1020

atcgagactc atgtgcttca ccactactgt tctaggatcc cattctacaa cgctagacct  1080

gcttctgagg ctatcaagaa agttatggga aagcactaca ggtctagcga cgagaacatg  1140

tggaagtcac tttggaagtc tttcaggtct tgccaatacg ttgacggtga taacggtgtt  1200

ctcatgttcc gtaacatcaa caactgcgga gttggagctg ctgagaagta atga         1254
```

<210> SEQ ID NO 4
<211> LENGTH: 416

<212> TYPE: PRT
<213> ORGANISM: Lachancea kluyveri

<400> SEQUENCE: 4

```
Met Ser Ala Val Thr Val Thr Gly Ser Asp Pro Lys Asn Arg Gly Ser
1               5                   10                  15

Ser Ser Asn Thr Glu Gln Glu Val Pro Lys Val Ala Ile Asp Thr Asn
            20                  25                  30

Gly Asn Val Phe Ser Val Pro Asp Phe Thr Ile Lys Asp Ile Leu Gly
        35                  40                  45

Ala Ile Pro His Glu Cys Tyr Glu Arg Arg Leu Ala Thr Ser Leu Tyr
    50                  55                  60

Tyr Val Phe Arg Asp Ile Phe Cys Met Leu Thr Thr Gly Tyr Leu Thr
65                  70                  75                  80

His Lys Ile Leu Tyr Pro Leu Leu Ile Ser Tyr Thr Ser Asn Ser Ile
                85                  90                  95

Ile Lys Phe Thr Phe Trp Ala Leu Tyr Thr Tyr Val Gln Gly Leu Phe
            100                 105                 110

Gly Thr Gly Ile Trp Val Leu Ala His Glu Cys Gly His Gln Ala Phe
        115                 120                 125

Ser Asp Tyr Gly Ile Val Asn Asp Phe Val Gly Trp Thr Leu His Ser
    130                 135                 140

Tyr Leu Met Val Pro Tyr Phe Ser Trp Lys Tyr Ser His Gly Lys His
145                 150                 155                 160

His Lys Ala Thr Gly His Met Thr Arg Asp Met Val Phe Val Pro Ala
                165                 170                 175

Thr Lys Glu Glu Phe Lys Lys Ser Arg Asn Phe Phe Gly Asn Leu Ala
            180                 185                 190

Glu Tyr Ser Glu Asp Ser Pro Leu Arg Thr Leu Tyr Glu Leu Leu Val
        195                 200                 205

Gln Gln Leu Gly Gly Trp Ile Ala Tyr Leu Phe Val Asn Val Thr Gly
    210                 215                 220

Gln Pro Tyr Pro Asp Val Pro Ser Trp Lys Trp Asn His Phe Trp Leu
225                 230                 235                 240

Thr Ser Pro Leu Phe Glu Gln Arg Asp Ala Leu Tyr Ile Phe Leu Ser
                245                 250                 255

Asp Leu Gly Ile Leu Thr Gln Gly Ile Val Leu Thr Leu Trp Tyr Lys
            260                 265                 270

Lys Phe Gly Gly Trp Ser Leu Phe Ile Asn Trp Phe Val Pro Tyr Ile
        275                 280                 285

Trp Val Asn His Trp Leu Val Phe Ile Thr Phe Leu Gln His Thr Asp
    290                 295                 300

Pro Thr Met Pro His Tyr Asn Ala Glu Glu Trp Thr Phe Ala Lys Gly
305                 310                 315                 320

Ala Ala Ala Thr Ile Asp Arg Lys Phe Gly Phe Ile Gly Pro His Ile
                325                 330                 335

Phe His Asp Ile Ile Glu Thr His Val Leu His His Tyr Cys Ser Arg
            340                 345                 350

Ile Pro Phe Tyr Asn Ala Arg Pro Ala Ser Glu Ala Ile Lys Lys Val
        355                 360                 365

Met Gly Lys His Tyr Arg Ser Ser Asp Glu Asn Met Trp Lys Ser Leu
    370                 375                 380

Trp Lys Ser Phe Arg Ser Cys Gln Tyr Val Asp Gly Asp Asn Gly Val
385                 390                 395                 400
```

```
Leu Met Phe Arg Asn Ile Asn Asn Cys Gly Val Gly Ala Ala Glu Lys
                405                 410                 415


<210> SEQ ID NO 5
<211> LENGTH: 1251
<212> TYPE: DNA
<213> ORGANISM: Pichia pastoris

<400> SEQUENCE: 5

atgtctaagg ttaccgtgtc tggatctgag atccttgagg gatctactaa gaccgttagg     60

cgttctggaa acgttgcatc tttcaagcag caaaagaccg ctatcgatac cttcggaaac    120

gttttcaagg tgccagatta caccatcaag gatatccttg acgctatccc taagcactgt    180

tacgagagat ctctcgtgaa gtctatgtct tacgtggtga gagatatcgt ggctatctct    240

gctatcgctt acgttggact tacctacatc cctcttctcc ctaacgaatt ccttagattc    300

gctgcttggt ctgcttacgt gttctctatc tcttgtttcg gattcggaat ctggatcctt    360

ggacatgagt gtggacattc tgctttctct aactacggat gggttaacga taccgttgga    420

tgggttctcc actctcttgt tatggttcct tacttcagct ggaagttctc tcatgctaag    480

caccataagg ctactggaca catgaccaga gatatggttt tcgttcctta caccgccgag    540

gaattcaaag agaagcacca agttaccagc cttcacgata tcgctgagga aactcctatc    600

tactctgttt tcgctctctt gttccaacag cttggaggac tttctcttta ccttgctact    660

aacgctactg gacaacctta ccctggtgtt tctaagttct tcaagtctca ctactggcct    720

tctagccctg ttttcgataa gaaggactac tggtacatcg ttctttctga tcttggaatc    780

cttgctaccc tcacttctgt ttacaccgct tacaaggttt tcggattctg gcctactttc    840

atcacatggt tctgtccttg gatccttgtt aaccactggc ttgttttcgt taccttcctt    900

cagcacaccg attcttctat gcctcattac gatgctcaag agtggacttt cgctaagggt    960

gctgctgcta ctatcgatag agagttcgga atcctcggaa tcatcttcca tgacatcatc   1020

gagactcatg tgctccatca ctacgtttca aggatcccat tctaccatgc tagagaagct   1080

accgagtgca tcaagaaagt tatgggagag cactacagac acaccgatga gaacatgtgg   1140

gttagccttt ggaaaacttg gagatcttgc cagttcgttg agaaccatga tggtgtgtac   1200

atgttccgta actgcaacaa cgttggagtg aagcctaagg atacctgatg a            1251


<210> SEQ ID NO 6
<211> LENGTH: 415
<212> TYPE: PRT
<213> ORGANISM: Pichia pastoris

<400> SEQUENCE: 6

Met Ser Lys Val Thr Val Ser Gly Ser Glu Ile Leu Glu Gly Ser Thr
1               5                   10                  15

Lys Thr Val Arg Arg Ser Gly Asn Val Ala Ser Phe Lys Gln Gln Lys
            20                  25                  30

Thr Ala Ile Asp Thr Phe Gly Asn Val Phe Lys Val Pro Asp Tyr Thr
        35                  40                  45

Ile Lys Asp Ile Leu Asp Ala Ile Pro Lys His Cys Tyr Glu Arg Ser
    50                  55                  60

Leu Val Lys Ser Met Ser Tyr Val Val Arg Asp Ile Val Ala Ile Ser
65                  70                  75                  80

Ala Ile Ala Tyr Val Gly Leu Thr Tyr Ile Pro Leu Leu Pro Asn Glu
                85                  90                  95
```

```
Phe Leu Arg Phe Ala Ala Trp Ser Ala Tyr Val Phe Ser Ile Ser Cys
            100                 105                 110

Phe Gly Phe Gly Ile Trp Ile Leu Gly His Glu Cys Gly His Ser Ala
        115                 120                 125

Phe Ser Asn Tyr Gly Trp Val Asn Asp Thr Val Gly Trp Val Leu His
    130                 135                 140

Ser Leu Val Met Val Pro Tyr Phe Ser Trp Lys Phe Ser His Ala Lys
145                 150                 155                 160

His His Lys Ala Thr Gly His Met Thr Arg Asp Met Val Phe Val Pro
                165                 170                 175

Tyr Thr Ala Glu Glu Phe Lys Glu Lys His Gln Val Thr Ser Leu His
            180                 185                 190

Asp Ile Ala Glu Glu Thr Pro Ile Tyr Ser Val Phe Ala Leu Leu Phe
        195                 200                 205

Gln Gln Leu Gly Gly Leu Ser Leu Tyr Leu Ala Thr Asn Ala Thr Gly
    210                 215                 220

Gln Pro Tyr Pro Gly Val Ser Lys Phe Phe Lys Ser His Tyr Trp Pro
225                 230                 235                 240

Ser Ser Pro Val Phe Asp Lys Lys Asp Tyr Trp Tyr Ile Val Leu Ser
                245                 250                 255

Asp Leu Gly Ile Leu Ala Thr Leu Thr Ser Val Tyr Thr Ala Tyr Lys
            260                 265                 270

Val Phe Gly Phe Trp Pro Thr Phe Ile Thr Trp Phe Cys Pro Trp Ile
        275                 280                 285

Leu Val Asn His Trp Leu Val Phe Val Thr Phe Leu Gln His Thr Asp
    290                 295                 300

Ser Ser Met Pro His Tyr Asp Ala Gln Glu Trp Thr Phe Ala Lys Gly
305                 310                 315                 320

Ala Ala Ala Thr Ile Asp Arg Glu Phe Gly Ile Leu Gly Ile Ile Phe
                325                 330                 335

His Asp Ile Ile Glu Thr His Val Leu His His Tyr Val Ser Arg Ile
            340                 345                 350

Pro Phe Tyr His Ala Arg Glu Ala Thr Glu Cys Ile Lys Lys Val Met
        355                 360                 365

Gly Glu His Tyr Arg His Thr Asp Glu Asn Met Trp Val Ser Leu Trp
    370                 375                 380

Lys Thr Trp Arg Ser Cys Gln Phe Val Glu Asn His Asp Gly Val Tyr
385                 390                 395                 400

Met Phe Arg Asn Cys Asn Asn Val Gly Val Lys Pro Lys Asp Thr
                405                 410                 415
```

<210> SEQ ID NO 7
<211> LENGTH: 1392
<212> TYPE: DNA
<213> ORGANISM: Micromonas pusilla

<400> SEQUENCE: 7

```
atgtgcccgc cgaagacgga cggccgatcg tccccgcgat cgccgctgac gcgcagcaaa      60

tcctccgcgg aggcgctcga cgccaaggac gcgtcgaccg cgcccgtcga tctcaaaacg     120

ctcgagccgc acgagctcgc ggcgacgttc gagacgcgat gggtgcgcgt ggaggacgtc     180

gagtacgacg tcacaaactt caaacacccg ggaggcagcg tgatattcta catgctcgcg     240

aacacgggcg cggacgccac ggaggcgttc aaggagttcc acatgcgatc gcttaaggcg     300
```

-continued

```
tggaagatgc tcagagcgct gccgtcgcgc cccgcggaga tcaaacgcag cgagagcgag    360

gacgcgccga tgttggagga tttcgcgcgg tggcgcgcgg agctcgaacg cgacgggttc    420

tttaagccct cgataacgca cgtcgcgtat cggttactcg agctcctcgc gaccttcgcc    480

ctcggcaccg ccctcatgta cgccgggtac ccgatcatcg cgtccgtcgt gtacggcgcg    540

ttcttcggcg ctcggtgcgg ttgggtccag cacgagggcg ggcacaactc gctcacgggg    600

tccgtctacg tcgacaagcg cctccaagcg atgacgtgcg ggttcgggct gtccacgagc    660

ggggagatgt ggaaccagat gcacaataag caccacgcga cgccgcagaa agtgaggcac    720

gacatggacc tggacacgac cccgcggtg gcgtttttta acaccgccgt ggaggacaac    780

cggccgaggg ggttctcccg cgcgtgggct cggcttcagg cgtggacgtt cgtcccggtg    840

acctccgggc tgctcgtcca ggcgttctgg atctacgtcc tgcacccgcg gcaggtgttg    900

cgaaagaaga actacgagga ggcgtcgtgg atgctcgtct ctcacgtcgt caggaccgcg    960

gtgattaaac tcgcgacggg gtactcgtgg cccgtcgcgt actggtggtt caccttcggc   1020

aactggatcg cgtacatgta cctcttcgcg cacttctcca cgagccacac gcacctcccg   1080

gtcgtgccct cggataagca cctgagctgg gtgaactacg cggtcgatca caccgtggac   1140

atcgacccgt cgcgcgggta cgtgaactgg ttgatgggat atctgaactg ccaggtcatt   1200

catcacctgt tcccggacat gccgcagttt cgccagccgg aggtgagccg gcggttcgtc   1260

ccgttcgcga agaagtgggg gctgaactac aaggtgctgt cctattacgg cgcctggaag   1320

gcgacgttct cgaacttgga taaggtcggg cagcactact acgtcaacgg caaggcggag   1380

aaggcgcact ga                                                       1392
```

<210> SEQ ID NO 8
<211> LENGTH: 1395
<212> TYPE: DNA
<213> ORGANISM: Artificial Sequence
<220> FEATURE:
<223> OTHER INFORMATION: Codon-optimized open reading frame for expression of Micromonas pusilla  6 desaturase in plants (version 1)

<400> SEQUENCE: 8

```
atgtgccctc ctaagactga tggaagatct tctcctagat ctccacttac caggtctaaa     60

tcttctgctg aggctcttga tgctaaggat gcttctactg ctcctgttga tcttaagact    120

cttgagcctc atgagcttgc tgctactttc gagactagat gggttagagt tgaggacgtt    180

gagtacgatg tgactaactt caagcaccct ggtggatctg tgatcttcta catgcttgct    240

aacactggtg ctgatgctac tgaggctttc aaagaattcc acatgcgttc tctcaaggct    300

tggaagatgc ttagagcttt gccttctaga cctgctgaga tcaagagatc tgagtctgag    360

gatgctccta tgcttgagga tttcgctaga tggcgtgctg agcttgagag agatggattc    420

ttcaagcctt ctatcaccca tgtggcttac agacttctcg agcttcttgc tacattcgct    480

cttggaactg ctcttatgta cgctggatac cctatcattg cttctgttgt ttacggtgct    540

ttcttcggag ctagatgtgg atgggttcaa catgagggtg gacataactc tcttaccgga    600

tctgtttacg tggacaagag acttcaggct atgacttgtg gattcggact ttctacttct    660

ggtgagatgt ggaaccagat gcataacaag caccatgcta cccctcaaaa ggttagacac    720

gatatggatc ttgataccac tcctgctgtg gctttcttca acactgctgt tgaggataac    780

agacctagag gattctctag agcttgggct agacttcaag cttggacttt cgttcctgtt    840

acctctggac ttcttgttca agctttctgg atctacgttc tccaccctag acaagttctc    900
```

-continued

```
cgtaagaaga actacgaaga ggcttcttgg atgctcgttt ctcatgttgt tagaaccgct    960

gttatcaagc ttgctactgg atactcttgg cctgttgctt actggtggtt cactttcgga   1020

aactggatcg cttacatgta ccttttcgct cacttctcta cttctcatac tcacctccct   1080

gttgttccat ctgataagca cctttcttgg gttaactacg ctgttgatca caccgttgat   1140

atcgatcctt ctagaggata cgtgaactgg cttatgggat accttaactg tcaggttatc   1200

caccacctct tccctgatat gcctcaattc agacagcctg aggttagcag aagattcgtt   1260

cctttcgcta agaagtgggg actcaactac aaggtgctct cttactacgg tgcttggaag   1320

gctactttct ctaaccttga taaggtggga cagcactact acgttaacgg aaaggctgag   1380

aaggctcact aatga                                                    1395
```

```
<210> SEQ ID NO 9
<211> LENGTH: 463
<212> TYPE: PRT
<213> ORGANISM: Micromonas pusilla

<400> SEQUENCE: 9

Met Cys Pro Pro Lys Thr Asp Gly Arg Ser Ser Pro Arg Ser Pro Leu
1               5                   10                  15

Thr Arg Ser Lys Ser Ser Ala Glu Ala Leu Asp Ala Lys Asp Ala Ser
            20                  25                  30

Thr Ala Pro Val Asp Leu Lys Thr Leu Glu Pro His Glu Leu Ala Ala
        35                  40                  45

Thr Phe Glu Thr Arg Trp Val Arg Val Glu Asp Val Glu Tyr Asp Val
    50                  55                  60

Thr Asn Phe Lys His Pro Gly Gly Ser Val Ile Phe Tyr Met Leu Ala
65                  70                  75                  80

Asn Thr Gly Ala Asp Ala Thr Glu Ala Phe Lys Glu Phe His Met Arg
                85                  90                  95

Ser Leu Lys Ala Trp Lys Met Leu Arg Ala Leu Pro Ser Arg Pro Ala
            100                 105                 110

Glu Ile Lys Arg Ser Glu Ser Glu Asp Ala Pro Met Leu Glu Asp Phe
        115                 120                 125

Ala Arg Trp Arg Ala Glu Leu Glu Arg Asp Gly Phe Phe Lys Pro Ser
    130                 135                 140

Ile Thr His Val Ala Tyr Arg Leu Leu Glu Leu Leu Ala Thr Phe Ala
145                 150                 155                 160

Leu Gly Thr Ala Leu Met Tyr Ala Gly Tyr Pro Ile Ile Ala Ser Val
                165                 170                 175

Val Tyr Gly Ala Phe Phe Gly Ala Arg Cys Gly Trp Val Gln His Glu
            180                 185                 190

Gly Gly His Asn Ser Leu Thr Gly Ser Val Tyr Val Asp Lys Arg Leu
        195                 200                 205

Gln Ala Met Thr Cys Gly Phe Gly Leu Ser Thr Ser Gly Glu Met Trp
    210                 215                 220

Asn Gln Met His Asn Lys His His Ala Thr Pro Gln Lys Val Arg His
225                 230                 235                 240

Asp Met Asp Leu Asp Thr Thr Pro Ala Val Ala Phe Phe Asn Thr Ala
                245                 250                 255

Val Glu Asp Asn Arg Pro Arg Gly Phe Ser Arg Ala Trp Ala Arg Leu
            260                 265                 270

Gln Ala Trp Thr Phe Val Pro Val Thr Ser Gly Leu Leu Val Gln Ala
```

```
        275                 280                 285

Phe Trp Ile Tyr Val Leu His Pro Arg Gln Val Leu Arg Lys Lys Asn
    290                 295                 300

Tyr Glu Glu Ala Ser Trp Met Leu Val Ser His Val Val Arg Thr Ala
305                 310                 315                 320

Val Ile Lys Leu Ala Thr Gly Tyr Ser Trp Pro Val Ala Tyr Trp Trp
                325                 330                 335

Phe Thr Phe Gly Asn Trp Ile Ala Tyr Met Tyr Leu Phe Ala His Phe
            340                 345                 350

Ser Thr Ser His Thr His Leu Pro Val Val Pro Ser Asp Lys His Leu
        355                 360                 365

Ser Trp Val Asn Tyr Ala Val Asp His Thr Val Asp Ile Asp Pro Ser
    370                 375                 380

Arg Gly Tyr Val Asn Trp Leu Met Gly Tyr Leu Asn Cys Gln Val Ile
385                 390                 395                 400

His His Leu Phe Pro Asp Met Pro Gln Phe Arg Gln Pro Glu Val Ser
                405                 410                 415

Arg Arg Phe Val Pro Phe Ala Lys Lys Trp Gly Leu Asn Tyr Lys Val
            420                 425                 430

Leu Ser Tyr Tyr Gly Ala Trp Lys Ala Thr Phe Ser Asn Leu Asp Lys
        435                 440                 445

Val Gly Gln His Tyr Tyr Val Asn Gly Lys Ala Glu Lys Ala His
    450                 455                 460


<210> SEQ ID NO 10
<211> LENGTH: 1449
<212> TYPE: DNA
<213> ORGANISM: Ostreococcus lucimarinus

<400> SEQUENCE: 10

atgtgcgtcg aaacgaccga aggcacatcg cgaacgatgg cgaacgaacg cacgagctcg      60

tcgtcgtcgc tgagcgaagg cggaacgccg acggtgacgg tcgggatggg aagcgaagac     120

gcggggaaga agactcgaaa cgcgagcgtc acggcgtgga cgaaagagtt ggagccgcac     180

gcgatcgcga agacgttcga acggcggtac gtgacgatcg aaggcgtgga atacgatgtg     240

acggatttta agcatcccgg aggatcggtt atttattaca tgctgtcgaa cacgggagcg     300

gacgcgacgg aggcttttaa agagtttcat tatcggtcga aaaaggcgcg caaggcgttg     360

gcggcgttgc cgcataagcc agtggacgcg gcgacgcggg aaccgatcga agatgaggcg     420

atgctgaagg atttcgcgca gtggcgcaag gaattggagc gtgagggatt ttttaagccc     480

tcgccggcgc acgtggcgta tcgattcgcc gagctcgcgg cgatgttcgc gctcggcacg     540

gcgttgatgc acgcgcgttg gcacgtcgct tccgtgatcg tgtactcgtg tttcttcggc     600

gcgcgatgcg gttgggtgca gcacgagggt gggcacaatt cgttgactgg aaacatttgg     660

tgggacaagc gaatccaagc cttcgccgcg gggttcggct tggcgtcgag tggcgacatg     720

tggaacaaca tgcacaacaa gcatcacgcg acgccccaaa aggtgcgaca cgatatggat     780

ctcgacacca ctcccacggt ggcgttcttc aactccgcgg ttgaagaaaa tcgcccgcgg     840

ggattcagta agttgtggtt gcgccttcaa gcgtggacct tcgtgcccgt gacgtccggt     900

atggttttgt tcttctggat gttcgtcttg cacccgcgta acgcgctgcg acgcaaaagc     960

ttcgaagaag cggcttggat gttttccgcg cacgtcattc gcacggcggt tatcaaagcc    1020

gtcaccggct actcctggat cgcctcgtac ggcttgttcg cggcgacgat gtgggcgagc    1080
```

```
ggatgttact tgttcgcgca cttttccacg tctcacacgc acttggatgt cgtgccgagc   1140

gataaacacc tctcgtgggt gcgatacgcc gtcgatcaca cgatcgacat caatccgaac   1200

aacagcgtcg tcaactggtt gatgggctac ttgaactgcc aagtcatcca tcacctgttc   1260

ccggatatgc ctcagttccg ccaacccgaa gtctcccgcc gattcgtccc gtttgcgaag   1320

aagtggaact taaactacaa ggtcttgacg tattatgggg cctggaaggc gacgttcggc   1380

aacttgaacg acgtcgggaa gcactattac gtgcacggat ctcagcgcgt caaatcaaag   1440

tcggcgtga                                                           1449
```

<210> SEQ ID NO 11
<211> LENGTH: 1449
<212> TYPE: DNA
<213> ORGANISM: Artificial Sequence
<220> FEATURE:
<223> OTHER INFORMATION: Codon-optimized open reading frame for
expression of Ostreococcus lucimarinus 6-desaturase in plants

<400> SEQUENCE: 11

```
atgtgtgttg agactactga gggaacctct agaactatgg ctaacgagag gacctcttct     60

tcttcttcac tctctgaggg tggaactcct actgttactg tgggaatggg atctgaggat    120

gctggaaaga aaaccagaaa cgcttctgtt actgcttgga ccaaagagct tgagcctcac    180

gctatcgcta agaccttcga gagaagatac gttaccatcg agggtgttga gtacgatgtg    240

accgatttca aacaccctgg tggatctgtg atctactaca tgctctctaa cactggtgct    300

gatgctactg aggctttcaa agagttccac taccgttcta agaaggctag aaaggctctt    360

gctgctcttc ctcacaagcc tgttgatgct gctactagag agcctattga ggacgaggct    420

atgcttaagg atttcgctca gtggagaaaa gagttggaga gagagggatt cttcaagcct    480

tctcctgctc atgttgctta ccgtttcgct gaactcgctg ctatgttcgc tcttggaacc    540

gctcttatgc atgctagatg gcacgttgct agcgttatcg tgtactcctg tttcttcgga    600

gctagatgtg gatgggttca acatgagggt ggacacaact ctcttaccgg aaacatctgg    660

tgggataaga gaatccaagc tttcgctgct ggattcggac ttgcttcttc tggtgacatg    720

tggaacaaca tgcacaacaa gcaccatgct actcctcaga aagtgagaca cgatatggat    780

cttgatacca cccctaccgt tgctttcttc aactctgctg tggaggaaaa cagacctagg    840

ggattctcta agctttggct cagacttcaa gcttggacct tcgttcctgt tacctctgga    900

atggtgctct tcttctggat gttcgttctc catcctagaa acgctctccg tcgtaagtct    960

ttcgaagagg ctgcttggat gttctctgct cacgttatca gaaccgctgt tatcaaggct   1020

gttaccggat actcttggat cgctagctac ggacttttcg ctgctactat gtgggcttct   1080

ggatgctacc ttttcgctca cttctctact tctcacaccc acctcgatgt tgttccatct   1140

gataagcacc ttagctgggt taggtacgct gttgatcaca ccatcgacat caaccctaac   1200

aactctgttg tgaactggct tatgggatac cttaactgcc aggttatcca ccatctcttc   1260

cctgatatgc ctcaattcag acagcctgag gtgtcaagaa gattcgtccc tttcgctaag   1320

aagtggaacc tcaactacaa ggtgctcact tactacggtg cttggaaggc tactttcgga   1380

aacctcaacg atgttggaaa gcactactac gttcacggat ctcagagagt gaagagcaag   1440

agcgcttga                                                           1449
```

<210> SEQ ID NO 12
<211> LENGTH: 482
<212> TYPE: PRT

<213> ORGANISM: Ostreococcus lucimarinus

<400> SEQUENCE: 12

```
Met Cys Val Glu Thr Thr Glu Gly Thr Ser Arg Thr Met Ala Asn Glu
1               5                   10                  15

Arg Thr Ser Ser Ser Ser Ser Leu Ser Glu Gly Gly Thr Pro Thr Val
            20                  25                  30

Thr Val Gly Met Gly Ser Glu Asp Ala Gly Lys Lys Thr Arg Asn Ala
        35                  40                  45

Ser Val Thr Ala Trp Thr Lys Glu Leu Glu Pro His Ala Ile Ala Lys
    50                  55                  60

Thr Phe Glu Arg Arg Tyr Val Thr Ile Glu Gly Val Glu Tyr Asp Val
65                  70                  75                  80

Thr Asp Phe Lys His Pro Gly Gly Ser Val Ile Tyr Tyr Met Leu Ser
                85                  90                  95

Asn Thr Gly Ala Asp Ala Thr Glu Ala Phe Lys Glu Phe His Tyr Arg
            100                 105                 110

Ser Lys Lys Ala Arg Lys Ala Leu Ala Ala Leu Pro His Lys Pro Val
        115                 120                 125

Asp Ala Ala Thr Arg Glu Pro Ile Glu Asp Glu Ala Met Leu Lys Asp
    130                 135                 140

Phe Ala Gln Trp Arg Lys Glu Leu Glu Arg Glu Gly Phe Phe Lys Pro
145                 150                 155                 160

Ser Pro Ala His Val Ala Tyr Arg Phe Ala Glu Leu Ala Ala Met Phe
                165                 170                 175

Ala Leu Gly Thr Ala Leu Met His Ala Arg Trp His Val Ala Ser Val
            180                 185                 190

Ile Val Tyr Ser Cys Phe Phe Gly Ala Arg Cys Gly Trp Val Gln His
        195                 200                 205

Glu Gly Gly His Asn Ser Leu Thr Gly Asn Ile Trp Trp Asp Lys Arg
    210                 215                 220

Ile Gln Ala Phe Ala Ala Gly Phe Gly Leu Ala Ser Ser Gly Asp Met
225                 230                 235                 240

Trp Asn Asn Met His Asn Lys His His Ala Thr Pro Gln Lys Val Arg
                245                 250                 255

His Asp Met Asp Leu Asp Thr Thr Pro Thr Val Ala Phe Phe Asn Ser
            260                 265                 270

Ala Val Glu Glu Asn Arg Pro Arg Gly Phe Ser Lys Leu Trp Leu Arg
        275                 280                 285

Leu Gln Ala Trp Thr Phe Val Pro Val Thr Ser Gly Met Val Leu Phe
    290                 295                 300

Phe Trp Met Phe Val Leu His Pro Arg Asn Ala Leu Arg Arg Lys Ser
305                 310                 315                 320

Phe Glu Glu Ala Ala Trp Met Phe Ser Ala His Val Ile Arg Thr Ala
                325                 330                 335

Val Ile Lys Ala Val Thr Gly Tyr Ser Trp Ile Ala Ser Tyr Gly Leu
            340                 345                 350

Phe Ala Ala Thr Met Trp Ala Ser Gly Cys Tyr Leu Phe Ala His Phe
        355                 360                 365

Ser Thr Ser His Thr His Leu Asp Val Val Pro Ser Asp Lys His Leu
    370                 375                 380

Ser Trp Val Arg Tyr Ala Val Asp His Thr Ile Asp Ile Asn Pro Asn
385                 390                 395                 400
```

```
Asn Ser Val Val Asn Trp Leu Met Gly Tyr Leu Asn Cys Gln Val Ile
                405                 410                 415

His His Leu Phe Pro Asp Met Pro Gln Phe Arg Gln Pro Glu Val Ser
            420                 425                 430

Arg Arg Phe Val Pro Phe Ala Lys Lys Trp Asn Leu Asn Tyr Lys Val
        435                 440                 445

Leu Thr Tyr Tyr Gly Ala Trp Lys Ala Thr Phe Gly Asn Leu Asn Asp
    450                 455                 460

Val Gly Lys His Tyr Tyr Val His Gly Ser Gln Arg Val Lys Ser Lys
465                 470                 475                 480

Ser Ala


<210> SEQ ID NO 13
<211> LENGTH: 456
<212> TYPE: PRT
<213> ORGANISM: Ostreococcus tauri

<400> SEQUENCE: 13

Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285
```

-continued

```
Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
            420                 425                 430

Ala Thr Leu Gly Asn Leu Asp Asn Val Gly Lys His Tyr Tyr Val His
        435                 440                 445

Gly Gln His Ser Gly Lys Thr Ala
    450                 455
```

<210> SEQ ID NO 14
<211> LENGTH: 894
<212> TYPE: DNA
<213> ORGANISM: Pyramimonas cordata

<400> SEQUENCE: 14

```
atggagttcg ctcagcctct tgtggctatg gcacaggagc agtatgccgc aattgacgcg     60

gtggtagccc ctgcaatttt ctcagctacc gacagcatcg gttggggtct taagcccatt    120

agcagcgcga caaaggatct tcctctcgtt gagagtccga cgccgctcat actgagcctg    180

ttggcctatt ttgcgatcgt cggctctggg ctggtgtacc gcaaagtatt ccctcgcaca    240

gtaaaggggc aagacccctt cctgctgaag gcgctcatgc ttgcgcacaa cgtgttcctc    300

attggcctca gtctatacat gtgcttgaag cttgtctacg aggcttacgt caacaagtac    360

tccttctggg gaaacgccta caaccccgca cagaccgaga tggcgaaggt catctggatt    420

ttctacgtct ccaagatcta tgagttcatg gacacgttca tcatgctctt gaagggcaac    480

gtcaaccagg tctctttcct gcatgtgtac catcatggct ccatctctgg tatctggtgg    540

atgatcacct acgctgcccc tggcggtgac gcgtacttct cggcggcgct caactcgtgg    600

gtgcacgtgt gcatgtacac gtactacttc atggcggcgg tgctgcccaa ggacgagaag    660

accaagcgca agtacctctg gtggggccgc tacctgaccc agatgcagat gttccagttc    720

ttcatgaacc tgctccaggc ggtctacctc ctctactcct ctagccccta ccccaagttc    780

atcgcccagc tgctggtggt gtacatggtc acgctgctga tgctcttcgg caacttctac    840

tacatgaagc accacgcgag caagaagcag aagctggcca gcaagaagca gtag          894
```

<210> SEQ ID NO 15
<211> LENGTH: 870
<212> TYPE: DNA
<213> ORGANISM: Artificial Sequence
<220> FEATURE:
<223> OTHER INFORMATION: Codon-optimized open reading frame for
      expression of Pyramimonas cordata  6 elongase in plants (truncated at 3' end and encoding functional elongase) (version 1)

<400> SEQUENCE: 15
atggaattcg cccagcctct tgttgctatg gctcaagagc aatacgctgc tatcgatgct 60
gttgttgctc ctgctatctt ctctgctact gattctatcg gatggggact taagcctatc 120
tcttctgcta ctaaggactt gcctcttgtt gagtctccta cacctctcat cctttctttg 180
cttgcttact tcgctatcgt tggatctgga ctcgtttaca gaaaggtttt ccctagaacc 240
gtgaagggac aagatccatt ccttttgaag gctcttatgc ttgctcacaa cgtgttcctt 300
atcggacttt ctctttacat gtgcctcaag cttgtgtacg aggcttacgt taacaagtac 360
tctttctggg gaaacgctta caaccctgct caaactgaga tggctaaggt tatctggatc 420
ttctacgtga gcaagatcta cgagttcatg gataccttca tcatgctcct caagggaaat 480
gttaaccagg ttagcttcct tcacgtttac catcacggat ctatctctgg aatctggtgg 540
atgattactt acgctgctcc tggtggtgat gcttacttct ctgctgctct taactcttgg 600
gttcacgtgt gtatgtacac ctactatttt atggctgccg tgcttcctaa ggacgagaaa 660
actaagagaa agtacctctg gtggggaaga taccttactc aaatgcagat gttccagttc 720
ttcatgaacc ttctccaggc tgtttacctt ctctactctt catctcctta ccctaagttt 780
atcgctcagc tcctcgtggt gtacatggtt actcttctca tgcttttcgg aaacttctac 840
tacatgaagc accacgctag caagtgatga 870

<210> SEQ ID NO 16
<211> LENGTH: 297
<212> TYPE: PRT
<213> ORGANISM: Pyramimonas cordata

<400> SEQUENCE: 16

Met Glu Phe Ala Gln Pro Leu Val Ala Met Ala Gln Glu Gln Tyr Ala
1 5 10 15

Ala Ile Asp Ala Val Val Ala Pro Ala Ile Phe Ser Ala Thr Asp Ser
20 25 30

Ile Gly Trp Gly Leu Lys Pro Ile Ser Ser Ala Thr Lys Asp Leu Pro
35 40 45

Leu Val Glu Ser Pro Thr Pro Leu Ile Leu Ser Leu Leu Ala Tyr Phe
50 55 60

Ala Ile Val Gly Ser Gly Leu Val Tyr Arg Lys Val Phe Pro Arg Thr
65 70 75 80

Val Lys Gly Gln Asp Pro Phe Leu Leu Lys Ala Leu Met Leu Ala His
85 90 95

Asn Val Phe Leu Ile Gly Leu Ser Leu Tyr Met Cys Leu Lys Leu Val
100 105 110

Tyr Glu Ala Tyr Val Asn Lys Tyr Ser Phe Trp Gly Asn Ala Tyr Asn
115 120 125

Pro Ala Gln Thr Glu Met Ala Lys Val Ile Trp Ile Phe Tyr Val Ser
130 135 140

Lys Ile Tyr Glu Phe Met Asp Thr Phe Ile Met Leu Leu Lys Gly Asn
145 150 155 160

Val Asn Gln Val Ser Phe Leu His Val Tyr His His Gly Ser Ile Ser
165 170 175

Gly Ile Trp Trp Met Ile Thr Tyr Ala Ala Pro Gly Gly Asp Ala Tyr
180 185 190

Phe Ser Ala Ala Leu Asn Ser Trp Val His Val Cys Met Tyr Thr Tyr

```
        195                 200                 205

Tyr Phe Met Ala Ala Val Leu Pro Lys Asp Glu Lys Thr Lys Arg Lys
    210                 215                 220

Tyr Leu Trp Trp Gly Arg Tyr Leu Thr Gln Met Gln Met Phe Gln Phe
225                 230                 235                 240

Phe Met Asn Leu Leu Gln Ala Val Tyr Leu Leu Tyr Ser Ser Ser Pro
                245                 250                 255

Tyr Pro Lys Phe Ile Ala Gln Leu Leu Val Val Tyr Met Val Thr Leu
            260                 265                 270

Leu Met Leu Phe Gly Asn Phe Tyr Tyr Met Lys His His Ala Ser Lys
        275                 280                 285

Lys Gln Lys Leu Ala Ser Lys Lys Gln
    290                 295


<210> SEQ ID NO 17
<211> LENGTH: 288
<212> TYPE: PRT
<213> ORGANISM: Pyramimonas cordata

<400> SEQUENCE: 17

Met Glu Phe Ala Gln Pro Leu Val Ala Met Ala Gln Glu Gln Tyr Ala
1               5                   10                  15

Ala Ile Asp Ala Val Val Ala Pro Ala Ile Phe Ser Ala Thr Asp Ser
            20                  25                  30

Ile Gly Trp Gly Leu Lys Pro Ile Ser Ser Ala Thr Lys Asp Leu Pro
        35                  40                  45

Leu Val Glu Ser Pro Thr Pro Leu Ile Leu Ser Leu Leu Ala Tyr Phe
    50                  55                  60

Ala Ile Val Gly Ser Gly Leu Val Tyr Arg Lys Val Phe Pro Arg Thr
65                  70                  75                  80

Val Lys Gly Gln Asp Pro Phe Leu Leu Lys Ala Leu Met Leu Ala His
                85                  90                  95

Asn Val Phe Leu Ile Gly Leu Ser Leu Tyr Met Cys Leu Lys Leu Val
            100                 105                 110

Tyr Glu Ala Tyr Val Asn Lys Tyr Ser Phe Trp Gly Asn Ala Tyr Asn
        115                 120                 125

Pro Ala Gln Thr Glu Met Ala Lys Val Ile Trp Ile Phe Tyr Val Ser
    130                 135                 140

Lys Ile Tyr Glu Phe Met Asp Thr Phe Ile Met Leu Leu Lys Gly Asn
145                 150                 155                 160

Val Asn Gln Val Ser Phe Leu His Val Tyr His His Gly Ser Ile Ser
                165                 170                 175

Gly Ile Trp Trp Met Ile Thr Tyr Ala Ala Pro Gly Gly Asp Ala Tyr
            180                 185                 190

Phe Ser Ala Ala Leu Asn Ser Trp Val His Val Cys Met Tyr Thr Tyr
        195                 200                 205

Tyr Phe Met Ala Ala Val Leu Pro Lys Asp Glu Lys Thr Lys Arg Lys
    210                 215                 220

Tyr Leu Trp Trp Gly Arg Tyr Leu Thr Gln Met Gln Met Phe Gln Phe
225                 230                 235                 240

Phe Met Asn Leu Leu Gln Ala Val Tyr Leu Leu Tyr Ser Ser Ser Pro
                245                 250                 255

Tyr Pro Lys Phe Ile Ala Gln Leu Leu Val Val Tyr Met Val Thr Leu
            260                 265                 270
```

-continued

```
Leu Met Leu Phe Gly Asn Phe Tyr Tyr Met Lys His His Ala Ser Lys
        275                 280                 285
```

<210> SEQ ID NO 18
<211> LENGTH: 1278
<212> TYPE: DNA
<213> ORGANISM: Pavlova salina

<400> SEQUENCE: 18

```
atgccgccgc gcgatagcta ctcgtacgcc gccccgccgt cggcccagct gcacgaggtc      60

gataccccgc aggagcatga taagaaggag ctcgtcatcg gtgaccgcgc gtacgacgtg     120

accaactttg tgaagcgcca cccgggtggc aagatcatcg cataccaggt tggcacagat     180

gcgacggacg cgtacaagca gttccatgtg cggtctgcca aggcggacaa gatgctcaag     240

tcgctgcctt cgcgcccggt gcacaagggc tactcgcccc gccgcgctga cctcattgcc     300

gacttccagg agttcaccaa gcagctggag gcggagggca tgtttgagcc gtcgctgccg     360

cacgtggcat accgcctggc ggaggtgatc gcgatgcacg tggccggcgc cgcgctcatc     420

tggcacgggt acaccttcgc gggcattgcc atgctcggcg ttgtgcaggg ccgctgcggc     480

tggctcatgc acgagggcgg ccactactcg ctcacgggca acattgcttt tgaccgtgcc     540

atccaagtcg cgtgctacgg ccttggctgc ggcatgtcgg gcgcgtggtg gcgcaaccag     600

cacaacaagc accacgcgac gccgcagaag ttgcagcacg acgtcgacct cgacaccctc     660

ccgctcgtcg ccttccacga gcggatagcc gccaaggtga agagccccgc gatgaaggcg     720

tggcttagta tgcaggcgaa gctcttcgcg ccagtgacca cgctgctggt cgcgctgggc     780

tggcagctgt acctgcaccc gcgccatatg ctgcgcacca agcactacga cgagctcgcg     840

atgctcggca ttcgctacgg ccttgtcggc tacctcgcgg cgaactacgg cgcggggtac     900

gtgctcgcgt gctacctgct gtacgtgcag ctcggcgcca tgtacatctt ctgcaacttt     960

gccgtgtcgc acacacacct gccggttgtc gagcctaacg agcacgcaac gtgggtggag    1020

tacgccgcga accacacgac caactgctcg ccctcgtggt ggtgcgactg gtggatgtcg    1080

tacctcaact accagatcga gcaccacctc tacccgtcca tgccgcagtt ccgccacccg    1140

aagattgcgc cgcgggtgaa gcagctcttc gagaagcacg gcctgcacta cgacgtgcgt    1200

ggctacttcg aggccatggc ggacacgttt gccaaccttg acaacgtcgc gcacgcgccg    1260

gagaagaaga tgcagtga                                                  1278
```

<210> SEQ ID NO 19
<211> LENGTH: 1281
<212> TYPE: DNA
<213> ORGANISM: Artificial Sequence
<220> FEATURE:
<223> OTHER INFORMATION: Codon-optimized open reading frame for expression of Pavlova salina 5 desaturase in plants (version 1)

<400> SEQUENCE: 19

```
atgcctccaa gggactctta ctcttatgct gctcctcctt ctgctcaact tcacgaagtt      60

gatactcctc aagagcacga caagaaagag cttgttatcg gagatagggc ttacgatgtt     120

accaacttcg ttaagagaca ccctggtgga aagatcattg cttaccaagt tggaactgat     180

gctaccgatg cttacaagca gttccatgtt agatctgcta aggctgacaa gatgcttaag     240

tctcttcctt ctcgtcctgt tcacaaggga tactctccaa gaagggctga tcttatcgct     300

gatttccaag agttcaccaa gcaacttgag gctgagggaa tgttcgagcc ttctcttcct     360

catgttgctt acagacttgc tgaggttatc gctatgcatg ttgctggtgc tgctcttatc     420
```

-continued

```
tggcatggat acactttcgc tggaatcgct atgcttggag ttgttcaggg aagatgtgga    480

tggcttatgc atgagggtgg acattactct ctcactggaa acattgcttt cgacagagct    540

atccaagttg cttgttacgg acttggatgt ggaatgtctg gtgcttggtg gcgtaaccag    600

cataacaagc accatgctac tcctcaaaag cttcagcacg atgttgatct tgataccctt    660

cctctcgttg ctttccatga gagaatcgct gctaaggtta agtctcctgc tatgaaggct    720

tggctttcta tgcaagctaa gcttttcgct cctgttacca ctcttcttgt tgctcttgga    780

tggcagcttt accttcatcc tagacacatg ctcaggacta agcactacga tgagcttgct    840

atgctcggaa tcagatacgg acttgttgga taccttgctg ctaactacgg tgctggatac    900

gttctcgctt gttaccttct ttacgttcag cttggagcta tgtacatctt ctgcaacttc    960

gctgtttctc atactcacct ccctgttgtt gagcctaacg agcatgctac ttgggttgag   1020

tacgctgcta accacactac taactgttct ccatcttggt ggtgtgattg gtggatgtct   1080

taccttaact accagatcga gcaccacctt tacccttcta tgcctcaatt cagacaccct   1140

aagatcgctc ctagagttaa gcagcttttc gagaagcacg gacttcacta cgatgttaga   1200

ggatacttcg aggctatggc tgatactttc gctaaccttg ataacgttgc ccatgctcct   1260

gagaagaaaa tgcagtaatg a                                             1281
```

```
<210> SEQ ID NO 20
<211> LENGTH: 425
<212> TYPE: PRT
<213> ORGANISM: Pavlova salina

<400> SEQUENCE: 20

Met Pro Pro Arg Asp Ser Tyr Ser Tyr Ala Ala Pro Pro Ser Ala Gln
1               5                   10                  15

Leu His Glu Val Asp Thr Pro Gln Glu His Asp Lys Lys Glu Leu Val
            20                  25                  30

Ile Gly Asp Arg Ala Tyr Asp Val Thr Asn Phe Val Lys Arg His Pro
        35                  40                  45

Gly Gly Lys Ile Ile Ala Tyr Gln Val Gly Thr Asp Ala Thr Asp Ala
    50                  55                  60

Tyr Lys Gln Phe His Val Arg Ser Ala Lys Ala Asp Lys Met Leu Lys
65                  70                  75                  80

Ser Leu Pro Ser Arg Pro Val His Lys Gly Tyr Ser Pro Arg Arg Ala
                85                  90                  95

Asp Leu Ile Ala Asp Phe Gln Glu Phe Thr Lys Gln Leu Glu Ala Glu
            100                 105                 110

Gly Met Phe Glu Pro Ser Leu Pro His Val Ala Tyr Arg Leu Ala Glu
        115                 120                 125

Val Ile Ala Met His Val Ala Gly Ala Ala Leu Ile Trp His Gly Tyr
    130                 135                 140

Thr Phe Ala Gly Ile Ala Met Leu Gly Val Val Gln Gly Arg Cys Gly
145                 150                 155                 160

Trp Leu Met His Glu Gly Gly His Tyr Ser Leu Thr Gly Asn Ile Ala
                165                 170                 175

Phe Asp Arg Ala Ile Gln Val Ala Cys Tyr Gly Leu Gly Cys Gly Met
            180                 185                 190

Ser Gly Ala Trp Trp Arg Asn Gln His Asn Lys His His Ala Thr Pro
        195                 200                 205

Gln Lys Leu Gln His Asp Val Asp Leu Asp Thr Leu Pro Leu Val Ala
```

```
    210                 215                 220

Phe His Glu Arg Ile Ala Ala Lys Val Lys Ser Pro Ala Met Lys Ala
225                 230                 235                 240

Trp Leu Ser Met Gln Ala Lys Leu Phe Ala Pro Val Thr Thr Leu Leu
                245                 250                 255

Val Ala Leu Gly Trp Gln Leu Tyr Leu His Pro Arg His Met Leu Arg
            260                 265                 270

Thr Lys His Tyr Asp Glu Leu Ala Met Leu Gly Ile Arg Tyr Gly Leu
        275                 280                 285

Val Gly Tyr Leu Ala Ala Asn Tyr Gly Ala Gly Tyr Val Leu Ala Cys
    290                 295                 300

Tyr Leu Leu Tyr Val Gln Leu Gly Ala Met Tyr Ile Phe Cys Asn Phe
305                 310                 315                 320

Ala Val Ser His Thr His Leu Pro Val Val Glu Pro Asn Glu His Ala
                325                 330                 335

Thr Trp Val Glu Tyr Ala Ala Asn His Thr Thr Asn Cys Ser Pro Ser
            340                 345                 350

Trp Trp Cys Asp Trp Trp Met Ser Tyr Leu Asn Tyr Gln Ile Glu His
        355                 360                 365

His Leu Tyr Pro Ser Met Pro Gln Phe Arg His Pro Lys Ile Ala Pro
    370                 375                 380

Arg Val Lys Gln Leu Phe Glu Lys His Gly Leu His Tyr Asp Val Arg
385                 390                 395                 400

Gly Tyr Phe Glu Ala Met Ala Asp Thr Phe Ala Asn Leu Asp Asn Val
                405                 410                 415

Ala His Ala Pro Glu Lys Lys Met Gln
            420                 425
```

<210> SEQ ID NO 21
<211> LENGTH: 1329
<212> TYPE: DNA
<213> ORGANISM: Pyramimonas cordata

<400> SEQUENCE: 21

```
atgggaaagg gaggcaatgc tagcgctcct actgcgaaga aggaggtgtt gatcgagggg      60

aagttttacg atgtcaccga cttcaggcac cccggtggtt cgatcatcaa gtttctctcg     120

ggttctggtg ctgacgccac cgcttcctac cgcgagttcc acgttaggtc agcgaaggca     180

gacaagttct tgaagacgct gccctcccgc gaagccactc cccaggagct gaagcaggcg     240

gttgagttct ccaagctcaa cccgccctcc gcggagagtg cctctgctcc cctgaccgac     300

cttgccaagg tggaagcgct gaacaaggac ttcgaggctt tccgtgagca gctcattcag     360

gagggcttct ttaagcccaa tatcccgcat gtggtcaagc gcatcacgga agtcgtggcg     420

atgatggccg tagcctcctg gatgatggtg cagaccaacg ctcttgttgt gaccctcgga     480

gttctgatcc gcggcattgc acagggccgg tgcggttggc ttatgcacga gggcggccac     540

tatagtctta ctgggaagat ctccattgat aggcgtctgc aggagtcaat ttacggattc     600

ggctgtggaa tgtccggcgc ctggtggcgc aaccagcaca acaagcacca cgcaacccca     660

cagaagctgc agcatgacgt cgacctggag acccttcctc tgatggcttt caacaacgct     720

gttaccgata gacgcaaggt gaagcctggt agtctccagg ctctgtggct caagtaccag     780

gccttcctct tcttccccgt gacctccctt ctggtcggcc tcggttggac caccgtcctc     840

caccccaggc acagcttgcg caccaagcac tatttcgagc tgctctgcat ggctgctcgt     900
```

```
tacgcgagtt tcgctgctct tttcgctccc aagtacggac ttgcaggagc tgccgggctc    960

tacctcgcca ccttcgctgt cgggtgcaac tatattttca tcaacttctc ggtctctcac   1020

actcacctgc ccgtgagcgg tgcgagcgag tacctgcatt gggtcgtgta ttcggccatc   1080

cacaccacta acatcaaatc cagcatgctg tgcgattggt ggatgtcatt cctcaacttc   1140

cagatcgagc atcacctgtt cccttcaatg ccccagttcc gccacaagat tatctccccg   1200

cgtgtaaagg ccttgtttga gaagcacggt cttgtgtatg atgtgcgccc ctattggggg   1260

gccatggctg acaccttcaa gaacttgaat gacgttggca ctcacgcatc tcactccaag   1320

gcgcactag                                                           1329


<210> SEQ ID NO 22
<211> LENGTH: 442
<212> TYPE: PRT
<213> ORGANISM: Pyramimonas cordata

<400> SEQUENCE: 22

Met Gly Lys Gly Gly Asn Ala Ser Ala Pro Thr Ala Lys Lys Glu Val
1               5                   10                  15

Leu Ile Glu Gly Lys Phe Tyr Asp Val Thr Asp Phe Arg His Pro Gly
            20                  25                  30

Gly Ser Ile Ile Lys Phe Leu Ser Gly Ser Gly Ala Asp Ala Thr Ala
        35                  40                  45

Ser Tyr Arg Glu Phe His Val Arg Ser Ala Lys Ala Asp Lys Phe Leu
    50                  55                  60

Lys Thr Leu Pro Ser Arg Glu Ala Thr Pro Gln Glu Leu Lys Gln Ala
65                  70                  75                  80

Val Glu Phe Ser Lys Leu Asn Pro Pro Ser Ala Glu Ser Ala Ser Ala
                85                  90                  95

Pro Leu Thr Asp Leu Ala Lys Val Glu Ala Leu Asn Lys Asp Phe Glu
            100                 105                 110

Ala Phe Arg Glu Gln Leu Ile Gln Glu Gly Phe Phe Lys Pro Asn Ile
        115                 120                 125

Pro His Val Val Lys Arg Ile Thr Glu Val Val Ala Met Met Ala Val
    130                 135                 140

Ala Ser Trp Met Met Val Gln Thr Asn Ala Leu Val Val Thr Leu Gly
145                 150                 155                 160

Val Leu Ile Arg Gly Ile Ala Gln Gly Arg Cys Gly Trp Leu Met His
                165                 170                 175

Glu Gly Gly His Tyr Ser Leu Thr Gly Lys Ile Ser Ile Asp Arg Arg
            180                 185                 190

Leu Gln Glu Ser Ile Tyr Gly Phe Gly Cys Gly Met Ser Gly Ala Trp
        195                 200                 205

Trp Arg Asn Gln His Asn Lys His His Ala Thr Pro Gln Lys Leu Gln
    210                 215                 220

His Asp Val Asp Leu Glu Thr Leu Pro Leu Met Ala Phe Asn Asn Ala
225                 230                 235                 240

Val Thr Asp Arg Arg Lys Val Lys Pro Gly Ser Leu Gln Ala Leu Trp
                245                 250                 255

Leu Lys Tyr Gln Ala Phe Leu Phe Phe Pro Val Thr Ser Leu Leu Val
            260                 265                 270

Gly Leu Gly Trp Thr Thr Val Leu His Pro Arg His Ser Leu Arg Thr
        275                 280                 285

Lys His Tyr Phe Glu Leu Leu Cys Met Ala Ala Arg Tyr Ala Ser Phe
```

```
    290                 295                 300

Ala Ala Leu Phe Ala Pro Lys Tyr Gly Leu Ala Gly Ala Ala Gly Leu
305                 310                 315                 320

Tyr Leu Ala Thr Phe Ala Val Gly Cys Asn Tyr Ile Phe Ile Asn Phe
                325                 330                 335

Ser Val Ser His Thr His Leu Pro Val Ser Gly Ala Ser Glu Tyr Leu
            340                 345                 350

His Trp Val Val Tyr Ser Ala Ile His Thr Thr Asn Ile Lys Ser Ser
        355                 360                 365

Met Leu Cys Asp Trp Trp Met Ser Phe Leu Asn Phe Gln Ile Glu His
    370                 375                 380

His Leu Phe Pro Ser Met Pro Gln Phe Arg His Lys Ile Ile Ser Pro
385                 390                 395                 400

Arg Val Lys Ala Leu Phe Glu Lys His Gly Leu Val Tyr Asp Val Arg
                405                 410                 415

Pro Tyr Trp Gly Ala Met Ala Asp Thr Phe Lys Asn Leu Asn Asp Val
            420                 425                 430

Gly Thr His Ala Ser His Ser Lys Ala His
        435                 440
```

<210> SEQ ID NO 23
<211> LENGTH: 804
<212> TYPE: DNA
<213> ORGANISM: Pyramimonas cordata

<400> SEQUENCE: 23

```
atggcgtcta ttgcgattcc ggctgcgctg gcagggactc ttggttatgt gacgtacaat      60
gtcgcaaacc cagatattcc tgcatccgag aaggtgcctg cttactttat gcaggtcgag     120
tattgggggc caacgattgg gaccatcggt tatcttctgt tcatctactt tggtaaacgg     180
attatgcaaa acaggagcca gccgtttggc ctgaagaacg ctatgctggt gtacaacttc     240
tatcagactt tcttcaactc gtactgcata tacctttttg tcacgtcgca ccgcgctcag     300
gggctgaaag tttggggaaa catccccgat atgactgcca acagctgggg gatctcacag     360
gtgatctggc tgcactacaa caacaagtac gttgagctgc tggacacgtt cttcatggtc     420
atgcgcaaga agtttgacca gctttcgttc ctgcacattt accatcatac cctgttgatc     480
tggtcttggt tcgtggtgat gaaattggag cccgttgggg actgctactt tggctctagc     540
gtcaacacgt ttgtgcacgt cattatgtac tcgtactatg gccttgccgc gctcggggtg     600
aattgcttct ggaagaagta cattacgcag attcagatgc tgcagttctg tatctgcgct     660
tcgcactcga tttataccgc ctatgtgcag aacaccgcgt tctggttgcc ttacttgcag     720
ctgtgggtga tggtgaacat gttcgtgttg ttcgccaact tctatcgcaa gcgctacaag     780
agcaagggtg ccaagaagca gtaa                                            804
```

<210> SEQ ID NO 24
<211> LENGTH: 807
<212> TYPE: DNA
<213> ORGANISM: Artificial Sequence
<220> FEATURE:
<223> OTHER INFORMATION: Codon-optimized open reading frame for expression of Pyramimonas cordata 5 elongase in plants (version 1)

<400> SEQUENCE: 24

```
atggcctcta tcgctatccc tgctgctctt gctggaactc ttggatacgt tacctacaat      60
```

```
gtggctaacc ctgatatccc agcttctgag aaagttcctg cttacttcat gcaggttgag    120

tactggggac ctactatcgg aactattgga tacctcctct tcatctactt cggaaagcgt    180

atcatgcaga acagatctca acctttcgga ctcaagaacg ctatgctcgt ttacaacttc    240

taccagacct tcttcaacag ctactgcatc taccttttcg ttacttctca tagggctcag    300

ggacttaagg tttggggaaa catccctgat atgactgcta actcttgggg aatctctcag    360

gttatctggc ttcactacaa caacaagtac gttgagcttc tcgacacctt cttcatggtg    420

atgaggaaga agttcgacca gctttctttc cttcacatct accaccacac tcttctcatc    480

tggtcatggt tcgttgttat gaagcttgag cctgttggag attgctactt cggatcttct    540

gttaacacct tcgtgcacgt gatcatgtac tcttactacg gacttgctgc tcttggagtt    600

aactgtttct ggaagaagta catcacccag atccagatgc ttcagttctg tatctgtgct    660

tctcactcta tctacaccgc ttacgttcag aataccgctt tctggcttcc ttaccttcaa    720

ctctgggtta tggtgaacat gttcgttctc ttcgccaact tctaccgtaa gaggtacaag    780

tctaagggtg ctaagaagca gtgataa                                         807
```

```
<210> SEQ ID NO 25
<211> LENGTH: 267
<212> TYPE: PRT
<213> ORGANISM: Pyramimonas cordata

<400> SEQUENCE: 25

Met Ala Ser Ile Ala Ile Pro Ala Ala Leu Ala Gly Thr Leu Gly Tyr
1               5                   10                  15

Val Thr Tyr Asn Val Ala Asn Pro Asp Ile Pro Ala Ser Glu Lys Val
            20                  25                  30

Pro Ala Tyr Phe Met Gln Val Glu Tyr Trp Gly Pro Thr Ile Gly Thr
        35                  40                  45

Ile Gly Tyr Leu Leu Phe Ile Tyr Phe Gly Lys Arg Ile Met Gln Asn
    50                  55                  60

Arg Ser Gln Pro Phe Gly Leu Lys Asn Ala Met Leu Val Tyr Asn Phe
65                  70                  75                  80

Tyr Gln Thr Phe Phe Asn Ser Tyr Cys Ile Tyr Leu Phe Val Thr Ser
                85                  90                  95

His Arg Ala Gln Gly Leu Lys Val Trp Gly Asn Ile Pro Asp Met Thr
            100                 105                 110

Ala Asn Ser Trp Gly Ile Ser Gln Val Ile Trp Leu His Tyr Asn Asn
        115                 120                 125

Lys Tyr Val Glu Leu Leu Asp Thr Phe Phe Met Val Met Arg Lys Lys
    130                 135                 140

Phe Asp Gln Leu Ser Phe Leu His Ile Tyr His His Thr Leu Leu Ile
145                 150                 155                 160

Trp Ser Trp Phe Val Val Met Lys Leu Glu Pro Val Gly Asp Cys Tyr
                165                 170                 175

Phe Gly Ser Ser Val Asn Thr Phe Val His Val Ile Met Tyr Ser Tyr
            180                 185                 190

Tyr Gly Leu Ala Ala Leu Gly Val Asn Cys Phe Trp Lys Lys Tyr Ile
        195                 200                 205

Thr Gln Ile Gln Met Leu Gln Phe Cys Ile Cys Ala Ser His Ser Ile
    210                 215                 220

Tyr Thr Ala Tyr Val Gln Asn Thr Ala Phe Trp Leu Pro Tyr Leu Gln
225                 230                 235                 240
```

-continued

```
Leu Trp Val Met Val Asn Met Phe Val Leu Phe Ala Asn Phe Tyr Arg
                245                 250                 255

Lys Arg Tyr Lys Ser Lys Gly Ala Lys Lys Gln
            260                 265
```

<210> SEQ ID NO 26
<211> LENGTH: 1344
<212> TYPE: DNA
<213> ORGANISM: Pavlova salina

<400> SEQUENCE: 26

```
atgcctccga gcgcggcgaa gcagatgggc gcgagcacgg gcgtgcatgc gggcgtcaca      60

gattcgtcgg ccttcacgcg caaggatgtc gccgacaggc cggacctcac gatcgtgggt     120

gacagcgtgt acgatgcgaa ggcgttccgc tccgagcatc cgggtggcgc gcactttgtg     180

tcgctgttcg gcgggcgcga tgccacggag gcgttcatgg agtaccaccg gcgcgcctgg     240

cccaagtcgc gcatgtcgcg cttccacgtc ggctctctgg catcgaccga ggagcccgtc     300

gccgccgatg agggctacct ccagctgtgc gctcgcatcg ccaagatggt gccgtcggtc     360

agcagcgggt tcgcgccggc gtcgtactgg gtgaaggccg ggctgatcct cggctccgcg     420

atcgcgctcg aggcgtacat gctgtacgcg ggcaagcgcc tgctcccgtc gatcgtgctc     480

gggtggctgt ttgcgctgat tggcctgaac atccagcacg atgccaacca cggcgcgctc     540

tccaagtcgg cctcggtcaa cctggcgctc gggttgtgcc aggactggat cggcgggagc     600

atgatcctct ggctgcagga gcacgttgtc atgcaccact tgcacaccaa cgacgttgac     660

aaggacccgg accagaaggc gcacggcgcc ctgcggctca agccgaccga cgcgtggagc     720

ccgatgcact ggctgcagca cctctacctg ctgcctgggg agacgatgta cgccttcaag     780

ctgctgtttc tcgacatcag cgagctggtg atgtggcggt gggagggcga gcccatcagc     840

aagctggccg ggtacctctt catgccctcg ctgctcctca agctcacctt ctgggcgcgc     900

tttgtcgcgc tgccgctgta cctcgcgccc agcgtgcaca cggcggtgtg catcgcggcg     960

acggtaatga cggggagctt ctacctcgcc ttcttcttct tcatctcgca caacttcgag    1020

ggcgtggcga gcgtcggacc ggacggcagc atcaccagca tgacgcgcgg cgcatccttc    1080

ctcaagcggc aggccgagac ctcgtccaac gtgggcggcc cgctgctcgc cacgctcaac    1140

ggcggcctca actaccaaat cgagcaccac ctcttcccca gggtgcacca cggcttctac    1200

cctcgcctcg cgccgttggt caaggcggag ctcgaggcgc gcggcattga gtacaagcac    1260

taccccacca tatggagcaa cctggcatcc acgctgaggc acatgtacgc gctcggccgc    1320

aggccgcgca gcaaggcgga gtga                                           1344
```

<210> SEQ ID NO 27
<211> LENGTH: 1347
<212> TYPE: DNA
<213> ORGANISM: Artificial Sequence
<220> FEATURE:
<223> OTHER INFORMATION: Codon-optimized open reading frame for
      expression of Pavlova salina  4 desaturase in plants (version 1)

<400> SEQUENCE: 27

```
atgccaccta gcgctgctaa gcaaatggga gcttctactg gtgttcatgc tggtgttact      60

gactcttctg ctttcaccag aaaggatgtt gctgatagac ctgatctcac catcgttgga     120

gattctgttt acgatgctaa ggctttcaga tctgagcatc ctggtggtgc tcatttcgtt     180

tctttgttcg gaggaagaga tgctactgag gctttcatgg aataccatag aagggcttgg     240
```

-continued

```
cctaagtcta gaatgtctag attccacgtt ggatctcttg cttctactga ggaacctgtt    300

gctgctgatg agggatacct tcaactttgt gctaggatcg ctaagatggt gccttctgtt    360

tcttctggat tcgctcctgc ttcttactgg gttaaggctg gacttatcct tggatctgct    420

atcgctcttg aggcttacat gctttacgct ggaaagagac ttctcccttc tatcgttctt    480

ggatggcttt tcgctcttat cggtcttaac atccagcatg atgctaacca tggtgctttg    540

tctaagtctg cttctgttaa ccttgctctt ggactttgtc aggattggat cggaggatct    600

atgatccttt ggcttcaaga gcatgttgtt atgcaccacc tccacactaa cgatgttgat    660

aaggatcctg atcaaaaggc tcacggtgct cttagactca agcctactga tgcttggtca    720

cctatgcatt ggcttcagca tctttacctt ttgcctggtg agactatgta cgctttcaag    780

cttttgttcc tcgacatctc tgagcttgtt atgtggcgtt gggagggtga gcctatctct    840

aagcttgctg gatacctctt tatgccttct ttgcttctca agcttacctt ctgggctaga    900

ttcgttgctt tgcctcttta ccttgctcct tctgttcata ctgctgtgtg tatcgctgct    960

actgttatga ctggatcttt ctacctcgct ttcttcttct tcatctccca caacttcgag   1020

ggtgttgctt ctgttggacc tgatggatct atcacttcta tgactagagg tgctagcttc   1080

cttaagagac aagctgagac ttcttctaac gttggaggac ctcttcttgc tactcttaac   1140

ggtggactca actaccaaat tgagcatcac ttgttcccta gagttcacca tggattctac   1200

cctagacttg ctcctcttgt taaggctgag cttgaggcta gaggaatcga gtacaagcac   1260

taccctacta tctggtctaa ccttgcttct accctcagac atatgtacgc tcttggaaga   1320

aggcctagat ctaaggctga gtaatga                                         1347


<210> SEQ ID NO 28
<211> LENGTH: 447
<212> TYPE: PRT
<213> ORGANISM: Pavlova salina

<400> SEQUENCE: 28

Met Pro Pro Ser Ala Ala Lys Gln Met Gly Ala Ser Thr Gly Val His
1               5                   10                  15

Ala Gly Val Thr Asp Ser Ser Ala Phe Thr Arg Lys Asp Val Ala Asp
            20                  25                  30

Arg Pro Asp Leu Thr Ile Val Gly Asp Ser Val Tyr Asp Ala Lys Ala
        35                  40                  45

Phe Arg Ser Glu His Pro Gly Gly Ala His Phe Val Ser Leu Phe Gly
    50                  55                  60

Gly Arg Asp Ala Thr Glu Ala Phe Met Glu Tyr His Arg Arg Ala Trp
65                  70                  75                  80

Pro Lys Ser Arg Met Ser Arg Phe His Val Gly Ser Leu Ala Ser Thr
                85                  90                  95

Glu Glu Pro Val Ala Ala Asp Glu Gly Tyr Leu Gln Leu Cys Ala Arg
            100                 105                 110

Ile Ala Lys Met Val Pro Ser Val Ser Ser Gly Phe Ala Pro Ala Ser
        115                 120                 125

Tyr Trp Val Lys Ala Gly Leu Ile Leu Gly Ser Ala Ile Ala Leu Glu
    130                 135                 140

Ala Tyr Met Leu Tyr Ala Gly Lys Arg Leu Leu Pro Ser Ile Val Leu
145                 150                 155                 160

Gly Trp Leu Phe Ala Leu Ile Gly Leu Asn Ile Gln His Asp Ala Asn
                165                 170                 175
```

```
His Gly Ala Leu Ser Lys Ser Ala Ser Val Asn Leu Ala Leu Gly Leu
            180                 185                 190

Cys Gln Asp Trp Ile Gly Gly Ser Met Ile Leu Trp Leu Gln Glu His
        195                 200                 205

Val Val Met His His Leu His Thr Asn Asp Val Asp Lys Asp Pro Asp
    210                 215                 220

Gln Lys Ala His Gly Ala Leu Arg Leu Lys Pro Thr Asp Ala Trp Ser
225                 230                 235                 240

Pro Met His Trp Leu Gln His Leu Tyr Leu Leu Pro Gly Glu Thr Met
                245                 250                 255

Tyr Ala Phe Lys Leu Leu Phe Leu Asp Ile Ser Glu Leu Val Met Trp
            260                 265                 270

Arg Trp Glu Gly Glu Pro Ile Ser Lys Leu Ala Gly Tyr Leu Phe Met
        275                 280                 285

Pro Ser Leu Leu Leu Lys Leu Thr Phe Trp Ala Arg Phe Val Ala Leu
    290                 295                 300

Pro Leu Tyr Leu Ala Pro Ser Val His Thr Ala Val Cys Ile Ala Ala
305                 310                 315                 320

Thr Val Met Thr Gly Ser Phe Tyr Leu Ala Phe Phe Phe Phe Ile Ser
                325                 330                 335

His Asn Phe Glu Gly Val Ala Ser Val Gly Pro Asp Gly Ser Ile Thr
            340                 345                 350

Ser Met Thr Arg Gly Ala Ser Phe Leu Lys Arg Gln Ala Glu Thr Ser
        355                 360                 365

Ser Asn Val Gly Gly Pro Leu Leu Ala Thr Leu Asn Gly Gly Leu Asn
    370                 375                 380

Tyr Gln Ile Glu His His Leu Phe Pro Arg Val His His Gly Phe Tyr
385                 390                 395                 400

Pro Arg Leu Ala Pro Leu Val Lys Ala Glu Leu Glu Ala Arg Gly Ile
                405                 410                 415

Glu Tyr Lys His Tyr Pro Thr Ile Trp Ser Asn Leu Ala Ser Thr Leu
            420                 425                 430

Arg His Met Tyr Ala Leu Gly Arg Arg Pro Arg Ser Lys Ala Glu
        435                 440                 445
```

<210> SEQ ID NO 29
<211> LENGTH: 263
<212> TYPE: PRT
<213> ORGANISM: Isochrysis galbana

<400> SEQUENCE: 29

```
Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110
```

```
Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260
```

<210> SEQ ID NO 30
<211> LENGTH: 801
<212> TYPE: DNA
<213> ORGANISM: Artificial Sequence
<220> FEATURE:
<223> OTHER INFORMATION: Codon-optimized open reading frame for expression of Emiliania huxleyi 9 elongase in plants

<400> SEQUENCE: 30

```
atgcttgata gagcttcatc tgatgctgct atttggagcg ctgtttctga tcctgagatc      60

cttatcggaa ccttctctta ccttttgctt aagcctctcc tcagaaactc tggacttgtg     120

gatgagagaa agggagctta ccgtacttct atgatctggt acaacgttgt tcttgctctt     180

ttctctgcta cctctttcta cgttactgct actgctcttg gatgggataa gggaactggt     240

gagtggctta gatctcttac tggtgattct cctcaacaac tttggcagtg cccttctaga     300

gtttgggaca gcaaactctt cttgtggact gctaaagcct tctactactc caagtacgtt     360

gagtaccttg atactgcttg gcttgttctc aagggaaaga aggtttcatt cctccaggga     420

ttccatcatt tcggtgctcc atgggatgtt taccttggaa tcaggcttaa gaacgaggga     480

gtttggatct tcatgttctt caacagcttc atccacactg ttatgtacac ttactacgga     540

cttactgctg ctggatacaa gatcagagga aagcctatca tcaccgctat gcaaatctct     600

caattcgttg gtggattcgt tcttgtgtgg gactacatca acgttccttg tttccatgct     660

gatgctggac aagttttctc ttgggtgttc aactacgctt atgtgggatc tgttttcctt     720

cttttctgcc acttcttcta catggacaac attgctaagg ctaaggctaa aaaggctgtt     780

gctaccagaa aggctctttg a                                               801
```

<210> SEQ ID NO 31
<211> LENGTH: 266
<212> TYPE: PRT
<213> ORGANISM: Emiliania huxleyi

<400> SEQUENCE: 31

```
Met Leu Asp Arg Ala Ser Ser Asp Ala Ala Ile Trp Ser Ala Val Ser
```

-continued

```
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Arg Lys Gly Ala Tyr Arg
        35                  40                  45

Thr Ser Met Ile Trp Tyr Asn Val Val Leu Ala Leu Phe Ser Ala Thr
    50                  55                  60

Ser Phe Tyr Val Thr Ala Thr Ala Leu Gly Trp Asp Lys Gly Thr Gly
65                  70                  75                  80

Glu Trp Leu Arg Ser Leu Thr Gly Asp Ser Pro Gln Gln Leu Trp Gln
                85                  90                  95

Cys Pro Ser Arg Val Trp Asp Ser Lys Leu Phe Leu Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Lys Val Ser Phe Leu Gln Gly Phe His His Phe
    130                 135                 140

Gly Ala Pro Trp Asp Val Tyr Leu Gly Ile Arg Leu Lys Asn Glu Gly
145                 150                 155                 160

Val Trp Ile Phe Met Phe Phe Asn Ser Phe Ile His Thr Val Met Tyr
                165                 170                 175

Thr Tyr Tyr Gly Leu Thr Ala Ala Gly Tyr Lys Ile Arg Gly Lys Pro
            180                 185                 190

Ile Ile Thr Ala Met Gln Ile Ser Gln Phe Val Gly Gly Phe Val Leu
        195                 200                 205

Val Trp Asp Tyr Ile Asn Val Pro Cys Phe His Ala Asp Ala Gly Gln
    210                 215                 220

Val Phe Ser Trp Val Phe Asn Tyr Ala Tyr Val Gly Ser Val Phe Leu
225                 230                 235                 240

Leu Phe Cys His Phe Phe Tyr Met Asp Asn Ile Ala Lys Ala Lys Ala
                245                 250                 255

Lys Lys Ala Val Ala Thr Arg Lys Ala Leu
            260                 265
```

<210> SEQ ID NO 32
<211> LENGTH: 819
<212> TYPE: DNA
<213> ORGANISM: Pavlova pinguis

<400> SEQUENCE: 32

```
atggttgcgc cacccatcac gctcgagtgg ctgctttcgc cgaagctcaa ggatgcagtg     60

ttcggtgggg aggtgctcta cttctccatt gcctacctgt ttcttgcgcc cattttgaag    120

cgcaccccgt tggtggacac gcggaagggc gcgtataaga gtggtatgat cgcgtacaac    180

gtgatcatgt gcgtgttctc gctggtgtgc ttcatctgcc agctcgcagc cctgggctat    240

gacatgggct acttgcagtg ggtgcgtgac ctcacagggg acgagattgt ccccctctac    300

caggacgtgt ccccgtcccc cgccttctcc aacaagctct tcaagtattc gtctattgcc    360

ttccactact ccaagtatgt tgagtacatg gacaccgcat ggctggtgat gaagggcaag    420

cccgtgtcct tgctccaggg cttccaccac tttggcgccg cctgggacac ctactttggc    480

atcaccttcc agaacgaggg catctacgtg ttcgtggtgc tcaacgcctt catccacacg    540

atcatgtacg catactacgc ggccactgcg gcgggtctca agttctcact gaagttcgtc    600

atcacgctca tgcagatcac ccaattcaac gtgggcttcg taatggtgta tcactacatc    660
```

```
accctggagt acttccgcaa ctcaccggag ctcgtcttct cctacctttt caactatgcg    720

tacgtctgca cggttctcct cctcttcatg cagttcttct acatggacaa ctttggcaag    780

aagaaggccg ctgccgccgc gggcaagaag aagaagtag                           819


<210> SEQ ID NO 33
<211> LENGTH: 272
<212> TYPE: PRT
<213> ORGANISM: Pavlova pinguis

<400> SEQUENCE: 33

Met Val Ala Pro Pro Ile Thr Leu Glu Trp Leu Leu Ser Pro Lys Leu
1               5                   10                  15

Lys Asp Ala Val Phe Gly Gly Glu Val Leu Tyr Phe Ser Ile Ala Tyr
            20                  25                  30

Leu Phe Leu Ala Pro Ile Leu Lys Arg Thr Pro Leu Val Asp Thr Arg
        35                  40                  45

Lys Gly Ala Tyr Lys Ser Gly Met Ile Ala Tyr Asn Val Ile Met Cys
    50                  55                  60

Val Phe Ser Leu Val Cys Phe Ile Cys Gln Leu Ala Ala Leu Gly Tyr
65                  70                  75                  80

Asp Met Gly Tyr Leu Gln Trp Val Arg Asp Leu Thr Gly Asp Glu Ile
                85                  90                  95

Val Pro Leu Tyr Gln Asp Val Ser Pro Ser Pro Ala Phe Ser Asn Lys
            100                 105                 110

Leu Phe Lys Tyr Ser Ser Ile Ala Phe His Tyr Ser Lys Tyr Val Glu
        115                 120                 125

Tyr Met Asp Thr Ala Trp Leu Val Met Lys Gly Lys Pro Val Ser Leu
    130                 135                 140

Leu Gln Gly Phe His His Phe Gly Ala Ala Trp Asp Thr Tyr Phe Gly
145                 150                 155                 160

Ile Thr Phe Gln Asn Glu Gly Ile Tyr Val Phe Val Val Leu Asn Ala
                165                 170                 175

Phe Ile His Thr Ile Met Tyr Ala Tyr Tyr Ala Ala Thr Ala Ala Gly
            180                 185                 190

Leu Lys Phe Ser Leu Lys Phe Val Ile Thr Leu Met Gln Ile Thr Gln
        195                 200                 205

Phe Asn Val Gly Phe Val Met Val Tyr His Tyr Ile Thr Leu Glu Tyr
    210                 215                 220

Phe Arg Asn Ser Pro Glu Leu Val Phe Ser Tyr Leu Phe Asn Tyr Ala
225                 230                 235                 240

Tyr Val Cys Thr Val Leu Leu Leu Phe Met Gln Phe Phe Tyr Met Asp
                245                 250                 255

Asn Phe Gly Lys Lys Lys Ala Ala Ala Ala Ala Gly Lys Lys Lys Lys
            260                 265                 270


<210> SEQ ID NO 34
<211> LENGTH: 840
<212> TYPE: DNA
<213> ORGANISM: Pavlova salina

<400> SEQUENCE: 34

atggcgactg aagggatgcc ggcgataacg ctggactggc tgctctcgcc cgggctgaag     60

gatgccgtaa ttggcgggga ggtgctctac ttttcgcttg ggtatctgct gctcgagccc    120

atcctcaagc gctcaccgtt tgtggacaag cgcaagggcg cataccgcaa cggcatgatc    180
```

```
gcgtacaaca tcctcatgtg cggtttctcg ctggtatgct tcgtgtgcca gatggcggcg    240

ctcggccttg atcgcggcca cctgcagttt gtccgcgacc tcacgggcga cagcgtggtg    300

cagctctacc aggacgtgag cccatcccct gcattcgcga acaagctctt ccggtactca    360

gcggtggcgt tccactactc aaagtacgtg gagtacatgg acacagcgtg gcttgtgctg    420

aagggcaagc ccgtctcgtt cctgcagggc ttccaccact tcggcgccgc gtgggacacc    480

tactttggca tcacgtttca gaacgagggc acctacgtct ttgtgctgct caacgcattc    540

atccacacaa tcatgtacac ctactacggc gcgacggcag cgggcatcaa aatctcgatg    600

aagccgctga tcaccctcat gcagatcacg cagttcctgc tgggcttcgc gctcgtctac    660

ccgtacattg acctcggcta cttccgtgcg tcgcccgagc tcgtgtggag ctacctgttc    720

aactatgcgt acgtactcat ggtgctcttc ctcttcatgc gcttcttcta ccacgacaac    780

tttagcaagc acaagccaat ctcgcgcatc gactccagca accgcatgaa aaccgagtag    840


<210> SEQ ID NO 35
<211> LENGTH: 279
<212> TYPE: PRT
<213> ORGANISM: Pavlova salina

<400> SEQUENCE: 35

Met Ala Thr Glu Gly Met Pro Ala Ile Thr Leu Asp Trp Leu Leu Ser
1               5                   10                  15

Pro Gly Leu Lys Asp Ala Val Ile Gly Gly Glu Val Leu Tyr Phe Ser
            20                  25                  30

Leu Gly Tyr Leu Leu Leu Glu Pro Ile Leu Lys Arg Ser Pro Phe Val
        35                  40                  45

Asp Lys Arg Lys Gly Ala Tyr Arg Asn Gly Met Ile Ala Tyr Asn Ile
    50                  55                  60

Leu Met Cys Gly Phe Ser Leu Val Cys Phe Val Cys Gln Met Ala Ala
65                  70                  75                  80

Leu Gly Leu Asp Arg Gly His Leu Gln Phe Val Arg Asp Leu Thr Gly
                85                  90                  95

Asp Ser Val Val Gln Leu Tyr Gln Asp Val Ser Pro Ser Pro Ala Phe
            100                 105                 110

Ala Asn Lys Leu Phe Arg Tyr Ser Ala Val Ala Phe His Tyr Ser Lys
        115                 120                 125

Tyr Val Glu Tyr Met Asp Thr Ala Trp Leu Val Leu Lys Gly Lys Pro
    130                 135                 140

Val Ser Phe Leu Gln Gly Phe His His Phe Gly Ala Ala Trp Asp Thr
145                 150                 155                 160

Tyr Phe Gly Ile Thr Phe Gln Asn Glu Gly Thr Tyr Val Phe Val Leu
                165                 170                 175

Leu Asn Ala Phe Ile His Thr Ile Met Tyr Thr Tyr Tyr Gly Ala Thr
            180                 185                 190

Ala Ala Gly Ile Lys Ile Ser Met Lys Pro Leu Ile Thr Leu Met Gln
        195                 200                 205

Ile Thr Gln Phe Leu Leu Gly Phe Ala Leu Val Tyr Pro Tyr Ile Asp
    210                 215                 220

Leu Gly Tyr Phe Arg Ala Ser Pro Glu Leu Val Trp Ser Tyr Leu Phe
225                 230                 235                 240

Asn Tyr Ala Tyr Val Leu Met Val Leu Phe Leu Phe Met Arg Phe Phe
                245                 250                 255
```

```
Tyr His Asp Asn Phe Ser Lys His Lys Pro Ile Ser Arg Ile Asp Ser
            260                 265                 270

Ser Asn Arg Met Lys Thr Glu
        275


<210> SEQ ID NO 36
<211> LENGTH: 1284
<212> TYPE: DNA
<213> ORGANISM: Pavlova salina

<400> SEQUENCE: 36

atgggacgcg gcggagacag cagtgggcag gcgcatccgg cggcggagct ggcggtcccg      60

agcgaccgcg cggaggtgag caacgctgac agcaaagcgc tgcacatcgt gctgtatggc     120

aagcgcgtgg atgtgaccaa gttccaacgc acgcacccgg gtggtagcaa ggtcttccgg     180

atcttccagg accgcgatgc gacggagcag ttcgagtcct accactcgaa gcgcgcgatc     240

aagatgatgg agggcatgct caagaagtct gaggatgctc ccgccgacac gcccttgccc     300

tcccagtcac cgatggggaa ggacttcaag gcgatgatcg agcggcacgt tgcagcgggt     360

tactacgatc catgcccgct cgatgagctg ttcaagctca gcctcgtgct cctcccgacc     420

tttgcgggca tgtacatgct caaggcgggc gtcggctccc cgctctgcgg cgccctcatg     480

gtgagctttg gctggtacct cgatggctgg ctcgcgcacg actatctgca ccactccgtc     540

ttcaaggggt ccgtcgcacg caccgtcggg tggaacaacg cggcgggcta cttcctcggc     600

ttcgtgcagg ggtatgcggt cgagtggtgg cgcgcgcggc ataacacgca ccacgtgtgc     660

accaatgagg acggctcgga ccccgacatc aaaacggcgc cgctgctcat atacgtgcgc     720

aacaagccga gcatcgccaa gcgcctgaac gccttccagc gctaccagca gtactactat     780

gtgccggtga tggcaatcct cgacctgtac tggcggctcg agtcgatcgc ctacgtcgcg     840

atgcgcctgc cgaagatgct gccgcaggcc ctcgcactcg tcgcgcacta cgccatcgtc     900

gcgtgggtct ttgcgggcaa ctaccacctg ctcccgctcg tgacggttct gcgcgggttt     960

ggcactggga tcaccgtttt cgcgacgcac tacggtgagg acattctcga cgcggaccag    1020

gtgcgtcaca tgacgctcgt cgagcagacg gcactcacct cgcgcaacat ctcgggcggc    1080

tggctcgtga acgtgctcac cggcttcatc tcactgcaga cggagcacca cctgttcccg    1140

atgatgccaa ccggcaacct catgactatc cagcccgagg tgcgcgcctt cttcaagaag    1200

cacggacttg agtaccgcga gggcaacctc attgagtgcg tgcggcagaa catccgtgcg    1260

cttgcattcg agcacctgct ttga                                           1284


<210> SEQ ID NO 37
<211> LENGTH: 427
<212> TYPE: PRT
<213> ORGANISM: Pavlova salina

<400> SEQUENCE: 37

Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
        35                  40                  45

Gln Arg Thr His Pro Gly Gly Ser Lys Val Phe Arg Ile Phe Gln Asp
    50                  55                  60

Arg Asp Ala Thr Glu Gln Phe Glu Ser Tyr His Ser Lys Arg Ala Ile
```

```
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
    130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175

His His Ser Val Phe Lys Gly Ser Val Ala Arg Thr Val Gly Trp Asn
            180                 185                 190

Asn Ala Ala Gly Tyr Phe Leu Gly Phe Val Gln Gly Tyr Ala Val Glu
        195                 200                 205

Trp Trp Arg Ala Arg His Asn Thr His His Val Cys Thr Asn Glu Asp
    210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
                245                 250                 255

Gln Tyr Tyr Tyr Val Pro Val Met Ala Ile Leu Asp Leu Tyr Trp Arg
            260                 265                 270

Leu Glu Ser Ile Ala Tyr Val Ala Met Arg Leu Pro Lys Met Leu Pro
        275                 280                 285

Gln Ala Leu Ala Leu Val Ala His Tyr Ala Ile Val Ala Trp Val Phe
    290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
                325                 330                 335

Asp Ala Asp Gln Val Arg His Met Thr Leu Val Glu Gln Thr Ala Leu
            340                 345                 350

Thr Ser Arg Asn Ile Ser Gly Gly Trp Leu Val Asn Val Leu Thr Gly
        355                 360                 365

Phe Ile Ser Leu Gln Thr Glu His His Leu Phe Pro Met Met Pro Thr
    370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
                405                 410                 415

Asn Ile Arg Ala Leu Ala Phe Glu His Leu Leu
            420                 425


<210> SEQ ID NO 38
<211> LENGTH: 116
<212> TYPE: PRT
<213> ORGANISM: Tomato yellow leaf curl virus

<400> SEQUENCE: 38

Met Trp Asp Pro Leu Leu Asn Glu Phe Pro Glu Ser Val His Gly Phe
1               5                   10                  15
```

```
Arg Cys Met Leu Ala Ile Lys Tyr Leu Gln Ser Val Glu Glu Thr Tyr
            20                  25                  30

Glu Pro Asn Thr Leu Gly His Asp Leu Ile Arg Asp Leu Ile Ser Val
        35                  40                  45

Val Arg Ala Arg Asp Tyr Val Glu Ala Thr Arg Arg Tyr Asn His Phe
    50                  55                  60

His Ala Arg Leu Glu Gly Ser Pro Lys Ala Glu Leu Arg Gln Pro Ile
65                  70                  75                  80

Gln Gln Pro Cys Cys Cys Pro His Cys Pro Arg His Lys Gln Ala Thr
                85                  90                  95

Ile Met Asp Val Gln Ala His Val Pro Glu Ala Gln Asn Ile Gln Asn
            100                 105                 110

Val Ser Lys Pro
        115


<210> SEQ ID NO 39
<211> LENGTH: 351
<212> TYPE: DNA
<213> ORGANISM: Tomato yellow leaf curl virus

<400> SEQUENCE: 39

atgtgggatc cacttctaaa tgaatttcct gaatctgttc acggatttcg ttgtatgtta      60

gctattaaat atttgcagtc cgttgaggaa acttacgagc ccaatacatt gggccacgat     120

ttaattaggg atcttatatc tgttgtaagg gcccgtgact atgtcgaagc gaccaggcga     180

tataatcatt tccacgcccg cctcgaaggt tcgccgaagg ctgaacttcg acagcccata     240

cagcagccgt gctgctgtcc ccattgtcca aggcacaaac aagcgacgat catggacgta     300

caggcccatg taccggaagc ccagaatata cagaatgtat cgaagccctg a              351


<210> SEQ ID NO 40
<211> LENGTH: 389
<212> TYPE: PRT
<213> ORGANISM: Arabidopsis thaliana

<400> SEQUENCE: 40

Met Val Ile Ala Ala Ala Val Ile Val Pro Leu Gly Leu Leu Phe Phe
1               5                   10                  15

Ile Ser Gly Leu Ala Val Asn Leu Phe Gln Ala Val Cys Tyr Val Leu
            20                  25                  30

Ile Arg Pro Leu Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60

Gly Val Lys Ile Gln Val Phe Ala Asp Asn Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ala
    130                 135                 140

Lys Asp Glu Ser Thr Leu Lys Ser Gly Leu Gln Arg Leu Ser Asp Phe
145                 150                 155                 160
```

```
Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Ile Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
    210                 215                 220

Val Thr Ile Pro Lys Thr Ser Pro Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Ser Asp Asp Ala Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Gln Glu Gln Asn Ile Gly Arg Pro Ile Lys Ser
    290                 295                 300

Leu Ala Val Val Leu Ser Trp Ala Cys Val Leu Thr Leu Gly Ala Ile
305                 310                 315                 320

Lys Phe Leu His Trp Ala Gln Leu Phe Ser Ser Trp Lys Gly Ile Thr
                325                 330                 335

Ile Ser Ala Leu Gly Leu Gly Ile Ile Thr Leu Cys Met Gln Ile Leu
            340                 345                 350

Ile Arg Ser Ser Gln Ser Glu Arg Ser Thr Pro Ala Lys Val Val Pro
        355                 360                 365

Ala Lys Pro Lys Asp Asn His His Pro Glu Ser Ser Ser Gln Thr Glu
    370                 375                 380

Thr Glu Lys Glu Lys
385
```

<210> SEQ ID NO 41
<211> LENGTH: 281
<212> TYPE: PRT
<213> ORGANISM: Limnanthes alba

<400> SEQUENCE: 41

```
Met Ala Lys Thr Arg Thr Ser Ser Leu Arg Asn Arg Arg Gln Leu Lys
1               5                   10                  15

Thr Ala Val Ala Ala Thr Ala Asp Asp Asp Lys Asp Gly Ile Phe Met
            20                  25                  30

Val Leu Leu Ser Cys Phe Lys Ile Phe Val Cys Phe Ala Ile Val Leu
        35                  40                  45

Ile Thr Ala Val Ala Trp Gly Leu Ile Met Val Leu Leu Leu Pro Trp
    50                  55                  60

Pro Tyr Met Arg Ile Arg Leu Gly Asn Leu Tyr Gly His Ile Ile Gly
65                  70                  75                  80

Gly Leu Val Ile Trp Leu Tyr Gly Ile Pro Ile Glu Ile Gln Gly Ser
                85                  90                  95

Glu His Thr Lys Lys Arg Ala Ile Tyr Ile Ser Asn His Ala Ser Pro
            100                 105                 110

Ile Asp Ala Phe Phe Val Met Trp Leu Ala Pro Ile Gly Thr Val Gly
        115                 120                 125

Val Ala Lys Lys Glu Val Ile Trp Tyr Pro Leu Leu Gly Gln Leu Tyr
    130                 135                 140
```

```
Thr Leu Ala His His Ile Arg Ile Asp Arg Ser Asn Pro Ala Ala Ala
145                 150                 155                 160

Ile Gln Ser Met Lys Glu Ala Val Arg Val Ile Thr Glu Lys Asn Leu
                165                 170                 175

Ser Leu Ile Met Phe Pro Glu Gly Thr Arg Ser Gly Asp Gly Arg Leu
            180                 185                 190

Leu Pro Phe Lys Lys Gly Phe Val His Leu Ala Leu Gln Ser His Leu
        195                 200                 205

Pro Ile Val Pro Met Ile Leu Thr Gly Thr His Leu Ala Trp Arg Lys
    210                 215                 220

Gly Thr Phe Arg Val Arg Pro Val Pro Ile Thr Val Lys Tyr Leu Pro
225                 230                 235                 240

Pro Ile Asn Thr Asp Asp Trp Thr Val Asp Lys Ile Asp Asp Tyr Val
                245                 250                 255

Lys Met Ile His Asp Ile Tyr Val Arg Asn Leu Pro Ala Ser Gln Lys
            260                 265                 270

Pro Leu Gly Ser Thr Asn Arg Ser Lys
        275                 280


<210> SEQ ID NO 42
<211> LENGTH: 303
<212> TYPE: PRT
<213> ORGANISM: Saccharomyces cerevisiae

<400> SEQUENCE: 42

Met Ser Val Ile Gly Arg Phe Leu Tyr Tyr Leu Arg Ser Val Leu Val
1               5                   10                  15

Val Leu Ala Leu Ala Gly Cys Gly Phe Tyr Gly Val Ile Ala Ser Ile
            20                  25                  30

Leu Cys Thr Leu Ile Gly Lys Gln His Leu Ala Gln Trp Ile Thr Ala
        35                  40                  45

Arg Cys Phe Tyr His Val Met Lys Leu Met Leu Gly Leu Asp Val Lys
    50                  55                  60

Val Val Gly Glu Glu Asn Leu Ala Lys Lys Pro Tyr Ile Met Ile Ala
65                  70                  75                  80

Asn His Gln Ser Thr Leu Asp Ile Phe Met Leu Gly Arg Ile Phe Pro
                85                  90                  95

Pro Gly Cys Thr Val Thr Ala Lys Lys Ser Leu Lys Tyr Val Pro Phe
            100                 105                 110

Leu Gly Trp Phe Met Ala Leu Ser Gly Thr Tyr Phe Leu Asp Arg Ser
        115                 120                 125

Lys Arg Gln Glu Ala Ile Asp Thr Leu Asn Lys Gly Leu Glu Asn Val
    130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
                165                 170                 175

Leu Ala Gln Gln Gly Lys Ile Pro Ile Val Pro Val Val Val Ser Asn
            180                 185                 190

Thr Ser Thr Leu Val Ser Pro Lys Tyr Gly Val Phe Asn Arg Gly Cys
        195                 200                 205

Met Ile Val Arg Ile Leu Lys Pro Ile Ser Thr Glu Asn Leu Thr Lys
    210                 215                 220

Asp Lys Ile Gly Glu Phe Ala Glu Lys Val Arg Asp Gln Met Val Asp
```

```
225                 230                 235                 240

Thr Leu Lys Glu Ile Gly Tyr Ser Pro Ala Ile Asn Asp Thr Thr Leu
                245                 250                 255

Pro Pro Gln Ala Ile Glu Tyr Ala Ala Leu Gln His Asp Lys Lys Val
            260                 265                 270

Asn Lys Lys Ile Lys Asn Glu Pro Val Pro Ser Val Ser Ile Ser Asn
        275                 280                 285

Asp Val Asn Thr His Asn Glu Gly Ser Ser Val Lys Lys Met His
    290                 295                 300


<210> SEQ ID NO 43
<211> LENGTH: 373
<212> TYPE: PRT
<213> ORGANISM: Micromonas pusilla

<400> SEQUENCE: 43

Met Thr Pro Tyr Gln Trp Phe Asn Val Val Ser Ser Leu Gly Tyr Val
1               5                   10                  15

Leu Phe Thr Ala Thr Thr Ser Thr Val Thr Met Leu Val Pro Ala Ile
            20                  25                  30

Ile Leu Leu Arg Pro Val Ser Ala Asn Leu Tyr Ala Arg Cys Thr Ser
        35                  40                  45

Trp Ile Phe Ala Cys Trp Trp Thr Ser Cys Leu Phe Ile Thr Glu Arg
    50                  55                  60

Leu Asn Gly Val Lys Val Arg Val Thr Gly Asp Ala Leu Pro Leu Asn
65                  70                  75                  80

Ala Pro Leu Leu Ile Met Ser Asn His Lys Cys Asn Leu Asp Trp Met
                85                  90                  95

Phe Leu Trp Ser Ser Ala Ile Arg Thr Gly Ser Met Phe His Val Gly
            100                 105                 110

Val Phe Lys Ala Val Ala Lys Ser Glu Ile Arg Val Ile Pro Ile Phe
        115                 120                 125

Gly Trp Gly Cys Lys Leu Asn Gly Phe Ala Tyr Val Arg Arg Arg Trp
    130                 135                 140

Ser Ser Asp Ala Ser His Leu Thr Ser Trp Ile Gln Ser Gln Ile Arg
145                 150                 155                 160

Arg Arg Leu Asn Ala Asn Trp Thr Leu Ile Phe Pro Glu Gly Thr Arg
                165                 170                 175

Tyr Thr Asp Arg Asn Lys Glu Arg Ser Asp Leu Ser Cys Ala Lys Asp
            180                 185                 190

Gly Leu Glu Pro Met Ala Gly Glu Ile Leu Arg Pro Arg Thr Lys Gly
        195                 200                 205

Leu Ala Leu Leu Leu Arg Glu Ser Ala Lys Gly Gly Gly Tyr Tyr Arg
    210                 215                 220

Lys Ile Val Asp Met Thr Ile Gln Tyr Thr Asp Ala Asp Gly Lys Pro
225                 230                 235                 240

Leu Lys Gly Ala Ala Leu Gly Thr Arg Cys Phe Gly Gln Leu Ala Lys
                245                 250                 255

Gly Gln Leu Pro Val Ala Thr Cys His Val His Phe Asp Val Phe Ser
            260                 265                 270

His Lys Asp Val Pro Ala Gly Glu Asp Glu Asp Glu Val Glu Ala Trp
        275                 280                 285

Val Trp Lys Arg Trp Arg Lys Lys Ala Asn Met Leu Glu Ala Cys Ala
    290                 295                 300
```

-continued

```
Ser Ala Gly Gln Phe Glu Gly Val Arg Glu Trp Ser Thr Ser Gly Thr
305                 310                 315                 320

Ala Val Pro Leu Lys Thr Gln Thr Ala Leu Arg Cys Phe Phe Val Leu
                325                 330                 335

Gln Gly Leu Val Cys Val Gly Val Ala Cys Ser Ser Thr Ala Phe Leu
            340                 345                 350

Ala Tyr Val Ala Cys Ala Ala Val Gly Ala Ala Val Ile Ala Gln Thr
        355                 360                 365

Asp Pro Ala Trp Trp
    370


<210> SEQ ID NO 44
<211> LENGTH: 314
<212> TYPE: PRT
<213> ORGANISM: Mortierella alpina

<400> SEQUENCE: 44

Met Ser Ile Gly Ser Ser Asn Pro Val Leu Leu Ala Ala Ile Pro Phe
1               5                   10                  15

Val Tyr Leu Phe Val Leu Pro Arg Val Leu Ala Phe Leu Pro Gln Lys
            20                  25                  30

Ala Gln Phe Leu Ala Lys Cys Ile Val Val Leu Ile Ala Thr Leu Ile
        35                  40                  45

Met Ser Val Ala Gly Cys Phe Ile Ser Ile Val Cys Ala Leu Leu Asp
    50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
                85                  90                  95

Leu Asp Lys Tyr Pro Ala Ile Val Val Cys Asn His Gln Ser Ser Met
            100                 105                 110

Asp Met Met Val Leu Gly Arg Val Phe Pro Lys His Cys Val Val Met
        115                 120                 125

Ala Lys Lys Glu Leu Leu Tyr Phe Pro Phe Leu Gly Met Phe Met Lys
    130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
            180                 185                 190

Leu Leu Pro Phe Lys Lys Gly Ala Phe His Leu Ala Ile Gln Ala Gln
        195                 200                 205

Leu Pro Ile Leu Pro Ile Ile Ser Gln Gly Tyr Ser His Ile Tyr Asp
    210                 215                 220

Ser Ser Lys Arg Tyr Phe Pro Gly Gly Glu Leu Glu Ile Arg Val Leu
225                 230                 235                 240

Glu Pro Ile Pro Thr Thr Gly Leu Thr Thr Asp Asp Val Asn Asp Leu
                245                 250                 255

Met Asp Lys Thr Arg Asn Leu Met Leu Lys His Leu Lys Glu Met Asp
            260                 265                 270

Ser Gln Tyr Ser Ser Ser Thr Ala Glu Asn Gly Ser Thr His Ile Asp
        275                 280                 285

Ala Asp Ile Ala Lys Ser Thr Ala Thr Ser Ile Gly Asn Thr Asp Asp
    290                 295                 300
```

Ala Ile Thr Lys Arg Arg Thr Pro Lys Glu
305 310

<210> SEQ ID NO 45
<211> LENGTH: 391
<212> TYPE: PRT
<213> ORGANISM: Braccisa napus

<400> SEQUENCE: 45

Met Ala Met Ala Ala Ala Ala Val Ile Val Pro Leu Gly Ile Leu Phe
1 5 10 15

Phe Ile Ser Gly Leu Val Val Asn Leu Leu Gln Ala Val Cys Tyr Val
20 25 30

Leu Ile Arg Pro Leu Ser Lys Asn Thr Tyr Arg Lys Ile Asn Arg Val
35 40 45

Val Ala Glu Thr Leu Trp Leu Glu Leu Val Trp Ile Val Asp Trp Trp
50 55 60

Ala Gly Val Lys Ile Gln Val Phe Ala Asp Asp Glu Thr Phe Asn Arg
65 70 75 80

Met Gly Lys Glu His Ala Leu Val Val Cys Asn His Arg Ser Asp Ile
85 90 95

Asp Trp Leu Val Gly Trp Ile Leu Ala Gln Arg Ser Gly Cys Leu Gly
100 105 110

Ser Ala Leu Ala Val Met Lys Lys Ser Ser Lys Phe Leu Pro Val Ile
115 120 125

Gly Trp Ser Met Trp Phe Ser Glu Tyr Leu Phe Leu Glu Arg Asn Trp
130 135 140

Ala Lys Asp Glu Ser Thr Leu Lys Ser Gly Leu Gln Arg Leu Asn Asp
145 150 155 160

Phe Pro Arg Pro Phe Trp Leu Ala Leu Phe Val Glu Gly Thr Arg Phe
165 170 175

Thr Glu Ala Lys Leu Lys Ala Ala Gln Glu Tyr Ala Ala Ser Ser Gln
180 185 190

Leu Pro Val Pro Arg Asn Val Leu Ile Pro Arg Thr Lys Gly Phe Val
195 200 205

Ser Ala Val Ser Asn Met Arg Ser Phe Val Pro Ala Ile Tyr Asp Met
210 215 220

Thr Val Ala Ile Pro Lys Thr Ser Pro Pro Pro Thr Met Leu Arg Leu
225 230 235 240

Phe Lys Gly Gln Pro Ser Val Val His Val His Ile Lys Cys His Ser
245 250 255

Met Lys Asp Leu Pro Glu Ser Asp Asp Ala Ile Ala Gln Trp Cys Arg
260 265 270

Asp Gln Phe Val Ala Lys Asp Ala Leu Leu Asp Lys His Ile Ala Ala
275 280 285

Asp Thr Phe Pro Gly Gln Lys Glu His Asn Ile Gly Arg Pro Ile Lys
290 295 300

Ser Leu Ala Val Val Val Ser Trp Ala Cys Leu Leu Thr Leu Gly Ala
305 310 315 320

Met Lys Phe Leu His Trp Ser Asn Leu Phe Ser Ser Leu Lys Gly Ile
325 330 335

Ala Leu Ser Ala Leu Gly Leu Gly Ile Ile Thr Leu Cys Met Gln Ile
340 345 350

Leu Ile Arg Ser Ser Gln Ser Glu Arg Ser Thr Pro Ala Lys Val Ala

```
        355                 360                 365

Pro Ala Lys Pro Lys Asp Lys His Gln Ser Gly Ser Ser Ser Gln Thr
    370                 375                 380

Glu Val Glu Glu Lys Gln Lys
385                 390


<210> SEQ ID NO 46
<211> LENGTH: 390
<212> TYPE: PRT
<213> ORGANISM: Braccisa napus

<400> SEQUENCE: 46

Met Ala Met Ala Ala Ala Val Ile Val Pro Leu Gly Ile Leu Phe Phe
1               5                   10                  15

Ile Ser Gly Leu Val Val Asn Leu Leu Gln Ala Ile Cys Tyr Val Leu
            20                  25                  30

Ile Arg Pro Leu Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60

Gly Val Lys Ile Gln Val Phe Ala Asp Asn Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ala
    130                 135                 140

Lys Asp Glu Ser Thr Leu Lys Ser Gly Leu Gln Arg Leu Asn Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Val Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
    210                 215                 220

Val Ala Ile Pro Lys Thr Ser Pro Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Ser Asp Asp Ala Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Gln Glu Gln Asn Ile Gly Arg Pro Ile Lys Ser
    290                 295                 300

Leu Ala Val Val Leu Ser Trp Ser Cys Leu Leu Ile Leu Gly Ala Met
305                 310                 315                 320

Lys Phe Leu His Trp Ser Asn Leu Phe Ser Ser Trp Lys Gly Ile Ala
                325                 330                 335
```

Phe Ser Ala Leu Gly Leu Gly Ile Ile Thr Leu Cys Met Gln Ile Leu
340 345 350

Ile Arg Ser Ser Gln Ser Glu Arg Ser Thr Pro Ala Lys Val Val Pro
355 360 365

Ala Lys Pro Lys Asp Asn His Asn Asp Ser Gly Ser Ser Ser Gln Thr
370 375 380

Glu Val Glu Lys Gln Lys
385 390

<210> SEQ ID NO 47
<211> LENGTH: 361
<212> TYPE: PRT
<213> ORGANISM: Phytophthora infestans

<400> SEQUENCE: 47

Met Ala Thr Lys Glu Ala Tyr Val Phe Pro Thr Leu Thr Glu Ile Lys
1 5 10 15

Arg Ser Leu Pro Lys Asp Cys Phe Glu Ala Ser Val Pro Leu Ser Leu
20 25 30

Tyr Tyr Thr Val Arg Cys Leu Val Ile Ala Val Ala Leu Thr Phe Gly
35 40 45

Leu Asn Tyr Ala Arg Ala Leu Pro Glu Val Glu Ser Phe Trp Ala Leu
50 55 60

Asp Ala Ala Leu Cys Thr Gly Tyr Ile Leu Leu Gln Gly Ile Val Phe
65 70 75 80

Trp Gly Phe Phe Thr Val Gly His Asp Ala Gly His Gly Ala Phe Ser
85 90 95

Arg Tyr His Leu Leu Asn Phe Val Val Gly Thr Phe Met His Ser Leu
100 105 110

Ile Leu Thr Pro Phe Glu Ser Trp Lys Leu Thr His Arg His His His
115 120 125

Lys Asn Thr Gly Asn Ile Asp Arg Asp Glu Val Phe Tyr Pro Gln Arg
130 135 140

Lys Ala Asp Asp His Pro Leu Ser Arg Asn Leu Ile Leu Ala Leu Gly
145 150 155 160

Ala Ala Trp Leu Ala Tyr Leu Val Glu Gly Phe Pro Pro Arg Lys Val
165 170 175

Asn His Phe Asn Pro Phe Glu Pro Leu Phe Val Arg Gln Val Ser Ala
180 185 190

Val Val Ile Ser Leu Leu Ala His Phe Phe Val Ala Gly Leu Ser Ile
195 200 205

Tyr Leu Ser Leu Gln Leu Gly Leu Lys Thr Met Ala Ile Tyr Tyr Tyr
210 215 220

Gly Pro Val Phe Val Phe Gly Ser Met Leu Val Ile Thr Thr Phe Leu
225 230 235 240

His His Asn Asp Glu Glu Thr Pro Trp Tyr Ala Asp Ser Glu Trp Thr
245 250 255

Tyr Val Lys Gly Asn Leu Ser Ser Val Asp Arg Ser Tyr Gly Ala Leu
260 265 270

Ile Asp Asn Leu Ser His Asn Ile Gly Thr His Gln Ile His His Leu
275 280 285

Phe Pro Ile Ile Pro His Tyr Lys Leu Lys Lys Ala Thr Ala Ala Phe
290 295 300

His Gln Ala Phe Pro Glu Leu Val Arg Lys Ser Asp Glu Pro Ile Ile
305 310 315 320

```
Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360


<210> SEQ ID NO 48
<211> LENGTH: 418
<212> TYPE: PRT
<213> ORGANISM: Thalassiosira pseudonana

<400> SEQUENCE: 48

Met Tyr Arg Leu Thr Ser Thr Phe Leu Ile Ala Leu Ala Phe Ser Ser
1               5                   10                  15

Ser Ile Asn Ala Phe Ser Pro Gln Arg Pro Pro Arg Thr Ile Thr Lys
            20                  25                  30

Ser Lys Val Gln Ser Thr Val Leu Pro Ile Pro Thr Lys Asp Asp Leu
        35                  40                  45

Asn Phe Leu Gln Pro Gln Leu Asp Glu Asn Asp Leu Tyr Leu Asp Asp
    50                  55                  60

Val Asn Thr Pro Pro Arg Ala Gly Thr Ile Met Lys Met Leu Pro Lys
65                  70                  75                  80

Glu Thr Phe Asn Ile Asp Thr Ala Thr Ser Leu Gly Tyr Phe Gly Met
                85                  90                  95

Asp Met Ala Ala Val Val Ser Ser Met Thr Leu Leu Asn Ala Ile Val
            100                 105                 110

Thr Ser Asp Gln Tyr His Ala Leu Pro Leu Pro Leu Gln Ala Ala Thr
        115                 120                 125

Val Ile Pro Phe Gln Leu Leu Ala Gly Phe Ala Met Trp Cys Met Trp
    130                 135                 140

Cys Ile Gly His Asp Ala Gly His Ser Thr Val Ser Lys Thr Lys Trp
145                 150                 155                 160

Ile Asn Arg Val Val Gly Glu Val Ala His Ser Val Val Cys Leu Thr
                165                 170                 175

Pro Phe Val Pro Trp Gln Met Ser His Arg Lys His His Leu Asn His
            180                 185                 190

Asn His Ile Glu Lys Asp Tyr Ser His Lys Trp Tyr Ser Arg Asp Glu
        195                 200                 205

Phe Asp Asp Ile Pro Gln Leu Tyr Lys Thr Phe Gly Tyr Asn Pro Arg
    210                 215                 220

Met Met Gln Leu Pro Phe Leu Tyr Phe Met Tyr Leu Ala Leu Gly Ile
225                 230                 235                 240

Pro Asp Gly Gly His Val Val Phe Tyr Gly Arg Met Trp Glu Gly Val
                245                 250                 255

Ser Leu Gln Lys Lys Phe Asp Ala Ala Ile Ser Val Ala Val Ser Cys
            260                 265                 270

Ala Thr Ala Gly Ser Leu Trp Met Asn Met Gly Thr Ala Asp Phe Thr
        275                 280                 285

Val Val Cys Met Val Pro Trp Leu Val Leu Ser Trp Trp Leu Phe Met
    290                 295                 300

Val Thr Tyr Leu Gln His His Ser Glu Asp Gly Lys Leu Tyr Thr Asp
305                 310                 315                 320

Glu Thr Phe Thr Phe Glu Lys Gly Ala Phe Glu Thr Val Asp Arg Ser
```

-continued

```
                325                 330                 335

Tyr Gly Lys Leu Ile Asn Arg Met Ser His His Met Met Asp Gly His
            340                 345                 350

Val Val His His Leu Phe Phe Glu Arg Val Pro His Tyr Arg Leu Glu
        355                 360                 365

Ala Ala Thr Glu Ala Leu Val Lys Gly Met Asp Glu Thr Gly Gln Lys
    370                 375                 380

His Leu Tyr Lys Tyr Ile Asp Thr Pro Asp Phe Asn Ala Glu Ile Val
385                 390                 395                 400

Asn Gly Phe Arg Asp Asn Trp Phe Leu Val Glu Glu Glu Asn Ile Lys
                405                 410                 415

Arg Glu


<210> SEQ ID NO 49
<211> LENGTH: 363
<212> TYPE: PRT
<213> ORGANISM: Pythium irregulare

<400> SEQUENCE: 49

Met Ala Ser Thr Ser Ala Ala Gln Asp Ala Ala Pro Tyr Glu Phe Pro
1               5                   10                  15

Ser Leu Thr Glu Ile Lys Arg Ala Leu Pro Ser Glu Cys Phe Glu Ala
            20                  25                  30

Ser Val Pro Leu Ser Leu Tyr Tyr Thr Ala Arg Ser Leu Ala Leu Ala
        35                  40                  45

Gly Ser Leu Ala Val Ala Leu Ser Tyr Ala Arg Ala Leu Pro Leu Val
    50                  55                  60

Gln Ala Asn Ala Leu Leu Asp Ala Thr Leu Cys Thr Gly Tyr Val Leu
65                  70                  75                  80

Leu Gln Gly Ile Val Phe Trp Gly Phe Phe Thr Val Gly His Asp Cys
                85                  90                  95

Gly His Gly Ala Phe Ser Arg Ser His Val Leu Asn Phe Ser Val Gly
            100                 105                 110

Thr Leu Met His Ser Ile Ile Leu Thr Pro Phe Glu Ser Trp Lys Leu
        115                 120                 125

Ser His Arg His His His Lys Asn Thr Gly Asn Ile Asp Lys Asp Glu
    130                 135                 140

Ile Phe Tyr Pro Gln Arg Glu Ala Asp Ser His Pro Val Ser Arg His
145                 150                 155                 160

Leu Val Met Ser Leu Gly Ser Ala Trp Phe Ala Tyr Leu Phe Ala Gly
                165                 170                 175

Phe Pro Pro Arg Thr Met Asn His Phe Asn Pro Trp Glu Ala Met Tyr
            180                 185                 190

Val Arg Arg Val Ala Ala Val Ile Ile Ser Leu Gly Val Leu Phe Ala
        195                 200                 205

Phe Ala Gly Leu Tyr Ser Tyr Leu Thr Phe Val Leu Gly Phe Thr Thr
    210                 215                 220

Met Ala Ile Tyr Tyr Phe Gly Pro Leu Phe Ile Phe Ala Thr Met Leu
225                 230                 235                 240

Val Val Thr Thr Phe Leu His His Asn Asp Glu Glu Thr Pro Trp Tyr
                245                 250                 255

Ala Asp Ser Glu Trp Thr Tyr Val Lys Gly Asn Leu Ser Ser Val Asp
            260                 265                 270

Arg Ser Tyr Gly Ala Leu Ile Asp Asn Leu Ser His Asn Ile Gly Thr
```

```
        275                 280                 285

His Gln Ile His His Leu Phe Pro Ile Ile Pro His Tyr Lys Leu Asn
    290                 295                 300

Asp Ala Thr Ala Ala Phe Ala Lys Ala Phe Pro Glu Leu Val Arg Lys
305                 310                 315                 320

Asn Ala Ala Pro Ile Ile Pro Thr Phe Phe Arg Met Ala Ala Met Tyr
                325                 330                 335

Ala Lys Tyr Gly Val Val Asp Thr Asp Ala Lys Thr Phe Thr Leu Lys
            340                 345                 350

Glu Ala Lys Ala Ala Ala Lys Thr Lys Ser Ser
        355                 360
```

<210> SEQ ID NO 50
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 50
gcgaagcaca tcgagtca 18

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 51
ggttgaggtg gtagctgagg 20

<210> SEQ ID NO 52
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 52
tctctacccg tctcacatga cgc 23

<210> SEQ ID NO 53
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 53
atacaagcac ggtggatgg 19

<210> SEQ ID NO 54
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 54
tggtctaaca ggtctaggag ga 22

<210> SEQ ID NO 55

-continued

```
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 55

tggcaaagag atttcgagct tcctgc                                           26


<210> SEQ ID NO 56
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 56

caagcaccgt agtaagagag ca                                               22


<210> SEQ ID NO 57
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 57

cagacagcct gaggttagca                                                  20


<210> SEQ ID NO 58
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 58

tccccacttc ttagcgaaag gaacga                                           26
```